United States Patent
Kobayashi et al.

(10) Patent No.: US 8,957,205 B2
(45) Date of Patent: Feb. 17, 2015

(54) CYCLOALKANE CARBOXAMIDE DERIVATIVES AND PRODUCTION PROCESS OF SAME

(75) Inventors: Nobuo Kobayashi, Higashiyamato (JP); Tsuneo Koji, Higashiyamato (JP); Hisatomo Kunii, Higashiyamato (JP); Mizuho Kataoka, Higashiyamato (JP)

(73) Assignee: Seikagaku Corporation, Chiyoda-ku (JP)

( * ) Notice: Subject to any disclaimer, the term of this patent is extended or adjusted under 35 U.S.C. 154(b) by 0 days.

(21) Appl. No.: 12/087,617

(22) PCT Filed: Jan. 10, 2007

(86) PCT No.: PCT/JP2007/050155
§ 371 (c)(1),
(2), (4) Date: Jul. 10, 2008

(87) PCT Pub. No.: WO2007/080885
PCT Pub. Date: Jul. 19, 2007

(65) Prior Publication Data
US 2009/0156805 A1    Jun. 18, 2009

(30) Foreign Application Priority Data

Jan. 11, 2006  (JP) ................ 2006-003689
Dec. 20, 2006  (JP) ................ 2006-343571

(51) Int. Cl.
| | | |
|---|---|---|
| C07D 307/02 | (2006.01) | |
| C07D 413/00 | (2006.01) | |
| C07D 417/00 | (2006.01) | |
| C07C 237/28 | (2006.01) | |
| C07C 271/24 | (2006.01) | |
| C07C 237/24 | (2006.01) | |
| C07C 237/38 | (2006.01) | |
| C07C 271/22 | (2006.01) | |
| C07C 323/59 | (2006.01) | |
| C07D 207/34 | (2006.01) | |
| C07D 277/42 | (2006.01) | |
| C07D 295/155 | (2006.01) | |
| C07D 295/215 | (2006.01) | |
| C07D 307/42 | (2006.01) | |
| C07D 307/54 | (2006.01) | |
| C07D 307/68 | (2006.01) | |
| C07D 333/70 | (2006.01) | |
| C07D 417/04 | (2006.01) | |

(52) U.S. Cl.
CPC ............ *C07C 271/24* (2013.01); *C07C 237/24* (2013.01); *C07C 237/38* (2013.01); *C07C 271/22* (2013.01); *C07C 323/59* (2013.01); *C07D 207/34* (2013.01); *C07D 277/42* (2013.01); *C07D 295/155* (2013.01); *C07D 295/215* (2013.01); *C07D 307/42* (2013.01); *C07D 307/54* (2013.01); *C07D 307/68* (2013.01); *C07D 333/70* (2013.01); *C07D 417/04* (2013.01); *C07B 2200/07* (2013.01); *C07C 2101/14* (2013.01)
USPC .......................................................... 544/129

(58) Field of Classification Search
None
See application file for complete search history.

(56) References Cited

U.S. PATENT DOCUMENTS

| | | |
|---|---|---|
| 5,837,807 A | 11/1998 | Abrecht et al. |
| 6,117,870 A | 9/2000 | Hosoda et al. |
| 6,162,828 A | 12/2000 | Fukuda et al. |
| 2003/0125315 A1 | 7/2003 | Mjalli et al. |
| 2005/0197299 A1 | 9/2005 | Babine et al. |
| 2009/0111983 A1 | 4/2009 | Kobayashi et al. |
| 2009/0137799 A1 | 5/2009 | Kobayashi et al. |

FOREIGN PATENT DOCUMENTS

| | | | |
|---|---|---|---|
| EP | 0 393 457 | 10/1990 | |
| JP | 59-89671 | 5/1984 | |
| JP | 2-256654 | 10/1990 | |
| JP | 2-268145 | 11/1990 | |
| JP | 04-202170 | * 7/1992 | ............ C07C 237/22 |
| JP | 4-202170 | 7/1992 | |

(Continued)

OTHER PUBLICATIONS

Translation of JP-04-202170. Schreiber Translation Inc. Jun. 2009.*

(Continued)

*Primary Examiner* — Nyeemah A Grazier
(74) *Attorney, Agent, or Firm* — Jordan and Hamburg LLP

(57) ABSTRACT

Novel cycloalkane carboxamide derivatives having an action that selectively inhibits cathepsin K, and a production process thereof, are provided, wherein
the cycloalkane carboxamide derivatives are represented by the following general formula (I), or a pharmaceutically acceptable salt thereof:

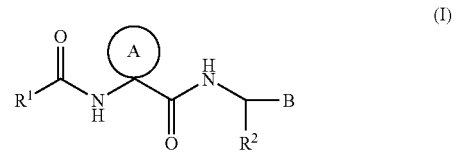

(I)

(wherein $R^1$ and $R^2$ represent (substituted) alkyl groups, (substituted) alkenyl groups, (substituted) alkynyl groups, (substituted) aromatic hydrocarbon groups or (substituted) heterocyclic groups, ring A represents an alkylidene group having 5 to 7 carbon atoms, and ring B represents a formyl group or a hydroxymethyl group).

8 Claims, No Drawings

(56) References Cited

FOREIGN PATENT DOCUMENTS

| | | |
|---|---|---|
| JP | 8-245692 | 9/1996 |
| JP | 9-165360 | 6/1997 |
| JP | 2000-204071 | 7/2000 |
| JP | 2001-139534 | 5/2001 |
| JP | 2002-513029 | 5/2002 |
| JP | 2002-513032 | 5/2002 |
| JP | 2005-504099 | 2/2005 |
| WO | WO-97/16177 | 5/1997 |
| WO | WO-98/01133 | 1/1998 |
| WO | WO-0037429 | 6/2000 |
| WO | WO-01/58886 | 8/2001 |
| WO | WO 2004/041203 * | 5/2004 |

OTHER PUBLICATIONS

Bratkovic et al. Biochem Biophys Res Commun, Jul. 8, 2005, Abstract Only.*
Vinsova, Folia Pharmaceutica Universitatis Carolinae (1996), 20, pp. 77-85.*
Olczyk Synthesis (2007) (12), 1807-1810.*
Babu Indian Journal of Chemistry, Section B: Organic Chemistry Including Medicinal Chemistry (2005), 44B(11), 2328-2332.*
Chen et al, JACS (2002), vol. 124(15), pp. 3840-3841.*
Christine E. Garrett, et al., "New observation on peptide bond formation using CDMT", Tetrahedron Letters, 2002, vol. 43, No. 23, pp. 4161-4165, Scheme 2.
Tetsuya Inaoka, et al., "Molecular Cloning of Human cDNA for Cathespin K: Novel Cysteine Proteinase Predominantly Expressed in Bone", Biochemical and Biophysical Research Communications, vol. 2006, No. 1, Jan. 5, 1995, pp. 89-96.
Fred H. Drake, et al., "Cathespin K, but Not Cathespins B, L, or S, Is Abundantly Expressed in Human Osteoclasts", The Journal of Biological Chemistry, vol. 271, No. 21, May 24, 1996, pp. 12511-12516.
Bruce D. Gelb, et al., "Pycnodysostosis, a Lysosomal Disease Caused by Cathespin K Deficiency", Science, vol. 273, Aug. 30, 1996, pp. 1236-1238.
Dieter Broemme, et al., "Human Cathespin O2, a Matrix Protein-degrading Cysteine Protease Expressed in Osteoclasts, Functional Expression of Human Cathespin O2 in Spodoptera Frugiperda and Characterization of the Enzyme", The Journal of Biological Chemistry, vol. 271, No. 4, Jan. 26, 1996, pp. 2126-2132.
Kazuhiko Aibe, et al., "Substrate Specificity of Recombinant Osteoclast-Specific Cathespin K from Rabbits", Biol. Pharm. Bull., vol. 19, No. 8, 1996, pp. 1026-1031.
Mary E. McGrath, et al., "Crystal structure of human cathespin K complexed with a potent inhibitor, The high resolution structure of the new therapeutic target, cathespin K. complexed with the ptent mechanism-based inhibitor, APC 3328, reveals the substrate-binding sites of this cysteine proteinase and validates the binding mode for this inhibitor class", Nature Structural Biology, vol. 4, No. 2, Feb. 1997, pp. 105-109.
James T. Palmer, et al., "Vinyl Sulfones as Mechanism-Based Cysteine Protease Inhibitors", J. Med. Chem., vol. 38, 1995, pp. 3193-3196.
Dieter Broemme, et al., "Peptide Methyl Ketones As Reversible Inhibitors of Cysteine Proteinases", J. Enzyme Inhibition, 1989, vol. 3, pp. 13-21.
Toshimasa Tsujinaka, et al., "Synthesis of a New Cell Penetrating Calpain Inhibitor (Calpeptin)", Biochemical and Biophysical Research Communications, vol. 153, No. 3, Jun. 30, 1988, pp. 1201-1208.
Seiichi Hashida, et al., "Inhibitions by E-64 Derivatives of Rat Liver Cathespin B and Cathespin L In Vitro and In Vivo", J. Biochem, vol. 88, No. 6, 1980, pp. 1805-1811.
Scott K. Thompson, et al., "Design of potent and selective human cathespin K inhibitors that span the active site", Proc. Natl. Acad. Sci. USA, vol. 94, Dec. 1997, pp. 14249-14254.
Baoguang Zhao, et al., "Crystal structure of human osteoclast cathespin K complex with E-64, The structure of human cathespin K, a potential target for treatment of osteoporosis, reveals active site differences with homologous cysteine proteinases that should enable the design of cathespin K selective inhibitors", Nature Structural Biology, vol. 4, No. 2, Feb. 1997, pp. 109-111.
Renee L. Desjarlais, et al., "Use of X-ray Co-crystal Structures and Molecular Modeling to Design Potent and Selective Non-peptide Inhibitors of Cathespin K", J. Am. Chem. Soc., vol. 120, 1998, vol. 120, pp. 9114-9115.
Robert W. Marquis, et al., "Conformationally Constrained 1,3-Diamino Ketones: A Series of Potent Inhibitors of the Cysteine Protease Cathespin K", J. Med. Chem. vol. 41, 1998, pp. 3563-3567.
David H. Sun, et al., "P4 cap modified tetrapeptidyl α-ketoamides as potent HCB NS3 protease inhibitors", Bioorganic & Medical Chemistry Letters 14, (2004), pp. 4333-4338.
David G. Barrett, et al., "Potent and selective $P^2$-$P^3$ ketoamide inhibitors of cathespin K with good pharmacokinetic properties via favorable $P^1$, $P^1$, and/or $P^3$ substitutions", Bioorganic & Medicinal Chemistry Letters 14, (2004), pp. 4897-4902.
Min Yang, et al., "Impact of methanol and acetonitrile on separations based on π-π interactions with a reserved-phase phenyl column", Journal of Chromatography A, vol. 1097, 2005, pp. 124-129.
Christine E. Garrett et al., "New observations on peptide bond formation using CDMT", Tetrahedron Letters, vol. 43, 2002, pp. 4161-4165.
Fariborz Firooznia, et al., "Synthesis and Biological Activity of Potent Heterocyclic Thiol-Based Inhibitors of Endothelin-Converting Enzyme-1", Bioorganic & Medicinal Chemistry Letters, vol. 12, 2002, pp. 3059-3062.
Bratkovic, et al. "Affinity selection to papain yields potent peptide inhibitors of cathepsins L, B, H, and K." Biochem Biophys Res Communi. U.S. National Library of Medicine National Institutes of Health. Jul. 8, 2005. Abstract Only.
Apr. 25, 2003 "Peptide backbone folding induced by the C-alpha-tetrasubstituted cyclic alpha-amino acids 4-amino-1,2-dithiolane-4-carboxylic acid (Adt) and 1-aminocyclopentane-l-carboxylic acid (Ac5c). A joint computational and experimental study", Massimiliano Aschi et al., Organic and Biomolecular Chemistry vol. 1, No. 11, pp. 1980-1988.
1961 "Syntheses de courts peptides renfermant des acides amino-1 cycloalkyl carboxyliques", Tailleur, Patrice and Louis Berlinguet, Canadian Journal of Chemistry vol. 39, pp. 1309-1320.
2001 "Synthesis and Biological Activity of Novel Potent Endothelin-Converting Enzyme-1 Inhibitors", Firooznia, et al., Bioorganic & Medicinal Chemistry Letters, vol. 11, No. 3 pp. 375-378.
"STN_preliminary_12087688_01272010" (U.S. Appl. No. 12/087,688, publication date not indicated).
Aug. 2, 1996 "Mercaptoacyl Dipeptides as Orally Active Dual Inhibitors of Angiotensin-Converting Enzyme and Neutral Endopeptidase" Cynthia A. Fink et al. Journal of Medicinal Chemistry vol. 39, No. 16 pp. 3158-3168.
Oct. 10, 1997 "Conformational restriction through C-alpha-i -C-alpha-i cyclization: 1-aminocycloheptane-1-carboxylic acid (Ac7c)" Ettore Benedetti et al. Journal of the Chemical Society: Perkin Transactions 2 vol. 1997, No. 10 pp. 2023-2032.
Aug. 1, 1971 "Peptides with Terminal Tyrosyl and Phenylalanyl Groups" Joseph A Skorcz Journal of Medicinal Chemistry vol. 14, No. 8 pp. 775-776.
H. Lynn, et al. "Angiotensin converting enzyme inhibitor use is associated with higher bone mineral density in elderly Chinese." Bone. 2006. pp. 584-588.
"Design and Synthesis of 1-Aminocycloalkane-1-carboxylic Acid-Substituted Deltorphin Analogues: Unique δ and μ Opioid Activity in Modified Peptides"; Angela Breveglieri, et al.; Journal of Medicinal Chemistry (1996) vol. 39, pp. 773-780.
"New α-Thiol Dipeptide Dual Inhibitors of Angiotensin-I Converting Enzyme and Neutral Endopeptidase EC 3.4.24.11"; Cynthia A. Fink, et al.; Journal of Medicinal Chemistry (1995) vol. 38, pp. 5023-5030.
"Utilization of a β-Aminophosphotyrosyl Mimetic in the Design and Synthesis of Macrocyclic Grb2 SH2 Domain-Binding Peptides"; Keyong Lee, et al.; Journal of Medicinal Chemistry (2003) vol. 46, pp. 2621-2630.

(56) References Cited

OTHER PUBLICATIONS

"Synthesis Approach to Peptides derived from α-Alkyl-serines involving Conversion of C-Terminal Amino-Acids", CODEN:SYNTBF ISSN: 0039-7881; J. Kaminski, et al.; Synthesis (1975) vol. 9, pp. 593-596.

"Solid Phase Combinatorial Library of 1,3-Azole Containing Peptides for the Discovery of Matrix Metallo Proteinase Inhibitors"; Caspar Christensen, et al.; QSAR & Combinatorial Science (2003) vol. 22(7), pp. 754-766.

"Conformational Behaviour of a Cyclolinopeptide A Analogue: Two-dimensional NMR study of cyclo(Pro$^1$-Pro-Phe-Phe-Ac$_6$c-Ile-ala-Val$^8$)"; Marco Mazzeo, et al.; Journal of Peptide Science (1995) vol. 1(5), pp. 330-340.

"Proctolin and its Analogues, Structure/Biological Function Relationship Studies"; D. Konopińska, et al.; Polish Journal of Chemistry (1994) vol. 68(7), pp. 1437-1439.

"New Proctolin Analogues Modified in Position 4 of the Peptide Chain and Their Influence on the Heart-Beat Frequency of Insects"; Danuta Konopińska, et al.; Bulletin of the Polish Academy of Sciences, Chemistry (1994), vol. Date 1993 vol. 41(1), pp. 27-39.

"Subtle Differences between Human and Rabbit Neutrophil Receptors Shown by the Secretagogue Activity of Constrained Formyl Peptides"; Andrew R. Dentino, et al.; Archives of Biochemistry and Biophysics (1997) vol. 337(2), pp. 267-274.

"A computergraphic Determination of the Chemotactic Peptide Preferred Conformation"; S.F. Semus, et al.; Biochemical and Biophysical Research Communications (1988) vol. 157(2), pp. 569-574.

"Conformation-Biological Activity Relationships of Conformationally Constrained Delta Specific Cyclic Enkephalins"; Victor J. Hruby, et al.; Pept.: Struct. Funct., Proc. Am. Pept. Symp., (1985) vol. 9, pp. 487-490.

"Synthesis and CCK-B Binding Affinities of Cyclic Analogues of the Potent and Selective CCK-B Receptor Antagonist C1-988"; Eric Didier, et al.; Tetrahedron (1992) vol. 48(39), pp. 8471-8490.

\* cited by examiner

CYCLOALKANE CARBOXAMIDE DERIVATIVES AND PRODUCTION PROCESS OF SAME

FIELD OF THE INVENTION

The present invention relates to novel cycloalkane carboxamide derivatives and a production process thereof. More particularly, the present invention relates to cycloalkane carboxamide derivatives having the action of selectively inhibiting cathepsin K which is the main cysteine protease involved in bone resorption, and to a production process thereof.

BACKGROUND OF THE INVENTION

Accompanying the rapid progression to an elderly society in recent years, the number of patients with geriatric diseases, and particularly those with bone diseases, is continuing to increase. In particular, osteoporosis, which is prevalent among women and especially postmenopausal women, is becoming a serious problem. Since accelerated bone resorption brought about by a loss of hormonal balance and aging phenomena in postmenopausal women is intimately related to the onset and progression of bone disease, bone resorption inhibitors have been used during the course of ordinary drug therapy for osteoporosis. However, drugs currently in use that demonstrate bone resorption inhibitory action, such as calcitonin preparations, estrogen preparations, vitamin K preparations and bisphosphonate preparations, have problems in terms of their therapeutic effects, rapid-acting, adverse side effects and patient compliance, thus desiring the development of a bone resorption inhibitor capable of being used as a more effective drug for the treatment or prevention of osteoporosis.

In the living body, bone calcium concentrations and blood calcium concentrations are in a state of equilibrium, and calcium is constantly migrating between the bone and blood. This migration of calcium is governed by dynamic shifts between bone formation and bone resorption. In the process of bone resorption, bone resorption is known to be accelerated as a result of activated osteoclasts eluting bone inorganic substances such as calcium simultaneous to cysteine proteases secreted from osteoclasts decomposing bone organic substances such as collagen. Cysteine proteases such as cathepsin B, cathepsin H, cathepsin L and cathepsin S are present in osteoclast lysosomes, and osteoclast-localized human cathepsin K was isolated in 1995, which was demonstrated to be expressed in osteoclasts in larger amounts than other cathepsins (Biochem. Biophys. Res. Commun., 206, 89 (1995); J. Biol. Chem., 271, 12511 (1996)). Moreover, the cathepsin K gene was demonstrated to mutate in patients with dwarfism presenting with bone resorption abnormalities (Science, 273, 1236 (1997)).

In this manner, attention has been focused on cathepsin K as the main cysteine protease involved in bone resorption, and considerable expectations are being placed on cathepsin K inhibitors as inhibitors of bone resorption. Previously reported examples of compounds having cathepsin K inhibitory action include aldehyde derivatives, epoxy succinic acid derivatives (J. Biol. Chem., 271, p. 2126 (1996); Biol. Pharm. Bull., 19, p. 1026 (1996)) and vinylsulfonic acid derivatives (Nature Structural Biology, 4, p. 105 (1997); J. Med. Chem., 38, p. 3139 (1995)), and these derivatives have low selectivity and are known to strongly inhibit other cysteine proteases in addition to cathepsin K (J. Enzyme Inhibition, 3, p. 13 (1989); Biochem. Biophys. Res. Commun., 153, p. 1201 (1988); J. Biochem., 87, p. 39 (1980); J. Biochem., 88, p. 805 (1980)).

Moreover, accompanying the growing interest in cathepsin K as described above, research has also been actively conducted in the area of X-ray crystal analyses of cathepsin K and inhibitors (Nature Structural Biology, 4, p. 105 (1997); Nature Structural Biology, 4, p. 109 (1997)), and compounds are known that has a selective inhibitory action on cathepsin K (Proc. Natl. Acad. Sci. USA, 94, 142, p. 49 (1997); WO9801133; J. Am. Chem. Soc., 120, 9, p. 114 (1998); J. Med. Chem., 41, p. 3563 (1988); Japanese Unexamined Patent Publication No. 2000-204071; Bioorg. Med. Chem., 14, p. 4333 (2004); Bioorg. Med. Chem., 14, p. 4897 (2004)). In addition, WO971677 identifies the catalyst active site of cathepsin K and discloses a method for inhibiting cathepsin K using a compound that interacts with this active site.

Moreover, although not containing descriptions of inhibition of cathepsin K, Japanese Unexamined Patent Publication Nos. Hei 2-256654 and Hei 2-268145 disclose various types of aldehyde derivatives as protease inhibitors.

[Non-patent document 1] Proc. Natl. Acad. Sci. USA., 94, 142, p. 49 (1997)

[Non-patent document 2] J. Am. Chem. Soc., 120. 9. p. 114 (1998)

[Non-patent document 3] J. Med. Chem., 41, p. 3563 (1998)

[Non-patent document 4] Bioorg. Med. Chem., 14, p. 4333 (2004)

[Non-patent document 5] Bioorg. Med. Chem., 14, p. 4897 (2004))

[Patent document 1] WO9801133

[Patent document 2] WO971677

[Patent document 3] Japanese Unexamined Patent Publication No. 2000-204071

[Patent document 4] Japanese Unexamined Patent Publication No. Hei 2-256654

[Patent document 5] Japanese Unexamined Patent Publication No. Hei 2-268145

DISCLOSURE OF THE INVENTION

Summary of the Invention

As has been described above, compounds that inhibit cathepsin K have attracted attention as bone resorption inhibitors, and although numerous derivatives have been reported, none has yet been able to be used practically as a therapeutic drug for metabolic bone diseases. As a result of extensive studies on novel compounds having potent and selective cathepsin K inhibitory action, the inventors of the present invention found that novel cycloalkane carboxamide derivatives represented by a specific structural formula selectively inhibit cathepsin K as compared with conventional aldehyde derivatives known to be protease inhibitors.

An object of the present invention is to provide these novel cycloalkane carboxamide derivatives and a production process thereof.

The present invention is based on the fact that cycloalkane carboxamide derivatives represented by general formula (I) having a non-naturally-occurring amino acid structure selectively inhibit cathepsin K as compared with conventional aldehyde derivatives, relates to compounds having more highly selective cathepsin K inhibitory action and a production process thereof, and the gist thereof lies in the cycloalkane carboxamide derivatives described in 1 to 11 below and a production process thereof.

1. A cycloalkane carboxamide derivative represented by formula (I):

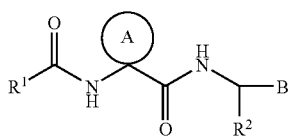

[wherein R¹ represents a substituted or unsubstituted alkyl group, substituted or unsubstituted alkenyl group, substituted or unsubstituted alkynyl group, substituted or unsubstituted aromatic hydrocarbon group, substituted or unsubstituted heterocyclic group, group represented by R⁴O—, group represented by R⁵S— (wherein R⁴ and R⁵ respectively and independently represent a substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group), or group represented by R⁶(R⁷)N— (wherein R⁶ and R⁷ respectively and independently represent a hydrogen atom, a substituted or unsubstituted alkyl group, substituted or unsubstituted alkenyl group, substituted or unsubstituted alkynyl group, substituted or unsubstituted aromatic hydrocarbon group or substituted or unsubstituted heterocyclic group, furthermore R⁶ and R⁷ may together form a ring); R² represents a substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group; ring A represents a cyclic alkylidene group having 5, 6 or 7 carbon atoms; and B represents a formyl group or hydroxymethyl group; provided that in the case B is a formyl group, R² is not a 2-carboxyethyl group] or a pharmaceutically acceptable salt thereof.

2. The cycloalkane carboxamide derivative or pharmaceutically acceptable salt thereof described in 1 above, wherein alkyl groups in the groups represented by R¹, R², R⁴, R⁵, R⁶ and R⁷ in the formula (I) are linear, branched or cyclic alkyl groups having 1 to 12 carbon atoms, the alkenyl groups are linear, branched or cyclic alkenyl groups having 2 to 12 carbon atoms, the alkynyl groups are linear, branched or cyclic alkynyl groups having 2 to 12 carbon atoms, the aromatic hydrocarbon groups are monocyclic or polycyclic aromatic hydrocarbon groups having 6 to 18 carbon atoms, and the heterocyclic groups are heterocyclic groups of 3- to 7-membered rings containing at least one nitrogen atom, oxygen atom or sulfur atom as a ring-constituting atom.

3. The cycloalkane carboxamide derivative or pharmaceutically acceptable salt thereof described in 1 or 2 above, wherein substituents of the alkyl groups in the groups represented by R¹, R², R⁴, R⁵, R⁶ and R⁷ in the formula (I) are a group selected from a hydroxyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein Rx and Ry respectively and independently represent a hydrogen atom, alkyl group, alkenyl group, alkynyl group, aromatic hydrocarbon group or heterocyclic group); and substituents of the alkenyl groups, alkynyl groups, aromatic hydrocarbon groups and heterocyclic groups are a group selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein Rx and Ry respectively and independently represent a hydrogen atom, alkyl group, alkenyl group, alkynyl group, aromatic hydrocarbon group or heterocyclic group).

4. The cycloalkane carboxamide derivative or pharmaceutically acceptable salt thereof described in any of 1 to 3 above, wherein B in the formula (I) is a hydroxymethyl group.

5. The cycloalkane carboxamide derivative or pharmaceutically acceptable salt thereof described in any of 1 to 3 above, wherein B in the formula (I) is a formyl group.

6. The cycloalkane carboxamide derivative or pharmaceutically acceptable salt thereof described in any of 1 to 5 above, wherein R¹ in the formula (I) is a substituted or unsubstituted alkyl group, substituted or unsubstituted alkenyl group, substituted or unsubstituted aromatic hydrocarbon group, or substituted or unsubstituted heterocyclic group, and R¹ is a substituted or unsubstituted alkyl group, or substituted or unsubstituted aromatic hydrocarbon group.

7. The cycloalkane carboxamide derivative or pharmaceutically acceptable salt thereof described in any of 1 to 4 above, wherein the substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group represented by R² in the formula (I) is a group derived from an α-amino acid, and the α-amino acid is an α-amino acid selected from alanine, arginine, asparagine, aspartic acid, isoasparagine, γ-carboxyglutamic acid, cysteine, cystine, glutamine, glutamic acid, histidine, homoarginine, homocysteine, homocystine, homoserine, homophenylalanine, isoleucine, leucine, lysine, methionine, norleucine, t-leucine, norvaline, ornithine, phenylalanine, phenylglycine, serine, threonine, tryptophan, tyrosine, valine, 3,4-dihydroxyphenylalanine, allylglycine, neopentylglycine, allothreonine, homolysine, naphthylalanine, α-aminoadipic acid, thienylglycine, pyridylalanine and cyclohexylalanine.

8. The cycloalkane carboxamide derivative or pharmaceutically acceptable salt thereof described in any of 1, 2, 3 and 5 above, wherein the substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group represented by R² in the formula (I) is a group derived from an α-amino acid, and the α-amino acid is an α-amino acid selected from alanine, arginine, asparagine, aspartic acid, isoasparagine, γ-carboxyglutamic acid, cysteine, cystine, glutamine, histidine, homoarginine, homocysteine, homocystine, homoserine, homophenylalanine, isoleucine, leucine, lysine, methionine, norleucine, norvaline, ornithine, phenylalanine, phenylglycine, serine, threonine, tryptophan, tyrosine, valine, 3,4-dihydroxyphenylalanine, allylglycine, neopentylglycine, allothreonine, homolysine, naphthylalanine, α-aminoadipic acid, thienylglycine, pyridylalanine and cyclohexylalanine.

9. The cycloalkane carboxamide derivative or pharmaceutically acceptable salt thereof described in any of 4 to 8 above, wherein $R^1$ in the formula (I) is a 3- to 7-membered substituted or unsubstituted heterocyclic group, containing at least one nitrogen atom, oxygen atom or sulfur atom as a ring-constituting atom, or a substituted aromatic hydrocarbon group, $R^2$ is an alkyl group having 1 to 4 carbon atoms and ring A is a cyclohexylidene group.

10. A process for producing a cycloalkylcarbonylamino aldehyde derivative represented by the following formula (XIII) by oxidizing a cycloalkylcarbonylamino alcohol derivative represented by the following formula (XI):

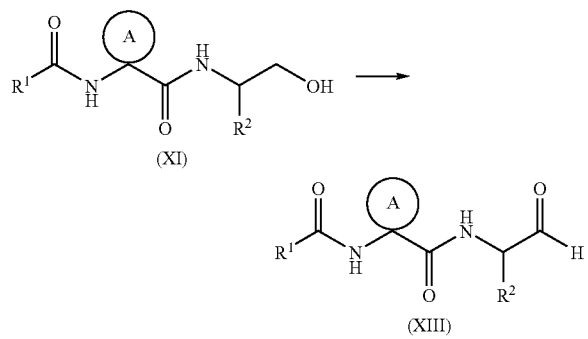

(wherein ring A, $R^1$ and $R^2$ in the formulas (XI) and (XIII) are the same as previously defined in 1 above).

11. A process for producing a cycloalkylcarbonylamino alcohol derivative represented by the following formula (XI) from an oxazolone derivative represented by the following formula ($I_o$) according to any of the following steps (A) to (C):

Step (A):
an oxazolone derivative represented by formula ($I_o$) is reacted with an amino acid derivative represented by formula (VII) to form a cycloalkylcarbonylamino acid derivative represented by formula (X), and the cycloalkylcarbonylamino acid derivative is followed by reduction;

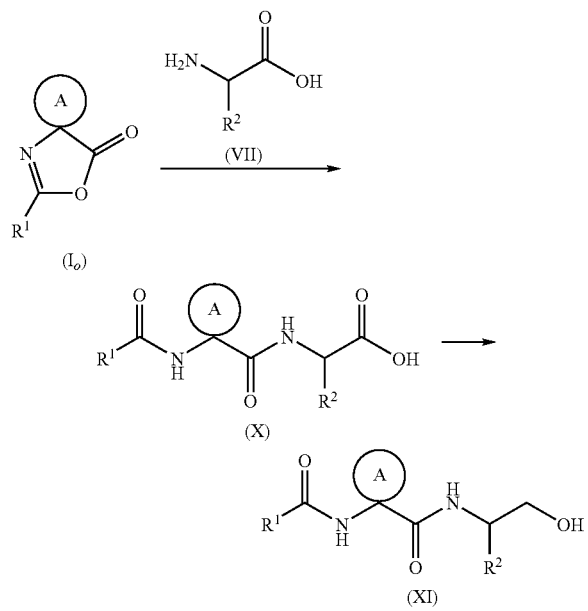

Step (B):
an oxazolone derivative represented by formula ($I_o$) is reacted with an amino acid ester derivative represented by formula (IX) to form a cycloalkylcarbonylamino acid ester derivative represented by formula (XII), and the cycloalkylcarbonylamino acid ester derivative is followed by reduction;

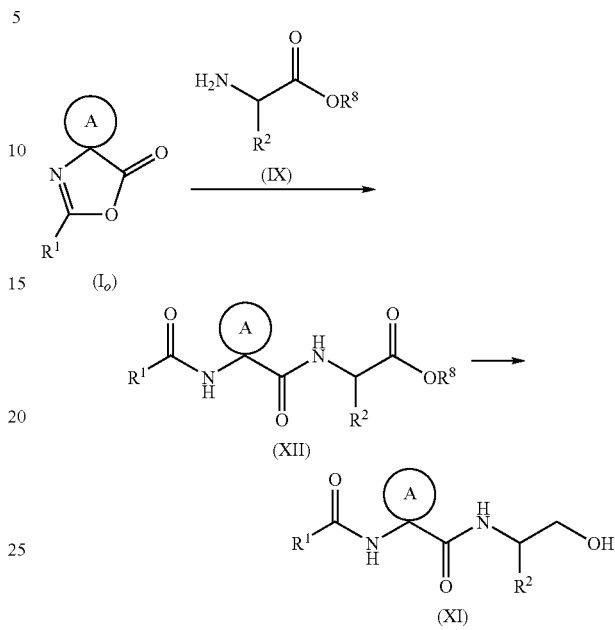

Step (C):
an oxazolone derivative represented by formula ($I_o$) is condensed with an amino alcohol derivative represented by formula (VIII);

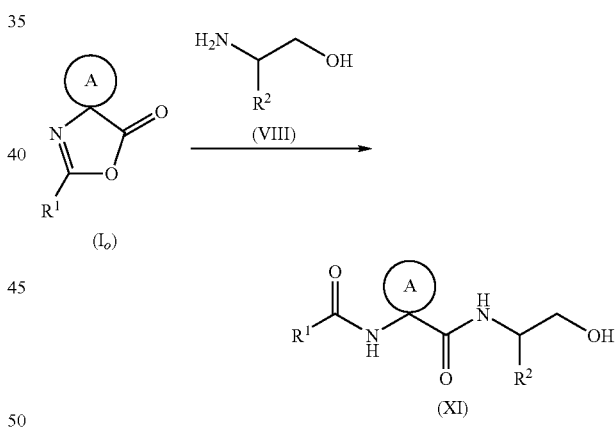

(wherein $R^1$, $R^2$ and ring A in the formulas ($I_o$), (VII), (VIII) (IX), (X), (XI) and (XII) above are the same as previously defined in 1 above, and $R^8$ in formulas (IX) and (XII) represents a substituted or unsubstituted alkyl group having 1 to 6 carbon atoms).

The novel cycloalkane carboxamide derivatives of the present invention have highly active and highly selective cathepsin K inhibitory activity. Thus, compounds of the present invention are useful in the prevention and treatment of such diseases as osteoporosis, hypercalcemia, Paget's disease, bone resorption diseases, osteogenesis imperfecta, osteoarthrosis, rheumatoid arthritis, arthritis, Klinefelter's syndrome, hereditary hyperphosphatasemia, Charcot's neuroarthopathy, mastocytosis, Gaucher's disease, cancer metastasis and multiple myeloma, and the contribution thereof to the medical care of these diseases is considerable.

DETAILED DESCRIPTION OF THE INVENTION

The cycloalkane carboxamide derivatives of the present invention are compounds represented by the aforementioned formula (I) and pharmaceutically acceptable salts thereof, and specific examples of alkyl groups, alkenyl groups, alkynyl groups, aromatic hydrocarbon groups and heterocyclic groups included by the groups represented by substituents $R^1$, $R^2$, $R^4$, $R^5$, $R^6$ and $R^7$ in these derivatives are listed below.

The alkyl group may be any of a linear, branched and cyclic alkyl group having 1 to 12 carbon atoms, examples of which include a methyl group, ethyl group, n-propyl group, 2-propyl group, cyclopropyl group, n-butyl group, 2-methylpropyl group, 2-butyl group, 1,1-dimethylethyl group, cyclobutyl group, n-pentyl group, 3-methylbutyl group, cyclopentyl group, 2,2-dimethylpropyl group, 1-methylcyclobutyl group, cyclobutylmethyl group, n-hexyl group, 4-methylpentyl group, cyclohexyl group, 1-methylcyclopentyl group, cyclopentylmethyl group, (1-methylcyclobutyl)methyl group, n-heptyl group, 5-methylhexyl group, 4,4-dimethylpentyl group, cycloheptyl group, cyclohexylmethyl group, (1-methylcyclopentyl)methyl group, n-octyl group, 6-methylheptyl group, 5,5-dimethylhexyl group, (1-methylcyclohexyl)methyl group, n-nonyl group, 7-methyloctyl group, 6,6-dimethylheptyl group, n-decyl group, 8-methylnonyl group, n-dodecacyl group, 10-methylundecacyl group and 9,9-dimethyldecacyl group.

The alkenyl group may be any of a linear, branched and cyclic alkenyl group having 2 to 12 carbon atoms, examples of which include a vinyl group, 1-propenyl group, 2-propenyl group, 1-methylethenyl group, 1-methyl-1-propenyl group, 1-methyl-2-propenyl group, 2-methyl-2-propenyl group, 1-propenyl group, 2-propenyl group, 1-butenyl group, 2-butenyl group, 2-pentenyl group, 1-pentenyl group, 1-hexenyl group and 2-hexenyl group.

The alkynyl group may be any of a linear, branched and cyclic group having 2 to 12 carbon atoms and may be substituted, examples of which include an ethynyl group, 1-propynyl group, 2-propynyl group and 2-butynyl group.

The aromatic hydrocarbon group may be a monocyclic or polycyclic group having 6 to 18 carbon atoms, examples of which include a phenyl group, naphthyl group and anthranyl group.

The heterocyclic group is a 3- to 7-membered ring group containing at least one heteroatom such as a nitrogen atom, oxygen atom or sulfur atom as a ring-constituting atom, and these may condense heterocyclic groups, aliphatic rings or aromatic rings or form a spiro ring, examples of which include a furanyl group, thienyl group, pyrrolyl group, pyrazolyl group, thiazolyl group, oxazolyl group, isoxazolyl group, pyridinyl group, pirazinyl group, pyrimidinyl group, pyridazinyl group, pyranyl group, indolyl group, benzofuranyl group, benzimidazolyl group, benzoxazolyl group, quinolyl group, isoquinolyl group, pyrrolidinyl group, piperidinyl group, piperazinyl group, morpholinyl group, indolinyl group and benzodioxolyl group. It is preferably a furanyl group or morpholinyl group.

However, in the case B is a formyl group in the formula (I), $R^2$ is not a 2-carboxyethyl group.

In addition, examples of substituents able to be possessed by the alkyl groups include groups selected from a hydroxyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and an Rx(Ry)N group (wherein Rx and Ry respectively and independently represent a hydrogen atom, alkyl group, alkenyl group, alkynyl group, aromatic hydrocarbon group or heterocyclic group).

Moreover, examples of substituents able to be possessed by the alkenyl groups, alkynyl groups, aromatic hydrocarbon groups and heterocyclic groups include groups selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and an Rx(Ry)N group (wherein Rx and Ry respectively and independently represent a hydrogen atom, alkyl group, alkenyl group, alkynyl group, aromatic hydrocarbon group or heterocyclic group).

Furthermore, the alkyl groups, alkenyl groups, alkynyl groups, aromatic hydrocarbon groups and heterocyclic groups listed as examples of Rx, Ry and substituents include the same types of groups as the groups represented by $R^1$, $R^2$, $R^4$, $R^5$, $R^6$ and $R^7$. In addition, the alkyl groups of alkoxy groups, alkylthio groups as the substituents, alkoxycarbonyl groups and alkoxycarbonylamino groups are also the same as the previously described alkyl groups having 1 to 12 carbon atoms, and the aryl groups of aryloxy groups and arylthio groups are also the same as the previously described aromatic hydrocarbon groups having 6 to 18 carbon atoms. In addition, examples of the guanidino groups, acyl groups, sulfonyl groups, heterocyclyloxy groups, heterocyclylthio groups, amido groups, ureido groups, carbamoyl groups, sulfamoyl groups, acyloxy groups, sulfonamido groups and alkoxycarbonylamino groups as the substituents are indicated below.

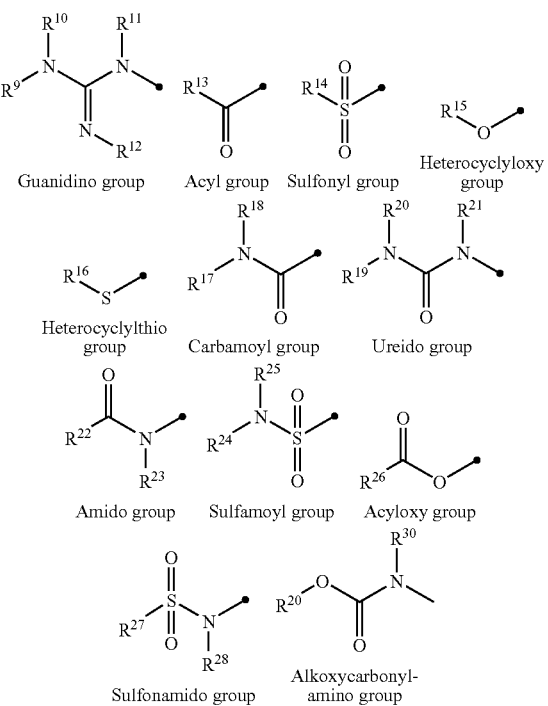

(In the examples of groups indicated above, $R^9$ to $R^{12}$, $R^{17}$ to $R^{21}$, $R^{23}$ to $R^{25}$, $R^{28}$ and $R^{30}$ represent hydrogen atoms, substituted or unsubstituted alkyl groups, substituted or unsubstituted alkenyl groups, substituted or unsubstituted alkynyl groups, substituted or unsubstituted aromatic hydrocarbon groups or substituted or unsubstituted heterocyclic groups. $R^{13}$, $R^{14}$, $R^{22}$, $R^{26}$, $R^{27}$ and $R^{29}$ represent substituted or unsubstituted alkyl groups, substituted or unsubstituted alkenyl groups, substituted or unsubstituted alkynyl groups, substituted or unsubstituted aromatic hydrocarbon groups or substituted or unsubstituted heterocyclic groups. $R^{15}$ and $R^{16}$ represent substituted or unsubstituted heterocyclic groups. In addition, examples of substituents of these substituted alkyl groups, substituted alkenyl groups, substituted alkynyl groups, substituted aromatic hydrocarbon groups and substituted heterocyclic groups include the same groups as the substituents of these groups listed for $R^1$ in 3 above.)

In the cycloalkane carboxamide derivatives represented by formula (I) of the present invention, ring A is a cyclopentylidene group, cyclohexylidene group or cycloheptylidene group, and preferably a cyclohexylidene group.

In formula (I), a compound wherein $R^1$ is a 3- to 7-membered ring heterocyclic group containing at least one nitrogen atom, oxygen atom or sulfur atom as a ring-constituting group, or a substituted aromatic hydrocarbon group, $R^2$ is an alkyl group having 1 to 4 carbon atoms, and ring A is a cyclohexylidene group is preferable.

In the case a cycloalkane carboxamide derivative represented by formula (I) of the present invention has a basic site in a molecule thereof, a salt can be formed with an inorganic acid or organic acid, and examples of inorganic acids include hydrochloric acid, sulfuric acid, nitric acid, phosphoric acid and hydrobromic acid. Examples of organic acids include acetic acid, propionic acid, benzoic acid, oxalic acid, malonic acid, succinic acid, phthalic acid, glycolic acid, lactic acid, glyceric acid, malic acid, tartaric acid, gallic acid, citric acid, maleic acid, fumaric acid, methanesulfonic acid, benzenesulfonic acid and toluenesulfonic acid.

Moreover, in the case the cycloalkane carboxamide derivative has an acidic site in a molecule thereof, a salt can be formed with, for example, an alkali metal such as lithium, sodium or potassium, an alkaline earth metal such as magnesium or calcium, aluminum or zinc. In addition, a salt can also be formed with an organic base, and examples of such an organic base include primary amines such as methylamine, ethylamine or aniline, secondary amines such as diethylamine, pyrrolidine, piperidine, morpholine, piperazine or dicyclohexylamine, tertiary amines such as trimethylamine, triethylamine, N,N-diisopropylethylamine or pyridine, and ammonia.

The following indicates an example of the production of a cycloalkane carboxamide derivative represented by formula (I) of the present invention.

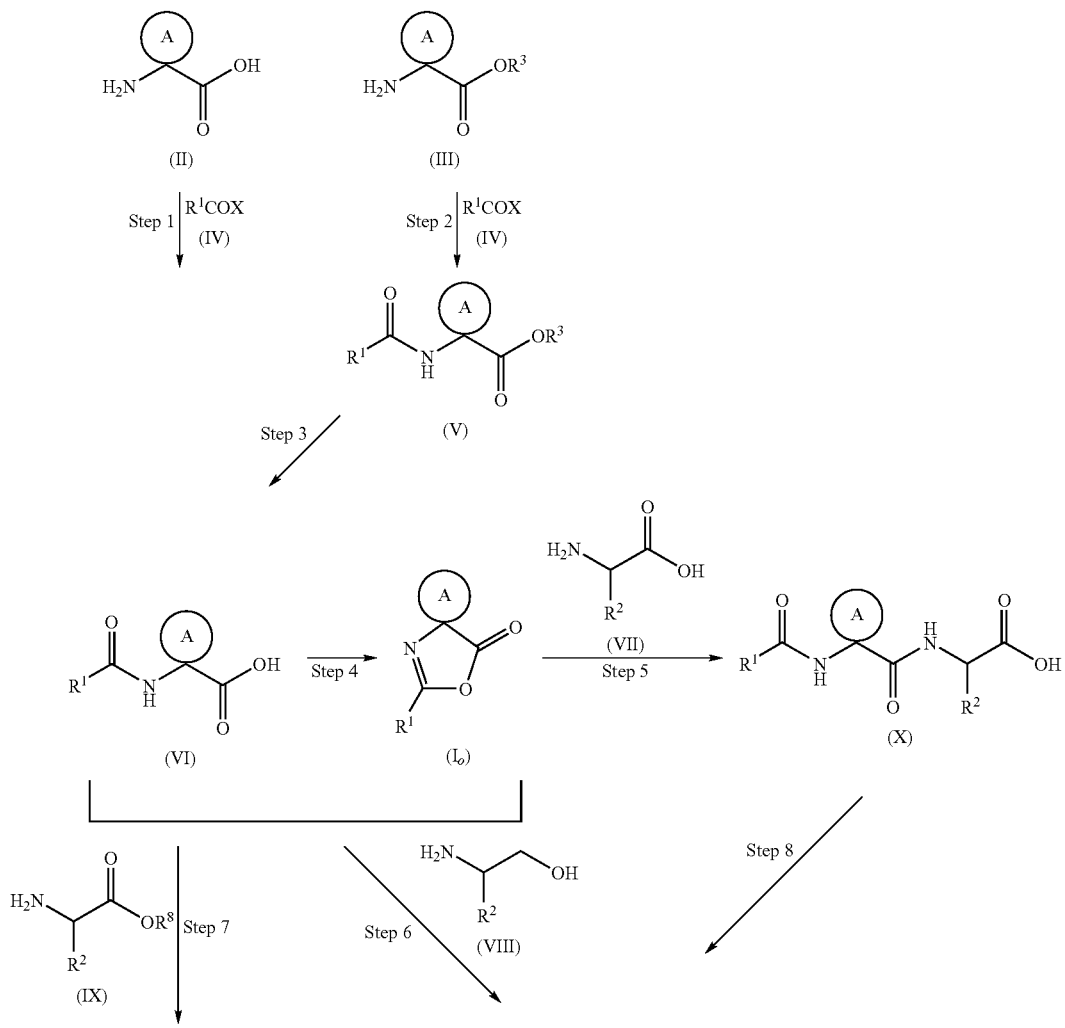

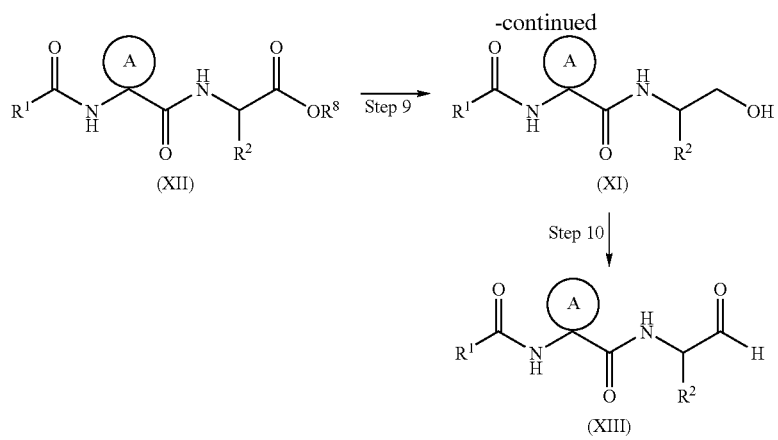

In the above formulas, $R^1$, $R^2$ and ring A are the same as previously defined in the formula (I), $R^3$ and $R^8$ represent substituted or unsubstituted alkyl groups having 1 to 6 carbon atoms, and X represents a hydroxyl group or a leaving group.

Step 1:

This step is a step for producing a cycloalkylcarboxylic acid derivative represented by formula (VI) above by condensing an amino acid represented by formula (II) above with a carboxylic acid or carboxylic acid derivative represented by formula (IV) above. As carboxylic acid derivatives, for example, acid halides, active esters and acid anhydrides can be used. In addition, in this step, reaction can be carried out by adding a base as necessary. As bases, for example, pyridine, triethylamine, N,N-diisopropylethylamine, 4-(dimethylamino)pyridine, N-methylmorpholine, sodium carbonate, potassium carbonate, sodium hydrogencarbonate, sodium hydroxide and potassium hydroxide can be used.

When this step is carried out, it is preferably carried out in a solvent, and organic solvents such as methylene chloride, chloroform, dichloroethane, ethyl acetate, acetone, benzene, toluene, xylene, dimethylformamide, acetonitrile, tetrahydrofuran, dioxane, diethyl ether, isopropyl ether or dimethoxyethane, and water can be used. A mixed solvent of an organic solvent and water can be used as necessary. The reaction is normally carried out at a reaction temperature within the range of −30 to 200° C. and is preferably allowed to proceed within the range of −15 to 100° C.

Step 2:

This step is a step for producing a cycloalkyl ester derivative represented by formula (V) above by a condensation reaction between an amino acid ester represented by formula (III) above with a carboxylic acid or carboxylic acid derivative represented by formula (IV) above. As carboxylic acid derivatives, for example, acid halides, active esters or acid anhydrides can be used. In this step, the reaction can be carried out by adding a condensation agent or base as necessary. As condensation agents, for example, dicyclohexylcarbodiimide, 1-ethyl-3-(3-dimethylaminopropyl) carbodiimide hydrochloride, diisopropylcarbodiimide and carbonyldiimidazole can be used. Here, an activator such as 1-hydroxybenzotriazole can also be added as necessary. As bases, pyridine, triethylamine, N,N-diisopropylethylamine, 4-(dimethylamino)pyridine, N-methylmorpholine, sodium carbonate, potassium carbonate and sodium hydrogencarbonate can be used.

When this step is carried out, it is preferably carried out in a solvent, and organic solvents such as methylene chloride, chloroform, dichloroethane, ethyl acetate, acetone, benzene, toluene, xylene, dimethylformamide, acetonitrile, tetrahydrofuran, dioxane, diethyl ether, isopropyl ether or dimethoxyethane, and water can be used. A mixed solvent of an organic solvent and water can be used as necessary. The reaction is normally carried out at a reaction temperature within the range of −30 to 200° C. and is preferably allowed to proceed within the range of −15 to 100° C.

Step 3:

This step is a step for producing a compound of formula (VI) above by a hydrolysis reaction or a hydrogenation reaction by catalytic reduction using a metal catalyst of the cycloalkyl ester derivative represented by formula (V) above. Hydrolysis can be carried out in the presence of an acid or base. As acids, for example, hydrochloric acid, sulfuric acid, nitric acid and acetic acid can be used. As bases, for example, sodium hydroxide, potassium hydroxide, lithium hydroxide, sodium carbonate and potassium carbonate can be used. When this step is carried out, it is preferably carried out in water or in a mixed solvent of an organic solvent and water, and as organic solvents, for example, methanol, ethanol, isopropyl alcohol, tetrahydrofuran and dimethoxyethane can be used. The reaction is normally carried out at a reaction temperature within the range of −20 to 200° C. and is preferably allowed to proceed within the range of 0 to 180° C. In addition, as metal catalysts in the catalytic hydrogenation reaction, for example, platinum, palladium, nickel, rhodium, ruthenium and copper can be used. When this step is carried out, it is preferably carried out in a solvent, and methanol, ethanol, isopropyl alcohol, isopropyl ether, tetrahydrofuran, benzene, toluene, xylene, dimethylformamide, dioxane and water can be used, for example. The reaction is normally carried out at a reaction temperature of −50 to 200° C. and is preferably allowed to proceed within the range of 10 to 100° C.

Examples of the carboxylic acid or carboxylic acid derivative represented by formula (IV) above include the compounds listed below.

Carboxylic acids: acetic acid, isobutyric acid, acrylic acid, propionic acid, cyclohexanecarboxylic acid, benzoic acid, cinnamic acid, 2-furancarboxylic acid, nicotinic acid, tetrahydrofuran-2-carboxylic acid, 1-acetyl-piperidine-2-carboxylic acid, 2-pyrrolecarboxylic acid, 5-indolecarboxylic acid;

acid halides: acetyl chloride, benzoyl chloride, pivaloyl chloride, 2-furancarbonyl chloride, 4-morpholinecarbonyl chloride, 2-thiophenecarbonyl chloride;

active esters: 1-acetylimidazole, benzoic acid p-nitrophenyl esters, benzoic acid N-hydroxysuccinimide esters, benzoic acid 1-hydroxybenzotriazole esters; and acid anhydrides: acid anhydrides of benzoic acid and methyl carbonate, acid anhydrides of benzoic acid and isobutyl carbonate, acid anhydrides of benzoic acid and pivalic acid, acid anhydrides of benzoic acid and methanesulfonic acid.

The cycloalkylcarboxylic acid derivatives represented by formula (VI) above include, for example, the compounds listed below:

1-[(phenylacetyl)amino]cyclohexanecarboxylic acid, 1-[(1-oxo-3-phenylpropyl)amino]cyclohexanecarboxylic acid, 1-(benzoylamino)cyclohexanecarboxylic acid, 1-[(4-biphenylcarbonyl)amino]cyclohexanecarboxylic acid, 1-[(2-naphthylcarbonyl)amino]cyclohexanecarboxylic acid, 1-[(1-naphthylcarbonyl)amino]cyclohexanecarboxylic acid, 1-[[[(RS)-2,3-tetrahydrobenzofuran-2-yl]carbonyl]amino]cyclohexanecarboxylic acid, 1-[(2-furanylcarbonyl)amino]cyclohexanecarboxylic acid, 1-[(3-furanylcarbonyl)amino]cyclohexanecarboxylic acid, 1-[[(E)-3-(2-furanyl)-1-oxo-2-propenyl]amino]cyclohexanecarboxylic acid, 1-[(2-benzofuranylcarbonyl)amino]cyclohexanecarboxylic acid, 1-[(cyclohexylcarbonyl)amino]cyclohexanecarboxylic acid, 1-[(6-benzothiazolylcarbonyl)amino]cyclohexanecarboxylic acid, 1-[[(6-hydroxy-3-pyridinyl)carbonyl]amino]cyclohexanecarboxylic acid, 1-[(2-thienylcarbonyl)amino]cyclohexanecarboxylic acid, 1-[(2-pyridinylcarbonyl)amino]cyclohexanecarboxylic acid, 1-[(3-thienylcarbonyl)amino]cyclohexanecarboxylic acid, 1-[[(3-ethoxy-2-thienyl)carbonyl]amino]cyclohexanecarboxylic acid, 1-[[(S)-1-oxo-2-phenylpropyl]amino]cyclohexanecarboxylic acid, 1-[(2-pyrazinylcarbonyl)amino]cyclohexanecarboxylic acid, 1-[[(5-methyl-2-thienyl)carbonyl]amino]cyclohexanecarboxylic acid, 1-[[(4-methoxyphenyl)carbonyl]amino]cyclohexanecarboxylic acid, 1-[[(3-methyl-2-thienyl)carbonyl]amino]cyclohexanecarboxylic acid, 1-[[(3-methyl-2-furanyl)carbonyl]amino]cyclohexanecarboxylic acid, 1-[(3-pyridinylcarbonyl)amino]cyclohexanecarboxylic acid, 1-[[(1-methyl-1H-pyrrol-2-yl)carbonyl]amino]cyclohexanecarboxylic acid, 1-[((R)-1-oxo-2-phenylpropyl)amino]cyclohexanecarboxylic acid, 1-[(1H-indol-5-ylcarbonyl)amino]cyclohexanecarboxylic acid, 1-[(1-cyclopentenylcarbonyl)amino]cyclohexanecarboxylic acid, 1-[(4-pyridinylcarbonyl)amino]cyclohexanecarboxylic acid, 1-[[(1H-pyrrol-2-yl)carbonyl]amino]cyclohexanecarboxylic acid, 1-[[(6-hydroxy-2-pyridinyl)carbonyl]amino]cyclohexanecarboxylic acid, 1-[[(2-hydroxy-3-pyridinyl)carbonyl]amino]cyclohexanecarboxylic acid, 1-[[(6-hydroxy-3-pyridinyl)carbonyl]amino]cyclohexanecarboxylic acid, 1-[[[1-(2-propoxycarbonyl)piperidin-4-yl]carbonyl]amino]cyclohexanecarboxylic acid, 1-[[[1-(ethoxycarbonyl)piperidin-4-yl]carbonyl]amino]cyclohexanecarboxylic acid, 1-[[[1-(2-furanylcarbonyl)piperidin-4-yl]carbonyl]amino]cyclohexanecarboxylic acid, 1-[[[(2-furanylcarbonyl)amino]acetyl]amino]cyclohexanecarboxylic acid, 1-[[(benzoylamino)acetyl]amino]cyclohexanecarboxylic acid, 1-[[(2-oxo-2H-pyran-5-yl)carbonyl]amino]cyclohexanecarboxylic acid, 1-[(4-fluorobenzoyl)amino]cyclohexanecarboxylic acid, 1-[[[4-(4-propylpiperazin-1-yl)phenyl]carbonyl]amino]cyclohexanecarboxylic acid, 1-[[[4-(4-propylpiperazin-1-yl)phenyl]carbonyl]amino]cyclohexanecarboxylic acid hydrochloride,

[[(2,3-dihydro-2-oxo-5-benzoxazole)carbonyl]amino]cyclohexanecarboxylic acid, [[(2,3-dihydro-1,4-benzodioxin-6-yl)carbonyl]amino]cyclohexanecarboxylic acid, [[(2,4-dioxo-3-thiazolidinyl)acetyl]amino]cyclohexanecarboxylic acid, [(1-oxo-3-phenyl-2-propenyl)amino]cyclohexanecarboxylic acid, [[1-oxo-3-(2-chlorophenyl)-2-propenyl]amino]cyclohexanecarboxylic acid, [[1-oxo-3-(4-chlorophenyl)-2-propenyl]amino]cyclohexanecarboxylic acid, [[1-oxo-3-(dichlorophenyl)-2-propenyl]amino]cyclohexanecarboxylic acid, [[1-oxo-3-(2-bromophenyl)-2-propenyl]amino]cyclohexanecarboxylic acid, [[1-oxo-3-(4-bromophenyl)-2-propenyl]amino]cyclohexanecarboxylic acid, [[1-oxo-3-(dibromophenyl)-2-propenyl]amino]cyclohexanecarboxylic acid, [[(1-oxo-3-(2-fluorophenyl)-2-propenyl)amino]cyclohexanecarboxylic acid,

[[1-oxo-3-(2-iodophenyl)-2-propenyl]amino]cyclohexanecarboxylic acid, [[oxo-3-(4-fluorophenyl)-2-propenyl]amino]cyclohexanecarboxylic acid, [[oxo-3-(difluorophenyl)-2-propenyl]amino]cyclohexanecarboxylic acid, [[1-oxo-3-(4-iodophenyl)-2-propenyl]amino]cyclohexanecarboxylic acid, [[1-oxo-3-(diiodophenyl)-2-propenyl]amino]cyclohexanecarboxylic acid, [[oxo-3-(trifluorophenyl)-2-propenyl]amino]cyclohexanecarboxylic acid, [[1-oxo-3-(2-methylphenyl)-2-propenyl]amino]cyclohexanecarboxylic acid, [[1-oxo-3-(3-methylphenyl)-2-propenyl]amino]cyclohexanecarboxylic acid, [[1-oxo-3-(4-methylphenyl)-2-propenyl]amino]cyclohexanecarboxylic acid,

[[1-oxo-3-(dimethylphenyl)-2-propenyl]amino]cyclohexanecarboxylic acid, [[1-oxo-3-(2-methoxyphenyl)-2-propenyl]amino]cyclohexanecarboxylic acid, [[1-oxo-3-(4-methoxyphenyl)-2-propenyl]amino]cyclohexanecarboxylic acid, [[1-oxo-3-(dimethoxyphenyl)-2-propenyl]amino]cyclohexanecarboxylic acid, [[1-oxo-3-(nitrophenyl)-2-propenyl]amino]cyclohexanecarboxylic acid, [[1-oxo-3-(dinitrophenyl)-2-propenyl]amino]cyclohexanecarboxylic acid, [[oxo-3-(acetaminophenyl)-2-propenyl]amino]cyclohexanecarboxylic acid, [[1-oxo-3-(2-pyridinyl)-2-propenyl]amino]cyclohexanecarboxylic acid, [[1-oxo-3-cyclohexyl-2-propenyl]amino]cyclohexanecarboxylic acid, [[1-oxo-3-cyclopentyl-2-propenyl]amino]cyclohexanecarboxylic acid, [(1-oxo-3-phenyl-2-propynyl)amino]cyclohexanecarboxylic acid, [[1-oxo-3-(fluorophenyl)-2-propynyl]amino]cyclohexanecarboxylic acid, [[1-oxo-3-(chlorophenyl)-2-propynyl]amino]cyclohexanecarboxylic acid, [[1-oxo-3-(bromophenyl)-2-propynyl]amino]cyclohexanecarboxylic acid, [[1-oxo-3-(iodophenyl)-2-propynyl]amino]cyclohexanecarboxylic acid,

[[1-oxo-3-(difluorophenyl)-2-propynyl]amino]cyclohexanecarboxylic acid, [[1-oxo-3-(dibromophenyl)-2-propynyl]amino]cyclohexanecarboxylic acid, [[1-oxo-3-(diiodophenyl)-2-propynyl]amino]cyclohexanecarboxylic acid, [[1-oxo-3-(trifluorophenyl)-2-propynyl]amino]cyclohexanecarboxylic acid, [(1-oxo-3-cyclohexyl-2-propynyl)amino]cyclohexanecarboxylic acid, [(1-oxo-3-cyclopentyl-2-propynyl)amino]cyclohexanecarboxylic acid, [[3-(2-furanyl)-1-oxo-2-propynyl]amino]cyclohexanecarboxylic acid, 1-[[[4-(4-propylpiperazin-1-yl)phenyl]carbonyl]amino]cyclohexanecarboxylic acid acetate, 1-[[[4-(4-propylpiperazin-1-yl)phenyl]carbonyl]amino]cyclohexanecarboxylic acid hydrobromide, 1-[[[4-(4-propylpiperazin-1-yl)phenyl]carbonyl]amino]cyclohexanecarboxylic acid benzensulfonate, 1-[[[4-(4-propylpiperazin-1-yl)phenyl]carbonyl]amino]cyclohexanecarboxylic acid toluenesulfonate, 1-[[[4-(4- propylpiperazin-1-yl)phenyl]carbonyl]amino]cyclohexanecarboxylic acid phtalate, 1-[[[4-(4-propylpiperazin-1-yl)phenyl]carbonyl]amino]cyclohexanecarboxylic acid fumarate, and 1-[[[4-(4-propylpiperazin-1-yl)phenyl]carbonyl]amino]cyclohexanecarboxylic acid citrate.

Step 4:

This step is a step for producing an oxazolone derivative represented by formula ($I_o$) above by ring-closing the cycloalkylcarboxylic acid derivative represented by formula (VI) above by a dehydration reaction. The dehydration reaction of this step is preferably carried out in the presence of a condensation agent, halogenating agent, acid, acid anhydride, acid chloride and the like, and as condensation agents, dicyclohexylcarbodiimide, 1-ethyl-3-(3-dimethylaminopropyl)carbodiimide hydrochloride, diisopropylcarbodiimide and carbonyldiimidazole can be used. As halogenating agents, for example, chlorine, bromine, iodine, phosphorous pentachloride, thionyl chloride, oxalyl chloride and thionyl bromide can be used. As acids, for example, acetic acid, sulfuric acid, hydrochloric acid, methanesulfonic acid and toluenesulfonic acid can be used. As acid anhydrides, for example, acetic anhydride, methanesulfonic anhydride, toluenesulfonic anhydride and trifluoromethanesulfonic anhydride can be used. As acid chlorides, for example, acetyl chloride, pivaloyl chloride, methanesulfonyl chloride, toluenesulfonyl chloride, methyl chloroformate, ethyl chloroformate, propyl chloroformate and isobutyl chloroformate can be used.

In addition, the reaction of this step can also be carried out by adding a base as necessary, and as bases, for example, pyridine, triethylamine, N,N-diisopropylethylamine, 4-(dimethylamino)pyridine, N-methylmorpholine, sodium carbonate, potassium carbonate and sodium hydrogencarbonate can be used.

When this step is carried out, it is preferably carried out in a solvent, and methylene chloride, chloroform, dichloroethane, ethyl acetate, acetone, benzene, toluene, xylene, dimethylformamide, acetonitrile, tetrahydrofuran, dioxane, diethyl ether, diisopropyl ether and dimethoxyethane can be used, for example. The reaction is normally carried out at a reaction temperature within the range of −30 to 200° C. and is preferably allowed to proceed within the range of 0 to 100° C.

Step 5:

This step is a step for producing a cycloalkylcarbonylamino acid derivative represented by the formula (X) by reacting the oxazolone derivative represented by formula ($I_o$) above with the amino acid derivative represented by formula (VII) above.

This step can be carried out in the presence of a base and in the presence or absence of a solvent, and as solvents, methylene chloride, chloroform, dichloroethane, ethyl acetate, acetone, benzene, toluene, xylene, dimethylformamide, acetonitrile, tetrahydrofuran, dioxane, diethyl ether, diisopropyl ether, dimethoxyethane, dimethyl sulfoxide, methanol, ethanol and 2-propanol can be used, for example. In addition, as bases, for example, pyridine, triethylamine, N,N-diisopropylethylamine, 4-(dimethylamino)pyridine, N-methylmorpholine, sodium carbonate, potassium carbonate, sodium hydrogencarbonate, sodium hydroxide and potassium hydroxide can be used. The reaction is normally carried out at a reaction temperature within the range of −30 to 200° C. and can be preferably allowed to proceed within the range of 20 to 200° C.

The amino acid derivatives represented by formula (VII) above include, for example, the compounds listed below:

alanine, arginine, $N^\omega$-nitro-arginine, asparagine, aspartic acid, β-benzyl ester, isoasparagine, γ-carboxyglutamic acid, cysteine, S-acetamido-cysteine, S-trityl-cysteine, cystine, glutamine, glutamic acid, glutaminic acid γ-t-butyl ester, histidine, homoarginine, homocysteine, homocystine, homoserine, homophenylalanine, isoleucine, leucine, t-leucine, lysine, $N^\epsilon$-t-butoxycarbonyl-lysine, methionine, norleucine, norvaline, ornithine, $N^\delta$-carbobenzoxy-ornithine, phenylalanine, phenylglycine, serine, O-benzyl-serine, threonine, O-t-butylthreonine, tryptophan, tyrosine, O-benzyl-tyrosine, valine, 3,4-dihydroxyphenylalanine, allylglycine, neopentylglycine, allothreonine, homolysine, naphthylalanine, α-aminoadipic acid, thienylglycine, pyridylalanine and cyclohexylalanine.

Step 6:

This step is a step for producing a cycloalkylcarbonylamino alcohol derivative represented by formula (XI) above. In this step, a cycloalkylcarbonylamino alcohol derivative represented by formula (XI) above can be produced by two types of methods, namely a method that uses a cycloalkylcarboxylic acid derivative represented by formula (VI) above for the starting raw material (Step 6-A), and a method that uses an oxazolone derivative represented by formula ($I_o$) above for the starting raw material (Step 6-B).

Step 6-A:

This step is a step for producing a cycloalkylcarbonylamino alcohol derivative represented by formula (XI) above by condensing a cycloalkylcarboxylic acid derivative represented by formula (VI) above with an amino alcohol derivative represented by formula (VIII) above.

As condensation agents in this step, for example, dicyclohexylcarbodiimide, 1-ethyl-3-(3-dimethylaminopropyl)carbodiimide hydrochloride, diisopropylcarbodiimide and carbonyldiimidazole can be used. Here, an activator such as 1-hydroxybenzotriazole or N-hydroxysuccinimide can be added as necessary.

In addition, this step can also be carried out by condensing in the presence of a base according to a mixed acid anhydride method with an acid chloride. As acid chlorides, for example, pivaloyl chloride, isobutyl chloroformate, methyl chloroformate, ethyl chloroformate, methanesulfonyl chloride and toluenesulfonyl chloride can be used. As bases, for example, pyridine, triethylamine, N,N-diisopropylethylamine, 4-(dimethylamino)pyridine and N-methylmorpholine can be used.

When this step is carried out, it is preferably carried out in a solvent, and methylene chloride, chloroform, dichloroethane, ethyl acetate, acetone, benzene, toluene, xylene, dimethylformamide, acetonitrile, tetrahydrofuran, dioxane, diethyl ether, diisopropyl ether and dimethoxyethane can be used, for example.

The reaction is normally carried out at a reaction temperature within the range of −30 to 200° C. and can be preferably allowed to proceed within the range of 0 to 100° C.

Step 6-B:

This step is a step for producing a cycloalkylcarbonylamino alcohol derivative represented by formula (XI) above by reacting an oxazolone derivative represented by formula ($I_o$) above with an amino alcohol derivative represented by formula (VIII) above.

This step can be carried out in the presence or absence of solvent, and as solvents, methylene chloride, chloroform, dichloroethane, ethyl acetate, acetone, benzene, toluene, xylene, dimethylformamide, acetonitrile, tetrahydrofuran, dioxane, diethyl ether, diisopropyl ether, dimethoxyethane, dimethyl sulfoxide, methanol, ethanol and 2-propanol can be used, for example. In addition, in this step, a base can be added as necessary. As bases, for example, pyridine, triethylamine, N,N-diisopropylethylamine, 4-(dimethylamino)pyridine and N-methylmorpholine can be used. The reaction is normally carried out at a reaction temperature within the range of −30 to 200° C. and can be preferably allowed to proceed within the range of 20 to 200° C.

Amino alcohol derivatives represented by formula (VIII) above used in step 6, include, for example, the compounds listed below:

alaminol, N$^\omega$-p-toluenesulfonyl-argininol, 3-amino-4-hydroxybutanamide, 3-amino-4-hydroxybutanoic acid t-butyl ester, 3-benzylthio-2-aminopropanol, 4-amino-5-hydroxypentanamide, 4-amino-5-hydroxypentanoic acid benzyl ester, histidinol, homoserinol, homophenylalaminol, isoleucinol, leucinol, t-leucinol, 2-amino-6-[(t-butoxycarbonyl)amino]hexanol, methioninol, norleucinol, norvalinol, 2-amino-5-(dibenzylamino)pentanol, phenylalaminol, phenylglycinol, 2-amino-3-(benzyloxy)propanol, threoninol, tryptophanol, tyrosinol, valinol, 3,4-dihydroxyphenylalaminol, allylglycinol, neopentylglycinol, allothreoninol, naphthylalaminol, thienylglycinol, pyridylalaminol, cyclohexylalaminol, 2-amino-1-phenyl-1,3-propanediol, 2-amino-1,3-propanediol and sphingosine.

Step 7:

This step is a step for producing a cycloalkylcarbonylamino acid ester derivative represented by formula (XII) above. In this step, a cycloalkylcarbonylamino acid derivative represented by formula (XII) above can be produced by two types of methods, namely a method that uses a cycloalkylcarboxylic acid derivative represented by formula (VI) above for the starting raw material (Step 7-A), and a method that uses an oxazolone derivative represented by formula (I$_o$) above for the starting raw material (Step 7-B).

Step 7-A:

This step is a step for producing a cycloalkylcarbonylamino acid ester derivative represented by formula (XII) above by condensing a cycloalkylcarboxylic acid derivative represented by formula (VI) above with an amino acid ester derivative represented by formula (IX) above.

As condensation agents in this step, for example, dicyclohexylcarbodiimide, 1-ethyl-3-(3-dimethylaminopropyl)carbodiimide hydrochloride, diisopropylcarbodiimide and carbonyldiimidazole can be used. Here, an activator such as 1-hydroxybenzotriazole or N-hydroxysuccinimide can be added as necessary.

In addition, this step can also be carried out by condensing in the presence of a base according to a mixed acid anhydride method with an acid chloride. As acid chlorides, for example, pivaloyl chloride, isobutyl chloroformate, methyl chloroformate, ethyl chloroformate, methanesulfonyl chloride and toluenesulfonyl chloride can be used. As bases, for example, pyridine, triethylamine, N,N-diisopropylethylamine, 4-(dimethylamino)pyridine and N-methylmorpholine can be used.

When this step is carried out, it is preferably carried out in a solvent, and methylene chloride, chloroform, dichloroethane, ethyl acetate, acetone, benzene, toluene, xylene, dimethylformamide, acetonitrile, tetrahydrofuran, dioxane, diethyl ether, diisopropyl ether and dimethoxyethane can be used, for example.

The reaction is normally carried out at a reaction temperature within the range of −30 to 200° C. and can be preferably allowed to proceed within the range of 0 to 100° C.

Step 7-B:

This step is a step for producing a cycloalkylcarbonylamino acid ester derivative represented by formula (XII) above by reacting an oxazolone derivative represented by formula (I$_o$) above with an amino acid ester derivative represented by formula (IX) above.

This step can be carried out in the presence or absence of solvent, and as solvents, for example, methylene chloride, chloroform, dichloroethane, ethyl acetate, acetone, benzene, toluene, xylene, dimethylformamide, acetonitrile, tetrahydrofuran, dioxane, diethyl ether, diisopropyl ether, dimethoxyethane, dimethyl sulfoxide, methanol, ethanol and 2-propanol can be used. In addition, in this step, a base can be added as necessary. As bases, for example, pyridine, triethylamine, N,N-diisopropylethylamine, 4-(dimethylamino)pyridine and N-methylmorpholine can be used. The reaction is normally carried out at a reaction temperature within the range of −30 to 200° C. and can be preferably allowed to proceed within the range of 20 to 200° C.

Oxazolone derivatives represented by formula (I$_o$) above include, for example, the compounds listed below: 2-phenylmethyl-3-oxa-1-azaspiro[4.5]dec-1-en-4-one, 2-phenylethyl-3-oxa-1-azaspiro[4.5]dec-1-en-4-one, 2-(4-biphenyl)-3-oxa-1-azaspiro[4.5]dec-1-en-4-one, 2-(2-naphthyl)-3-oxa-1-azaspiro[4.5]dec-1-en-4-one, 2-[(RS)-2,3-tetrahydrobenzofuran-2-yl]-3-oxa-1-azaspiro[4.5]dec-1-en-4-one, 2-(6-benzothiazolyl)-3-oxa-1-azaspiro[4.5]dec-1-en-4-one, 2-(2-thienyl)-3-oxa-1-azaspiro[4.5]dec-1-en-4-one, 2-(1,3-benzoxol-5-yl)-3-oxa-1-azaspiro[4.5]dec-1-en-4-one, 2-(2-benzofuranyl)-3-oxa-1-azaspiro[4.5]dec-1-en-4-one, 2-(2-pyridinyl)-3-oxa-1-azaspiro[4.5]dec-1-en-4-one, 2-(3-ethoxy-2-thienyl)-3-oxa-1-azaspiro[4.5]dec-1-en-4-one, 2-(2-pyrazinyl)-3-oxa-1-azaspiro[4.5]dec-1-en-4-one, 2-(5-methylisoxazol-4-yl)-3-oxa-1-azaspiro[4.5]dec-1-en-4-one, 2-cyclopentyl-3-oxa-1-azaspiro[4.5]dec-1-en-4-one, 2-(5-methyl-2-thienyl)-3-oxa-1-azaspiro[4.5]dec-1-en-4-one, 2-(4-methoxyphenyl)-3-oxa-1-azaspiro[4.5]dec-1-en-4-one, 2-(3-methyl-2-furanyl)-3-oxa-1-azaspiro[4.5]dec-1-en-4-one, 2-(1-methyl-1H-pyrrol-2-yl)-3-oxa-1-azaspiro[4.5]dec-1-en-4-one, 2-(1H-indol-5-yl)-3-oxa-1-azaspiro[4.5]dec-1-en-4-one, 2-(1-cyclopentenyl)-3-oxa-1-azaspiro[4.5]dec-1-en-4-one, 2-(6-hydroxy-2-pyridinyl)-3-oxa-1-azaspiro[4.5]dec-1-en-4-one, 2-[2-(furanyl)ethyl]-3-oxa-1-azaspiro[4.5]dec-1-en-4-one, 2-[1-[(2-propoxy)carbonyl]piperidin-4-yl]-3-oxa-1-azaspiro[4.5]dec-1-en-4-one, 2-[1-(ethoxycarbonyl)piperidin-4-yl]-3-oxa-1-azaspiro[4.5]dec-1-en-4-one, 2-[1-(2-furanylcarbonyl)piperidin-4-yl]-3-oxa-1-azaspiro[4.5]dec-1-en-4-one, 2-[(2-furanylcarbonyl)amino]methyl]-3-oxa-1-azaspiro[4.5]dec-1-en-4-one, 2-[(benzoylamino)methyl]-3-oxa-1-azaspiro[4.5]dec-1-en-4-one, 2-(4-fluorophenyl)-3-oxa-1-azaspiro[4.5]dec-1-en-4-one, 2-[[4-[(1-propyl)piperazin-1-yl]phenyl]-3-oxa-1-azaspiro[4.5]dec-1-en-4-one, 2-(2-furyl)-3-oxa-1-azaspiro[4.5]dec-1-en-4-one, 2-cyclohexyl-3-oxa-1-azaspiro[4.5]dec-1-en-4-one, 2-(2-propyl)-3-oxa-1-azaspiro[4.5]dec-1-en-4-one, 2-(1-acetyl-piperidin-4-yl)-3-oxa-1-azaspiro[4.5]dec-1-en-4-one, 2-[4-[2-(4-methyl-1-piperazinyl)-4-thiazolyl]phenyl]-3-oxa-1-azaspiro[4.5]dec-1-en-4-one, 2-[4-[2-[4-(4-morpholinyl)-1-piperidinyl]-4-thiazolyl]phenyl]-3-oxa-1-azaspiro[4.5]dec-1-en-4-one, 2-[4-(2-[1,4-bipiperidin]-1'-yl-4-thiazolyl)phenyl]-3-oxa-1-azaspiro[4.5]dec-1-en-4-one, 2-[4-[2-[4-(1,1-dimethylethyl)-1-piperazinyl]-4-thiazolyl]phenyl]-3-oxa-1-azaspiro[4.5]dec-1-en-4-one, 2-([1,1'-biphenyl]-3-yl)-3-oxa-1-azaspiro[4.5]dec-1-en-4-one, 2-[2-(4-pyridinyl)-4-thiazolyl]-3-oxa-1-azaspiro[4.5]dec-1-en-4-one, 2-(4-aminophenyl)-3-oxa-1-azaspiro[4.5]dec-1-en-4-one, 2-[4-(4-morpholinyl)phenyl]-3-oxa-1-azaspiro[4.5]dec-1-en-4-one, 2-(5-bromo-2-thienyl)-3-oxa-1-azaspiro[4.5]dec-1-en-4-one, 2-[4-[(4-methyl-1-piperazinyl)carbonyl]phenyl]-3-oxa-1-azaspiro[4.5]dec-1-en-4-one, 2-[4-[(4-methyl-1-piperazinyl)sulfonyl]phenyl]-3-oxa-1-azaspiro[4.5]dec-1-en-4-one, 2-[4-(dimethylamino)phenyl]-3-oxa-1-azaspiro[4.5]dec-1-en-4-one, 2-(4-ethynylphenyl)-3-oxa-1-azaspiro[4.5]dec-1-en-4-one, 2-[4'-(dimethylamino)[1,1'-biphenyl]-4-yl]-3-oxa-1-azaspiro[4.5]dec-1-en-4-one, 2-[4-(4-methyl-1-piperazinyl)phenyl]-3-oxa-1-azaspiro[4.5]dec-1-en-4-one, 2-[4'-(1-piperazinyl)[1,1'-biphenyl]-4-yl]-3-oxa-1-azaspiro[4.5]dec-1-en-4-one, 2-[4'-[[1-(2-hydroxyethyl)-4-piperidinyl]oxy][1,1'-biphenyl]-4-yl]-3-oxa-1-azaspiro[4.5]dec-1-en-4-one, 2-[4'-[(1-methyl-4-piperidinyl)oxy][1,1'-biphenyl]-4-yl]-3-oxa-1-azaspiro[4.5]dec-1-en-4-one, 2-[4'-[methyl(1-methyl-3-pyrrolidinyl)amino][1,1'-biphenyl]-4-yl]-3-oxa-1-azaspiro[4.5]dec-1-en-4-one, 2-[4'-[4-(1,1-dimethylethyl)-1-piperidinyl][1,1'-biphenyl]-4-yl]-3-oxa-1-azaspiro[4.5]dec-1-en-4-one, 2-[4'-(1-piperazinylsulfonyl)[1,1'-biphenyl]-4-yl]-3-oxa-1-azaspiro[4.5]dec-1-en-4-one, 2-[4'-(4-fluoro-4-piperidinyl)[1,1'-biphenyl]-4-yl]-3-oxa-1-azaspiro[4.5]dec-1-en-4-one, 2-[4'-[[4-(2,2,2-trifluoroethyl)-1-piperazinyl]sulfonyl][1,1'-biphenyl]-4-yl]-3-oxa-1-azaspiro[4.5]dec-1-en-4-one, 2-[4'-[(1-methyl-3-piperidinyl)oxy][1,1'-biphenyl]-4-yl]-3-oxa-1-azaspiro[4.5]dec-1-en-4-one, 2-[4'-[[1-(2-methoxyethyl)-4-piperidinyl]oxy][1,1'-biphenyl]-4-yl]]-3-oxa-1-azaspiro[4.5]dec-1-en-4-one, 2-[4'-[[(2S)-1-methyl-2-pyrrolidinyl]methoxy][1,1'-biphenyl]-4-yl]-3-oxa-1-azaspiro[4.5]dec-1-en-4-one, 2-[4'-[4-[(1,1-dimethylethyl)amino]-1-piperidinyl][1,1'-biphenyl]-4-yl]-3-oxa-1-azaspiro[4.5]dec-1-en-4-one, 2-[4'-(5-isoxazolyl)[1,1'-biphenyl]-4-yl]-3-oxa-1-azaspiro[4.5]dec-1-en-4-one, 2-[4-[2-(4-morpholinylmethyl)-4-thiazolyl]phenyl]-3-oxa-1-azaspiro[4.5]dec-1-en-4-one, 2-[4-[2-[3-(dimethylamino)-1-pyrrolidinyl]-4-thiazolyl]phenyl]-3-oxa-1-azaspiro[4.5]dec-1-en-4-one, 2-[4-[2-(4-methyl-1-piperazinylmethyl)-4-thiazolyl]phenyl]-3-oxa-1-azaspiro[4.5]dec-1-en-4-one, 2-[4-[2-(1,4-dimethyl-4-piperidinyl)-4-thiazolyl]phenyl]-3-oxa-1-azaspiro[4.5]dec-1-en-4-one, 2-[4-[2-(1-methyl-4-piperidinyl)-4-thiazolyl]phenyl]-3-oxa-1-azaspiro[4.5]dec-1-en-4-one, 2-[4-[2-[(3R)-3-amino-1-pyrrolidinyl]-4-thiazolyl]phenyl]-3-oxa-1-azaspiro[4.5]dec-1-en-4-one, 2-[4-[2-(4-piperidinyloxy)-4-thiazolyl]phenyl]-3-oxa-1-azaspiro[4.5]dec-1-en-4-one, 2-[4-[2-(4-morpholinyl)-4-thiazolyl]phenyl]-3-oxa-1-azaspiro[4.5]dec-1-en-4-one, 2-[4-[2-[4-[(1-methylethyl)amino]-1-piperidinyl]-4-thiazolyl]phenyl]-3-oxa-1-azaspiro[4.5]dec-1-en-4-one, 2-[4-[2-[methyl(4-methyl-1-piperazinyl)amino]-4-thiazolyl]phenyl]-3-oxa-1-azaspiro[4.5]dec-1-en-4-one, 2-[4-[2-[4-[methyl(1-methylethyl)amino]-1-piperidinyl]-4-thiazolyl]phenyl]-3-oxa-1-azaspiro[4.5]dec-1-en-4-one, 2-[4-[2-[4-(tetrahydro-2H-pyran-4-yl)-1-piperazinyl]-4-thiazolyl]phenyl]-3-oxa-1-azaspiro[4.5]dec-1-en-4-one, 2-[4-[2-[4-(2-methoxyethyl)-1-piperazinyl]-4-thiazolyl]phenyl]-3-oxa-1-azaspiro[4.5]dec-1-en-4-one, 2-[3-(4-morpholinyl)-1-propynyl]-3-oxa-1-azaspiro[4.5]dec-1-en-4-one, 2-cycloheptyl-3-oxa-1-azaspiro[4.5]dec-1-en-4-one, 2-[4-(4-morpholinylmethyl)phenyl]-3-oxa-1-azaspiro[4.5]dec-1-en-4-one, 2-cyclopropyl-3-oxa-1-azaspiro[4.5]dec-1-en-4-one, 2-[2-(diethylamino)ethyl]-3-oxa-1-azaspiro[4.5]dec-1-en-4-one, 2-[4-[(dimethylamino)methyl]phenyl]-3-oxa-1-azaspiro[4.5]dec-1-en-4-one, 2-(2-benzothienyl)-3-oxa-1-azaspiro[4.5]dec-1-en-4-one, 2-(1-methyl-4-piperazinyl)-3-oxa-1-azaspiro[4.5]dec-1-en-4-one, 2-[2-(1-piperazinyl)ethyl]-3-oxa-1-azaspiro[4.5]dec-1-en-4-one, 2-[3-(trifluoromethyl)phenyl]-3-oxa-1-azaspiro[4.5]dec-1-en-4-one, 2-[4-(trifluoromethoxy)phenyl]-3-oxa-1-azaspiro[4.5]dec-1-en-4-one, 2-[4-(trifluoromethyl)phenyl]-3-oxa-1-azaspiro[4.5]dec-1-en-4-one, 2-[2-(trifluoromethyl)phenyl]-3-oxa-1-azaspiro[4.5]dec-1-en-4-one, 2-[3-(trifluoromethoxy)phenyl]-3-oxa-1-azaspiro[4.5]dec-1-en-4-one, 2-(4-pyridinyl)-3-oxa-1-azaspiro[4.5]dec-1-en-4-one, 2-(3-fluorophenyl)-3-oxa-1-azaspiro[4.5]dec-1-en-4-one, 2-(2-fluorophenyl)-3-oxa-1-azaspiro[4.5]dec-1-en-4-one, 2-[2-(trifluoromethoxy)phenyl]-3-oxa-1-azaspiro[4.5]dec-1-en-4-one, 2-(3-methylphenyl)-3-oxa-1-azaspiro[4.5]dec-1-en-4-one, 2-[4-[(methoxymethylamino)methyl]phenyl]-3-oxa-1-azaspiro[4.5]dec-1-en-4-one, 2-(3-methoxyphenyl)-3-oxa-1-azaspiro[4.5]dec-1-en-4-one, 2-(4-chlorophenyl)-3-oxa-1-azaspiro[4.5]dec-1-en-4-one, 2-(4-cyanophenyl)-3-oxa-1-azaspiro[4.5]dec-1-en-4-one, 2-[3-(4-morpholinylmethyl)phenyl]-3-oxa-1-azaspiro[4.5]dec-1-en-4-one, 2-(phenoxymethyl)-3-oxa-1-azaspiro[4.5]dec-1-en-4-one, 2-(2-chlorophenyl)-3-oxa-1-azaspiro[4.5]dec-1-en-4-one, 2-(2-thienylmethyl)-3-oxa-1-azaspiro[4.5]dec-1-en-4-one, 2-(2-methylphenyl)-3-oxa-1-azaspiro[4.5]dec-1-en-4-one, 2-(4-hydroxyphenyl)-3-oxa-1-azaspiro[4.5]dec-1-en-4-one, 2-[3-[(dimethylamino)methyl]phenyl]-3-oxa-1-azaspiro[4.5]dec-1-en-4-one, 2-(4-methyl-1,2,3-thiadiazol-5-yl)-3-oxa-1-azaspiro[4.5]dec-1-en-4-one, and 2-(2,5-dimethyl-3-furanyl)-3-oxa-1-azaspiro[4.5]dec-1-en-4-one.

In addition, amino acid ester derivatives represented by formula (IX) above include, for example, the compounds listed below:

alanine methyl ester, $N^\omega$-p-toluenesulfonyl-arginine ethyl ester, asparagine t-butyl ester, aspartic acid α-benzyl ester, aspartic acid dimethyl ester, isoasparagine ethyl ester, γ-carboxyglutamic acid dibenzyl ester, cysteine ethyl ester, S-benzyl cysteine methyl ester, cystine dimethyl ester, glutamine ethyl ester, glutamic acid di-t-butyl ester, histidine methyl ester, homoarginine ethyl ester, homocysteine methyl ester, homocystine diethyl ester, homoserine benzyl ester, homophenyl alanine methyl ester, isoleucine t-butyl ester, leucine cyclohexyl ester, $N^\epsilon$-carbobenzoxy-lysine methyl ester, methionine ethyl ester, norleucine isopropyl ester, t-leucine butyl ester, norvaline methyl ester, $N^\delta$-carbobenzoxy-ornithine benzyl ester, phenylalanine t-butyl ester, phenylglycine 3-pentyl ester, serine ethyl ester, threonine benzyl ester, tryptophan methyl ester, tyrosine ethyl ester, valine cyclopentyl ester, 3,4-dihydroxyphenylalanine ethyl ester, allylglycine methyl ester, neopentyl glycine t-butyl ester, allothreonine benzyl ester, homolysine methyl ester, naphthyl alanine ethyl ester, α-aminoadipic acid t-butyl ester, thienyl glycine methyl ester, pyridylalanine benzyl ester, and cyclohexylalanine t-butyl ester.

Step 8:

This step is a step for producing a cycloalkylcarbonylamino alcohol derivative represented by formula (XI) above by carrying out a reduction reaction after activating a cycloalkylcarbonylamino acid represented by formula (X) above by a mixed acid anhydride method.

As acid chlorides employable in the reaction for forming a mixed acid anhydride in this step, for example, pivaloyl chloride, isobutyl chloroformate, methyl chloroformate, ethyl chloroformate, methanesulfonyl chloride and toluenesulfonyl chloride can be used. As bases, for example, pyridine, triethylamine, N,N-diisopropylethylamine, 4-(dimethylamino)pyridine and N-methylmorpholine can be used.

When this reaction is carried out, it is preferably carried out in a solvent, and methylene chloride, chloroform, dichloroethane, benzene, toluene, xylene, dimethylformamide, acetonitrile, tetrahydrofuran, dioxane, diethyl ether, diisopropyl ether and dimethoxyethane can be used.

The reaction is normally carried out at a reaction temperature within the range of −50 to 200° C. and can be preferably allowed to proceed within the range of −20 to 50° C.

In addition, as reducing agents employable in this step, sodium borohydride, lithium aluminum hydride, diisobutyl aluminum hydride, and sodium dihydro-bis(2-methoxyethoxy)aluminate (Red-Al) can be used.

When this step is carried out, it is preferably carried out in a solvent, and methylene chloride, chloroform, dichloroethane, benzene, toluene, xylene, dimethylformamide, acetonitrile, tetrahydrofuran, dioxane, diethyl ether, diisopropyl ether, dimethoxyethane, ethanol, 2-propanol or water, etc., can be used. The reaction is normally carried out at a reaction temperature within the range of −30 to 200° C. and can be preferably allowed to proceed within the range of −20 to 80° C.

Cycloalkylcarbonylamino acids represented by formula (X) above include, for example, the compounds listed below:
N-[[1-[[(phenylmethoxy)carbonyl]amino]cyclohexyl]carbonyl]-L-valine, N-[[1-[[(phenylmethoxy) carbonyl]amino]cyclohexyl]carbonyl]-L-norleucine, N-[[1-[(2-furanylcarbonyl)amino]cyclohexyl]carbonyl]-L-valine, N-[[1-[(4-morpholinylcarbonyl)amino]cyclohexyl]carbonyl]-L-norleucine, N-[[1-[[(phenylmethoxy)carbonyl]amino]cyclohexyl]carbonyl]-L-methionine, N-[[1-[(2-furanylcarbonyl)amino]cyclohexyl]carbonyl]-L-phenylalanine, N-[[1-[(4-morpholinylcarbonyl)amino]cyclohexyl]carbonyl]-L-tryptophan, N-[[1-[[(phenylmethoxy)carbonyl]amino]cyclohexyl]carbonyl]-L-tyrosine, N-[[1-[(2-furanylcarbonyl)amino]cyclohexyl]carbonyl]-L-phenylglycine, N-[[1-[(4-morpholinylcarbonyl)amino]cyclohexyl]carbonyl]-L-histidine, N-[[1-[[(phenylmethoxy)carbonyl]amino]cyclohexyl]carbonyl]-L-pyridylglycine, N-[[1-(acetamide)cyclohexyl]carbonyl]-L-valine, N-[[1-[[(phenylmethylthio)carbonyl]amino]cyclohexyl]carbonyl]-L-valine, N-[[1-[(1-oxo-3-phenyl-2-propenyl)amino]cyclohexyl]carbonyl]-L-valine, N-[[1-[(1-oxo-3-phenyl-2-propynyl)amino]cyclohexyl]carbonyl]-L-valine, and N-[[1-[(1-oxo-3-phenyl-2-propynyl)amino]cyclohexyl]carbonyl]-L-allylglycine.

Step 9:

This step is a step for producing a cycloalkylcarbonylamino alcohol derivative represented by formula (XI) above by reducing a cycloalkylcarbonylamino acid ester derivative represented by formula (XII) above.

As reducing agents employable in this step, for example, sodium borohydride, lithium aluminum hydride, diisobutyl aluminum hydride, and Red-Al can be used.

When this reaction is carried out, it is preferably carried out in a solvent, and methylene chloride, chloroform, dichloroethane, benzene, toluene, xylene, dimethylformamide, acetonitrile, tetrahydrofuran, dioxane, diethyl ether, diisopropyl ether and dimethoxyethane can be used, for example.

The reaction is normally carried out at a reaction temperature within the range of −100 to 200° C. and can be preferably allowed to proceed within the range of −80 to 100° C.

Cycloalkylcarbonylamino acid ester derivatives represented by formula (XII) above include, for example, the compounds listed below:
N-[[1-[[(phenylmethoxy)carbonyl]amino]cyclohexyl]carbonyl]-L-valine methyl ester, N-[[1-[[(phenylmethoxy)carbonyl]amino]cyclohexyl]carbonyl]-L-norleucine ethyl ester, N-[[1-[(2-furanylcarbonyl)amino]cyclohexyl]carbonyl]-L-valine benzyl ester, N-[[1-[(4-morpholinylcarbonyl)amino]cyclohexyl]carbonyl]-L-norleucine t-butyl ester, N-[[1-[[(phenylmethoxy)carbonyl]amino]cyclohexyl]carbonyl]-L-methionine ethyl ester, N-[[1-[(2-furanylcarbonyl)amino]cyclohexyl]carbonyl]-L-phenylalanine benzyl ester, N-[[1-[(4-morpholinylcarbonyl)amino]cyclohexyl]carbonyl]-L-tryptophan methyl ester, N-[[1-[[(phenylmethoxy)carbonyl]amino]cyclohexyl]carbonyl]-L-tyrosine propyl ester, N-[[1-[(2-furanylcarbonyl)amino]cyclohexyl]carbonyl]-L-phenylglycine 2-propyl ester, N-[[1-[(4-morpholinylcarbonyl)amino]cyclohexyl]carbonyl]-L-hystidine butyl ester, N-[[1-[[(phenylmethoxy)carbonyl]amino]cyclohexyl]carbonyl]-L-pyridyl glycine t-butyl ester, N-[[1-(acetamido)cyclohexyl]carbonyl]-L-valine methyl ester, N-[[1-[[(phenylmethylthio)carbonyl]amino]cyclohexyl]carbonyl]-L-valine benzyl ester, N-[[1-[(1-oxo-3-phenyl-2-propenyl)amino]cyclohexyl]carbonyl]-L-valine ethyl ester, N-[[1-[(1-oxo-3-phenyl-2-propynyl)amino]cyclohexyl]carbonyl]-L-valine benzyl ester, and N-[[1-[(1-oxo-3-phenyl-2-propynyl)amino]cyclohexyl]carbonyl]-L-allylglycine t-butyl ester.

Step 10:

This step is a step for producing a cycloalkylcarbonylamino aldehyde derivative represented by formula (XIII) above by oxidizing a cycloalkylcarbonylamino alcohol derivative represented by formula (XI) above.

In the oxidation reaction employable in this step, activated DMSO (dimethyl sulfoxide) oxidation can be used. Electrophilic activating reagents used here include, for example, dicyclohexylcarbodiimide, phosphorous pentoxide, pyridine-sulfur trioxide complex, acetic anhydride, mercury (II) acetate and oxalyl chloride. A hydrogen donor such as phosphoric acid, trifluoroacetic acid, dichloroacetic acid, pyridine-phosphoric acid or pyridine-trifluoroacetic acid can also be added in this step as necessary. In addition, an amine such as triethylamine, N,N-diisopropylethylamine or N-methylmorpholine can also be added as necessary.

This step can be carried out in dimethyl sulfoxide, and a solvent such as methylene chloride, chloroform, dichloroethane, toluene, acetone or tetrahydrofuran can also be added as necessary.

The reaction is normally carried out at a reaction temperature within the range of −80 to 200° C. and can be preferably allowed to proceed within the range of −40 to 40° C.

In addition, in this step, an oxidation reaction can also be carried out by preparing an active species having a structure resembling an activated DMSO reaction from a sulfide and halogen.

As sulfides employable in this step, dimethyl sulfide or methyl phenyl sulfide can be used, for example. As halogenating agents, N-chlorosuccinimide, chlorine, etc. can be used.

In this step, an amine such as triethylamine, N,N-diisopropylethylamine, N-methylmorpholine or 1,8-diazabicyclo [5.4.0]undec-7-ene (DBU) can also be added as necessary.

This step is preferably carried out in a solvent, and as solvents, methylene chloride, chloroform, dichloroethane, toluene; tetrahydrofuran, etc. can be used.

The reaction is normally carried out at a reaction temperature within the range of −80 to 200° C. and can be preferably allowed to proceed within the range of −40 to 40° C.

In addition, oxidation can also be carried out in this step using a hypervalent iodine compound reagent. As hypervalent iodine compounds employable in this step, Dess-Martin reagent (1,1,1-tris(acetoxy)-1,1-dihydro-1,2-benziodoxol-3-(1H)-one), IBX (1-hydroxy-1,2-benziodoxol-3-(1H)-1-oxide), etc. can be used.

A base such as pyridine or sodium hydrogencarbonate can be added in this step as necessary.

This step is preferably carried out in a solvent, and as solvents, for example, methylene chloride, chloroform, dichloroethane, benzene, toluene, xylene, dimethylformamide, acetonitrile, tetrahydrofuran, dioxane and dimethoxyethane can be used.

The reaction is normally carried out at a reaction temperature within the range of −20 to 200° C. and can be preferably allowed to proceed within the range of 0 to 40° C.

In addition, this step can also be carried out using oxidation (oppenauer's oxidation) with aluminum alkoxide and a hydrogen acceptor. As aluminum alkoxides, aluminum isopropoxide and aluminum t-butoxide can be used, for example.

As hydrogen acceptors, for example, benzoquinone, benzophenone, acetone, cyclohexanone and benzaldehyde can be used.

This step is preferably carried out in a solvent, and as solvents, for example, benzene, toluene and xylene can be used.

The reaction is normally carried out at a reaction temperature within the range of −20 to 200° C. and can be preferably allowed to proceed within the range of 0 to 150° C.

In addition, this step can also be carried out using an oxidation reaction with tetrapropylammonium perruthenate (TPAP). N-methylmorpholine-N-oxide or molecular oxygen can be used for the oxidizing agent.

This step is preferably carried out in a solvent, and as solvents, for example, methylene chloride, acetonitrile and toluene can be used.

A type 4A molecular sieve can be added in this step as necessary.

The reaction is normally carried out at a reaction temperature within the range of −20 to 200° C. and can be preferably allowed to proceed within the range of 0 to 40° C.

In addition, this step can also use an oxidation reaction with 2,2,6,6-tetramethyl-1-piperidinyloxy radical (TEMPO) or derivative thereof.

As the oxidizing agent, hypochlorous acid salt is preferable, and bromous acid salt, N-chlorosuccinimide, etc. can be used.

This step is preferably carried out in a solvent, and as solvents, for example, dimethyl sulfoxide, N,N-dimethylformamide, methylene chloride, acetonitrile, toluene and ethyl acetate can be used.

In addition, sodium bromide or water can also be added in this step as necessary.

The reaction is normally carried out at a reaction temperature within the range of −20 to 200° C. and can be preferably allowed to proceed within the range of 0 to 40° C.

Specific examples of an alcohol derivative (XI), in which B is a hydroxymethyl group, and an aldehyde derivative (XIII), in which B is a formyl group, in the cycloalkane carboxamide derivatives represented by general formula (I) above of the present invention include the compounds listed below.

N-[[1-[[(phenylmethoxy)carbonyl]amino]cyclohexyl]carbonyl]-L-valinol, N-[[1-[[(phenylmethoxy)carbonyl]amino]cyclohexyl]carbonyl]-L-norleucinol, N-[[1-[(2-furanylcarbonyl)amino]cyclohexyl]carbonyl]-L-valinol, N-[[1-[(2-furanylcarbonyl)amino]cyclohexyl]carbonyl]-L-valinol, N-[[1-[(2-furanylcarbonyl)amino]cyclohexyl]carbonyl]-L-valinol, N-[[1-[(4-morpholinylcarbonyl)amino]cyclohexyl]carbonyl]-L-norleucinol, N-[[1-[(2-benzothienylcarbonyl)amino]cyclohexyl]carbonyl]-L-phenylglycinol, N-[[1-[(2-benzothienylcarbonyl)amino]cyclohexyl]carbonyl]-L-methioninol, N-[[1-[[[4-(4-morpholinylmethyl)phenyl]carbonyl]amino]cyclohexyl]carbonyl]-L-phenylglycinol, N-[[1-[[[4-(4-morpholinylmethyl)phenyl]carbonyl]amino]cyclohexyl]carbonyl]-L-methioninol, N-[[1-[[[4-[2-(4-methyl-1-piperazinyl)-4-thiazolyl]phenyl]carbonyl]amino]cyclohexyl]carbonyl]-L-methioninol, N-[[1-[[[4-[2-(4-methyl-1-piperazinyl)-4-thiazolyl]phenyl]carbonyl]amino]cyclohexyl]carbonyl]-L-phenylglycinol, N-[[1-[[[2-[4-(4-morpholinyl)-1-piperazinyl]-4-thiazolyl]phenyl]carbonyl]amino]cyclohexyl]carbonyl]-L-methioninol, N-[[1-[[[2-[4-(4-morpholinyl)-1-piperazinyl]-4-thiazolyl]phenyl]carbonyl]amino]cyclohexyl]carbonyl]-L-phenylglycinol, N-[[1-[[(2-furanylmethoxy)carbonyl]amino]cyclohexyl]carbonyl]-L-valinol, N-[[1-[[(E)-3-(2-furanyl)-1-oxo-2-propenyl]amino]cyclohexyl]carbonyl]-L-valinol, N-[[1-[(3-furanylcarbonyl)amino]cyclohexyl]carbonyl]-L-valinol, N-[[1-[[(4-methoxyphenyl)carbonyl]amino]cyclohexyl]carbonyl]-L-valinol, N-[[1-[[(phenylmethoxy)carbonyl]amino]cyclohexyl]carbonyl]-L-valinal, N-[[1-[[(phenylmethoxy)carbonyl]amino]cyclohexyl]carbonyl]-L-norleucinal, N-[[1-[(2-furanylcarbonyl)amino]cyclohexyl]carbonyl]-L-valinal, N-[[1-[(4-morpholinylcarbonyl)amino]cyclohexyl]carbonyl]-L-norleucinal, N-[[1-[(2-benzothienylcarbonyl)amino]cyclohexyl]carbonyl]-L-phenylglycinal, N-[[1-[(2-benzothienylcarbonyl)amino]cyclohexyl]carbonyl]-L-methioninal, N-[[1-[[[4-(4-morpholinylmethyl)phenyl]carbonyl]amino]cyclohexyl]carbonyl]-L-phenylglycinal, N-[[1-[[[4-(4-morpholinylmethyl)phenyl]carbonyl]amino]cyclohexyl]carbonyl]-L-methioninal, N-[[1-[[[4-[2-(4-methyl-1-piperazinyl)-4-thiazolylphenyl]carbonyl]amino]cyclohexyl]carbonyl]-L-methioninal, N-[[1-[[[4-[2-(4-methyl-1-piperazinyl)-4-thiazolyl]phenyl]carbonyl]amino]cyclohexyl]carbonyl]-L-phenylglycinal, N-[[1-[[[2-[4-(4-morpholinyl)-1-piperazinyl]-4-thiazolyl]phenyl]carbonyl]amino]cyclohexyl]carbonyl]-L-methioninal, N-[[1-[[[2-[4-(4-morpholinyl)-1-piperazinyl]-4-thiazolyl]phenyl]carbonyl]amino]cyclohexyl]carbonyl]-L-phenylglycinal, N-[[1-[[(2-furanylmethoxy)carbonyl]amino]cyclohexyl]carbonyl]-L-valinal, N-[[1-[[(E)-3-(2-furanyl)-1-oxo-2-propenyl]amino]cyclohexyl]carbonyl]-L-valinal, N-[[1-[(3-furanylcarbonyl)amino]cyclohexyl]carbonyl]-L-valinal, and N-[[1-[[(4-methoxyphenyl)carbonyl]amino]cyclohexyl]carbonyl]-L-valinal.

The effective amount of these compounds or pharmaceutically acceptable salts thereof as pharmaceuticals in the case of administering to humans varies depending on such factors as the degree of the effective activity thereof, patient age and symptoms of the target disease, and the effective amount is normally 0.001 to 100 mg and preferably 0.01 to 50 mg per kilogram of human body weight per day. In addition, in the case of administering these compounds for the purpose of treatment, these compounds or pharmaceutically acceptable salts thereof are used in the form of a pharmaceutical composition containing one of these compounds or a salt thereof as an active ingredient in combination with a pharmaceutically allowable carrier, examples of which include an organic or inorganic solid or liquid excipient, etc. suitable for not only oral administration but also parenteral administration, external use or inhalation. Examples of the forms of these pharmaceutical compositions include capsules, tablets, sugar-coated tablets, granules, liquids, suspensions and emulsions. An adjuvant, stabilizer, lubricant, emulsifier, buffer or other commonly used additive can be added to these preparations as necessary.

A cycloalkane carboxamide derivative represented by formula (I) of the present invention has highly active and highly selective inhibitory activity against cathepsin K as is clear from the test examples to be described later, as a result of having this selective inhibitory activity against cathepsin K, and thus, it is expected to be used as a useful drug for prevention or treatment of osteoporosis, hypercalcemia, osteoarthrosis and rheumatoid arthritis.

The present invention is explained below in further detail by way of reference examples and examples, but the present invention is not limited to these examples provided they do not exceed the gist thereof.

Furthermore, "%" refers to "1% by weight" unless specifically indicated otherwise.

In addition, synthesis examples of the cycloalkylcarboxylic acid represented by formula (VI) above and esters thereof, as well as synthesis examples of the oxazolone derivative represented by formula ($I_O$), which are intermediates for producing the cycloalkane carboxamide derivatives of the present invention, are indicated as reference examples.

Reference Example 1

1-[(Phenylacetyl)amino]cyclohexanecarboxylic acid phenylmethyl ester

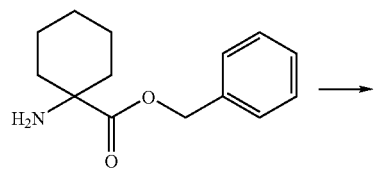

1.21 g (12 mmol) of triethylamine was added to a solution of 2.33 g (10 mmol) of 1-aminocyclohexanecarboxylic acid phenylmethyl ester in 100 ml of tetrahydrofuran, and 1.55 g (10 mmol) of phenylacetyl chloride was added dropwise thereto under ice-cooling, followed by stirring of the mixture overnight. The reaction mixture was concentrated under reduced pressure, ethyl acetate was added thereto, and the mixture was successively washed with water, a 10% aqueous potassium hydrogen sulfate solution, a saturated aqueous sodium hydrogencarbonate solution and saturated brine, followed by drying with anhydrous sodium sulfate. After the solvent was distilled off under reduced pressure, the residue was purified by silica gel chromatography to obtain 3.21 g (91%) of the title compound.

1H-NMR (CDCl$_3$, δ): 1.10-1.23 (3H, m), 1.50-1.58 (3H, m), 1.74-1.80 (2H, m), 1.95-1.98 (2H, m), 3.57 (2H, s), 5.12 (2H, s), 5.48 (1H, br-s), 7.24-7.38 (10H, m)

Reference Example 2

1-[(Phenylacetyl)amino]cyclohexanecarboxylic acid

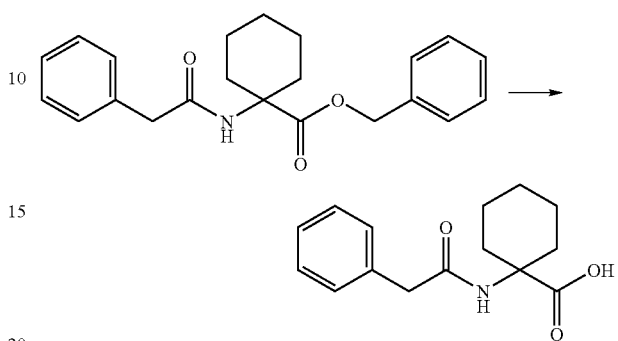

2.69 g (9.1 mmol) of 1-[(phenylacetyl)amino]cyclohexanecarboxylic acid phenylmethyl ester obtained in Reference example 1 was dissolved in 100 ml of methanol, and 300 mg of 10% palladium-carbon was added thereto, followed by stirring of the mixture at room temperature under a hydrogen atmosphere overnight. After the reaction solution was filtered, the filtrate was concentrated under reduced pressure to obtain 1.96 g (98%) of the title compound.

1H-NMR (CDCl$_3$, δ): 1.01-1.10 (2H, m), 1.18-1.26 (1H, m), 1.49-1.59 (3H, m), 1.75-1.82 (2H, m), 1.97-2.00 (2H, m), 3.66 (2H, s), 5.67 (1H, br-s), 7.29-7.34 (3H, m), 7.37-7.40 (2H, m)

Reference Example 3

1-[(1-Oxo-3-phenylpropyl)amino]cyclohexanecarboxylic acid phenylmethyl ester

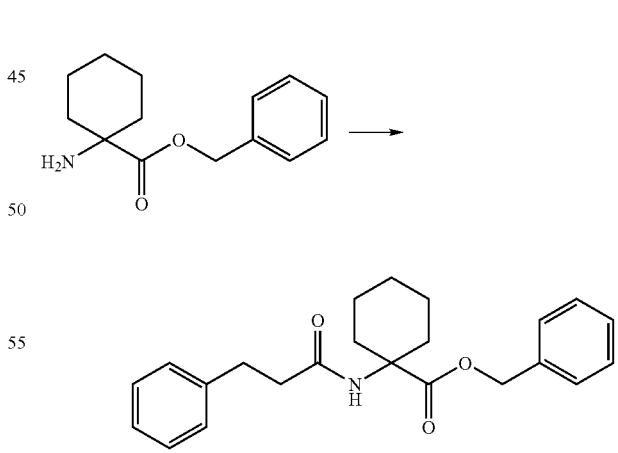

1.68 g (10 mmol) of 3-phenylpropionyl chloride was used instead of phenylacetyl chloride in the process according to Reference example 1 to obtain 3.47 g (95%) of the title compound.

1H-NMR (CDCl$_3$, δ): 1.19-1.26 (3H, m), 1.50-1.61 (3H, m), 1.78-1.84 (2H, m), 1.96-2.05 (2H, m), 2.50 (2H, t, J=7

Hz), 2.93 (2H, t, J=7 Hz), 5.13 (2H, s), 5.45 (1H, br-s), 7.18-7.21 (4H, m), 7.26-7.37 (6H, m)

Reference Example 4

1-[(1-Oxo-3-phenylpropyl)amino]cyclohexanecarboxylic acid

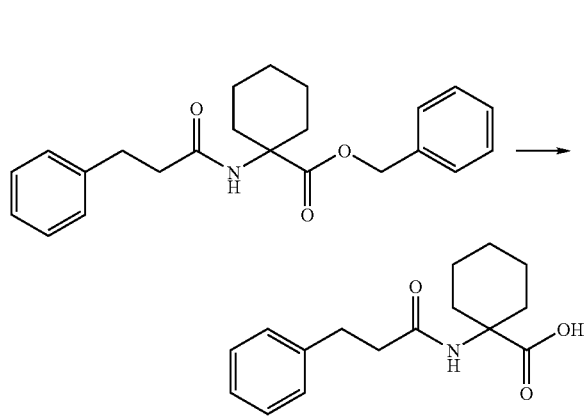

3.47 g (9.5 mmol) of 1-[(1-oxo-3-phenylpropyl)amino]cyclohexanecarboxylic acid phenylmethyl ester was used instead of 1-[(phenylacetyl)amino]cyclohexanecarboxylic acid phenylmethyl ester in the process according to Reference example 2 to obtain 2.35 g (90%) of the title compound.

1H-NMR (CDCl$_3$, δ): 1.16-1.25 (3H, m), 1.48-1.51 (1H, m), 1.52-1.62 (2H, m), 1.84-1.97 (4H, m), 2.62 (2H, t, J=7 Hz), 3.00 (2H, t, J=7 Hz), 5.43 (1H, br-s), 7.21-7.26 (3H, m), 7.29-7.33 (2H, m)

Reference Example 5

1-(Benzoylamino)cyclohexanecarboxylic acid phenylmethyl ester

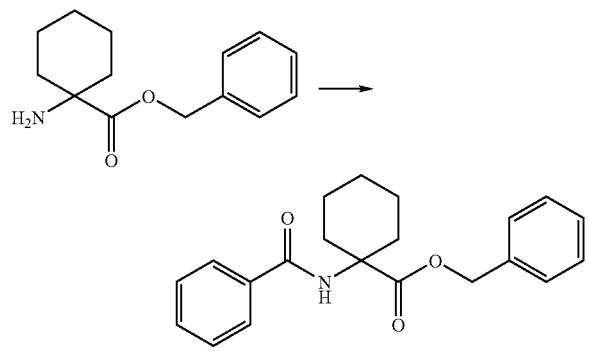

1.41 g (10 mmol) of benzoyl chloride was used instead of phenylacetyl chloride in the process according to Reference example 1 to obtain 3.39 g (quantitative) of the title compound.

1H-NMR (CDCl$_3$, δ): 1.33-1.40 (1H, m), 1.45-1.54 (2H, m), 1.62-1.76 (3H, m), 1.93-1.99 (2H, m), 2.19-2.22 (2H, m), 5.17 (2H, s), 6.25 (1H, br-s), 7.25-7.32 (4H, m), 7.41-7.45 (3H, m), 7.49-7.52 (1H, m), 7.75-7.77 (2H, m)

Reference Example 6

1-(Benzoylamino)cyclohexanecarboxylic acid

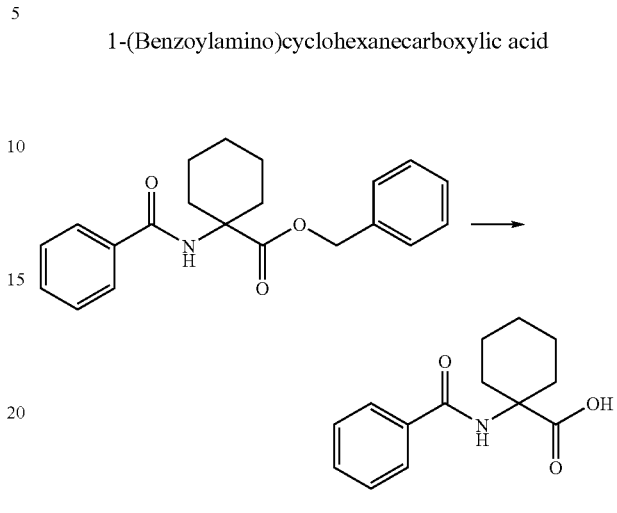

3.39 g (10 mmol) of 1-(benzoylamino)cyclohexanecarboxylic acid phenylmethyl ester was used instead of 1-[(phenylacetyl)amino]cyclohexanecarboxylic acid phenylmethyl ester in the process according to Reference example 2 to obtain 2.44 g (99%) of the title compound.

1H-NMR (CDCl$_3$, δ): 1.38-1.55 (3H, m), 1.67-1.71 (1H, m), 1.75-1.79 (2H, m), 1.98-2.04 (2H, m), 2.24-2.27 (2H, m), 6.26 (1H, br-s), 7.46 (1H, td, J=7 Hz, 1 Hz), 7.48 (1H, td, J=7 Hz, 1 Hz), 7.57 (1H, td, 7 Hz, 1 Hz), 7.79-7.82 (2H, m)

Reference Example 7

1-[(4-Biphenylcarbonyl)amino]cyclohexanecarboxylic acid phenylmethyl ester

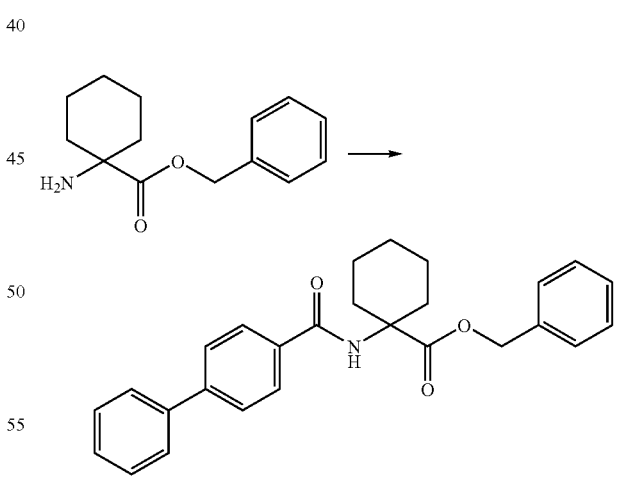

2.11 g (11 mmol) of 1-ethyl-3-(3-dimethylaminopropyl)carbodiimide hydrochloride was added to a solution of 2.33 g (10 mmol) of 1-aminocyclohexanecarboxylic acid phenylmethyl ester, 1.68 g (11 mmol) of 1-hydroxybenzotriazole and 3.23 g (10 mmol) of 4-biphenylcarboxylic acid in 120 ml of methylene chloride under ice-cooling. After the mixture was stirred at room temperature overnight, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. After the solvent was distilled off under reduced pressure, the residue was purified by silica gel chromatography to obtain 3.51 g (85%) of the title compound.

1H-NMR (CDCl$_3$, δ): 1.38-1.41 (1H, m), 1.51-1.61 (2H, m), 1.66-1.80 (3H, m), 1.95-2.05 (2H, m), 2.23-2.31 (2H, m), 5.20 (2H, s), 6.38 (1H, br-s), 7.24-7.34 (7H, m), 7.55-7.60 (2H, m), 7.81 (1H, dd, J=8 Hz, 1 Hz), 7.87-7.91 (3H, m), 8.26 (1H, d, J=1 Hz)

Reference Example 8

1-[(4-Biphenylcarbonyl)amino]cyclohexanecarboxylic acid

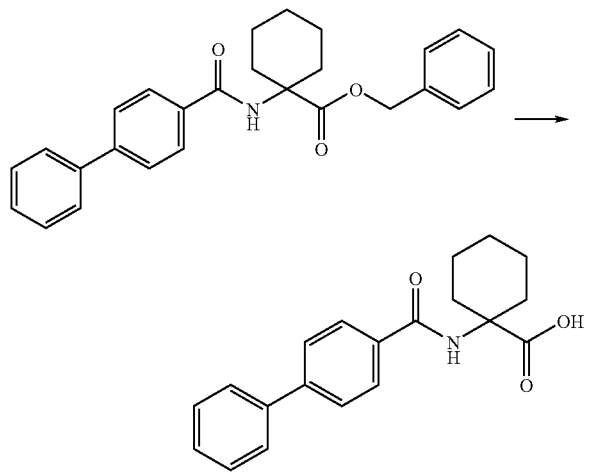

3.51 g (8.5 mmol) of 1-[(4-biphenylcarbonyl)amino]cyclohexanecarboxylic acid phenylmethyl ester was used instead of 1-[(phenylacetyl)amino]cyclohexanecarboxylic acid phenylmethyl ester in the process according to Reference example 2 to obtain 2.75 g (quantitative) of the title compound.

1H-NMR (CDCl$_3$, δ): 1.37-1.48 (1H, m), 1.48-1.60 (2H, m), 1.66-1.73 (1H, m), 1.73-1.82 (2H, m), 2.00-2.10 (2H, m), 2.27-2.35 (2H, m), 6.32 (1H, br-s), 7.39-7.43 (1H, m), 7.46-7.49 (2H, m), 7.61-7.66 (2H, m), 7.68-7.70 (2H, m), 7.87-7.89 (2H, m)

Reference Example 9

1-[(2-Naphthylcarbonyl)amino]cyclohexanecarboxylic acid phenylmethyl ester

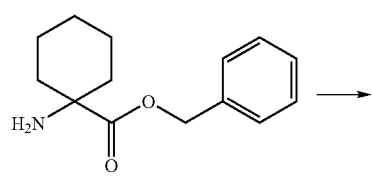

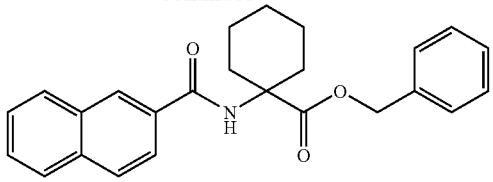

1.28 g (7.4 mmol) of 2-naphthoeic acid was used instead of 4-biphenylcarboxylic acid in the process according to Reference example 7 to obtain 2.12 g (74%) of the title compound.

1H-NMR (CDCl$_3$, δ): 1.32-1.41 (1H, m), 1.48-1.61 (2H, m), 1.64-1.78 (3H, m), 1.95-2.01 (2H, m), 2.21-2.24 (2H, m), 5.19 (2H, s), 6.27 (1H, br-s), 7.27-7.36 (3H, m), 7.40 (1H, td, J=7 Hz, 1 Hz), 7.46-7.49 (2H, m), 7.61-7.63 (2H, m), 7.65-7.67 (2H, m), 7.83-7.85 (2H, m)

Reference Example 10

1-[(2-Naphthylcarbonyl)amino]cyclohexanecarboxylic acid

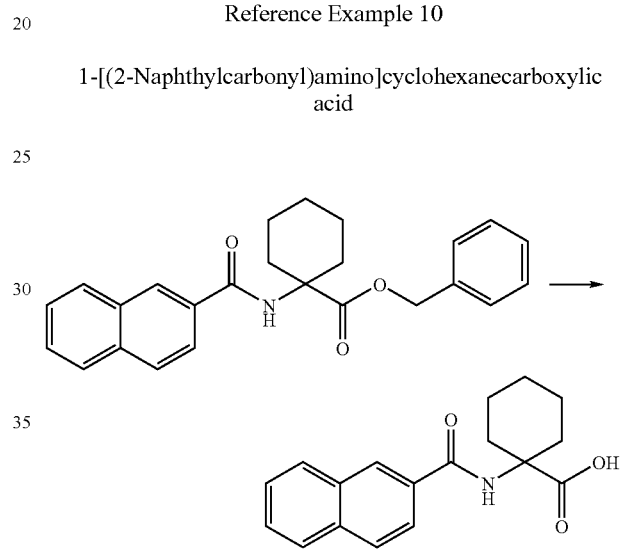

2.12 g (5.5 mmol) of 1-[(2-naphthylcarbonyl)amino]cyclohexanecarboxylic acid phenylmethyl ester was used instead of 1-[(phenylacetyl)amino]cyclohexanecarboxylic acid phenylmethyl ester in the process according to Reference example 2 to obtain 1.63 g (quantitative) of the title compound.

1H-NMR (CDCl$_3$, δ): 1.41-1.45 (1H, m), 1.52-1.60 (2H, m), 1.70-1.74 (1H, m), 1.77-1.82 (2H, m), 2.03-2.09 (2H, m), 2.29-2.32 (2H, m), 6.41 (1H, br-s), 7.56-7.63 (2H, m), 7.83 (1H, dd, J=8 Hz, 2 Hz), 7.89-7.96 (3H, m), 8.33 (1H, s)

Reference Example 11

1-[(1-Naphthylcarbonyl)amino]cyclohexanecarboxylic acid phenylmethyl ester

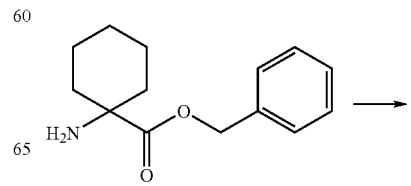

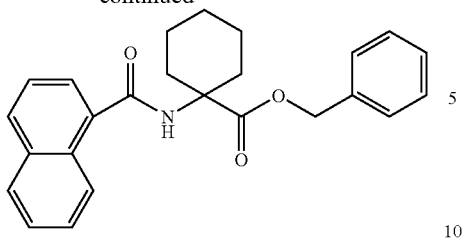

1.72 g (10 mmol) of 1-naphthoeic acid was used instead of 4-biphenylcarboxylic acid in the process according to Reference example 7 to obtain 3.87 g (quantitative) of the title compound.

1H-NMR (CDCl$_3$, δ): 1.31-1.42 (1H, m), 1.45-1.60 (2H, m), 1.65-1.71 (1H, m), 1.71-1.80 (2H, m), 1.98-2.05 (2H, m), 2.24-2.32 (2H, m), 5.26 (2H, s), 6.10 (1H, br-s), 7.32-7.37 (3H, m), 7.40-7.45 (4H, m), 7.48-7.52 (1H, m), 7.57 (1H, dd, J=7 Hz, 1 Hz), 7.85 (1H, dd, J=7 Hz, 1 Hz), 7.91 (1H, dd, J=7 Hz, 1 Hz), 8.25 (1H, dd, J=7 Hz, 1 Hz)

Reference Example 12

1-[(2-Benzofuranylcarbonyl)amino]cyclohexanecarboxylic acid phenylmethyl ester

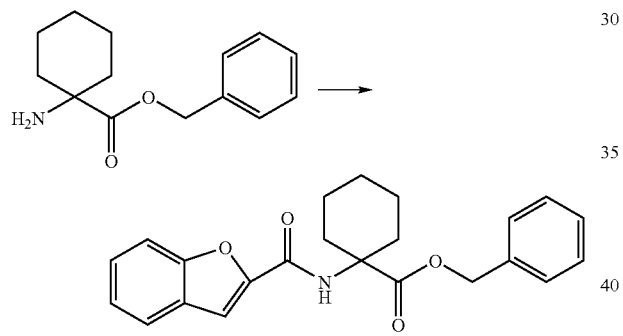

12.22 g (75.4 mmol) of benzofuran-2-carboxylic acid was used instead of 4-biphenylcarboxylic acid in the process according to Reference example 7 to obtain 21.3 g (75%) of the title compound.

1H-NMR (CDCl$_3$, δ): 1.26-1.42 (1H, m), 1.50-1.61 (2H, m), 1.64-1.77 (3H, m), 1.95-2.04 (2H, m), 2.21-2.28 (2H, m), 5.19 (2H, s), 6.77 (1H, br-s), 7.25-7.34 (6H, m), 7.44 (1H, td, J=8 Hz, 2 Hz), 7.52 (1H, dd, J=8 Hz, 2 Hz), 7.57 (1H, dd, J=8 Hz, 2 Hz), 7.68 (1H, dd, J=8 Hz, 2 Hz)

Reference Example 13

1-[[[(RS)-2,3-Tetrahydrobenzofuran-2-yl]carbonyl]amino]cyclohexanecarboxylic acid

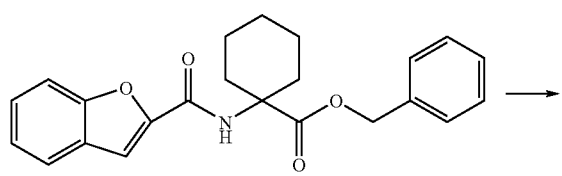

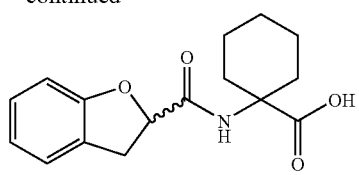

1.5 g of 10% palladium-carbon was added to a solution of 15 g (40 mmol) of 1-[(2-benzofuranylcarbonyl)amino]cyclohexanecarboxylic acid phenylmethyl ester in 300 ml of 2-propanol, and the mixture was stirred at 60° C. under a hydrogen atmosphere for 20 hours. After the reaction solution was filtered, the filtrate was concentrated under reduced pressure to obtain 11.57 g (quantitative) of the title compound.

1H-NMR (CDCl$_3$, δ): 1.07-1.19 (1H, m), 1.21-1.36 (2H, m), 1.50-1.63 (2H, m), 1.65-1.71 (1H, m), 1.80-1.88 (1H, m), 1.89-1.95 (1H, m), 2.04-2.15 (2H, m), 3.42 (1H, dd, J=17 Hz, 7 Hz), 3.60 (1H, dd, J=17 Hz, 7 Hz), 5.18 (1H, dd, J=7 Hz, 7 Hz), 6.84 (1H, br-s), 6.91 (1H, d, J=8 Hz), 6.96 (1H, dd, J=8 Hz, 1 Hz), 7.18 (1H, td, J=8 Hz, 1 Hz), 7.22 (1H, dd, J=8 Hz, 1 Hz)

Reference Example 14

1-[(2-Furanylcarbonyl)amino]cyclohexanecarboxylic acid

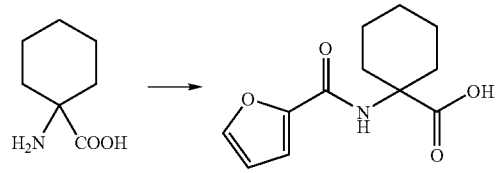 [SMILES: NC1(C(=O)O)CCCCC1 ; O=C(NC1(C(=O)O)CCCCC1)c1ccco1]

71.6 g (0.5 mol) of 1-aminocyclohexanecarboxylic acid was added to 250 ml of an aqueous solution of 20 g (0.5 mol) of sodium hydroxide, and the mixture was stirred at 80° C. for 2 hours. The mixed solution was cooled with ice-water, and 71.8 g (0.2 mol) of 2-furancarbonyl chloride and 100 ml of an aqueous solution of 24 g (0.6 mol) of sodium hydroxide were simultaneously added thereto over approximately 1 hour. The temperature of the reaction solution was slowly returned to room temperature and the solution was stirred overnight. After 80 ml of ethyl acetate was added to the reaction solution and the solution was stirred for 1 hour, the insolubles were removed by filtration. The aqueous layer was separately collected and 49 ml of concentrated hydrochloric acid was added thereto under ice-cooling. The precipitated crystal was collected by filtration and dried under reduced pressure to obtain 112.6 g (95%) of the title compound.

1H-NMR (CDCl$_3$, δ): 1.35-1.41 (1H, m), 1.48-1.53 (2H, m), 1.64-1.67 (1H, m), 1.71-1.76 (2H, m), 1.96-2.02 (2H, m), 2.20-2.24 (2H, m), 6.48 (1H, br-s), 6.55 (1H, dd, J=4 Hz, 2 Hz), 7.19 (1H, dd, J=4 Hz, 1 Hz), 7.50 (1H, dd, J=2 Hz, 1 Hz)

Reference Example 15

1-[(3-Furanylcarbonyl)amino]cyclohexanecarboxylic acid methyl ester

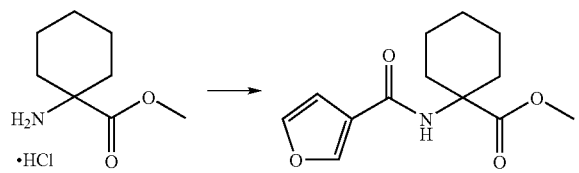 [SMILES: Cl ; COC(=O)C1(N)CCCCC1 ; COC(=O)C1(NC(=O)c2ccoc2)CCCCC1]

105 g (550 mmol) of 1-ethyl-3-(3-dimethylaminopropyl) carbodiimide hydrochloride was added to a solution of 98.8 g (500 mmol) of 1-aminocyclohexanecarboxylic acid methyl ester hydrochloride, 84.2 g (550 mmol) of 1-hydroxybenzotriazole, 56.0 g (500 mmol) of 3-furancarboxylic acid and 152 g (1.5 mol) of triethylamine in 1000 ml of methylene chloride under ice-cooling. After the mixture was stirred at room temperature overnight, the reaction solution was concentrated under reduced pressure. Ethyl acetate was added to the residue and the mixture was successively washed with water, a 10% aqueous potassium hydrogensulfate solution, a saturated aqueous sodium hydrogencarbonate solution and saturated brine, followed by drying with anhydrous sodium sulfate. After the solvent was distilled off under reduced pressure, the obtained crystal was washed with diisopropyl ether to give 114 g (91%) of the title compound.

1H-NMR (CDCl$_3$, δ): 1.34-1.40 (1H, m), 1.43-1.44 (2H, m), 1.62-1.73 (3H, m), 1.90-1.96 (2H, m), 2.10-2.14 (2H, m), 3.73 (3H, s), 5.87 (1H, br-s), 6.23 (1H, dd, J=2 Hz, 1 Hz), 7.44 (1H, dd, J=2 Hz, 1 Hz), 7.94 (1H, dd, J=2 Hz, 1 Hz)

Reference Example 16

1-[(3-Furanylcarbonyl)amino]cyclohexanecarboxylic acid

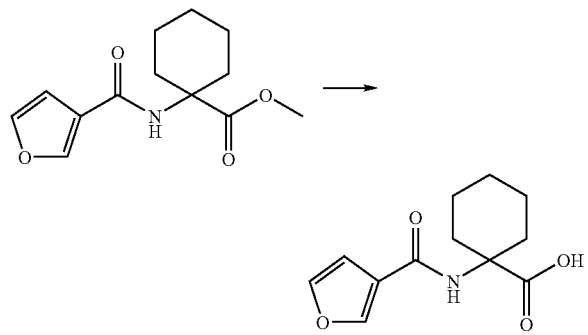

450 ml of 2N aqueous sodium hydroxide solution was added to a solution of 75.4 g (300 mmol) of 1-[(3-furanylcarbonyl)amino]cyclohexanecarboxylic acid methyl ester in 450 ml of tetrahydrofuran, and the mixture was refluxed under heating for 3 hours. After ether was added to the reaction solution to wash, the aqueous layer was neutralized by concentrated hydrochloric acid and extracted with ethyl acetate. After the obtained organic layer was washed with saturated brine and it was dried with anhydrous sodium sulfate. The solvent was distilled off under reduced pressure to obtain 68.8 g (97%) of the title compound.

1H-NMR (CDCl$_3$, δ): 1.37-1.50 (3H, m), 1.58-1.64 (1H, m), 1.68-1.80 (2H, m), 1.98-2.05 (2H, m), 2.14-2.23 (2H, m), 5.87 (1H, s), 6.63 (1H, d, J=2 Hz), 7.49 (1H, d, J=2 Hz), 8.00 (1H, s)

Reference Example 17

1-[[(E)-3-(2-Furanyl)-1-oxo-2-propenyl]amino]cyclohexanecarboxylic acid methyl ester

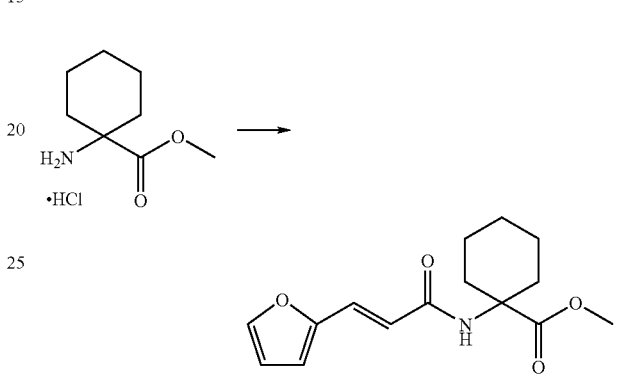

80 g (362 mmol) of 2-furanacrylic acid was used instead of 3-furancarboxylic acid in the process according to Reference example 15 to obtain 89 g (89%) of the title compound.

1H-NMR (CDCl$_3$, δ): 1.29-1.39 (1H, m), 1.40-1.51 (2H, m), 1.58-1.71 (3H, m), 1.88-1.95 (2H, m), 2.05-2.14 (2H, m), 3.73 (3H, s), 5.67 (1H, br-s), 6.35 (1H, d, J=16 Hz), 6.45 (1H, dd, J=3 Hz, 2 Hz), 6.54 (1H, d, J=3 Hz), 7.37 (1H, d, J=16 Hz), 7.40 (1H, d, J=2 Hz)

Reference Example 18

1-[[(E)-3-(2-Furanyl)-1-oxo-2-propenyl]amino]cyclohexanecarboxylic acid

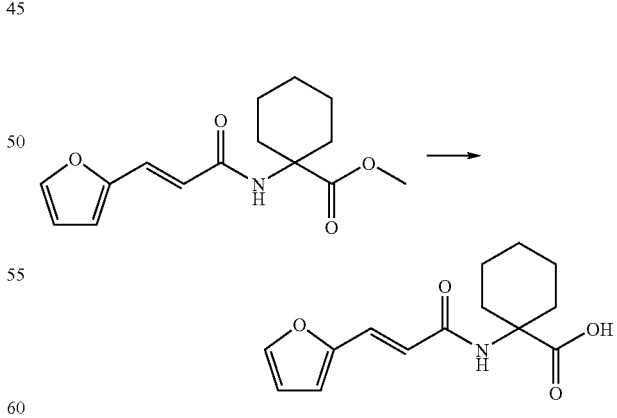

44.9 g (162 mmol) of 1-[[(E)-3-(2-furanyl)-1-oxo-2-propenyl]amino]cyclohexanecarboxylic acid methyl ester was used instead of 1-[(3-furanylcarbonyl)amino]cyclohexanecarboxylic acid methyl ester in the process according to Reference example 16 to obtain 37.5 g (quantitative) of the title compound.

1H-NMR (CDCl₃, δ): 1.32-1.85 (6H, m), 1.96-2.05 (2H, m), 2.15-2.18 (2H, m), 5.66 (1H, br-s), 6.36 (1H, d, J=15 Hz), 6.49 (1H, dd, J=3 Hz, 2 Hz), 6.64 (1H, d, J=3 Hz), 7.48 (1H, d, J=15 Hz), 7.49 (1H, d, J=2 Hz)

Reference Example 19

1-[(2-Benzofuranylcarbonyl)amino]cyclohexanecarboxylic acid ethyl ester

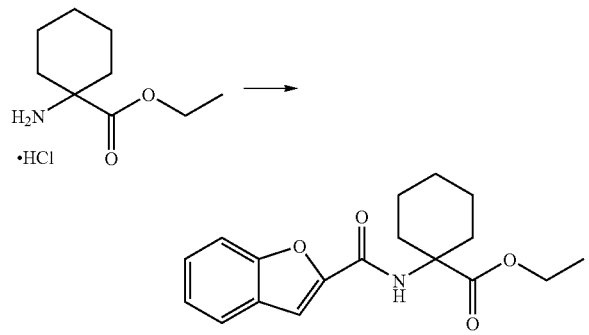

3.11 g (15 mmol) of 1-aminocyclohexanecarboxylic acid ethyl ester hydrochloride was used instead of 1-aminocyclohexanecarboxylic acid methyl ester hydrochloride and 2.43 g (15 mmol) of benzofuran-2-carboxylic acid was used instead of 3-furancarboxylic acid in the process according to Reference example 15 to obtain 3.80 g (80%) of the title compound.

1H-NMR (CDCl₃, δ): 1.26 (3H, t, J=7 Hz), 1.33-1.42 (1H, m) 1.50-1.62 (2H, m), 1.65-1.78 (3H, m), 1.94-2.02 (2H, m), 2.19-227 (2H, m), 4.21 (2H, q, J=7 Hz), 6.75 (1H, br-s), 7.30 (1H, td, J=8 Hz, 1 Hz), 7.43 (1H, td, J=8 Hz, 1 Hz), 7.45 (1H, d, J=1 Hz), 7.53 (1H, dd, J=8 Hz, 1 Hz), 7.67 (1H, dd, J=8 Hz, 1 Hz)

Reference Example 20

1-[(2-Benzofuranylcarbonyl)amino]cyclohexanecarboxylic acid

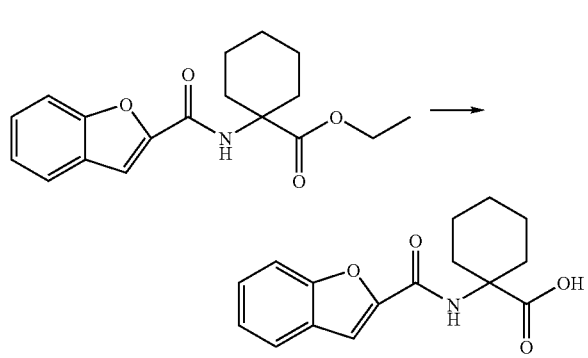

3.80 g (12 mmol) of 1-[(2-benzofuranylcarbonyl)amino]cyclohexanecarboxylic acid ethyl ester was used instead of 1-[(3-furanylcarbonyl)amino]cyclohexanecarboxylic acid methyl ester in the process according to Reference example 16 to obtain 3.42 g (quantitative) of the title compound.

1H-NMR (CDCl₃, δ): 1.35-1.44 (1H, m), 1.50-1.62 (2H, m), 1.65-1.73 (1H, m), 1.74-1.82 (2H, m), 2.00-2.08 (2H, m), 2.25-2.33 (2H, m), 6.77 (1H, br-s), 7.32 (1H, td, J=8 Hz, 1 Hz), 7.46 (1H, td, J=8 Hz, 1 Hz), 7.53 (1H, d, J=1 Hz), 7.55 (1H, dd, J=8 Hz, 1 Hz), 7.70 (1H, dd, J=8 Hz, 1 Hz)

Reference Example 21

1-[(Cyclohexylcarbonyl)amino]cyclohexanecarboxylic acid phenylmethyl ester

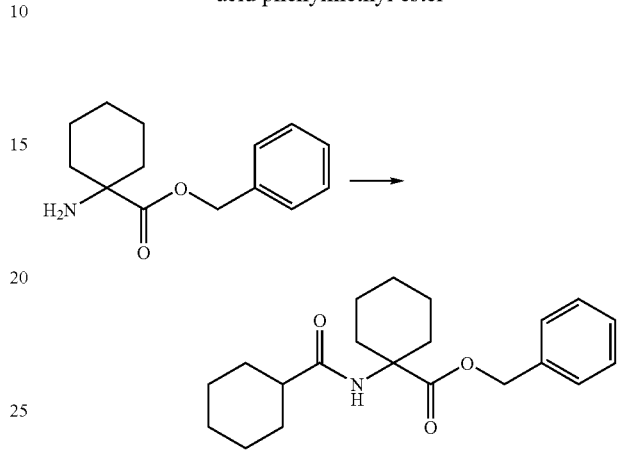

3.85 g (30 mmol) of cyclohexanecarboxylic acid was used instead of 4-biphenylcarboxylic acid in the process according to Reference example 7 to obtain 4.77 g (46%) of the title compound.

1H-NMR (CDCl₃, δ): 1.17-1.45 (8H, m), 1.59-1.77 (4H, m), 1.73-1.88 (6H, m), 2.03-2.11 (3H, m), 5.12 (2H, s), 5.55 (1H, br-s), 7.23-7.36 (5H, m)

Reference Example 22

1-[(Cyclohexylcarbonyl)amino]cyclohexanecarboxylic acid

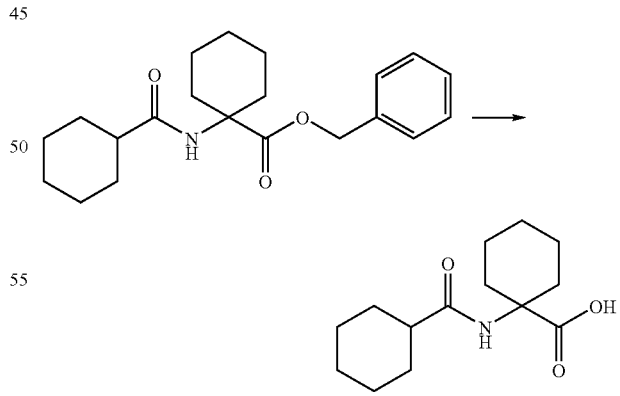

5.62 g (16.3 mmol) of 1-[(cyclohexylcarbonyl)amino]cyclohexanecarboxylic acid phenylmethyl ester was used instead of 1-[(phenylacetyl)amino]cyclohexanecarboxylic acid phenylmethyl ester in the process according to Reference example 2 to obtain 4.15 g (quantitative) of the title compound.

1H-NMR (CDCl$_3$, δ): 1.18-1.50 (8H, m), 1.60-1.76 (4H, m), 1.78-1.95 (6H, m), 2.06-2.14 (2H, m), 2.16-2.23 (1H, m), 5.58 (1H, br-s)

Reference Example 23

1-[(6-Benzothiazolylcarbonyl)amino]cyclohexanecarboxylic acid phenylmethyl ester

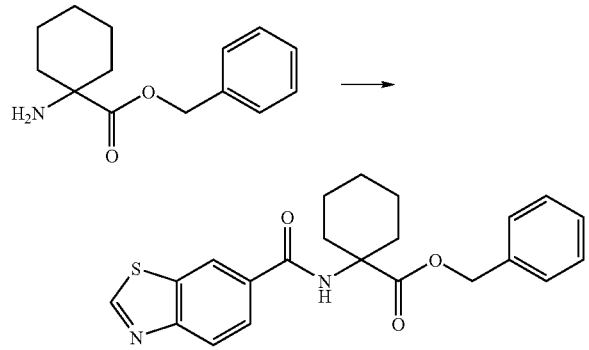

1.15 g (6.4 mmol) of benzothiazole-6-carboxylic acid was used instead of 4-biphenylcarboxylic acid in the process according to Reference example 7 to obtain 1.58 g (62%) of the title compound.

1H-NMR (CDCl$_3$, δ): 1.35-1.43 (1H, m), 1.49-1.60 (2H, m), 1.61-1.78 (3H, m), 1.96-2.06 (2H, m), 2.20-2.27 (2H, m), 5.19 (2H, s), 6.30 (1H, br-s), 7.28-7.75 (5H, m), 7.86 (1H, dd, J=7 Hz, 2 Hz), 8.17 (1H, dd, J=7 Hz, 1 Hz), 8.41 (1H, dd, J=2 Hz, 1 Hz), 9.12 (1H, s)

Reference Example 24

1-[(6-Benzothiazolylcarbonyl)amino]cyclohexanecarboxylic acid

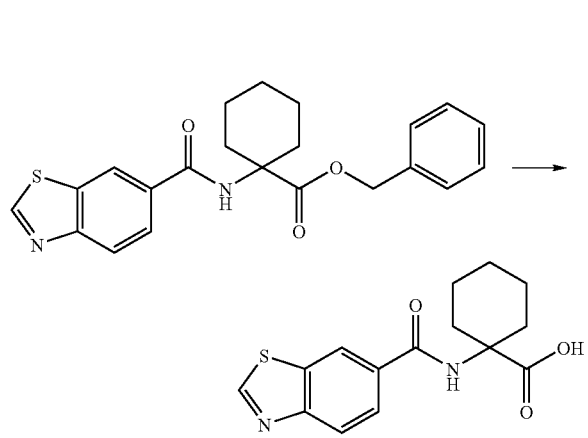

1.18 g (30 mmol) of 1-[(6-benzothiazolylcarbonyl)amino]cyclohexanecarboxylic acid phenylmethyl ester was used instead of 1-[(3-furanylcarbonyl)amino]cyclohexanecarboxylic acid methyl ester in the process according to Reference example 16 to obtain 0.77 g (84%) of the title compound.

1H-NMR (CD$_3$OD, δ): 1.38-1.46 (1H, m), 1.60-1.76 (5H, m), 1.91-2.01 (2H, m), 2.21-2.28 (2H, m), 7.98 (1H, dd, J=7 Hz, 2 Hz), 8.12 (1H, dd, J=7 Hz, 1 Hz), 8.54 (1H, dd, J=2 Hz, 1 Hz), 9.37 (1H, s)

Reference Example 25

1-[[(6-Hydroxy-3-pyridinyl)carbonyl]amino]cyclohexanecarboxylic acid phenylmethyl ester

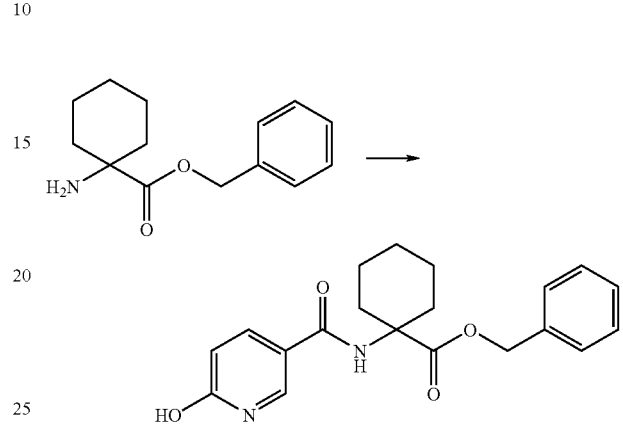

139 mg (1.0 mmol) of 6-hydroxy-3-pyridinecarboxylic acid was used instead of 4-biphenylcarboxylic acid in the process according to Reference example 7 to obtain 222 mg (62%) of the title compound.

1H-NMR (CDCl$_3$, δ): 1.30-1.40 (1H, m), 1.42-1.54 (2H, m), 1.62-1.73 (3H, m), 1.91-1.98 (2H, m), 2.13-2.20 (2H, m), 5.17 (2H, s), 6.22 (1H, s), 6.54 (1H, d, J=10 Hz), 7.26-7.35 (5H, m), 7.76 (1H, dd, J=10 Hz, 3 Hz), 7.93 (1H, d, J=3 Hz)

Reference Example 26

1-[[(6-Hydroxy-3-pyridinyl)carbonyl]amino]cyclohexanecarboxylic acid

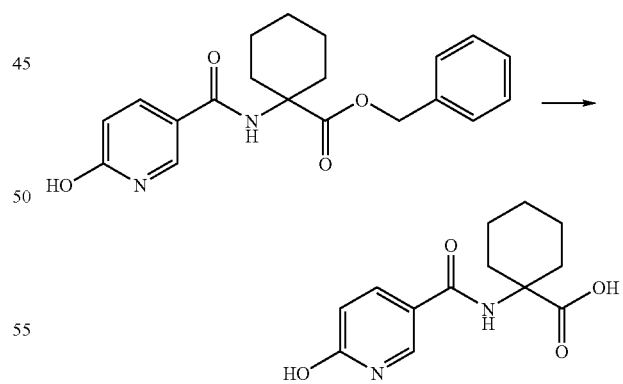

760 mg (2.2 mmol) of 1-[[(6-hydroxy-3-pyridinyl)carbonyl]amino]cyclohexanecarboxylic acid phenylmethyl ester was used instead of 1-[(phenylacetyl)amino]cyclohexanecarboxylic acid phenylmethyl ester in the process according to Reference example 2 to obtain 565 mg (quantitative) of the title compound.

1H-NMR (CD$_3$OD, δ): 1.21-1.30 (1H, m), 1.43-1.54 (5H, m), 1.67-1.74 (2H, m), 2.03-2.09 (2H, m), 6.33 (1H, d, J=9 Hz), 7.84 (1H, dd, J=9 Hz, 3 Hz), 8.05 (1H, d, J=3 Hz)

Reference Example 27

1-[(2-Thienylcarbonyl)amino]cyclohexanecarboxylic acid

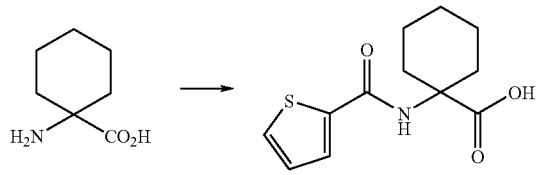 [SMILES: NC1(C(=O)O)CCCCC1 ; O=C(NC1(C(=O)O)CCCCC1)c1cccs1]

100 g (680 mmol) of 2-thiophenecarbonyl chloride was used instead of 2-furancarbonyl chloride in the process according to Reference example 14 to obtain 57.6 g (51) of the title compound.

1H-NMR (CDCl$_3$, δ): 1.35-1.54 (3H, m), 1.65-1.80 (3H, m), 1.98-2.05 (2H, m), 2.21-2.27 (2H, m), 6.06 (1H, br-s), 7.13 (1H, dd, J=5 Hz, 3 Hz), 7.57 (1H, dd, J=5 Hz, 1 Hz), 7.59 (1H, dd, J=3 Hz, 1 Hz)

Reference Example 28

1-[(2-Pyridinylcarbonyl)amino]cyclohexanecarboxylic acid methyl ester

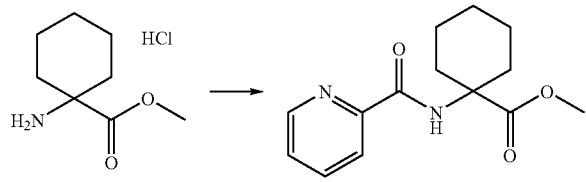 [SMILES: COC(=O)C1(N)CCCCC1 ; Cl ; COC(=O)C1(NC(=O)c2ccccn2)CCCCC1]

370 mg (3 mmol) of 2-pyridinecarboxylic acid was used instead of 3-furancarboxylic acid in the process according to Reference example 15 to obtain 600 mg (76%) of the title compound.

1H-NMR (CDCl$_3$, δ): 1.31-1.42 (1H, m), 1.51-1.73 (5H, m), 1.95 (2H, td, J=13 Hz, 4 Hz), 1.99-2.08 (2H, m), 3.73 (3H, s), 7.44 (1H, ddd, J=8 Hz, 5 Hz, 2 Hz), 7.84 (1H, dd, J=8 Hz, 2 Hz), 8.16 (1H, d, J=8 Hz), 8.33 (1H, s), 8.57 (1H, dd, J=5 Hz, 2 Hz)

Reference Example 29

1-[(2-Pyridinylcarbonyl)amino]cyclohexanecarboxylic acid

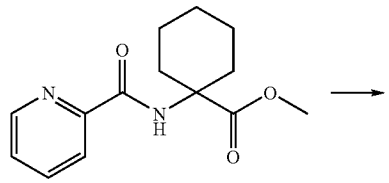

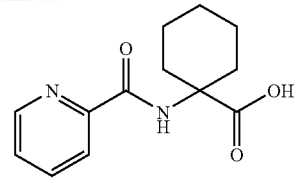

539 mg (2 mmol) of 1-[(2-pyridinylcarbonyl)amino]cyclohexanecarboxylic acid methyl ester was used instead of 1-[(3-furanylcarbonyl)amino]cyclohexanecarboxylic acid methyl ester in the process according to Reference example 16 to obtain 479 mg (quantitative) of the title compound.

1H-NMR (CDCl$_3$, δ): 1.32-1.41 (1H, m), 1.48-1.57 (2H, m), 1.62-1.78 (3H, m), 1.98 (2H, m), 2.25-2.35 (2H, m), 7.50 (1H, ddd, J=8 Hz, 5 Hz, 2 Hz), 7.89 (1H, dd, J=8 Hz, 2 Hz), 8.19 (1H, d, J=8 Hz), 8.59 (1H, s), 8.60 (1H, dd, J=5 Hz, 2 Hz)

Reference Example 30

1-[(3-Thienylcarbonyl)amino]cyclohexanecarboxylic acid methyl ester

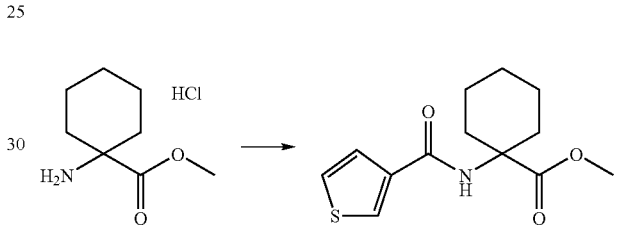

384 mg (3 mmol) of 3-thiophenecarboxylic acid was used instead of 3-furancarboxylic acid in the process according to Reference example 15 to obtain 759 mg (95%) of the title compound.

1H-NMR (CDCl$_3$, δ): 1.32-1.41 (1H, m), 1.42-1.55 (2H, m), 1.61-1.75 (3H, m), 1.90-1.99 (2H, m), 2.11-2.18 (2H, m), 3.74 (3H, s), 6.26 (1H, br-s), 7.35 (1H, dd, J=5 Hz, 2 Hz), 7.39 (1H, dd, J=5 Hz, 2 Hz), 7.88 (1H, dd, J=3 Hz, 2 Hz)

Reference Example 31

1-[(3-Thienylcarbonyl)amino]cyclohexanecarboxylic acid

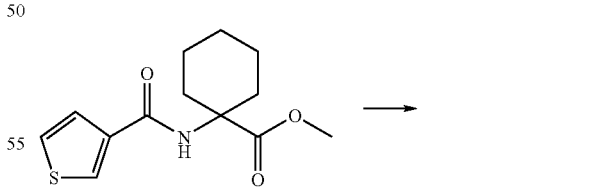

759 mg (2.8 mmol) of 1-[(3-thienylcarbonyl)amino]cyclohexanecarboxylic acid methyl ester was used instead of 1-[(3-furanylcarbonyl)amino]cyclohexanecarboxylic acid methyl ester in the process according to Reference example 16 to obtain 692 mg (96%) of the title compound.

1H-NMR (DMSO-d$_6$, δ): 1.24-1.32 (1H, m), 1.45-1.55 (5H, m), 1.72-1.78 (2H, m), 2.05-2.12 (2H, m), 7.50 (1H, dd, J=5 Hz, 2 Hz), 7.57 (1H, dd, J=5 Hz, 2 Hz), 7.96 (1H, br-s), 8.21 (1H, dd, J=3 Hz, 2 Hz)

Reference Example 32

1-[[(3-Ethoxy-2-thienyl)carbonyl]amino]cyclohexanecarboxylic acid

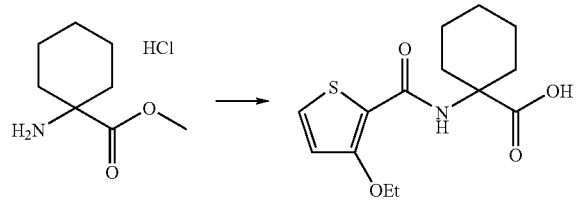 [SMILES: COC(=O)C1(N)CCCCC1 ; Cl ; CCOc1ccsc1C(=O)NC1(C(=O)O)CCCCC1]

633 mg (3.3 mmol) of 1-ethyl-3-(3-dimethylaminopropyl) carbodiimide hydrochloride was added to a solution of 581 mg (3 mmol) of 1-aminocyclohexanecarboxylic acid methyl ester hydrochloride, 482 mg (3.1 mmol) of 1-hydroxybenzotriazole, 517 mg (3 mmol) of 3-ethoxy-2-thiophenecarboxylic acid and 1.16 g (9 mmol) of diisopropylethylamine in 10 ml of methylene chloride under ice-cooling. After the solution was stirred at room temperature overnight, the reaction solution was concentrated under reduced pressure, ethyl acetate was added thereto, and the mixture was washed with water, a 10% aqueous potassium hydrogensulfate solution, a saturated aqueous sodium hydrogencarbonate solution and then saturated brine, followed by drying with anhydrous sodium sulfate. After the solvent was distilled off under reduced pressure, diisopropyl ether was added to the residue, followed by stirring overnight and the crystal was collected by filtration. Subsequently, the obtained crystal was dissolved in 3 ml of tetrahydrofuran solution, 2.8 ml of 2N—NaOH aqueous solution was added thereto, and the mixture was refluxed under heating for 3 hours. Ether was added to the reaction solution and the aqueous layer was separated. After the separated aqueous layer was neutralized by concentrated hydrochloric acid, the layer was extracted with ethyl acetate. After the obtained organic layer was washed with saturated brine, it was dried with anhydrous sodium sulfate. The solvent was distilled off under reduced pressure to obtain 656 mg (73%) of the title compound.

1H-NMR (CDCl$_3$, δ): 1.29-1.40 (1H, m), 1.43-1.54 (2H, m), 1.50 (3H, t, J=7 Hz), 1.62-1.76 (3H, m), 1.90-2.00 (2H, m), 2.22-2.30 (2H, m), 4.30 (2H, q, J=7 Hz), 6.87 (1H, d, J=6 Hz), 7.49 (1H, d, J=6 Hz), 7.60 (1H, s)

Reference Example 33

1-[[(S)-1-Oxo-2-phenylpropyl]amino]cyclohexanecarboxylic acid methyl ester

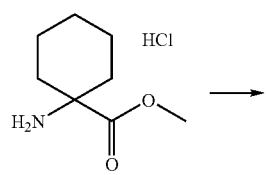

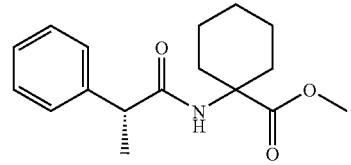

451 mg (3 mmol) of (S)-(+)-2-phenylpropionic acid was used instead of 3-furancarboxylic acid in the process according to Reference example 15 to obtain 601 mg (69%) of the title compound.

1H-NMR (CDCl$_3$, δ): 1.06-1.22 (2H, m), 1.48-1.61 (7H, m), 1.71-1.77 (2H, m), 1.90-1.96 (2H, m), 3.60 (1H, q, 7 Hz), 3.67 (3H, s), 5.40 (1H, br-s), 7.27-7.39 (5H, m)

Reference Example 34

1-[[(S)-1-Oxo-2-phenylpropyl]amino]cyclohexanecarboxylic acid

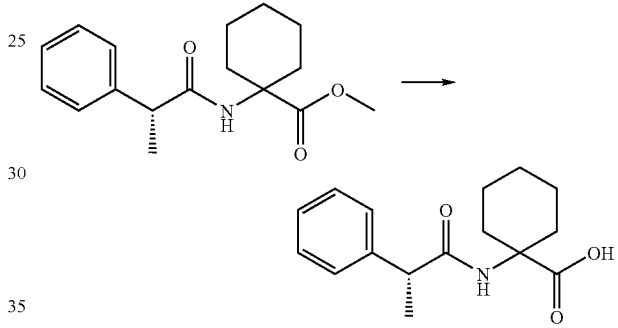

608 mg (2.1 mmol) of 1-[[(S)-1-oxo-2-phenylpropyl] amino]cyclohexanecarboxylic acid methyl ester was used instead of 1-[(3-furanylcarbonyl)amino]cyclohexanecarboxylic acid methyl ester in the process according to Reference example 16 to obtain 366 mg (63%) of the title compound.

1H-NMR (DMSO-d$_6$, δ): 1.08-1.21 (2H, m), 1.28-1.47 (7H, m), 1.53-1.62 (2H, m), 1.93 (2H, br-s), 3.79 (1H, q, J=7 Hz), 7.18-7.21 (1H, m), 7.27-7.33 (4H, m), 7.90 (1H, s), 12.00 (1H, s)

Reference Example 35

1-[(2-Pyrazinylcarbonyl)amino]cyclohexanecarboxylic acid methyl ester

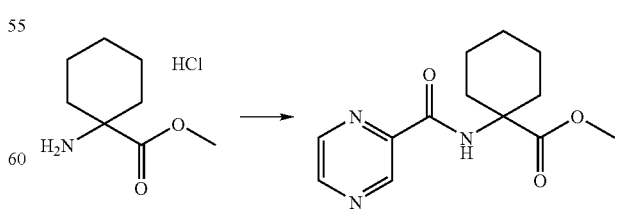

372 mg (3 mmol) of 2-pyrazinecarboxylic acid was used instead of 3-furancarboxylic acid in the process according to Reference example 15 to obtain 476 mg (60%) of the title compound.

1H-NMR (CDCl$_3$, δ): 1.35-1.40 (1H, m), 1.47-1.59 (2H, m), 1.65-1.75 (3H, m), 1.94-2.00 (2H, m), 2.18-2.29 (2H, m), 3.75 (3H, s), 8.03 (1H, s), 8.55 (1H, dd, J=3 Hz, 1 Hz), 8.77 (1H, d, J=3 Hz), 9.38 (1H, d, J=1 Hz)

Reference Example 36

1-[(2-Pyrazinylcarbonyl)amino]cyclohexanecarboxylic acid

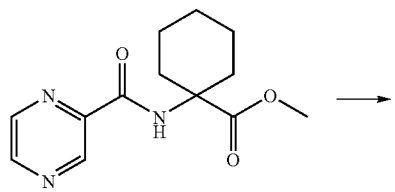

476 mg (1.8 mmol) of 1-[(2-pyrazinylcarbonyl)amino]cyclohexanecarboxylic acid methyl ester was used instead of 1-[(3-furanylcarbonyl)amino]cyclohexanecarboxylic acid methyl ester in the process according to Reference example 16 to obtain 356 mg (79%) of the title compound.

1H-NMR (DMSO-d$_6$, δ): 1.28-1.59 (6H, m), 1.79 (2H, td, J=12 Hz, 4 Hz), 2.10-2.19 (2H, m), 8.35 (1H, s), 8.75 (1H, d, J=2 Hz), 8.89 (1H, d, J=2 Hz), 9.14 (1H, d, J=2 Hz), 12.42 (1H, s)

Reference Example 37

1-[[(5-Methyl-2-thienyl)carbonyl]amino]cyclohexanecarboxylic acid methyl ester

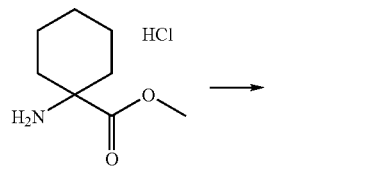

427 mg (3 mmol) of 5-methyl-2-thiophenecarboxylic acid was used instead of 3-furancarboxylic acid in the process according to Reference example 15 to obtain 812 mg (96%) of the title compound.

1H-NMR (CDCl$_3$, δ): 1.36-1.72 (6H, m), 1.92 (2H, td, J=13 Hz, 4 Hz), 2.11-2.19 (2H, m), 2.51 (3H, s), 3.73 (3H, s), 5.95 (1H, s), 6.74 (1H, d, J=4 Hz), 7.34 (1H, d, J=4 Hz)

Reference Example 38

1-[[(5-Methyl-2-thienyl)carbonyl]amino]cyclohexanecarboxylic acid

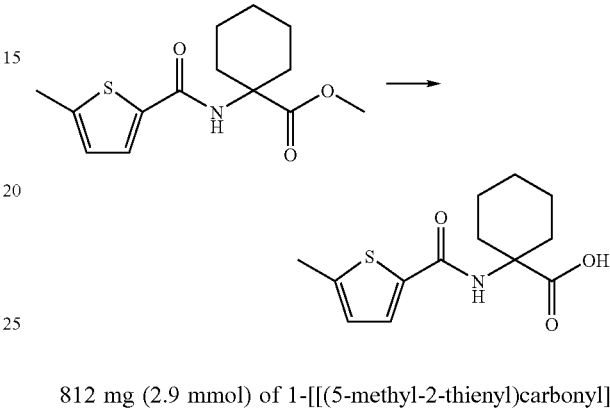

812 mg (2.9 mmol) of 1-[[(5-methyl-2-thienyl)carbonyl]amino]cyclohexanecarboxylic acid methyl ester was used instead of 1-[(3-furanylcarbonyl)amino]cyclohexanecarboxylic acid methyl ester in the process according to Reference example 16 to obtain 771 mg (99%) of the title compound.

1H-NMR (DMSO-d$_6$, δ): 1.21-1.38 (1H, m), 1.52 (5H, br-s), 1.68-1.80 (2H, m), 2.01-2.12 (2H, m), 2.46 (3H, s), 6.84 (1H, d, J=4 Hz), 7.70 (1H, s), 8.02 (1H, s)

Reference Example 39

1-[[(4-Methoxyphenyl)carbonyl]amino]cyclohexanecarboxylic acid methyl ester

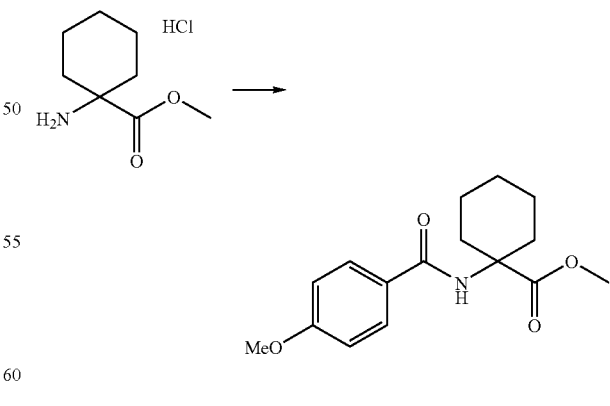

581 mg (3 mmol) of 1-aminocyclohexanecarboxylic acid methyl ester hydrochloride was used instead of 1-aminocyclohexanecarboxylic acid phenylmethyl ester and 512 mg (3 mmol) of 4-methoxybenzoyl chloride was used instead of phenylacetyl chloride in the process according to Reference example 1 to obtain 619 mg (71%) of the title compound.

1H-NMR (CDCl₃, δ): 1.32-1.41 (1H, m), 1.49-1.74 (5H, m), 1.94 (2H, td, J=13 Hz, 4 Hz), 2.12-2.22 (2H, m), 3.73 (3H, s), 3.85 (3H, s), 6.16 (1H, br-s), 6.92 (2H, dd, J=7 Hz, 2 Hz), 7.76 (2H, dd, J=7 Hz, 2 Hz)

Reference Example 40

1-[[(4-Methoxyphenyl)carbonyl]amino]cyclohexanecarboxylic acid

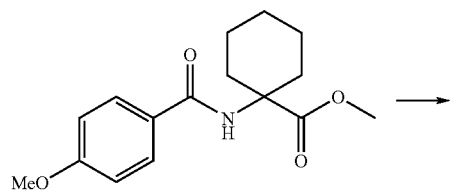

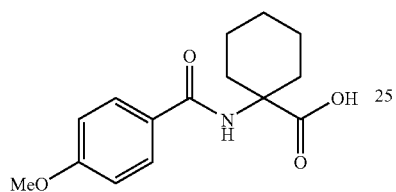

619 mg (2.1 mmol) of 1-[[(4-methoxyphenyl)carbonyl]amino]cyclohexanecarboxylic acid methyl ester was used instead of 1-[(3-furanylcarbonyl)amino]cyclohexanecarboxylic acid methyl ester in the process according to Reference example 16 to obtain 552 mg (94%) of the title compound.

1H-NMR (DMSO-d₆, δ): 1.22-1.38 (1H, m), 1.51-1.60 (5H, br-s), 1.65-1.79 (2H, m), 2.04-2.19 (2H, m), 3.81 (3H, s), 6.98 (2H, d, J=9 Hz), 7.83 (2H, d, J=9 Hz), 8.04 (1H, s), 12.3 (1H, br-s)

Reference Example 41

1-[[(3-Methyl-2-thienyl)carbonyl]amino]cyclohexanecarboxylic acid methyl ester

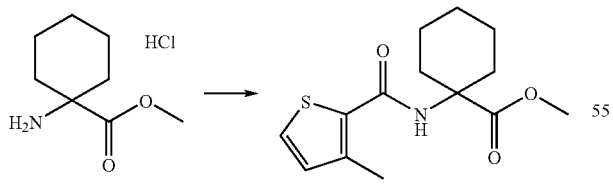

581 mg (3 mmol) of 1-aminocyclohexanecarboxylic acid methyl ester hydrochloride was used instead of 1-aminocyclohexanecarboxylic acid phenylmethyl ester and 482 mg (3 mmol) of 3-methyl-2-thiophenecarbonyl chloride was used instead of phenylacetyl chloride in the process according to Reference example 1 to obtain 394 mg (47%) of the title compound.

1H-NMR (CDCl₃, δ): 1.32-1.42 (1H, m), 1.49-1.53 (2H, m), 1.70-1.72 (3H, m), 1.92 (2H, td, J=12 Hz, 4 Hz), 2.11-2.22 (2H, m), 2.36 (3H, s), 3.74 (3H, s), 6.33 (1H, d, J=2 Hz), 6.44 (1H, br-s), 7.30 (1H, d, J=2 Hz)

Reference Example 42

1-[[(3-Methyl-2-thienyl)carbonyl]amino]cyclohexanecarboxylic acid

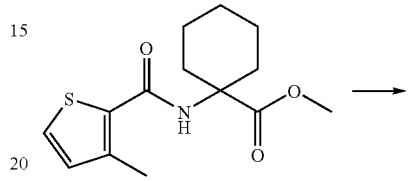

394 mg (1.4 mmol) of 1-[[(3-methyl-2-thienyl)carbonyl]amino]cyclohexanecarboxylic acid methyl ester was used instead of 1-[(3-furanylcarbonyl)amino]cyclohexanecarboxylic acid methyl ester in the process according to Reference example 16 to obtain 330 mg (88%) of the title compound.

1H-NMR (CDCl₃, δ): 1.36-1.53 (3H, m), 1.68-1.78 (3H, m), 1.96-2.05 (2H, m), 1.99-2.08 (2H, m), 2.55 (3H, s), 5.91 (1H, s), 6.94 (1H, d, J=5 Hz), 7.35 (1H, d J=5 Hz)

Reference Example 43

1-[[(3-Methyl-2-furanyl)carbonyl]amino]cyclohexanecarboxylic acid

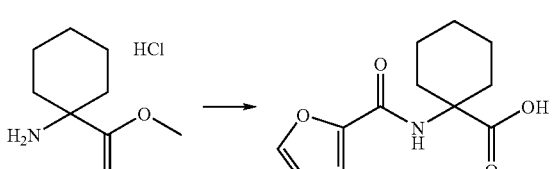

756 mg (6 mmol) of 3-methyl-2-furancarboxylic acid was used instead of 3-ethoxy-2-thiophenecarboxylic acid in the process according to Reference example 32 to obtain 902 mg (59%) of the title compound.

1H-NMR (DMSO-d₆, δ): 1.20-1.38 (1H, m), 1.40-1.59 (5H, m), 1.70-1.80 (2H, m), 2.02-2.18 (2H, m), 2.25 (3H, s), 6.50 (1H, d, J=1 Hz), 7.67 (1H, s), 7.68 (1H, d, J=1 Hz)

Reference Example 44

1-[(3-Pyridinylcarbonyl)amino]cyclohexanecarboxylic acid methyl ester

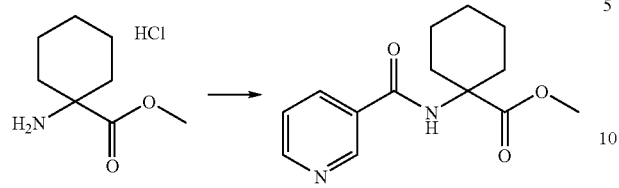

370 mg (3 mmol) of 3-pyridinecarboxylic acid was used instead of 3-furancarboxylic acid in the process according to Reference example 15 to obtain 539 mg (68%) of the title compound.

1H-NMR (CDCl$_3$, δ): 1.32-1.42 (1H, m), 1.45-1.55 (2H, m), 1.62-1.78 (3H, m), 1.92-2.01 (2H, m), 2.12-2.21 (2H, m), 3.75 (3H, s), 6.27 (1H, s), 7.40 (1H, dd, J=8 Hz, 5 Hz), 8.12 (1H, d, J=8 Hz), 8.74 (1H, d, J=5 Hz), 9.00 (1H, s)

Reference Example 45

1-[(3-Pyridinylcarbonyl)amino]cyclohexanecarboxylic acid

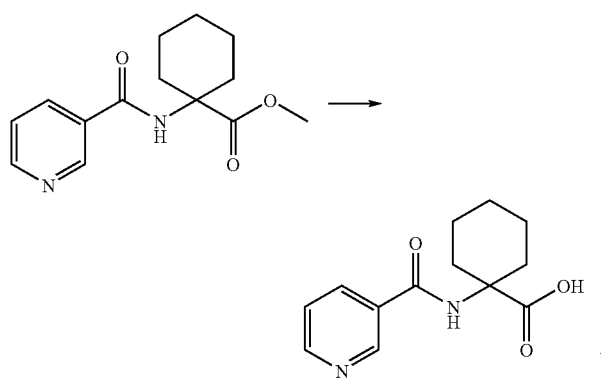

539 mg (2 mmol) of 1-[(3-pyridinylcarbonyl)amino]cyclohexanecarboxylic acid methyl ester was used instead of 1-[(3-furanylcarbonyl)amino]cyclohexanecarboxylic acid methyl ester in the process according to Reference example 16 to obtain 508 mg (quantitative) of the title compound.

1H-NMR (DMSO-d$_6$, δ): 1.22-1.35 (1H, m), 1.49-1.62 (5H, m), 1.69-1.82 (2H, m), 2.09-2.17 (2H, m), 7.50 (1H, dd, J=8 Hz, 5 Hz), 8.16 (1H, d, J=8 Hz), 8.44 (1H, s), 8.71 (1H, d, J=5 Hz), 8.97 (1H, s), 12.24 (1H, br-s)

Reference Example 46

1-[[(1-Methyl-1H-pyrrol-2-yl)carbonyl]amino]cyclohexanecarboxylic acid methyl ester

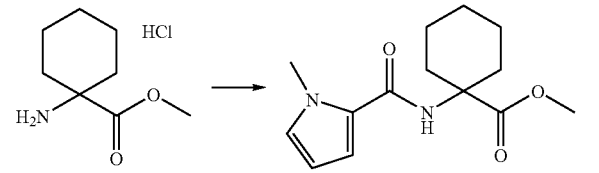 [SMILES: COC(=O)C1(N)CCCCC1 ; Cl ; COC(=O)C1(NC(=O)c2cccn2C)CCCCC1]

375 mg (3 mmol) of 1-methyl-2-pyrrolecarboxylic acid was used instead of 3-furancarboxylic acid in the process according to Reference example 15 to obtain 320 mg (40%) of the title compound.

1H-NMR (CDCl$_3$, δ): 1.28-1.40 (1H, m), 1.44-1.55 (2H, m), 1.61-1.74 (3H, m), 1.86-1.95 (2H, m), 2.05-2.16 (2H, m), 3.73 (3H, s), 3.89 (3H, s), 5.97 (1H, s), 6.09 (1H, dd, J=4 Hz, 3 Hz), 6.59 (1H, dd, J=4 Hz, 2 Hz), 6.71 (1H, dd, J=3 Hz, 2 Hz)

Reference Example 47

1-[[(1-Methyl-1H-pyrrol-2-yl)carbonyl]amino]cyclohexanecarboxylic acid

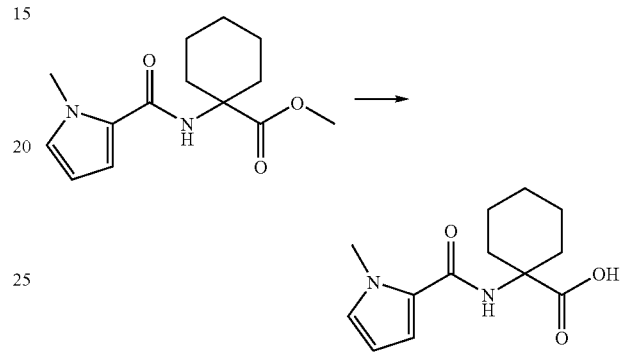

320 mg (1.2 mmol) of 1-[[(1-methyl-1H-pyrrol-2-yl)carbonyl]amino]cyclohexanecarboxylic acid methyl ester was used instead of 1-[(3-furanylcarbonyl)amino]cyclohexanecarboxylic acid methyl ester in the process according to Reference example 16 to obtain 187 mg (62%) of the title compound.

1H-NMR (CDCl$_3$, δ): 1.31-1.53 (3H, m), 1.62-1.79 (3H, m), 1.91-2.02 (2H, m), 2.18-2.24 (2H, m), 3.93 (3H, s), 5.92 (1H, s), 6.14 (1H, dd, J=4 Hz, 3 Hz), 6.68 (1H, dd, J=4 Hz, 2 Hz), 6.81 (1H, dd, J=3 Hz, 2 Hz)

Reference Example 48

1-[((R)-1-Oxo-2-phenylpropyl)amino]cyclohexanecarboxylic acid methyl ester

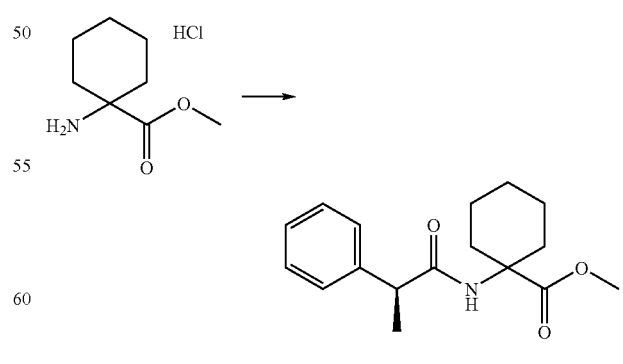

451 mg (3 mmol) of (R)-(−)-2-phenylpropionic acid was used instead of 3-furancarboxylic acid in the process according to Reference example 15 to obtain 435 mg (50%) of the title compound.

1H-NMR (CDCl$_3$, δ): 1.03-1.22 (3H, m), 1.48-1.62 (6H, m), 1.88-2.00 (2H, m), 3.60 (3H, q, J=7 Hz), 3.68 (3H, s), 5.40 (1H, br-s), 7.27-7.39 (5H, m)

Reference Example 49

1-[((R)-1-Oxo-2-phenylpropyl)amino]cyclohexanecarboxylic acid

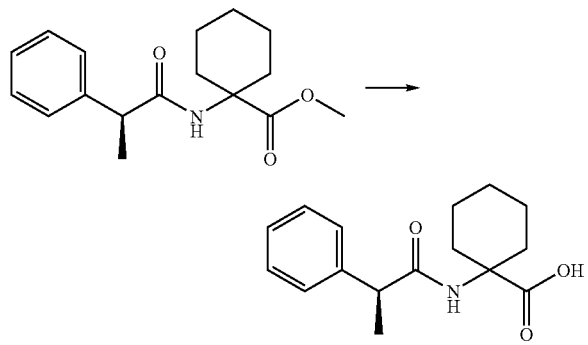

435 mg (1.5 mmol) of 1-[((R)-1-oxo-2-phenylpropyl)amino]cyclohexanecarboxylic acid methyl ester was used instead of 1-[(3-furanylcarbonyl)amino]cyclohexanecarboxylic acid methyl ester in the process according to Reference example 16 to obtain 349 mg (84%) of the title compound.

1H-NMR (DMSO-d$_6$, δ): 1.15-1.23 (2H, m), 1.29 (3H, d, J=7 Hz), 1.35-1.53 (4H, m), 1.53-1.63 (2H, m), 1.91 (2H, br-s), 3.78 (1H, q, J=7 Hz), 7.18-7.20 (1H, m), 7.21-7.32 (4H, m), 7.90 (1H, s), 12.00 (1H, s)

Reference Example 50

1-[(1H-Indol-5-ylcarbonyl)amino]cyclohexanecarboxylic acid methyl ester

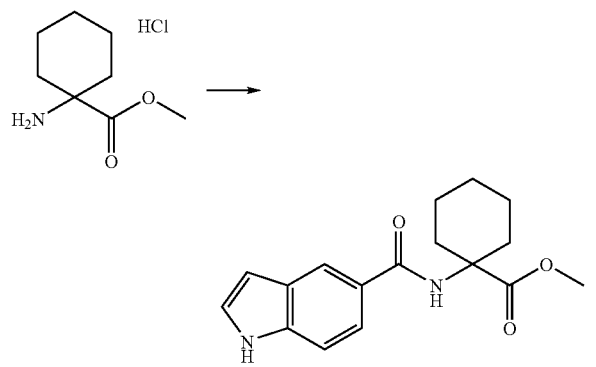

483 mg (3 mmol) of indole-5-carboxylic acid was used instead of 3-furancarboxylic acid in the process according to Reference example 15 to obtain 766 mg (85%) of the title compound.

1H-NMR (DMSO-d$_6$, δ): 1.16-1.33 (1H, m), 1.54-1.63 (5H, m), 1.75-1.80 (2H, m), 2.04-2.18 (2H, m), 3.33 (3H, s), 6.52-6.56 (1H, m), 7.40 (1H, s), 7.41-7.44 (1H, m), 7.60 (1H, dd, J=9 Hz, 2 Hz), 8.14 (1H, d, J=2 Hz), 8.18 (1H, s), 11.32 (1H, s)

Reference Example 51

1-[(1H-Indol-5-ylcarbonyl)amino]cyclohexanecarboxylic acid

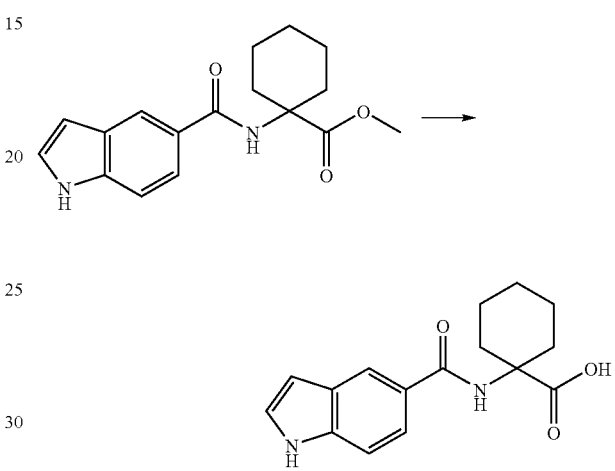

766 mg (2.6 mmol) of 1-[(1H-indol-5-ylcarbonyl)amino]cyclohexanecarboxylic acid methyl ester was used instead of 1-[(3-furanylcarbonyl)amino]cyclohexanecarboxylic acid methyl ester in the process according to Reference example 16 to obtain 561 mg (77%) of the title compound.

1H-NMR (DMSO-d$_6$, δ): 1.22-1.38 (1H, m), 1.55-1.62 (5H, m), 1.63-1.79 (2H, m), 2.10-2.22 (2H, m), 6.54 (1H, d, J=3 Hz), 7.40-7.43 (2H, m), 7.60 (1H, dd, J=3 Hz, 1 Hz), 8.03 (1H, s), 8.14 (1H, s), 11.31 (1H, s), 12.04 (1H, s)

Reference Example 52

1-[(1-Cyclopentenylcarbonyl)amino]cyclohexanecarboxylic acid methyl ester

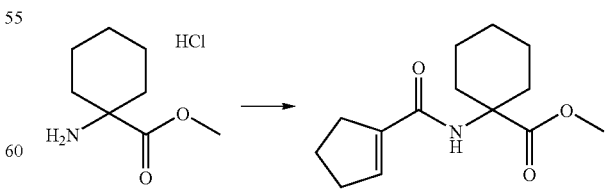

366 mg (3 mmol) of 1-cyclopentenecarboxylic acid was used instead of 3-furancarboxylic acid in the process according to Reference example 15 to obtain 717 mg (95%) of the title compound.

1H-NMR (CDCl₃, δ): 1.34-1.44 (2H, m), 1.60-1.70 (4H, m), 1.87 (2H, td, J=9 Hz, 4 Hz), 1.99-2.09 (4H, m), 2.49 (2H, m), 2.58 (2H, m), 3.72 (3H, s), 5.75 (1H, br-s), 6.55 (1H, t, J=2 Hz)

Reference Example 53

1-[(1-Cyclopentenylcarbonyl)amino]cyclohexanecarboxylic acid

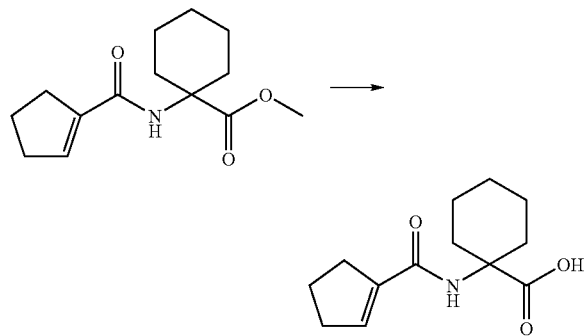

717 mg (2.9 mmol) of 1-[(1-cyclopentenylcarbonyl)amino]cyclohexanecarboxylic acid methyl ester was used instead of 1-[(3-furanylcarbonyl)amino]cyclohexanecarboxylic acid methyl ester in the process according to Reference example 16 to obtain 588 mg (87%) of the title compound.

1H-NMR (DMSO-d₆, δ): 1.24 (1H, d, J=8 Hz), 1.40-1.50 (5H, m), 1.67 (2H, td, J=10 Hz, 9 Hz), 1.81-1.89 (2H, m), 1.91-2.09 (2H, m), 2.40-2.50 (4H, m), 6.53 (1H, t, J=3 Hz), 7.46 (1H, s), 12.03 (1H, s)

Reference Example 54

1-[(4-Pyridinylcarbonyl)amino]cyclohexanecarboxylic acid methyl ester

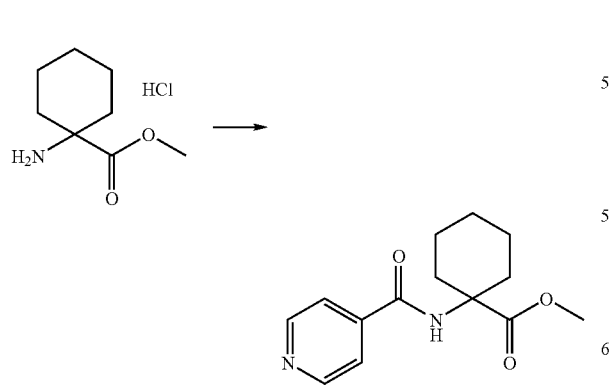

370 mg (3 mmol) of 4-pyridinecarboxylic acid was used instead of 3-furancarboxylic acid in the process according to Reference example 15 to obtain 609 mg (77%) of the title compound.

1H-NMR (CDCl₃, δ): 1.32-1.53 (3H, m), 1.62-1.77 (3H, m), 1.92-2.03 (2H, m), 2.13-2.21 (2H, m), 3.75 (3H, s), 6.29 (1H, br-s), 7.62 (2H, dd, J=5 Hz, 2 Hz), 8.76 (2H, dd, J=5 Hz, 2 Hz)

Reference Example 55

1-[(4-Pyridinylcarbonyl)amino]cyclohexanecarboxylic acid

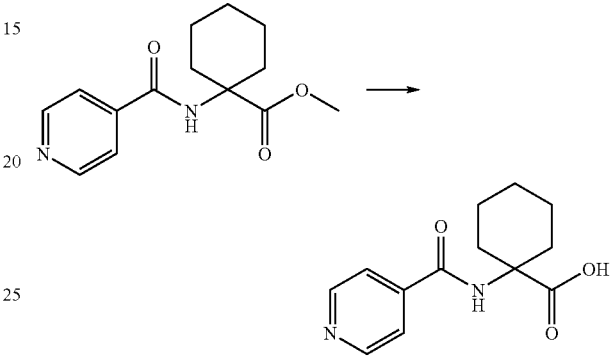

609 mg (2.3 mmol) of 1-[(4-pyridinylcarbonyl)amino]cyclohexanecarboxylic acid methyl ester was used instead of 1-[(3-furanylcarbonyl)amino]cyclohexanecarboxylic acid methyl ester in the process according to Reference example 16 to obtain 522 mg (97%) of the title compound.

1H-NMR (DMSO-d₆, δ): 1.22-1.33 (1H, m), 1.46-1.59 (5H, m), 1.70-1.80 (2H, m), 2.09-2.15 (2H, m), 7.73 (2H, dd, J=5 Hz, 2 Hz), 8.51 (1H, s), 8.72 (2H, dd, J=5 Hz, 2 Hz)

Reference Example 56

1-[(1H-Pyrrol-2-ylcarbonyl)amino]cyclohexanecarboxylic acid methyl ester

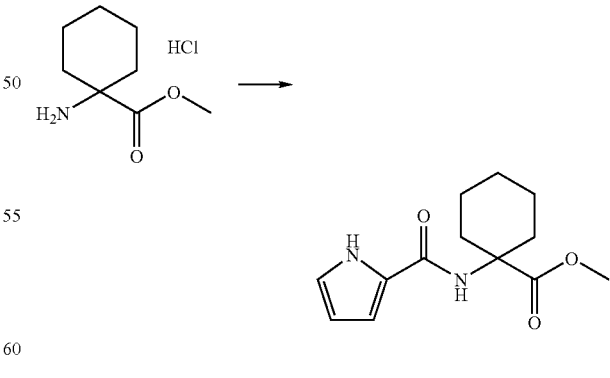

278 mg (2.5 mmol) of 2-pyrrolecarboxylic acid was used instead of 3-furancarboxylic acid in the process according to Reference example 15 to obtain 534 mg (85%) of the title compound.

1H-NMR (CDCl₃, δ): 1.32-1.45 (2H, m), 1.45-1.53 (2H, m), 1.62-1.72 (2H, m), 1.93 (2H td, J=13 Hz, 4 Hz), 2.08-2.19

(2H, m), 3.70 (3H, s), 6.05 (1H, br-s), 6.23-6.25 (1H, m), 6.61 (1H, d, J=2 Hz), 6.94 (1H, d, J=2 Hz)

Reference Example 57

1-[(1H-Pyrrol-2-ylcarbonyl)amino]cyclohexanecarboxylic acid

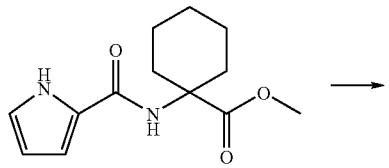

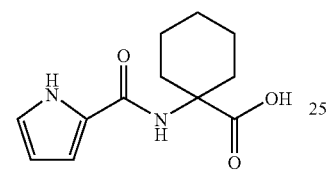

500 mg (2 mmol) of 1-[[(1H-pyrrol-2-yl)carbonyl]amino]cyclohexanecarboxylic acid methyl ester was used instead of 1-[(3-furanylcarbonyl)amino]cyclohexanecarboxylic acid methyl ester in the process according to Reference example 16 to obtain 338 mg (71%) of the title compound.

1H-NMR (DMSO-$d_6$, δ): 1.20-1.31 (1H, m), 1.52 (5H, br-s), 1.70-1.80 (2H, m), 2.04-2.18 (2H, m), 6.08 (1H, dd, J=4 Hz, 2 Hz), 6.85-6.89 (2H, m), 7.59 (1H, s), 11.39 (1H, s), 12.09 (1H, br-s)

Reference Example 58

1-[[(6-Hydroxy-2-pyridinyl)carbonyl]amino]cyclohexanecarboxylic acid methyl ester

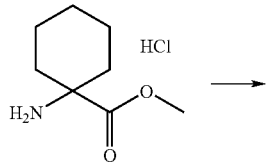

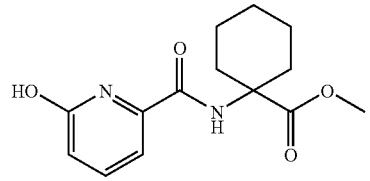

1.39 g (10 mmol) of 6-hydroxy-2-pyridinecarboxylic acid was used instead of 3-furancarboxylic acid in the process according to Reference example 15 to obtain 1.32 g (47%) of the title compound.

1H-NMR (CDCl$_3$, δ): 1.30-1.42 (1H, m), 1.65 (5H, m), 1.96 (2H, td, J=12 Hz, 4 Hz), 2.10-2.21 (2H, m), 3.73 (3H, s), 6.71 (1H, d, J=9 Hz), 7.20 (1H, d, J=7 Hz), 7.62 (1H, dd, J=9 Hz, 7 Hz), 8.00 (1H, s)

Reference Example 59

1-[[(6-Hydroxy-2-pyridinyl)carbonyl]amino]cyclohexanecarboxylic acid

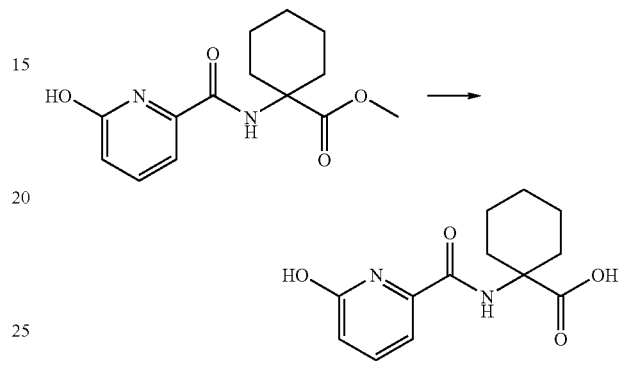

1.32 mg (4.7 mmol) of 1-[[(6-hydroxy-2-pyridinyl)carbonyl]amino]cyclohexanecarboxylic acid methyl ester was used instead of 1-[(3-furanylcarbonyl)amino]cyclohexanecarboxylic acid methyl ester in the process according to Reference example 16 to obtain 1.16 g (88%) of the title compound.

1H-NMR (DMSO-$d_6$, δ): 1.39-1.50 (1H, m), 1.39-1.50 (2H, m), 1.51-1.63 (3H, m), 1.70-1.82 (2H, m), 2.01-2.12 (2H, d, m), 6.78 (1H, d, J=8 Hz), 7.32 (1H, br-s), 7.74 (1H, t, J=8 Hz), 8.18 (1H, s)

Reference Example 60

1-[[(2-Hydroxy-3-pyridinyl)carbonyl]amino]cyclohexanecarboxylic acid methyl ester

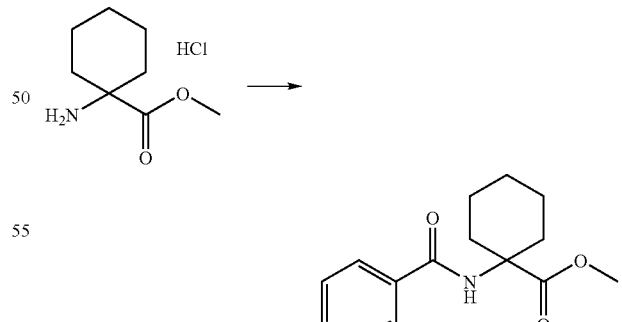

1.39 g (10 mmol) of 2-hydroxynicotinic acid was used instead of 3-furancarboxylic acid in the process according to Reference example 15 to obtain 697 mg (25%) of the title compound.

1H-NMR (CDCl$_3$, δ): 1.24-1.38 (1H, m), 1.50-1.62 (2H, m), 1.64-1.74 (3H, m), 1.82-1.93 (2H, m), 2.15-2.24 (2H, m), 3.74 (3H, s), 6.53 (1H, t, J=7 Hz), 7.49 (1H, d, J=7 Hz), 8.57 (1H, d, J=7 Hz), 10.04 (1H, s)

Reference Example 61

1-[[(2-Hydroxy-3-pyridinyl)carbonyl]amino]cyclohexanecarboxylic acid

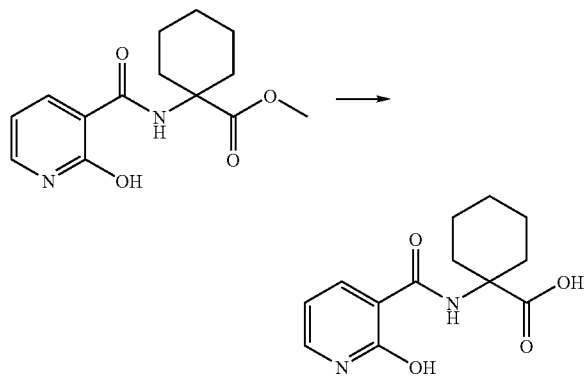

698 mg (2.5 mmol) of 1-[[(2-hydroxy-3-pyridinyl)carbonyl]amino]cyclohexanecarboxylic acid methyl ester was used instead of 1-[(3-furanylcarbonyl)amino]cyclohexanecarboxylic acid methyl ester in the process according to Reference example 16 to obtain 580 mg (83%) of the title compound.

1H-NMR (DMSO-$d_6$, δ): 1.21-1.31 (1H, m), 1.38-1.41 (2H, m), 1.59 (3H, d, J=10 Hz), 1.67-1.72 (2H, m), 1.98-2.04 (2H, m), 6.49 (1H, t, J=7 Hz), 7.73 (1H, br-s), 8.28 (1H, d, J=7 Hz), 10.21 (1H, s), 12.19 (1H, s), 12.53 (1H, br-s)

Reference Example 62

1-[[(6-Hydroxy-3-pyridinyl)carbonyl]amino]cyclohexanecarboxylic acid methyl ester

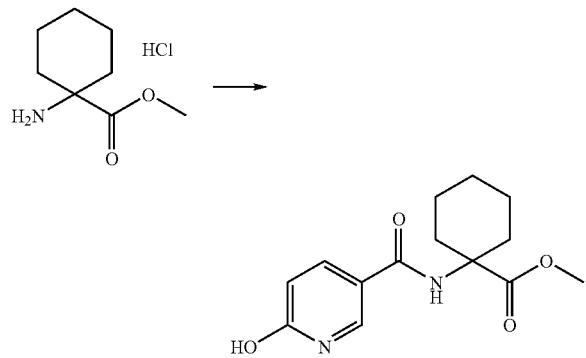

1.39 g (10 mmol) of 6-hydroxynicotinic acid was used instead of 3-furancarboxylic acid in the process according to Reference example 15 to obtain 869 mg (31%) of the title compound.

1H-NMR (CDCl$_3$, δ): 1.30-1.41 (1H, m), 1.43-1.58 (2H, m), 1.61-1.75 (3H, m), 1.89-1.99 (2H, m), 2.11-2.19 (2H, m),
3.74 (3H, s), 6.43 (1H, s), 6.53 (1H, d, J=10 Hz), 7.82 (1H, dd, J=10 Hz, 2 Hz), 8.05 (1H, d, J=2 Hz)

Reference Example 63

1-[[(6-Hydroxy-3-pyridinyl)carbonyl]amino]cyclohexanecarboxylic acid

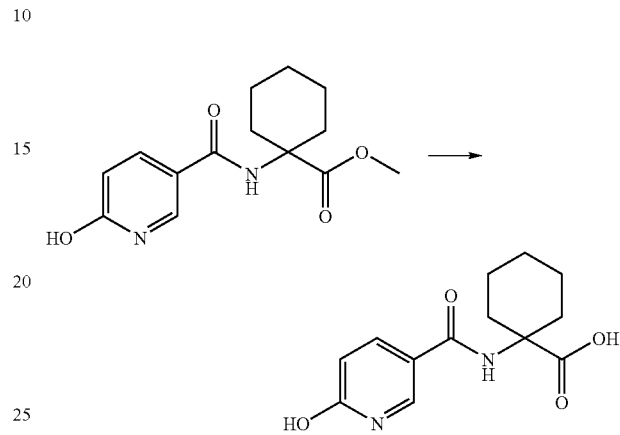

869 mg (3.1 mmol) of 1-[[(6-hydroxy-3-pyridinyl)carbonyl]amino]cyclohexanecarboxylic acid methyl ester was used instead of 1-[(3-furanylcarbonyl)amino]cyclohexanecarboxylic acid methyl ester in the process according to Reference example 16 to obtain 818 mg (94%) of the title compound.

1H-NMR (DMSO-$d_6$, δ): 1.19-1.31 (1H, m), 1.42-1.57 (5H, m), 1.67-1.78 (2H, m), 2.01-2.11 (2H, m), 6.34 (1H, d, J=10 Hz), 7.84 (1H, dd, J=10 Hz, 2 Hz), 7.95 (1H, s), 8.05 (1H, d, J=2 Hz), 11.90-12.18 (2H, m)

Reference Example 64

1-[[1-Oxo-3-(2-furanyl)propyl]amino]cyclohexanecarboxylic acid methyl ester

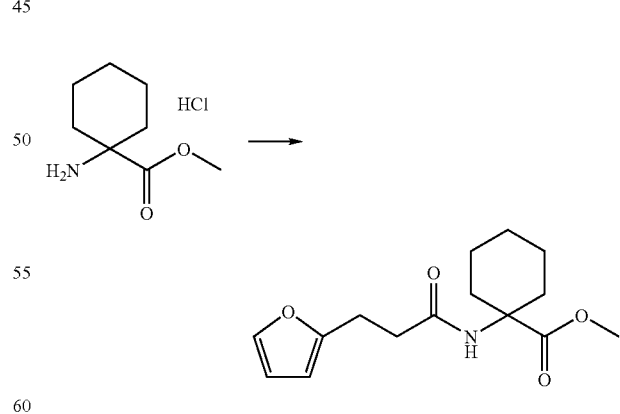

420 mg (3 mmol) of 3-(2-furyl)propionic acid was used instead of 3-furancarboxylic acid in the process according to Reference example 15 to obtain 478 mg (57%) of the title compound.

1H-NMR (CDCl$_3$, δ): 1.25-1.38 (3H, m), 1.57-1.65 (3H, m), 1.78-1.85 (2H, m), 1.96-2.01 (2H, m), 2.56 (2H, t, J=7

Hz), 2.98 (2H, t, J=7 Hz), 3.69 (3H, s), 5.56 (1H, br-s), 6.06 (1H, dd, J=3 Hz, 2 Hz), 6.29 (1H, dd, J=3 Hz, 2 Hz), 7.31 (1H, dd, J=3 Hz, 2 Hz)

Reference Example 65

1-[[[1-(2-Propoxycarbonyl)piperidin-4-yl]carbonyl]amino]cyclohexanecarboxylic acid methyl ester

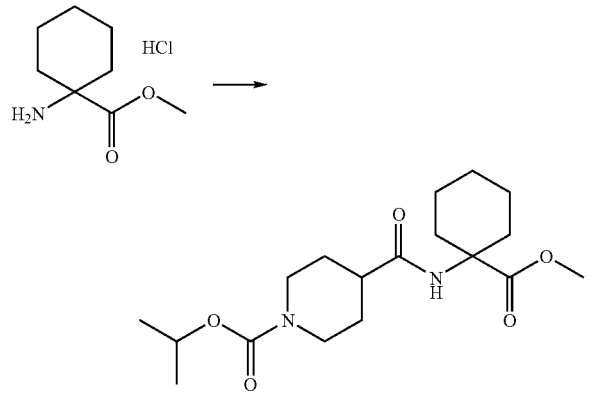

646 mg (3 mmol) of 1-(2-propoxycarbonyl)nipecotic acid was used instead of 3-furancarboxylic acid in the process according to Reference example 15 to obtain 979 mg (92%) of the title compound.

1H-NMR (CDCl$_3$, δ): 1.24 (6H, d, J=6 Hz), 1.25-1.44 (3H, m), 1.56-1.70 (5H, m), 1.79-1.90 (4H, m), 1.98-2.07 (2H, m), 2.26-2.34 (1H, m), 2.75-2.88 (2H, m), 3.69 (3H, s), 4.17 (2H, br-s), 4.86-4.96 (1H, m), 5.58 (1H, s)

Reference Example 66

1-[[[1-(2-Propoxycarbonyl)piperidin-4-yl]carbonyl]amino]cyclohexanecarboxylic acid

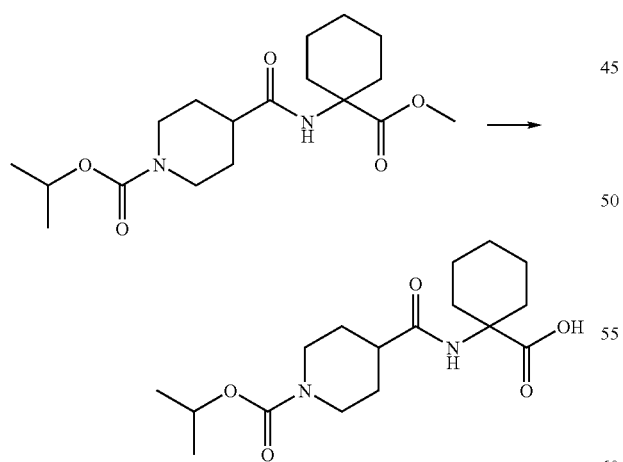

979 mg (2.76 mmol) of 1-[[[1-(2-propoxycarbonyl)piperidin-4-yl]carbonyl]amino]cyclohexanecarboxylic acid methyl ester was used instead of 1-[(3-furanylcarbonyl)amino]cyclohexanecarboxylic acid methyl ester in the process according to Reference example 16 to obtain 940 mg (quantitative) of the title compound.

1H-NMR (CDCl$_3$, δ): 1.23-1.28 (7H, m), 1.34-1.39 (3H, m), 1.62-1.71 (6H, m), 1.85-1.91 (4H, m), 2.05-2.09 (2H, m), 2.33-2.36 (1H, m), 2.74-2.84 (2H, m), 4.21 (1H, br-s), 4.91 (1H, q, J=7 Hz), 5.67 (1H, s)

Reference Example 67

1-[[[1-(Ethoxycarbonyl)piperidin-4-yl]carbonyl]amino]cyclohexanecarboxylic acid methyl ester

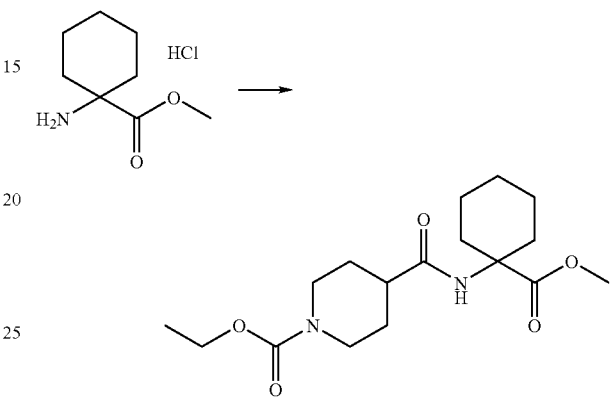

604 mg (3 mmol) of 1-ethoxycarbonylnipecotic acid was used instead of 3-furancarboxylic acid in the process according to Reference example 15 to obtain 976 mg (95%) of the title compound.

1H-NMR (CDCl$_3$, δ): 1.26 (3H, t, J=7 Hz), 1.25-1.42 (3H, m), 1.55-1.70 (3H, m), 1.81-1.86 (4H, m), 2.01-2.05 (3H, m), 2.26-2.32 (1H, m), 2.80-2.89 (2H, m), 3.69 (3H, s), 4.08-4.23 (3H, m), 4.13 (2H, q, J=7 Hz), 5.54 (1H, br-s)

Reference Example 68

1-[[[1-(Ethoxycarbonyl)piperidin-4-yl]carbonyl]amino]cyclohexanecarboxylic acid

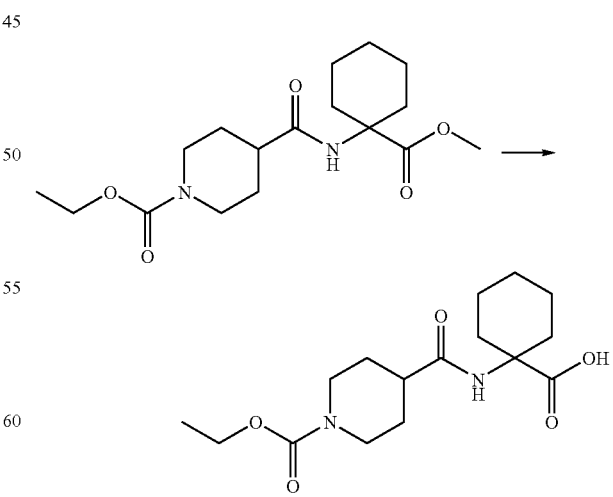

976 mg (2.87 mmol) of 1-[[[1-(ethoxycarbonyl)piperidin-4-yl]carbonyl]amino]cyclohexanecarboxylic acid methyl ester was used instead of 1-[(3-furanylcarbonyl)amino]cyclohexanecarboxylic acid methyl ester in the process according to Reference example 16 to obtain 935 mg (quantitative) of the title compound.

1H-NMR (CDCl₃, δ): 1.25 (3H, t, J=7 Hz), 1.30-1.42 (3H, m), 1.62-1.72 (5H, m), 1.85-1.91 (4H, m), 2.06-2.09 (2H, m), 2.34-2.39 (1H, m), 2.79-2.90 (2H, m), 4.10-4.25 (3H, m), 4.13 (2H, q, J=7 Hz), 5.69 (1H, s)

Reference Example 69

1-[[[1-(2-Furanylcarbonyl)piperidin-4-yl]carbonyl]amino]cyclohexanecarboxylic acid methyl ester

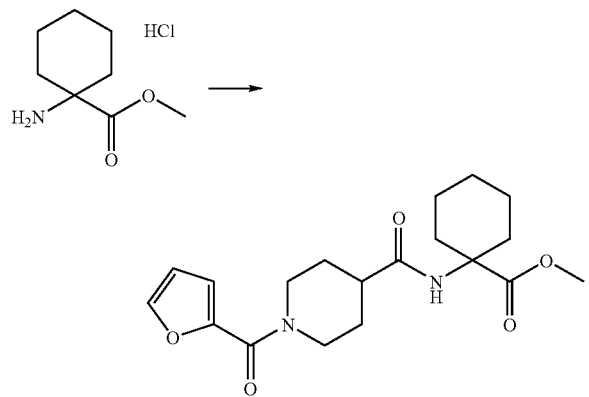

670 mg (3 mmol) of 1-(2-furanylcarbonyl)piperidine-4-carboxylic acid was used instead of 3-furancarboxylic acid in the process according to Reference example 15 to obtain 910 mg (80%) of the title compound.

1H-NMR (CDCl₃, δ): 1.30-1.43 (3H, m), 1.53-1.69 (3H, m), 1.74-1.90 (4H, m), 1.91-2.05 (4H, m), 2.43-2.48 (1H, m), 2.89-3.21 (2H, m), 3.79 (3H, s), 4.40-4.56 (2H, m), 5.58 (1H, br-s), 6.47 (1H, dd, J=3 Hz, 1 Hz), 6.95 (1H, dd, J=3 Hz, 1 Hz), 7.48 (1H, dd, J=3 Hz, 1 Hz)

Reference Example 70

1-[[[1-(2-Furanylcarbonyl)piperidin-4-yl]carbonyl]amino]cyclohexanecarboxylic acid

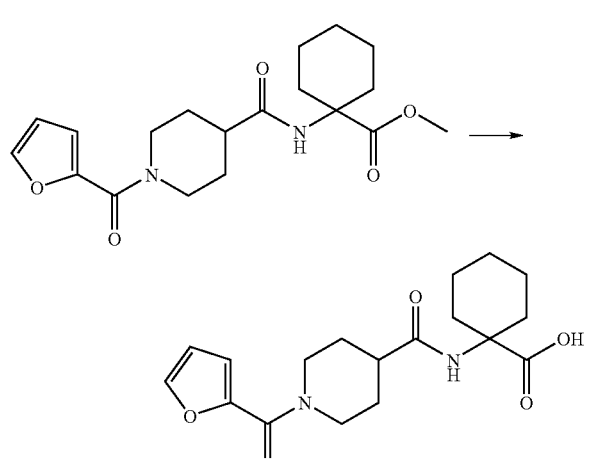

910 mg (2.4 mmol) of 1-[[[1-(2-furanylcarbonyl)piperidin-4-yl]carbonyl]amino]cyclohexanecarboxylic acid methyl ester was used instead of 1-[(3-furanylcarbonyl)amino]cyclohexanecarboxylic acid methyl ester in the process according to Reference example 16 to obtain 196 mg (23%) of the title compound.

1H-NMR (DMSO-d₆, δ): 1.17-1.25 (1H, m), 1.40-1.58 (7H, m), 1.58-1.62 (2H, m), 1.73-1.76 (2H, m), 1.93-1.96 (2H, m), 2.51-2.61 (1H, m), 2.80-3.11 (2H, m), 4.22-4.33 (2H, m), 6.61 (1H, dd, J=3 Hz, 1 Hz), 6.95 (1H, dd, J=3 Hz, 1 Hz), 7.78 (1H, s), 7.82 (1H, dd, J=3 Hz, 1 Hz)

Reference Example 71

1-[[[(2-Furanylcarbonyl)amino]acetyl]amino]cyclohexanecarboxylic acid methyl ester

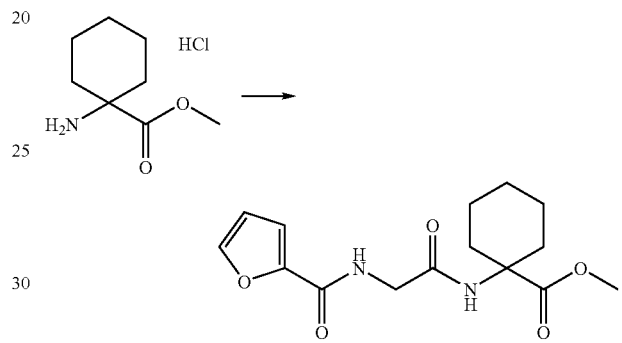

507 mg (3 mmol) of N-(2-furanylcarbonyl)glycine was used instead of 3-furancarboxylic acid in the process according to Reference example 15 to obtain 781 mg (88%) of the title compound.

1H-NMR (CDCl₃, δ): 1.22-1.38 (1H, m), 1.39-1.50 (2H, m), 1.58-1.69 (3H, m), 1.85 (2H, td, J=9 Hz, 4 Hz), 2.02-2.10 (2H, m), 3.70 (3H, s), 4.15 (2H, d, J=6 Hz), 6.51 (1H, dd, J=2 Hz, 1 Hz), 6.67 (1H, s), 7.13 (2H, m), 7.47 (1H, dd, J=2 Hz, 1 Hz)

Reference Example 72

1-[[[(2-Furanylcarbonyl)amino]acetyl]amino]cyclohexanecarboxylic acid

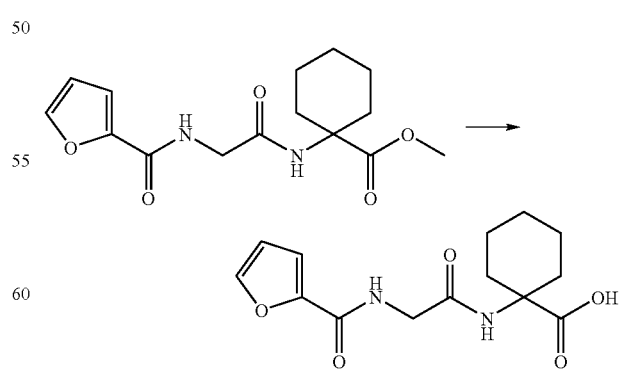

781 mg (2.7 mmol) of 1-[[[(2-furanylcarbonyl)amino]acetyl]amino]cyclohexanecarboxylic acid methyl ester was used instead of 1-[(3-furanylcarbonyl)amino]cyclohexanecarboxylic acid methyl ester in the process according to Reference example 16 to obtain 320 mg (41%) of the title compound.

1H-NMR (DMSO-d$_6$, δ): 1.12-1.25 (1H, m), 1.39-1.58 (5H, m), 1.64 (2H, td, J=13 Hz, 4 Hz), 1.90-2.02 (2H, m), 3.88 (2H, d, J=6 Hz), 6.62 (1H, dd, J=3 Hz, 1 Hz), 7.13 (1H, dd, J=3 Hz, 1 Hz), 7.84 (1H, d, J=1 Hz), 7.87 (1H, s), 8.38 (1H, d, J=6 Hz)

Reference Example 73

1-[[(Benzoylamino)acetyl]amino]cyclohexanecarboxylic acid methyl ester

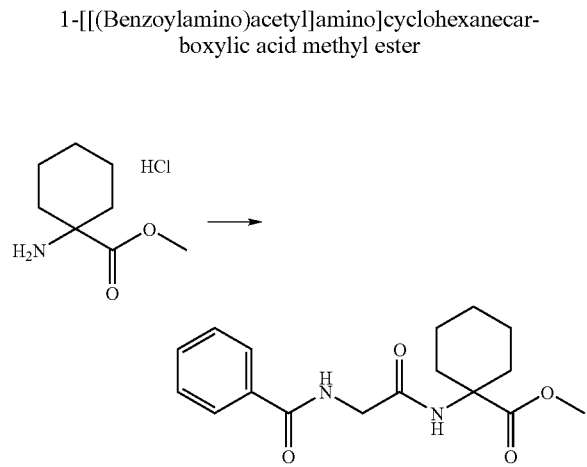

538 mg (3 mmol) of N-benzoylglycine was used instead of 3-furancarboxylic acid in the process according to Reference example 15 to obtain 812 mg (81%) of the title compound.

1H-NMR (CDCl$_3$, δ): 1.23-1.38 (1H, m), 1.48 (2H, td, J=9 Hz, 4 Hz) 1.58-1.71 (3H, m), 1.84 (2H, dt, J=9 Hz, 4 Hz), 2.02-2.10 (2H, m), 3.70 (3H, s), 4.21 (2H, d, J=7 Hz), 7.08 (1H, br-s), 7.26-7.46 (3H, m), 7.54 (1H, td, J=8 Hz, 1 Hz), 7.84 (2H, dd, J=8 Hz, 1 Hz)

Reference Example 74

1-[[(Benzoylamino)acetyl]amino]cyclohexanecarboxylic acid

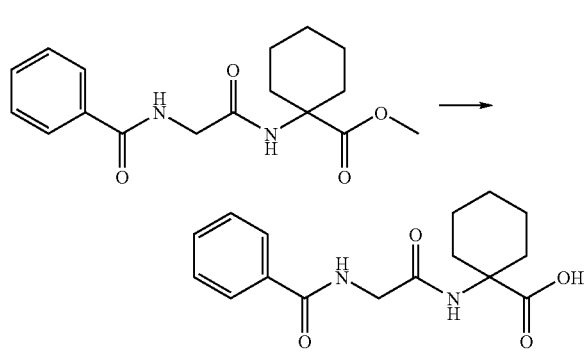

812 mg (2.4 mmol) of 1-[[(benzoylamino)acetyl]amino]cyclohexanecarboxylic acid methyl ester was used instead of 1-[(3-furanylcarbonyl)amino]cyclohexanecarboxylic acid methyl ester in the process according to Reference example 16 to obtain 724 mg (93%) of the title compound.

1H-NMR (DMSO-d$_6$, δ): 1.09-1.67 (8H, m), 1.96 (2H, d, J=11 Hz), 3.93 (2H, d, J=6 Hz), 7.47 (2H, td, J=6 Hz, 1 Hz), 7.52-7.55 (1H, m), 7.86-7.89 (3H, m), 8.64 (1H, t, J=6 Hz)

Reference Example 75

1-[[(2-Furanylmethoxy)carbonyl]amino]cyclohexanecarboxylic acid methyl ester

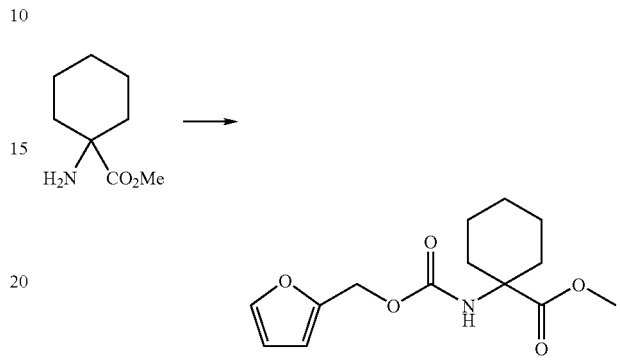

3.67 g (30 mmol) of dimethylaminopyridine was added to a solution of 65.48 g (0.3 mol) of di-t-butyl dicarbonate in 300 ml of anhydrous toluene, and the mixture was stirred at room temperature for 15 minutes. A solution of 47.17 g (0.3 mol) of 1-aminocyclohexanecarboxylic acid methyl ester in 100 ml of anhydrous toluene was added to the reaction solution, and the mixture was stirred at room temperature for 1 hour. After 60.71 g (0.6 mol) of triethylamine and 44.1 g (0.45 mol) of furfuryl alcohol were further added thereto, the mixture was heated under reflux for 3 hours. The reaction solution was returned to room temperature and concentrated under reduced pressure. The obtained residue was triturated in a mortal and stirred in a mixed solution of 5 ml of hydrochloric acid and 3 liters of water for 18 hours. The obtained crystal was collected by filtration to give 74.37 g (88%) of the title compound.

1H-NMR (CDCl$_3$, δ): 1.23-1.36 (1H, m), 1.38-1.51 (2H, m), 1.55-1.65 (3H, m), 1.80-1.88 (2H, m), 1.93-2.04 (2H, m), 3.71 (3H, br-s), 4.93 (1H, br-s), 5.04 (2H, s), 6.36 (1H, dd, J=3 Hz, 2 Hz), 6.41 (1H, d, J=3 Hz), 7.43 (1H, d, J=2 Hz)

Reference Example 76

1-[[(2-Furanylmethoxy)carbonyl]amino]cyclohexanecarboxylic acid

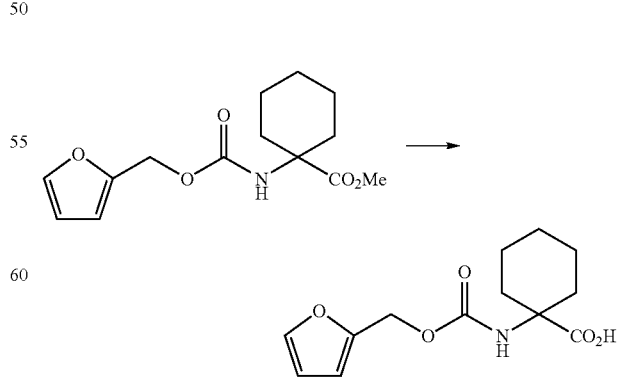

28.13 g (0.1 mol) of 1-[[(2-furanylmethoxy)carbonyl]amino]cyclohexanecarboxylic acid methyl ester was added to a mixture solution of 150 ml of 2N-sodium hydroxide aqueous solution and 200 ml of tetrahydrofuran, and the mixture was refluxed under heating for 18 hours. After the solvent was distilled off, water was added to the residue and the mixture was washed with diethyl ether. After potassium hydrogensulfate was added to the aqueous layer to acidify it, the layer was extracted with ethyl acetate twice. After the organic layer was washed with saturated brine and dried with anhydrous magnesium sulfate, the solvent was distilled off under reduced pressure. Diisopropyl ether was added to the residue, and the mixture was stirred for 18 hours. The obtained crystal was collected by filtration to give 19.89 g (74%) of the title compound.

1H-NMR (CDCl$_3$, δ): 1.24-1.37 (1H, m), 1.38-1.52 (2H, m), 1.59-1.71 (3H, m), 1.82-1.93 (2H, m), 1.99-2.12 (2H, m), 4.99 (1H, br-s), 5.07 (2H, s), 6.37 (1H, dd, J=3 Hz, 2 Hz), 6.42 (1H, d, J=3 Hz), 7.43 (1H, d, J=2 Hz)

Reference Example 77

1-[[(4-Phenyl-1-piperazinyl)carbonyl]amino]cyclohexanecarboxylic acid phenylmethyl ester

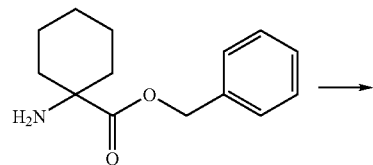

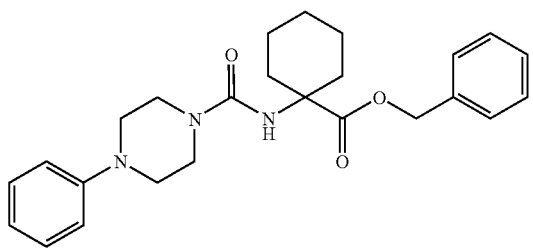

A solution of 366 mg (3 mmol) of N,N-dimethylaminopyridine and 6.99 g (30 mmol) of 1-aminocyclohexanecarboxylic acid phenylmethyl ester in methylene chloride was added to a solution of 6.55 g (30 mmol) of di-t-butyl dicarbonate in 150 ml of methylene chloride, and the mixture was stirred at room temperature for 30 minutes. Thereafter, a solution of 6.07 mg (60 mmol) of triethylamine and 5.11 g (33 mmol) of 1-phenylpiperazine in methylene chloride was added thereto, and the mixture was stirred at room temperature overnight. The reaction solution was concentrated, ethyl acetate was added thereto, and the mixture was successively washed with water, a saturated aqueous sodium hydrogencarbonate solution and saturated brine, followed by drying with anhydrous sodium sulfate. After the solvent was distilled off under reduced pressure, the obtained crystal was washed with diethyl ether to give 8.88 g (70%) of the title compound.

1H-NMR (CDCl$_3$, δ): 1.25-1.37 (1H, m), 1.42-1.51 (2H, m), 1.50-1.69 (3H, m), 1.82-1.91 (2H, m), 2.03-2.10 (2H, m), 3.17 (4H, t, J=5 Hz), 3.54 (4H, t, J=5 Hz), 4.60 (1H, br-s), 5.15 (2H, s), 6.89-6.94 (3H, m), 7.26-7.35 (7H, m)

Reference Example 78

1-[[(4-Phenyl-1-piperazinyl)carbonyl]amino]cyclohexanecarboxylic acid

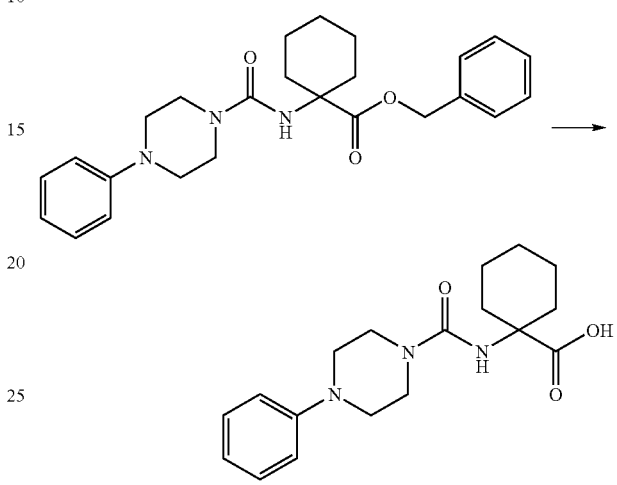

8.88 g (21 mmol) of 1-[[(4-phenyl-1-piperazinyl)carbonyl]amino]cyclohexanecarboxylic acid phenylmethyl ester obtained in Reference example 77 was dissolved in 200 ml of methanol, 900 mg of 10% palladium-carbon was added thereto, and the mixture was stirred under a hydrogen atmosphere at room temperature overnight. After the reaction solution was filtered, the filtrate was concentrated under reduced pressure to obtain 6.96 g (quantitative) of the title compound.

1H-NMR (CDCl$_3$, δ): 1.22-1.30 (1H, m), 1.36-1.42 (2H, m), 1.50-2.05 (5H, m), 2.06-2.14 (2H, m), 3.24 (4H, t, J=5 Hz), 4.61 (4H, t, J=5 Hz), 4.51 (1H, br-s), 6.92-6.95 (2H, m), 7.28-7.32 (3H, m)

Reference Example 79

1-[[[4-(2-Pyridinyl)-1-piperazinyl]carbonyl]amino]cyclohexanecarboxylic acid phenylmethyl ester

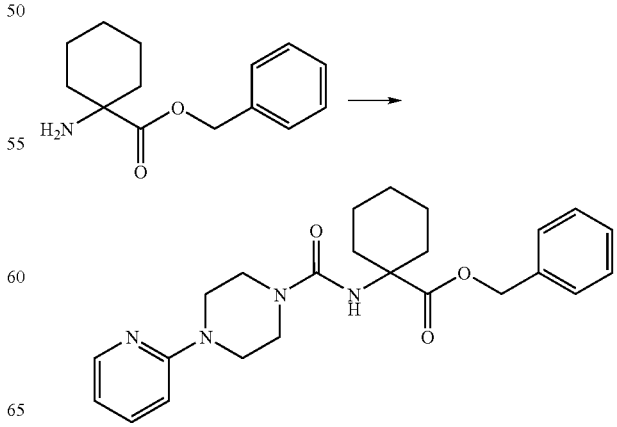

3.43 g (21 mmol) of 1-(2-pyridinyl)piperazine was used instead of 1-phenylpiperazine in the process according to Reference example 77 to obtain 7.33 g (87%) of the title compound.

1H-NMR (CDCl₃, δ): 1.26-1.35 (1H, m), 1.42-1.53 (2H, m), 1.60-1.68 (3H, m), 1.83-1.92 (2H, m), 2.02-2.10 (2H, m), 3.52 (4H, t, J=5 Hz), 3.57 (4H, t, J=5 Hz), 4.58 (1H, br-s), 5.15 (2H, s), 6.63 (1H, d, J=8 Hz), 6.67 (1H, td, J=8 Hz, 1 Hz), 7.25-7.34 (5H, m), 7.51 (1H, td, J=8 Hz, 1 Hz), 8.20 (1H, dd, J=8 Hz, 1 Hz)

Reference Example 80

1-[[[4-(2-Pyridinyl)-1-piperazinyl]carbonyl]amino]cyclohexanecarboxylic acid

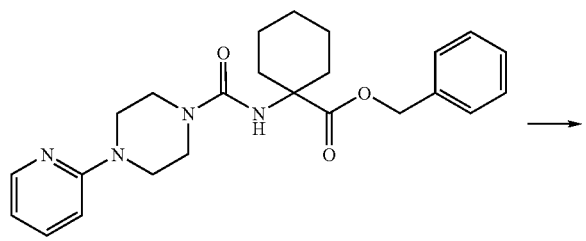

7.33 g (17.4 mmol) of 1-[[[4-(2-pyridinyl)-1-piperazinyl]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 5.75 g (quantitative) of the title compound.

1H-NMR (CDCl₃, δ): 1.30-1.43 (2H, m), 1.60-1.72 (4H, m), 1.89-1.99 (2H, m), 2.06-2.13 (2H, m), 3.61 (4H, t, J=5 Hz), 3.66 (4H, t, J=5 Hz), 4.61 (1H, br-s), 6.65 (1H, dd, J=8 Hz, 1 Hz), 6.69 (1H, td, J=8 Hz, 1 Hz), 7.52 (1H, td, J=8 Hz, 1 Hz), 8.20 (1H, dd, J=8 Hz, 1 Hz)

Reference Example 81

1-[[[4-(4-Fluorophenyl)-1-piperazinyl]carbonyl]amino]cyclohexanecarboxylic acid phenylmethyl ester

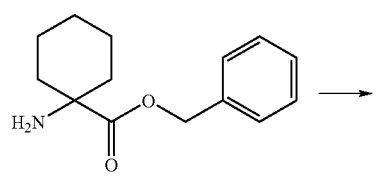

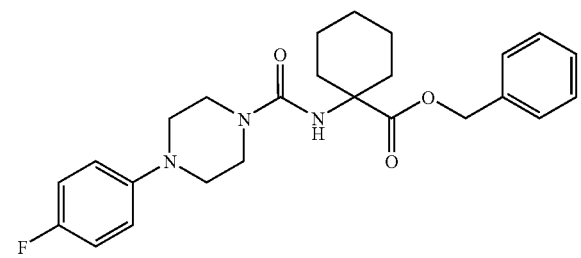

3.78 g (21 mmol) of 1-(4-fluorophenyl)piperazine was used instead of 1-phenylpiperazine in the process according to Reference example 77 to obtain 4.48 g (51%) of the title compound.

1H-NMR (CDCl₃, δ): 1.22-1.35 (1H, m), 1.40-1.51 (2H, m), 1.55-1.70 (3H, m), 1.85-1.93 (2H, m), 2.02-2.09 (2H, m), 3.07 (4H, t, J=5 Hz), 3.53 (4H, t, J=5 Hz), 4.60 (1H, br-s), 5.15 (2H, s), 6.87 (2H, ddd, J=9 Hz, 6 Hz, 2 Hz), 6.98 (2H, ddd, J=9 Hz, 6 Hz, 2 Hz), 7.25-7.35 (5H, m)

Reference Example 82

1-[[[4-(4-Fluorophenyl)-1-piperazinyl]carbonyl]amino]cyclohexanecarboxylic acid

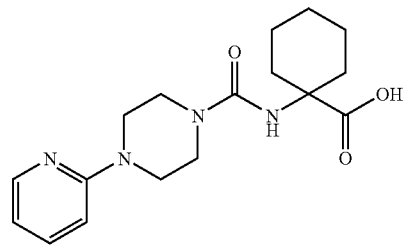

4.48 g (10 mmol) of 1-[[[4-(4-fluorophenyl)-1-piperazinyl]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 3.56 g (quantitative) of the title compound.

1H-NMR (CDCl₃, δ): 1.31-1.43 (3H, m), 1.60-1.75 (3H, m), 1.89-2.01 (2H, m), 2.05-2.13 (2H, m), 3.14 (4H, t, J=5 Hz), 3.61 (4H, t, J=5 Hz), 4.55 (1H, br-s), 6.89 (2H, ddd, J=8 Hz, 5 Hz, 2 Hz), 6.99 (2H, ddd, J=8 Hz, 5 Hz, 2 Hz)

Reference Example 83

1-[[[4-[3-(Trifluoromethyl)phenyl]-1-piperazinyl]carbonyl]amino]cyclohexanecarboxylic acid phenylmethyl ester

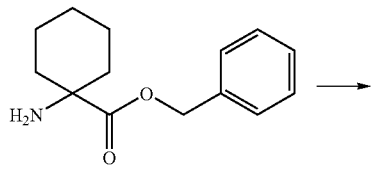

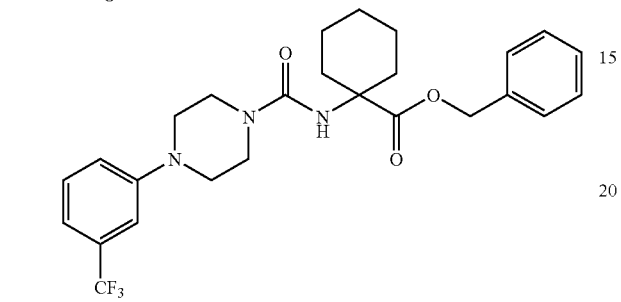

4.83 g (21 mmol) of 1-[3-(trifluoromethyl)phenyl]piperazine was used instead of 1-phenylpiperazine in the process according to Reference example 77 to obtain 7.54 g (77%) of the title compound.

1H-NMR (CDCl$_3$, δ): 1.23-1.37 (1H, m), 1.42-1.53 (2H, m), 1.59-1.70 (3H, m), 1.85-1.94 (2H, m), 2.02-2.10 (2H, m), 3.21 (4H, t, J=5 Hz), 3.55 (4H, t, J=5 Hz), 4.60 (1H, br-s), 5.15 (2H, s), 7.05 (1H, dd, J=8 Hz, 2 Hz), 7.09 (1H, s), 7.12 (1H, dd, J=8 Hz, 2 Hz), 7.25-7.40 (6H, m)

Reference Example 84

1-[[[4-[3-(Trifluoromethyl)phenyl]-1-piperazinyl]carbonyl]amino]cyclohexanecarboxylic acid

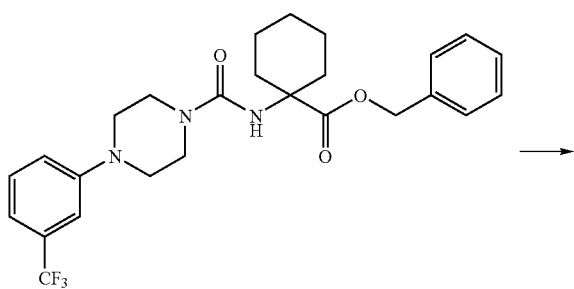

7.54 g (15.4 mmol) of 1-[[[4-[3-(trifluoromethyl)phenyl]-1-piperazinyl]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 5.92 g (96%) of the title compound.

1H-NMR (CDCl$_3$, δ): 1.36-1.44 (2H, m), 1.60-1.75 (4H, m), 1.91-2.00 (2H, m), 2.05-2.14 (2H, m), 3.30 (4H, t, J=5 Hz), 3.63 (4H, t, J=5 Hz), 4.63 (1H, br-s), 7.07 (1H, d, J=8 Hz), 7.11 (1H, s), 7.15 (1H, d, J=8 Hz), 7.38 (1H, t, J=8 Hz)

Reference Example 85

1-[[(4-Cyclohexyl-1-piperazinyl)carbonyl]amino]cyclohexanecarboxylic acid phenylmethyl ester

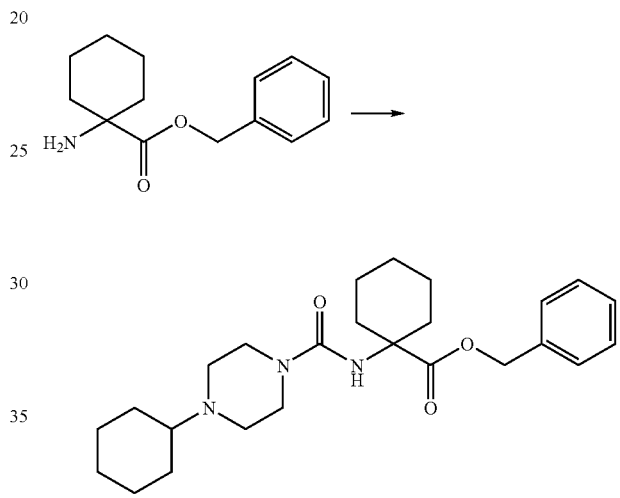

2.66 g (15.8 mmol) of 1-(cyclohexyl)piperazine was used instead of 1-phenylpiperazine in the process according to Reference example 77 to obtain 3.21 g (50%) of the title compound.

1H-NMR (CDCl$_3$, δ): 1.22-1.45 (3H, m), 1.39-1.50 (3H, m), 1.51-1.67 (6H, m), 1.89-1.90 (6H, m), 2.01-2.07 (2H, m), 2.22-2.30 (1H, m), 2.54 (4H, t, J=5 Hz), 3.38 (4H, t, J=5 Hz), 4.53 (1H, br-s), 5.14 (2H, s), 7.25-7.34 (5H, m)

Reference Example 86

1-[[(4-Cyclohexyl-1-piperazinyl)carbonyl]amino]cyclohexanecarboxylic acid

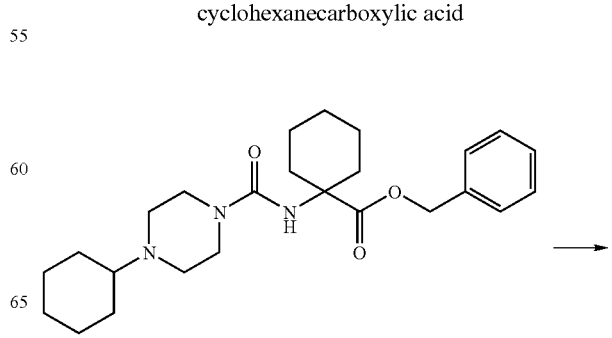

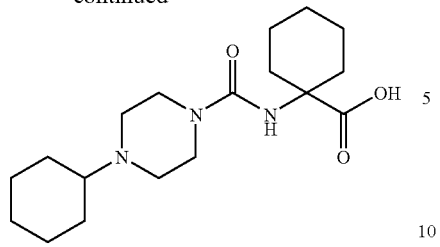

3.21 g (7.5 mmol) of 1-[[(4-cyclohexyl-1-piperazinyl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 2.53 g (quantitative) of the title compound.

1H-NMR (CDCl$_3$, δ): 1.05-1.19 (1H, m), 1.10-1.19 (2H, m), 1.20-1.32 (2H, m), 1.58-1.97 (13H, m), 2.03-2.12 (2H, m), 2.35-2.44 (1H, m), 2.67 (4H, t, J=5 Hz), 3.48 (4H, t, J=5 Hz), 4.59 (1H, br-s)

Reference Example 87

1-[[(4-Benzoyl-1-piperazinyl)carbonyl]amino]cyclohexanecarboxylic acid phenylmethyl ester

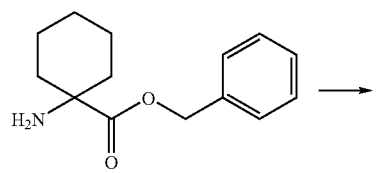

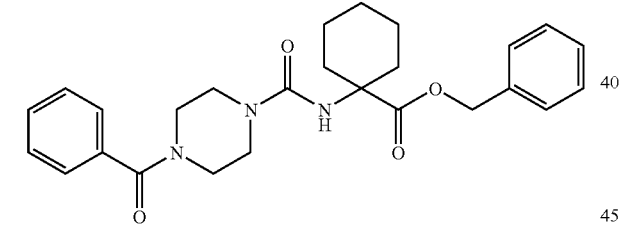

A solution of 114 mg (0.9 mmol) of N,N-dimethylaminopyridine and 2.17 g (9.3 mmol) of 1-aminocyclohexanecarboxylic acid phenylmethyl ester in methylene chloride was added to a solution of 2.03 g (9.3 mmol) of di-t-butyl dicarbonate in 60 ml of methylene chloride, and the mixture was stirred at room temperature for 30 minutes. Thereafter, a solution of 1.88 g (18.6 mmol) of triethylamine and 1.86 g (9.8 mmol) of 1-(benzoyl)piperazine in methylene chloride was added thereto, and the mixture was stirred at room temperature overnight. After the reaction solution was concentrated, the residue was dissolved in ethyl acetate and successively washed with water, a 10% aqueous potassium hydrogensulfate solution, a saturated aqueous sodium hydrogencarbonate solution and saturated brine, followed by drying with anhydrous sodium sulfate. After the solvent was distilled off under reduced pressure, the obtained crystal was washed with diethyl ether to give 3.60 g (86%) of the title compound.

1H-NMR (CDCl$_3$, δ): 1.26-1.38 (1H, m), 1.39-1.50 (2H, m), 1.53-1.68 (3H, m), 1.85-1.93 (2H, m), 2.02-2.08 (2H, m), 3.28-3.57 (6H, m), 3.66-3.85 (2H, m), 4.57 (1H, br-s), 5.15 (2H, s), 7.31-7.39 (4H, m), 7.40-7.48 (6H, m)

Reference Example 88

1-[[(4-Benzoyl-1-piperazinyl)carbonyl]amino]cyclohexanecarboxylic acid

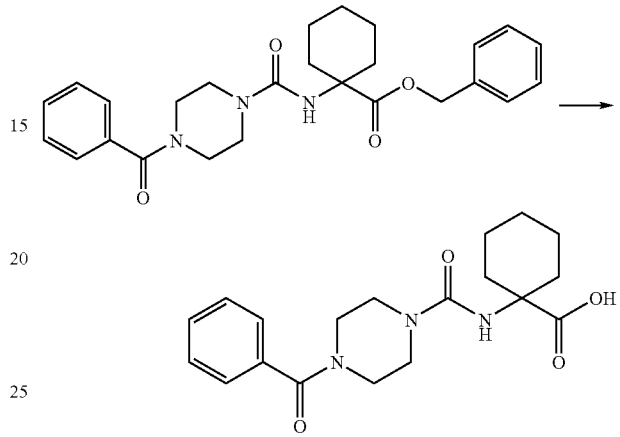

3.60 g (8 mmol) of 1-[[(4-benzoyl-1-piperazinyl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 2.88 g (quantitative) of the title compound.

1H-NMR (CDCl$_3$, δ): 1.34-1.42 (2H, m), 1.59-1.74 (2H, m), 1.85-2.10 (6H, m), 3.42-3.58 (6H, m), 3.70-3.87 (2H, m), 4.60 (1H, br-s), 7.39-7.47 (5H, m)

Reference Example 89

1-[[[4-(Phenylmethyl)-1-piperazinyl]carbonyl]amino]cyclohexanecarboxylic acid ethyl ester

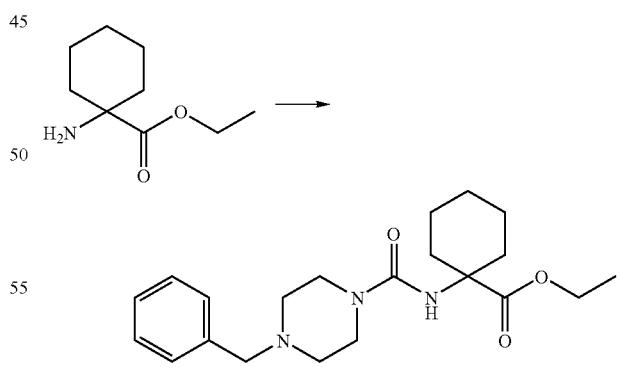

5.82 g (33 mmol) of 4-(phenylmethyl)piperazine was used instead of 1-phenylpiperazine and 5.14 g (30 mmol) of 1-aminocyclohexanecarboxylic acid ethyl ester was used instead of 1-aminocyclohexanecarboxylic acid phenylmethyl ester in the process according to Reference example 77 to obtain 7.62 g (68%) of the title compound.

1H-NMR (CDCl$_3$, δ): 1.24 (3H, t, J=7 Hz), 1.24-1.39 (1H, m) 1.40-1.49 (2H, m), 1.55-1.64 (3H, m), 1.80-1.89 (2H, m), 1.97-2.04 (2H, m), 2.44 (4H, t, J=5 Hz), 3.39 (4H, t, J=5 Hz), 3.52 (2H, s), 4.17 (2H, q, J=7 Hz), 4.50 (1H, br-s), 7.23-7.30 (1H, m), 7.30-7.37 (4H, m)

Reference Example 90

1-[[[4-(Phenylmethyl)-1-piperazinyl]carbonyl]amino]cyclohexanecarboxylic acid

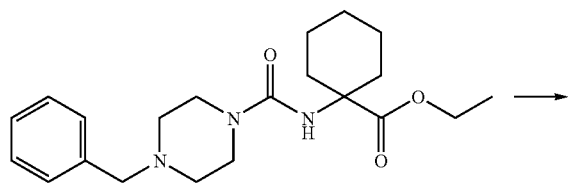

600 ml of 1N aqueous sodium hydroxide solution was added to a solution of 7.62 g (20 mmol) of 1-[[(4-phenylmethyl-1-piperazinyl)carbonyl]amino]cyclohexanecarboxylic acid ethyl ester in 300 ml of ethanol, and the mixture was heated under reflux for 2 hours. After ether was added to the reaction solution and the mixture was washed, the aqueous layer was neutralized by concentrated hydrochloric acid and extracted with ethyl acetate. After the obtained organic layer was washed with saturated brine, the layer was dried with anhydrous sodium sulfate. The solvent was distilled off under reduced pressure to obtain 2.90 g (42%) of the title compound.

1H-NMR (CDCl$_3$, δ): 1.28-1.38 (2H, m), 1.60-1.71 (4H, m), 1.88-1.98 (2H, m), 2.01-2.10 (2H, m), 2.49 (4H, t, J=5 Hz), 3.45 (4H, t, J=5 Hz), 3.55 (2H, s), 4.43 (1H, br-s), 7.24-7.34 (5H, m)

Reference Example 91

1-[[4-(1-Oxo-3-phenylpropyl)-1-piperazinyl]carbonyl]amino]cyclohexanecarboxylic acid phenylmethyl ester

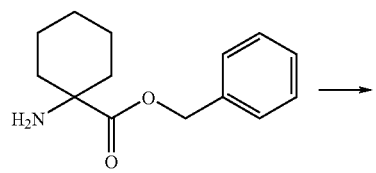

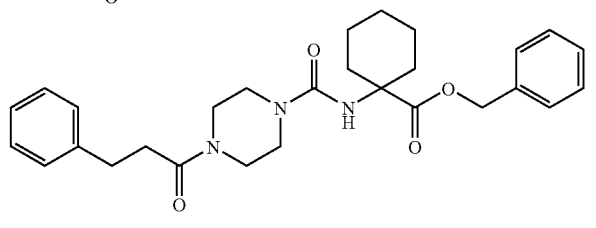

2.40 g (11 mmol) of 1-(1-oxo-3-phenylpropyl)piperazine was used instead of 1-(benzoyl)piperazine in the process according to Reference example 87 to obtain 3.53 g (74%) of the title compound.

1H-NMR (CDCl$_3$, δ): 1.22-1.39 (1H, m), 1.40-1.49 (2H, m), 1.58-1.67 (3H, m), 1.84-1.93 (2H, m), 2.00-2.07 (2H, m), 2.62 (2H, t, J=6 Hz), 2.98 (2H, t, J=6 Hz), 3.25-3.33 (6H, m), 3.59-3.65 (2H, m), 4.52 (1H, br-s), 5.14 (2H, br-s), 7.18-7.23 (4H, m), 7.28-7.34 (6H, m)

Reference Example 92

1-[[[4-(1-Oxo-3-phenylpropyl)-1-piperazinyl]carbonyl]amino]cyclohexanecarboxylic acid

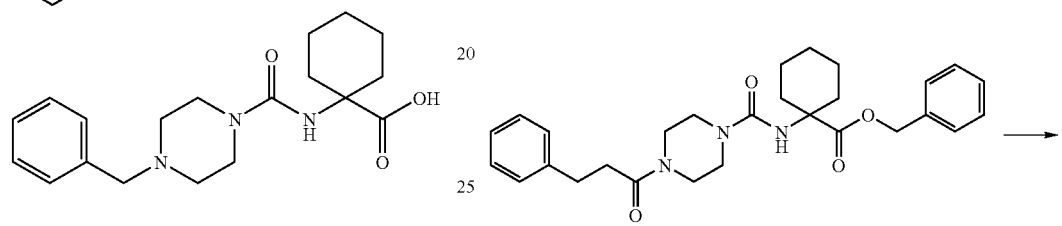

3.53 g (7.4 mmol) of 1-[[[4-(1-oxo-3-phenylpropyl)-1-piperazinyl]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 2.87 g (quantitative) of the title compound.

1H-NMR (CDCl$_3$, δ): 1.28-1.53 (3H, m), 1.57-1.70 (3H, m), 1.84-1.97 (2H, m), 2.00-2.08 (2H, m), 2.63 (2H, t, J=6 Hz), 2.98 (2H, m, J=6 Hz), 3.33-3.41 (6H, m), 3.67-3.71 (2H, m), 4.78 (1H, br-s), 7.18-7.25 (3H, m), 7.27-7.34 (2H, m)

Reference Example 93

1-[[[4-(Phenylacetyl)-1-piperazinyl]carbonyl]amino]cyclohexanecarboxylic acid phenylmethyl ester -continued

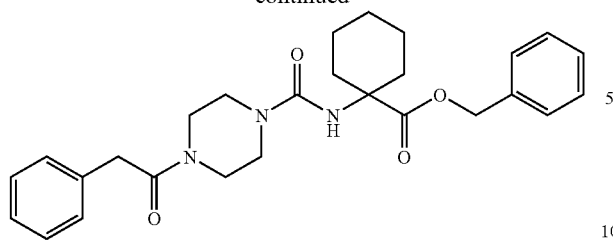

1.23 g (6 mmol) of 1-(phenylacetyl)piperazine was used instead of 1-(1-oxo-3-phenylpropyl)piperazine in the process according to Reference example 87 to obtain 2.39 g (87%) of the title compound.

1H-NMR (CDCl$_3$, δ): 1.22-1.36 (1H, m), 1.37-2.06 (2H, m), 1.55-1.66 (3H, m), 1.83-1.92 (2H, m), 1.98-2.03 (2H, m), 3.20 (2H, t, J=5 Hz), 3.31 (2H, t, J=5 Hz), 3.41 (2H, t, J=5 Hz), 3.63 (2H, t, J=5 Hz), 3.74 (2H, s), 4.49 (1H, br-s), 5.12 (2H, s), 7.24-7.32 (10H, m)

Reference Example 94

1-[[[4-(Phenylacetyl)-1-piperazinyl]carbonyl]amino]cyclohexanecarboxylic acid

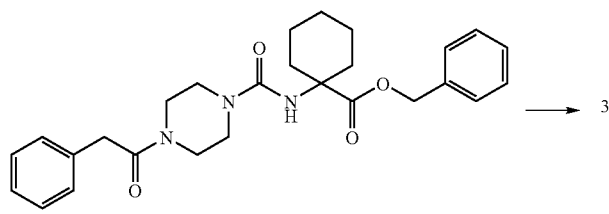

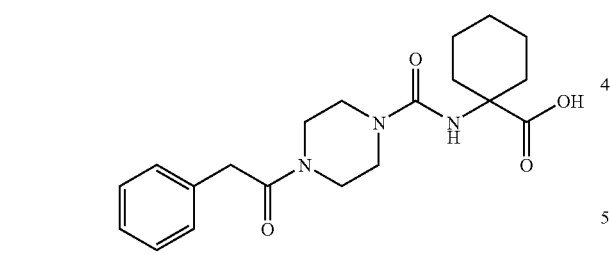

2.39 g (5.2 mmol) of 1-[[[4-(phenylacetyl)-1-piperazinyl]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 1.94 g (quantitative) of the title compound.

1H-NMR (CDCl$_3$, δ): 1.29-1.39 (3H, m), 1.58-1.70 (3H, m), 1.86-1.96 (2H, m), 1.99-2.07 (2H, m), 3.26 (2H, t, J=5 Hz), 3.38 (2H, t, J=5 Hz), 3.50 (2H, t, J=5 Hz), 3.72 (2H, t, J=5 Hz), 3.76 (2H, s), 4.50 (1H, br-s), 7.23-7.30 (3H, m), 7.30-7.35 (2H, m)

Reference Example 95

1-[(1-Piperidinylcarbonyl)amino]cyclohexanecarboxylic acid phenylmethyl ester

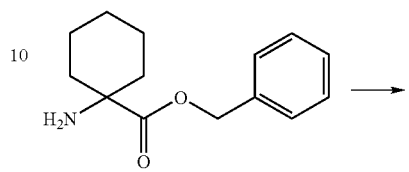

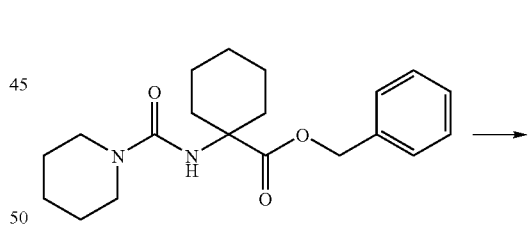

1.34 g (15.8 mmol) of piperidine was used instead of 1-(1-oxo-3-phenylpropyl)piperazine in the process according to Reference example 87 to obtain 4.59 g (89%) of the title compound.

1H-NMR (CDCl$_3$, δ): 1.22-1.34 (1H, m), 1.40-1.65 (11H, m), 1.82-1.90 (2H, m), 2.02-2.08 (2H, m), 3.32 (4H, t, J=5 Hz), 4.53 (1H, br-s), 5.14 (2H, s), 7.29-7.35 (5H, m)

Reference Example 96

1-[(1-Piperidinylcarbonyl)amino]cyclohexanecarboxylic acid 4.59 g (12 mmol) of 1-[(1-piperidinylcarbonyl)amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 3.05 g (quantitative) of the title compound.

1H-NMR (CDCl$_3$, δ): 1.30-1.41 (4H, m), 1.56-1.70 (8H, m), 1.85-1.96 (2H, m), 2.05-2.13 (2H, m), 3.89 (4H, t, J=5 Hz), 4.51 (1H, br-s)

Reference Example 97

1-[(1-Pyrrolidinylcarbonyl)amino]cyclohexanecarboxylic acid phenylmethyl ester

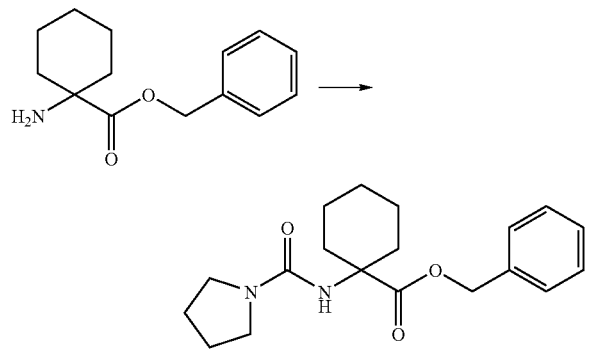

1.12 g (15.8 mmol) of pyrrolidine was used instead of 1-(1-oxo-3-phenylpropyl)piperazine in the process according to Reference example 87 to obtain 3.23 g (65%) of the title compound.

1H-NMR (CDCl$_3$, δ): 1.23-1.33 (1H, m), 1.42-1.51 (2H, m), 1.51-1.68 (3H, m), 1.82-1.95 (2H, m), 1.89 (4H, t, J=7 Hz), 2.02-2.10 (2H, m), 3.35 (4H, t, J=7 Hz), 4.33 (1H, br-s), 5.16 (2H, s), 7.26-7.36 (5H, m)

Reference Example 98

1-[(1-Pyrrolidinylcarbonyl)amino]cyclohexanecarboxylic acid

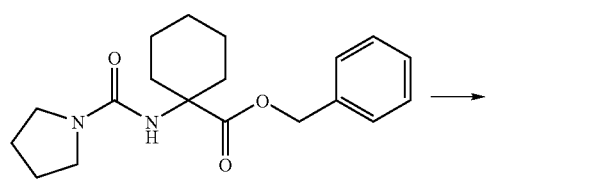

3.23 g (9.8 mmol) of 1-[(1-pyrrolidinylcarbonyl)amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 2.35 g (quantitative) of the title compound.

1H-NMR (CDCl$_3$, δ): 1.29-1.42 (3H, m), 1.58-1.72 (3H, m), 1.88-2.00 (6H, m), 2.05-2.14 (2H, m), 3.40 (4H, t, J=6 Hz), 4.34 (1H, br-s)

Reference Example 99

1-[[(2-Oxo-1-piperidinyl)carbonyl]amino]cyclohexanecarboxylic acid phenylmethyl ester

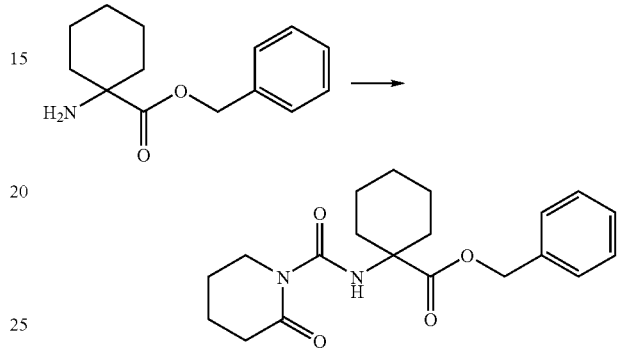

A solution of 183 mg (1.5 mmol) of N,N-dimethylaminopyridine and 3.50 g (15 mmol) of 1-aminocyclohexanecarboxylic acid phenylmethyl ester in toluene was added to a solution of 3.27 g (15 mmol) of di-t-butyl dicarbonate in 60 ml of toluene, and the mixture was stirred at room temperature for 30 minutes. Thereafter, 3.04 g (30 mmol) of triethylamine, 1.83 g (15 mmol) of N,N-dimethylaminopyridine and 1.56 g (15.8 mmol) of 2-piperidone were added thereto, and the mixture was refluxed under heating overnight. Ethyl acetate was added to the reaction solution and the mixture was successively washed with water, a 10% aqueous potassium hydrogensulfate solution, a saturated aqueous sodium hydrogencarbonate solution and saturated brine, followed by drying with anhydrous sodium sulfate. The solvent was distilled off under reduced pressure and the obtained residue was purified by silica gel chromatography to give 4.10 g (76%) of the title compound.

1H-NMR (CDCl$_3$, δ): 1.21-1.30 (1H, m), 1.42-1.53 (2H, m), 1.61-1.69 (3H, m), 1.78-1.90 (6H, m), 2.06-2.15 (2H, m), 2.54 (2H, t, J=6 Hz), 3.73 (2H, t, J=6 Hz), 5.16 (2H, s), 7.27-7.35 (5H, m), 9.85 (1H, br-s)

Reference Example 100

1-[[(2-Oxo-1-piperidinyl)carbonyl]amino]cyclohexanecarboxylic acid

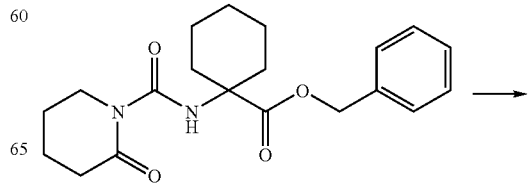

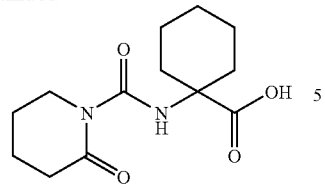

4.10 g (11.4 mmol) of 1-[[1-(2-oxo-1-piperidinyl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 2.95 g (96%) of the title compound.

1H-NMR (CDCl$_3$, δ): 1.24-1.35 (1H, m), 1.45-1.64 (2H, m), 1.50-1.71 (3H, m), 1.82-1.92 (6H, m), 2.12-2.16 (2H, m), 2.58 (2H, t, J=6 Hz), 3.80 (2H, t, J=6 Hz), 9.96 (1H, br-s)

Reference Example 101

1-[(1,4-Dioxa-8-azaspiro[4.5]dec-8-ylcarbonyl)amino]cyclohexanecarboxylic acid phenylmethyl ester

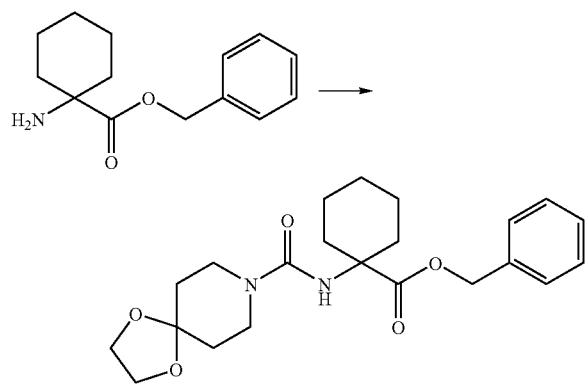

3.00 g (21 mmol) of 1,4-dioxa-8-azaspiro[4.5]decane was used instead of 1-(benzoyl)piperazine in the process according to Reference example 87 to obtain 5.70 g (71%) of the title compound.

1H-NMR (CDCl$_3$, δ): 1.23-1.34 (1H, m), 1.40-1.48 (2H, m), 1.59-1.67 (3H, m), 1.69 (4H, t, J=6 Hz), 1.84-1.93 (2H, m), 2.00-2.08 (2H, m), 3.47 (4H, t, J=6 Hz), 3.98 (4H, s), 4.59 (1H, br-s), 5.14 (2H, s), 7.27-7.36 (5H, m)

Reference Example 102

1-[(1,4-Dioxa-8-azaspiro[4.5]dec-8-ylcarbonyl)amino]cyclohexanecarboxylic acid

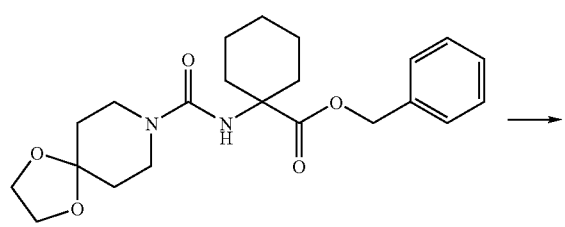

5.70 g (14.2 mmol) of 1-[(1,4-dioxa-8-azaspiro[4,5]dec-8-ylcarbonyl)amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 4.38 g (quantitative) of the title compound.

1H-NMR (CDCl$_3$, δ): 1.30-1.42 (3H, m), 1.60-1.77 (3H, m), 1.75 (4H, t, J=6 Hz), 1.88-2.01 (2H, m), 2.05-2.14 (2H, m), 3.54 (4H, t, J=6 Hz), 3.99 (4H, s), 4.55 (1H, br-s)

Reference Example 103

1-[[[(1,3-Dioxolan-2-ylmethyl)methylamino]carbonyl]amino]cyclohexanecarboxylic acid phenylmethyl ester

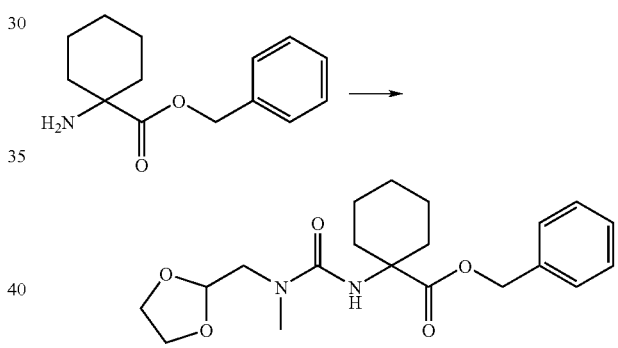

2.46 g (21 mmol) of 2-[(methylamino)methyl]-1,3-dioxolane was used instead of 1-(benzoyl)piperazine in the process according to Reference example 87 to obtain 6.05 g (80%) of the title compound.

1H-NMR (CDCl$_3$, δ): 1.22-1.34 (1H, m), 1.39-1.50 (2H, m), 1.59-1.68 (2H, m), 1.68-1.74 (3H, m), 1.82-1.91 (2H, m), 2.00-2.08 (2H, m), 3.44-3.50 (4H, m), 3.98 (4H, s), 4.59 (1H, br-s), 5.14 (2H, s), 7.27-7.36 (5H, m)

Reference Example 104

1-[[[(1,3-Dioxolan-2-ylmethyl)methylamino]carbonyl]amino]cyclohexanecarboxylic acid

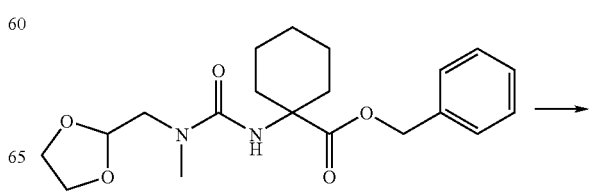

-continued

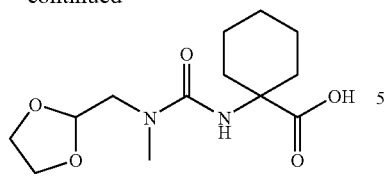

6.05 g (16 mmol) of 1-[[[(1,3-dioxolan-2-ylmethyl)methylamino]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 4.45 g (97%) of the title compound.

1H-NMR (CDCl$_3$, δ): 1.30-1.41 (3H, m), 1.60-1.75 (5H, m), 1.88-1.97 (2H, m), 2.04-2.13 (2H, m), 3.48-3.59 (4H, m), 3.99 (4H, s), 4.53 (1H, br-s)

Reference Example 105

1-[[(1,3-Dihydro-2H-isoindol-2-yl)carbonyl]amino]cyclohexanecarboxylic acid phenylmethyl ester

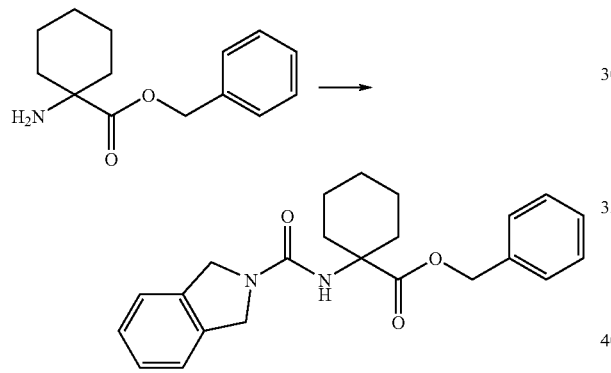

2.50 g (21 mmol) of isoindoline was used instead of 1-(benzoyl)piperazine in the process according to Reference example 87 to obtain 5.95 g (79%) of the title compound.

1H-NMR (CDCl$_3$, δ): 1.23-1.38 (1H, m), 1.45-1.70 (5H, m), 1.89-1.97 (2H, m), 2.07-2.16 (2H, m), 4.48 (1H, br-s), 4.73 (4H, s), 5.17 (2H, s), 7.25-7.31 (7H, m), 7.31-7.36 (2H, m)

Reference Example 106

1-[[(1,3-Dihydro-2H-isoindol-2-yl)carbonyl]amino]cyclohexanecarboxylic acid

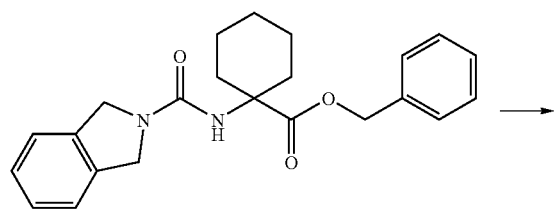

-continued

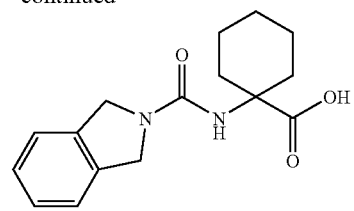

5.95 g (15.8 mmol) of 1-[[(1,3-dihydro-2H-isoindol-2-yl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 3.09 g (68%) of the title compound.

1H-NMR (CDCl$_3$, δ): 1.23-1.30 (1H, m), 1.35-1.48 (2H, m), 1.59-1.76 (3H, m), 1.96-2.05 (2H, m), 2.10-2.17 (2H, m), 4.40 (1H, br-s), 4.78 (4H, br-s), 7.24-7.35 (4H, m)

Reference Example 107

1-[[(2-Oxo-1-imidazolidinyl)carbonyl]amino]cyclohexanecarboxylic acid phenylmethyl ester

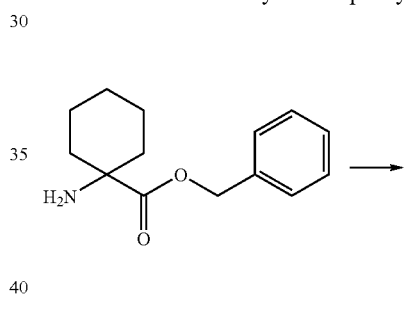

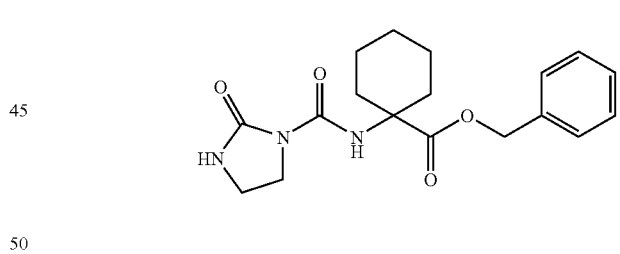

1.38 g (9.3 mmol) of 2-oxo-1-imidazolidinecarbonyl chloride was added to a solution of 2.17 g (9.3 mmol) of 1-aminocyclohexanecarboxylic acid phenylmethyl ester and 1.04 g (10 mmol) of triethylamine in 100 ml of chloroform, and the mixture was stirred at 60° C. for 4 days. The reaction solution was successively washed with water, a 10% aqueous potassium hydrogensulfate solution, a saturated aqueous sodium hydrogencarbonate solution and saturated brine, and the mixture was dried with anhydrous sodium sulfate. The solvent was distilled off under reduced pressure and the obtained crystal was washed with diethyl ether to obtain 2.64 g (82%) of the title compound.

1H-NMR (CDCl$_3$, δ): 1.22-1.31 (1H, m), 1.44-1.54 (2H, m), 1.60-1.68 (3H, m), 1.81-1.88 (2H, m), 2.08-2.16 (2H, m), 3.48 (2H, t, J=7 Hz), 3.93 (2H, t, J=7 Hz), 4.75 (1H, br-s), 5.17 (2H, s), 7.26-7.36 (5H, m), 8.45 (1H, br-s)

Reference Example 108

1-[[(2-Oxo-1-imidazolidinyl)carbonyl]amino]cyclohexanecarboxylic acid

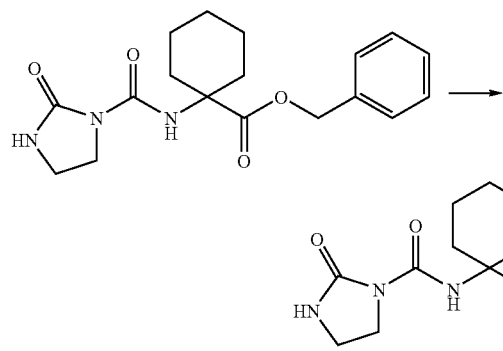

2.64 g (7.6 mmol) of 1-[[(2-oxo-1-imidazolidinyl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 1.95 g (quantitative) of the title compound.

1H-NMR (CDCl$_3$, δ): 1.23-1.38 (1H, m), 1.41-1.70 (5H, m), 1.83-1.92 (2H, m), 2.11-2.20 (2H, m), 3.54 (2H, t, J=8 Hz), 4.01 (2H, t, J=8 Hz), 4.92 (1H, br-s), 8.53 (1H, br-s)

Reference Example 109

1-[[(3-Methyl-2-oxo-1-imidazolidinyl)carbonyl]amino]cyclohexanecarboxylic acid phenylmethyl ester

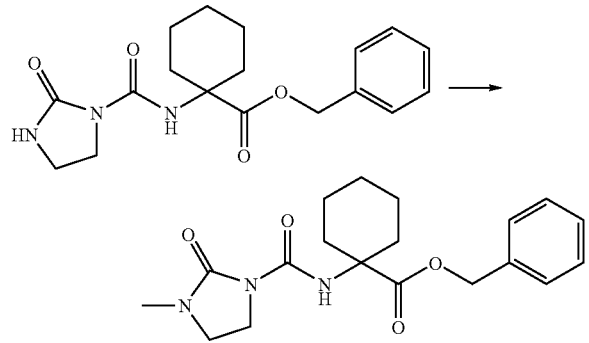

1.83 g (12.9 mmol) of methyl iodide was added to a solution of 1.50 g (4.3 mmol) of 1-[[(2-oxo-1-imidazolidinyl)carbonyl]amino]cyclohexanecarboxylic acid phenylmethyl ester and 1.78 g (12.9 mmol) of potassium carbonate in 100 ml of acetonitrile, and the mixture was refluxed under heating overnight. The reaction solution was concentrated, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. After the solvent was distilled off under reduced pressure, the residue was purified by silica gel chromatography to obtain 710 mg (50%) of the title compound.

1H-NMR (CDCl$_3$, δ): 1.21-1.30 (1H, m), 1.42-1.56 (2H, m), 1.61-1.69 (3H, m), 1.79-1.88 (2H, m), 2.08-2.17 (2H, m), 2.86 (3H, s), 3.40 (2H, t, J=8 Hz), 3.81 (2H, t, J=8 Hz), 5.17 (2H, s), 7.30-7.36 (5H, m), 8.55 (1H, br-s)

Reference Example 110

1-[[(3-Methyl-2-oxo-1-imidazolidinyl)carbonyl]amino]cyclohexanecarboxylic acid

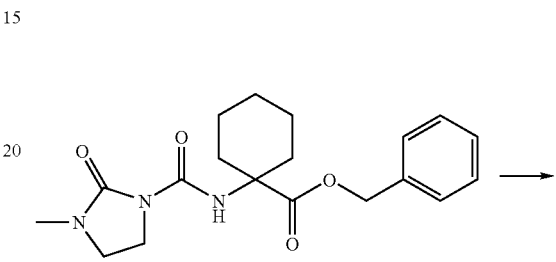

710 mg (2 mmol) of 1-[[(3-methyl-2-oxo-1-imidazolidinyl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference example 78 to obtain 539 mg (quantitative) of the title compound.

1H-NMR (CDCl$_3$, δ): 1.23-1.33 (1H, m), 1.42-1.53 (2H, m), 1.61-1.70 (3H, m), 1.82-1.89 (2H, m), 2.11-2.20 (2H, m), 2.89 (3H, s), 3.46 (2H, dd, J=10 Hz, 8 Hz), 3.91 (2H, dd, J=10 Hz, 8 Hz), 8.66 (1H, br-s)

Reference Example 111

1-[[(2,5-Dihydro-1H-pyrrol-1-yl)carbonyl]amino]cyclohexanecarboxylic acid methyl ester

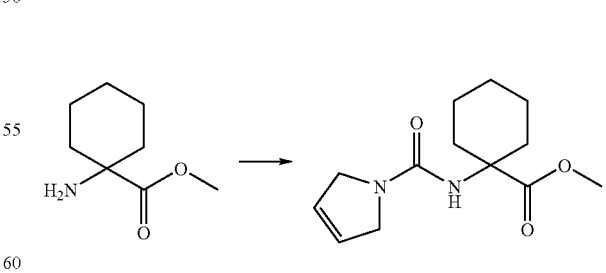

472 mg (3 mmol) of 1-aminocyclohexanecarboxylic acid methyl ester was used instead of 1-aminocyclohexanecarboxylic acid phenylmethyl ester and 311 mg (4.5 mmol) of 2,5-dihydropyrrole was used instead of 1-phenylpiperazine in the process according to Reference example 77 to obtain 698 mg (92%) of the title compound.

1H-NMR (CDCl$_3$, δ): 1.23-1.38 (1H, m), 1.42-1.53 (2H, m), 1.53-1.69 (3H, m), 1.82-1.92 (2H, m), 2.01-2.10 (2H, m), 3.73 (3H, s), 4.18 (4H, s), 4.31 (1H, s), 5.82 (2H, s)

Reference Example 112

1-[[(2,5-Dihydro-1H-pyrrol-1-yl)carbonyl]amino]cyclohexanecarboxylic acid

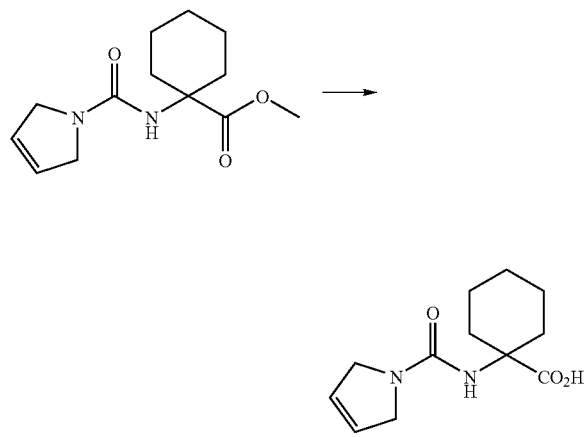

698 mg (2.8 mmol) of 1-[[(2,5-dihydro-1H-pyrrol-1-yl)carbonyl]amino]cyclohexanecarboxylic acid methyl ester was used instead of 1-[[[4-(phenylmethyl)-1-piperazinyl]carbonyl]amino]cyclohexanecarboxylic acid ethyl ester in the process according to Reference example 90 to obtain 453 mg (69%) of the title compound.

1H-NMR (CDCl$_3$, δ): 1.34-1.73 (6H, m), 1.92-2.22 (2H, m), 2.24-2.36 (2H, m), 4.23 (4H, br-s), 4.23 (1H, br-s), 5.87 (2H, br-s)

Reference Example 113

1-[(1H-Pyrrol-1-ylcarbonyl)amino]cyclohexanecarboxylic acid methyl ester

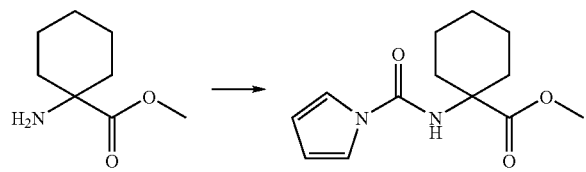 [SMILES: COC(=O)C1(N)CCCCC1 ; COC(=O)C1(NC(=O)n2cccc2)CCCCC1]

1 g (6.36 mmol) of 1-aminocyclohexanecarboxylic acid methyl ester was used instead of 1-aminocyclohexanecarboxylic acid phenylmethyl ester and 512 mmol (7.6 mmol) of pyrrole was used instead of 1-phenylpiperazine in the process according to Reference example 77 to obtain 1.52 g (95%) of the title compound.

1H-NMR (CDCl$_3$, δ): 1.36-1.57 (3H, m), 1.65-1.74 (3H, m), 1.91-2.02 (2H, m), 2.08-2.19 (2H, m), 3.74 (3H, s), 5.58 (1H, s), 6.28 (2H, dd, J=2 Hz, 1 Hz), 7.19 (2H, dd, J=2 Hz, 1 Hz)

Reference Example 114

1-[(1H-Pyrrol-1-ylcarbonyl)amino]cyclohexanecarboxylic acid

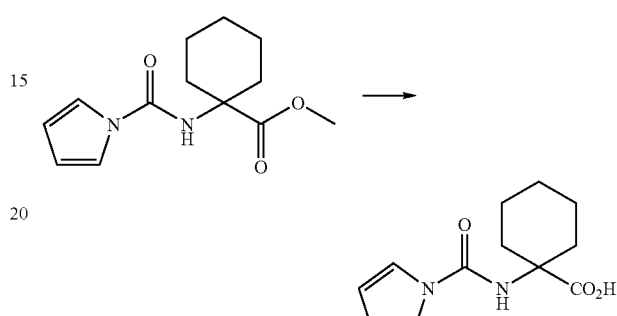

1.52 g (6 mmol) of 1-[[(1H-pyrrol-1-yl)carbonyl]amino]cyclohexanecarboxylic acid methyl ester was used instead of 1-[[[4-(phenylmethyl)-1-piperazinyl]carbonyl]amino]cyclohexanecarboxylic acid ethyl ester in the process according to Reference example 90 to obtain 839 mg (58%) of the title compound.

1H-NMR (DMSO-d$_6$, δ): 1.15-1.61 (4H, m), 1.69-1.81 (2H, m), 1.83-1.98 (2H, m), 2.08-2.19 (2H, m), 6.12 (2H, s), 6.21 (1H, d, J=2 Hz), 7.42 (2H, d, J=2 Hz), 7.88 (1H, dr-s)

Reference Example 115

1-[(3-Thiazolidinylcarbonyl)amino]cyclohexanecarboxylic acid

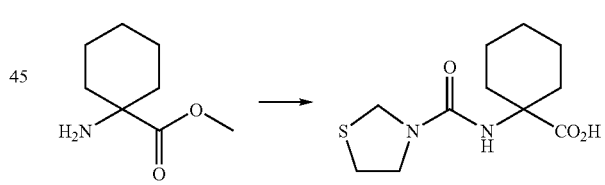

A solution of 78 mg (0.6 mmol) of N,N-dimethylaminopyridine and 1 g (6.36 mmol) of 1-aminocyclohexanecarboxylic acid methyl ester in methylene chloride was added to a solution of 1.39 mg (6.36 mmol) of di-t-butyl dicarbonate in 10 ml of methylene chloride, and the mixture was stirred at room temperature for 30 minutes. Thereafter, a solution of 1.29 g (12.7 mmol) of triethylamine and 680 mg (7.6 mmol) of thiazolidine in methylene chloride was added thereto, and the mixture was stirred at room temperature overnight. After the reaction mixture was concentrated, the residue was dissolved in ethyl acetate, and the mixture was washed with water, a 10% aqueous potassium hydrogensulfate solution, a saturated aqueous sodium hydrogencarbonate solution, and then saturated brine, followed by drying with anhydrous sodium sulfate. After the solvent was distilled off under reduced pressure, tetrahydrofuran and a 1N aqueous sodium hydroxide solution were added to the residue, and the mixture was heated under reflux for 3 hours. After ether was added to the reaction solution to wash it, the aqueous layer was neutralized by concentrated hydrochloric acid and extracted with ethyl acetate. After the obtained organic layer was washed with saturated brine, the layer was dried with anhydrous sodium sulfate. The solvent was distilled off under reduced pressure to obtain 1.1 g (66%) of the title compound.

1H-NMR (DMSO-$d_6$, δ): 1.08-1.25 (1H, m), 1.36-1.69 (6H, m), 1.82-2.01 (3H, m), 2.93 (2H, t, J=7 Hz), 3.59 (2H, t, J=7 Hz), 4.43 (2H, s), 6.44 (1H, s), 11.99 (1H, br-s)

Reference Example 116

1-[[[(2-Furanylmethyl)methylamino]carbonyl] amino]cyclohexanecarboxylic acid methyl ester

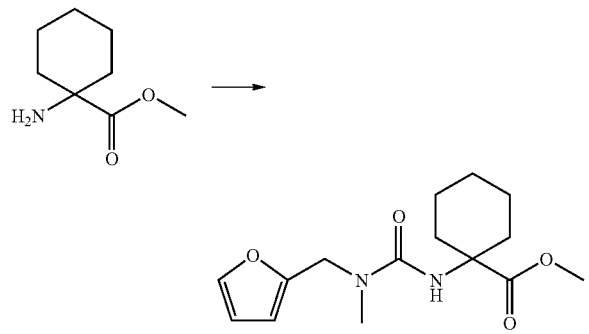

2.83 g (18 mmol) of 1-aminocyclohexanecarboxylic acid methyl ester was used instead of 1-aminocyclohexanecarboxylic acid phenylmethyl ester and 2.18 g (18 mmol) of (2-furanylmethyl)methylamine was used instead of 1-phenylpiperazine in the process according to Reference example 77 to obtain 4.27 g (78%) of the title compound.

1H-NMR (CDCl$_3$, δ): 1.25-1.47 (3H, m), 1.57-1.68 (3H, m), 1.80-1.85 (2H, m), 1.97-2.20 (2H, m), 2.94 (3H, s), 3.71 (3H, s), 4.42 (2H, s), 4.74 (1H, s), 6.24 (1H, dd, J=3 Hz, 1 Hz), 6.34 (1H, dd, J=3 Hz, J=3 Hz, 2 Hz), 7.37 (1H, dd, J=2 Hz, 1 Hz)

Reference Example 117

1-[[[(2-Furanylmethyl)methylamino]carbonyl] amino]cyclohexanecarboxylic acid

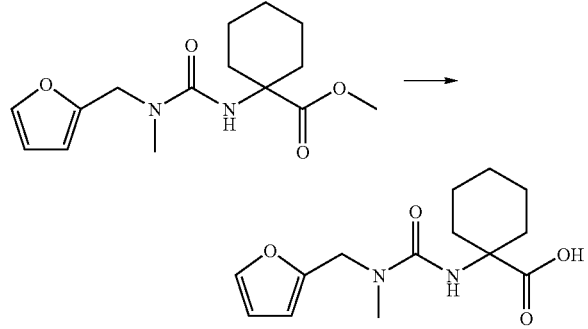

4.27 g (14 mmol) of 1-[[[(2-furanylmethyl)methylamino] carbonyl]amino]cyclohexanecarboxylic acid methyl ester was used instead of 1-[[[4-(phenylmethyl)-1-piperazinyl]carbonyl]amino]cyclohexanecarboxylic acid ethyl ester in the process according to Reference example 90 to obtain 3.47 g (84%) of the title compound.

1H-NMR (DMSO-$d_6$, δ): 1.12-1.23 (1H, m), 1.38-1.52 (5H, m), 1.58-1.64 (2H, m), 1.80-2.22 (2H, m), 2.81 (3H, s), 4.42 (2H, s), 6.03 (1H, s), 6.24 (1H, dd, J=3 Hz, 1 Hz), 6.40 (1H, dd, J=3 Hz, 2 Hz), 7.57 (1H, dd, J=2 Hz, 1 Hz)

Reference Example 118

1-[[(Methylphenylamino)carbonyl]amino]cyclohexanecarboxylic acid methyl ester

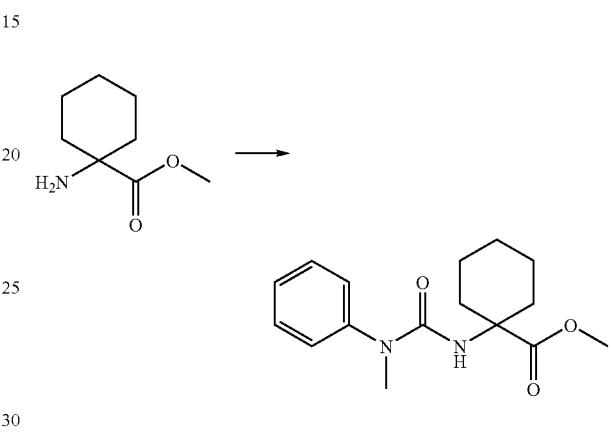

472 mg (3 mmol) of 1-aminocyclohexanecarboxylic acid methyl ester was used instead of 1-aminocyclohexanecarboxylic acid phenylmethyl ester and 643 mg (6 mmol) of N-methylaniline was used instead of 1-phenylpiperazine in the process according to Reference example 77 to obtain 834 mg (96%) of the title compound.

1H-NMR (CDCl$_3$, δ): 1.12-1.28 (2H, m), 1.48-1.62 (4H, m), 1.64-1.70 (2H, m), 1.90-1.98 (2H, m), 3.25 (3H, s), 3.74 (3H, s), 4.49 (1H, s), 7.26-7.36 (3H, m), 7.43-7.46 (2H, m)

Reference Example 119

1-[[(Methylphenylamino)carbonyl]amino]cyclohexanecarboxylic acid

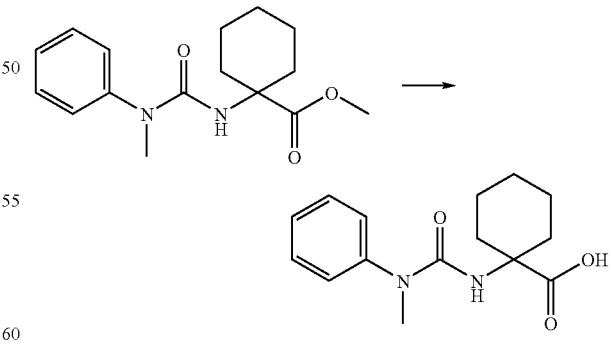

834 mg (2.87 mmol) of 1-[[(methylphenylamino)carbonyl]amino]cyclohexanecarboxylic acid methyl ester was used instead of 1-[[[4-(phenylmethyl)-1-piperazinyl]carbonyl]amino]cyclohexanecarboxylic acid ethyl ester in the process according to Reference example 90 to obtain 464 mg (59%) of the title compound.

1H-NMR (CDCl$_3$, δ): 0.96-1.05 (2H, m), 1.19-1.30 (1H, m), 1.50-1.60 (3H, m), 1.70-1.81 (2H, m), 1.96-2.02 (2H, m), 3.31 (3H, s), 4.30 (1H, s), 7.26-7.33 (2H, m), 7.44 (1H, t, J=9 Hz), 7.51 (2H, t, J=9 Hz)

Reference Example 120

1-[[[Methyl(phenylmethyl)amino]carbonyl]amino]cyclohexanecarboxylic acid methyl ester

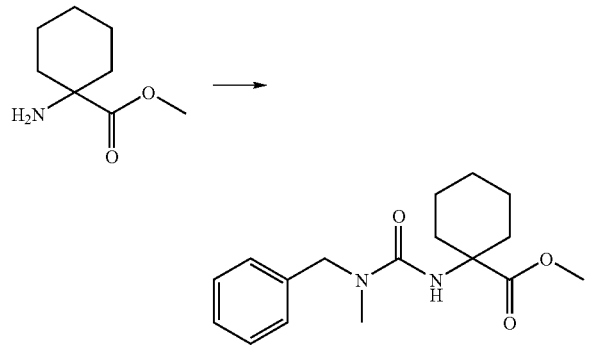

2.83 g (18 mmol) of 1-aminocyclohexanecarboxylic acid methyl ester was used instead of 1-aminocyclohexanecarboxylic acid phenylmethyl ester and 2.18 g (18 mmol) of N-methylbenzylamine was used instead of 1-phenylpiperazine in the process according to Reference example 77 to obtain 4.27 g (78%) of the title compound.

1H-NMR (CDCl$_3$, δ): 1.20-1.38 (3H, m), 1.50-1.63 (3H, m), 1.78-1.85 (2H, m), 1.97-2.03 (2H, m), 2.94 (3H, s), 3.73 (3H, s), 4.49 (2H, s), 4.51 (1H, s), 7.25-7.30 (3H, m), 7.35 (2H, dt, J=8 Hz, 1 Hz)

Reference Example 121

1-[[[Methyl(phenylmethyl)amino]carbonyl]amino]cyclohexanecarboxylic acid

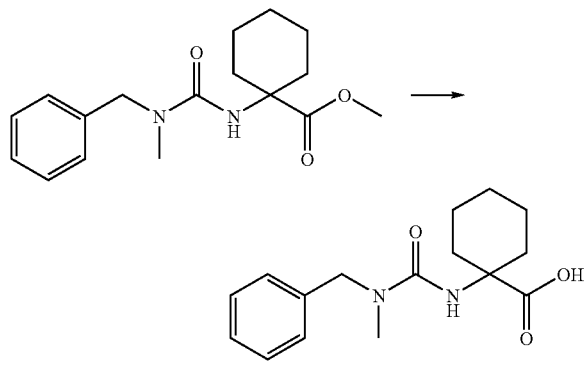

4.27 g (14 mmol) of 1-[[[methyl(phenylmethyl)amino]carbonyl]amino]cyclohexanecarboxylic acid methyl ester was used instead of 1-[[[4-(phenylmethyl)-1-piperazinyl]carbonyl]amino]cyclohexanecarboxylic acid ethyl ester in the process according to Reference example 90 to obtain 3.54 g (86%) of the title compound.

1H-NMR (DMSO-d$_6$, δ): 1.16-2.04 (1H, m), 1.39-1.47 (5H, m), 1.58-1.65 (2H, m), 1.97-2.22 (2H, m), 2.79 (3H, s), 4.44 (2H, s), 6.00 (1H, s), 7.21-7.34 (5H, m)

Reference Example 122

1-[[(2-Oxo-2H-pyran-5-yl)carbonyl]amino]cyclohexanecarboxylic acid

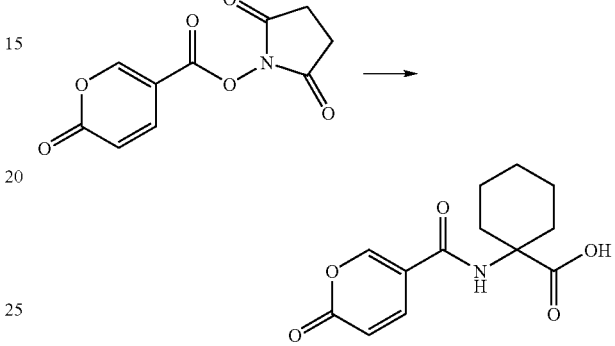

A solution of 2.37 g (10 mmol) of 5-coumarincarboxylic acid N-hydroxysuccinimide ester, 1.43 g (10 mmol) of 1-aminocyclohexanecarboxylic acid and 3.04 g (30 mmol) of triethylamine in 20 ml of dimethylformamide was stirred overnight. Ethyl acetate was added to the reaction solution, and the mixture was washed with a 10% aqueous potassium hydrogensulfate solution and then saturated brine. After it was dried with anhydrous sodium sulfate, the solvent was distilled off under reduced pressure to obtain 1.42 g (60%) of the title compound.

1H-NMR (DMSO-d$_6$, δ): 1.30-1.44 (3H, m), 1.44-1.63 (3H, m), 1.95-2.09 (4H, m), 5.26 (1H, d, J=9 Hz), 7.62 (1H, d, J=9 Hz), 8.28 (1H, d, J=15 Hz), 9.68 (1H, d, J=15 Hz)

Reference Example 123

1-[(4-Fluorobenzoyl)amino]cyclohexanecarboxylic acid

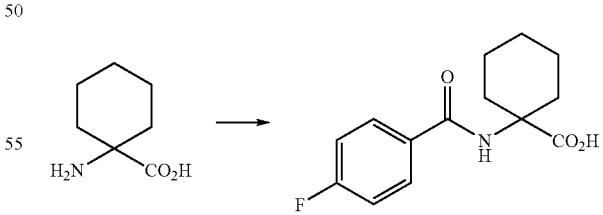

A solution of 25.0 g (15.8 mmol) of 4-fluorobenzoyl chloride in 30 ml of ether was added dropwise to a mixture solution of 22.6 g (15.8 mmol) of 1-aminocyclohexanecarboxylic acid and 25.0 g (23.7 mmol) of sodium carbonate in 100 ml of ether and 300 ml of water under ice-cooling, and the mixture was stirred at room temperature overnight. After the ether layer was separated, the aqueous layer was neutralized with concentrated hydrochloric acid under ice-cooling and the precipitated crystal was collected by filtration to obtain 27.7 g (66%) of the title compound.

Reference Example 124

1-[[[4-(4-Propylpiperazin-1-yl)phenyl]carbonyl]amino]cyclohexanecarboxylic acid phenylmethyl ester

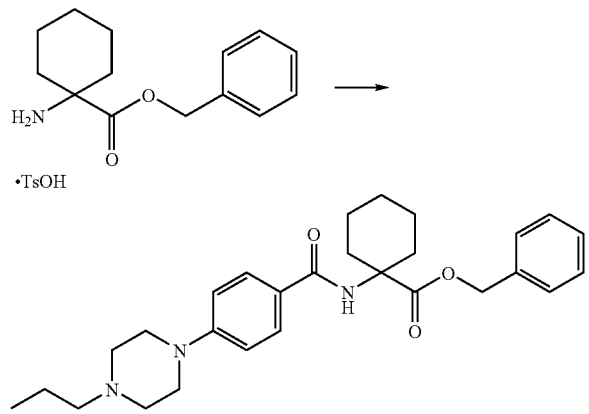

2.36 g (8.44 mmol) of 4-(4-propylpiperazin-1-yl)benzoic acid hydrochloride was used instead of phenylacetyl chloride in the process according to Reference example 1 to obtain 1.79 g (46%) of the title compound.

1H-NMR (CDCl$_3$, δ): 0.94 (3H, t, J=7 Hz), 1.28-1.40 (1H, m), 1.45-1.61 (4H, m), 1.61-1.72 (3H, m), 1.90-1.98 (2H, m), 2.15-2.23 (2H, m), 2.36 (1H, t, J=6 Hz), 2.37 (1H, t, J=6 Hz), 2.59 (4H, t, J=5 Hz), 3.31 (4H, t, J=5 Hz), 5.16 (2H, s), 6.13 (1H, br-s), 6.89 (2H, d, J=8 Hz), 7.25-7.33 (5H, m), 7.68 (2H, d, J=8 Hz)

Reference Example 125

1-[[[4-(4-Propylpiperazin-1-yl)phenyl]carbonyl]amino]cyclohexanecarboxylic acid

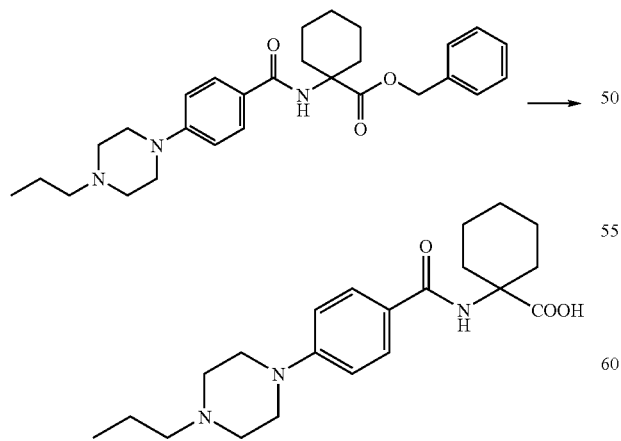

1.79 g (3.86 mmol) of 1-[[[4-(4-propylpiperazin-1-yl)phenyl]carbonyl]amino]cyclohexanecarboxylic acid phenylmethyl ester was used instead of 1-[(phenylacetyl)amino]cyclohexanecarboxylic acid phenylmethyl ester in the process according to Reference example 2 to obtain 1.43 g (quantitative) of the title compound.

1H-NMR (CDCl$_3$, δ): 0.95 (3H, t, J=8 Hz), 1.39-1.61 (3H, m), 1.65-1.78 (4H, m), 1.94-2.03 (3H, m), 2.21-2.41 (2H, m), 2.45-2.54 (2H, m), 2.65-2.70 (4H, m), 3.27-3.35 (4H, m), 6.06 (1H, br-s), 6.85 (2H, d, J=8 Hz), 7.65 (2H, d, J=8 Hz)

Reference Example 126

1-[[[4-(4-Propylpiperazin-1-yl)phenyl]carbonyl]amino]cyclohexanecarboxylic acid methyl ester

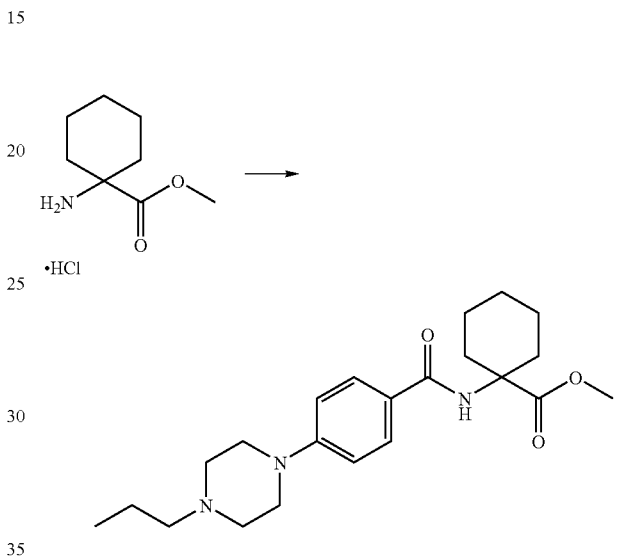

1.00 g (3.57 mmol) of 4-(4-propylpiperazin-1-yl)benzoic acid hydrochloride was used instead of 3-furancarboxylic acid in the process according to Reference example 15 to obtain 602 g (44%) of the title compound.

1H-NMR (CDCl$_3$, δ): 0.94 (3H, t, J=8 Hz), 1.31-1.40 (1H, m), 1.44-1.58 (4H, m), 1.62-1.74 (3H, m), 1.88-1.96 (2H, m), 2.11-2.19 (2H, m), 2.36 (1H, t, J=6 Hz), 2.37 (1H, t, J=6 Hz), 2.59 (4H, t, J=5 Hz), 3.30 (4H, t, J=5 Hz), 3.72 (3H, s), 6.12 (1H, br-s), 6.89 (2H, dd, J=2 Hz, 7 Hz), 7.69 (2H, dd, J=2 Hz, 7 Hz)

Reference Example 127

1-[[[4-(4-Propylpiperazin-1-yl)phenyl]carbonyl]amino]cyclohexanecarboxylic acid methyl ester hydrochloride

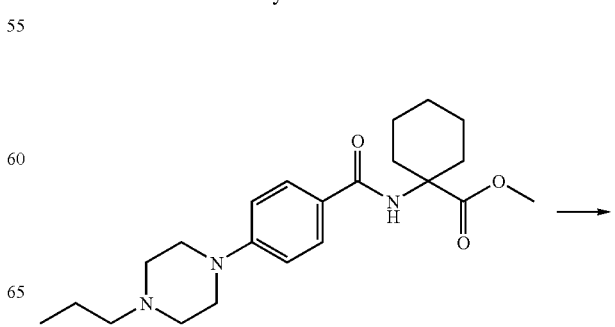

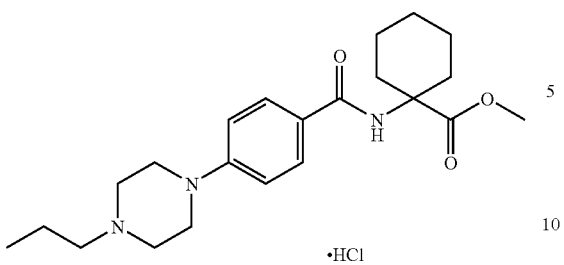
·HCl 1 ml of 4N hydrochloric acid/ethyl acetate solution was added to a solution of 120 mg (0.31 mmol) of 1-[[[4-(4-propylpiperazin-1-yl)phenyl]carbonyl]amino]cyclohexanecarboxylic acid methyl ester in 10 ml of ethyl acetate, and the mixture was stirred at room temperature for 30 minutes. The precipitated crystal was collected by filtration to obtain 87 mg (66%) of the title compound.

1H-NMR (DMSO-$d_6$, δ): 0.91 (3H, t, J=8 Hz), 1.21-1.35 (1H, m), 1.47-1.62 (5H, m), 1.70-1.81 (4H, m), 2.02-2.10 (2H, m), 3.01-3.14 (4H, m), 3.15-3.28 (2H, m), 3.50-3.58 (2H, m), 3.82-4.02 (5H, m), 7.04 (2H, dd, J=2 Hz, 7 Hz), 7.79 (2H, dd, J=2 Hz, 7 Hz), 8.11 (1H, s)

Reference Example 128

1-[[[4-(4-Propylpiperazin-1-yl)phenyl]carbonyl]amino]cyclohexanecarboxylic acid hydrochloride

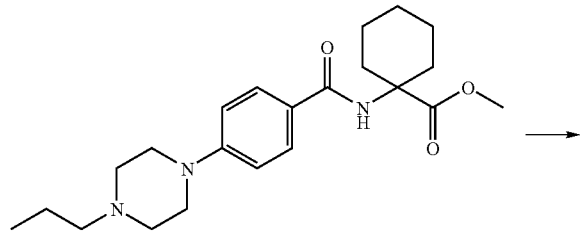
·HCl 3 ml of 4N hydrochloric acid was added to 600 mg (1.55 mmol) of 1-[[[4-(4-propylpiperazin-1-yl)phenyl]carbonyl]amino]cyclohexanecarboxylic acid methyl ester, and the mixture was refluxed under heating for 6 hours. The precipitated crystal obtained by cooling it to room temperature was collected by filtration to obtain 258 mg (41%) of the title compound.

1H-NMR (CDCl₃, δ): 1.05 (3H, t, J=7 Hz), 1.31-1.43 (1H, m), 1.45-1.56 (2H, m), 1.64-1.78 (3H, m), 1.90-2.02 (4H, m), 2.16-2.25 (2H, m), 2.95-3.28 (5H, m), 3.60-3.75 (4H, m), 3.78-3.89 (2H, m), 6.65 (1H, br-s), 6.92 (2H, d, J=8 Hz), 7.97 (2H, d, J=8 Hz)

Reference Example 129

1-[[[4-(4-Propylpiperazin-1-yl)phenyl]carbonyl]amino]cyclohexanecarboxylic acid ethyl ester

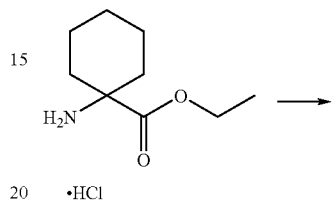
·HCl

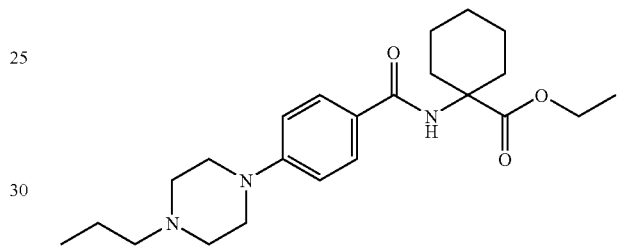

741 mg (3.57 mmol) of 1-aminocyclohexanecarboxylic acid ethyl ester hydrochloride was used instead of 1-aminocyclohexanecarboxylic acid methyl ester hydrochloride and 1.00 g (3.57 mmol) of 4-(4-propylpiperazin-1-yl)benzoic acid hydrochloride was used instead of 3-furancarboxylic acid in the process according to Reference example 15 to obtain 928 mg (65%) of the title compound.

1H-NMR (CDCl₃, δ): 0.94 (3H, t, J=8 Hz), 1.24 (3H, t, J=7 Hz), 1.30-1.41 (1H, m), 1.43-1.71 (7H, m), 1.88-1.97 (2H, m), 2.10-2.20 (2H, m), 2.36 (1H, t, J=6 Hz), 2.37 (1H, t, J=6 Hz), 3.31 (4H, t, J=5 Hz), 4.18 (4H, t, J=5 Hz), 4.20 (2H, q, J=7 Hz), 6.10 (1H, br-s), 6.89 (2H, dd, J=2 Hz, 8 Hz), 7.69 (2H, dd, J=2 Hz, 8 Hz)

Reference Example 130

1-[[[4-(4-Propylpiperazin-1-yl)phenyl]carbonyl]amino]cyclohexanecarboxylic acid ethyl ester hydrochloride

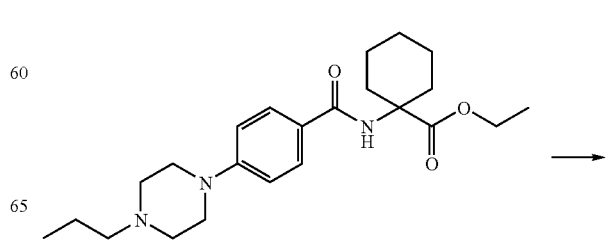

-continued

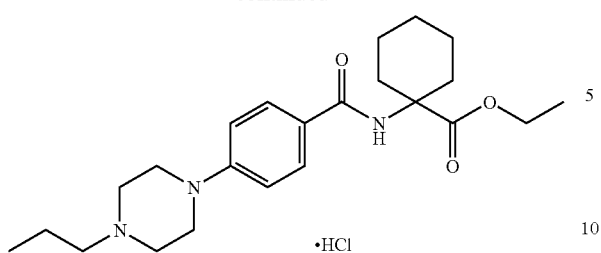

120 mg (0.3 mmol) of 1-[[[4-(4-propylpiperazin-1-yl)phenyl]carbonyl]amino]cyclohexanecarboxylic acid ethyl ester was used instead of 1-[[[4-(4-propylpiperazin-1-yl)phenyl]carbonyl]amino]cyclohexanecarboxylic acid methyl ester in the process according to Reference example 127 to obtain 114 mg (87%) of the title compound.

1H-NMR (DMSO-$d_6$, δ): 0.93 (3H, t, J=8 Hz), 1.11 (3H, t, J=7 Hz), 1.23-1.32 (1H, m), 1.45-1.55 (5H, m), 1.68-1.80 (4H, m), 2.02-2.10 (2H, m), 3.03-3.18 (6H, m), 3.51-3.62 (2H, m), 3.95-4.04 (2H, m), 4.02 (2H, q, J=7 Hz), 7.04 (2H, d, J=8 Hz), 7.78 (2H, d, J=8 Hz), 8.10 (1H, s)

Reference Example 131

1-[[[4-(4-Propylpiperazin-1-yl)phenyl]carbonyl]amino]cyclohexanecarboxylic acid hydrochloride

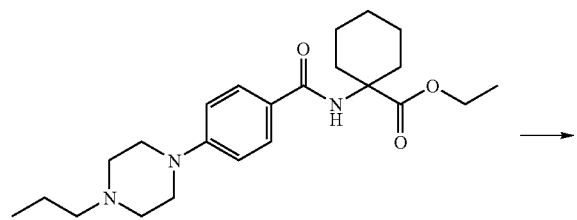

800 mg (1.99 mmol) of 1-[[[4-(4-propylpiperazin-1-yl)phenyl]carbonyl]amino]cyclohexanecarboxylic acid ethyl ester was used instead of 1-[[[4-(4-propylpiperazin-1-yl)phenyl]carbonyl]amino]cyclohexanecarboxylic acid methyl ester in the process according to Reference example 128 to obtain 197 mg (24%) of the title compound.

1H-NMR (CDCl$_3$, δ): 1.05 (3H, t, J=7 Hz), 1.31-1.43 (1H, m), 1.45-1.56 (2H, m), 1.64-1.78 (3H, m), 1.90-2.02 (4H, m), 2.16-2.25 (2H, m), 2.95-3.28 (5H, m), 3.60-3.75 (4H, m), 3.78-3.89 (2H, m), 6.65 (1H, br-s), 6.92 (2H, d, J=8 Hz), 7.97 (2H, d, J=8 Hz)

Reference Example 132

2-(Phenylmethyl)-3-oxa-1-azaspiro[4.5]dec-1-en-4-one

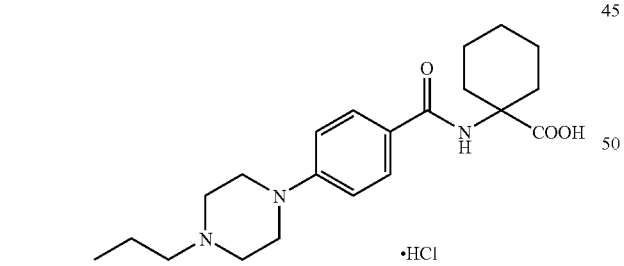

633 mg (3.3 mmol) of 1-ethyl-3-(3-dimethylaminopropyl)carbodiimide hydrochloride was added to a solution of 784 mg (3 mmol) of 1-[(phenylacetyl)amino]cyclohexanecarboxylic acid obtained in Reference example 2 in 20 ml of methylene chloride. After the mixture was stirred at room temperature for 4 hours, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. The solvent was distilled off under reduced pressure to obtain 625 mg (86%) of the title compound.

1H-NMR (CDCl$_3$, δ): 1.48-1.51 (1H, m), 1.56-1.70 (3H, m), 1.70-1.79 (6H, m), 3.79 (2H, s), 7.28-7.36 (5H, m)

Reference Example 133

2-(2-Phenylethyl)-3-oxa-1-azaspiro[4.5]dec-1-en-4-one

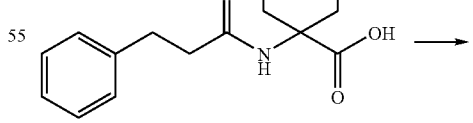

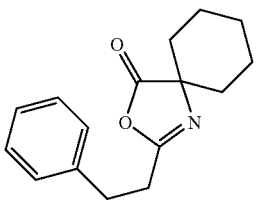

826 mg (3 mmol) of 1-[(1-oxo-3-phenylpropyl)amino]cyclohexanecarboxylic acid was used instead of 1-[(phenylacetyl)amino]cyclohexanecarboxylic acid in the process according to Reference example 132 to obtain 764 mg (99%) of the title compound.

1H-NMR (CDCl₃, δ): 1.47-1.55 (4H, m), 1.57-1.78 (6H, m), 2.79 (2H, t, J=7 Hz), 3.02 (2H, t, J=7 Hz), 7.20-7.23 (3H, m), 7.28-7.31 (2H, m)

Reference Example 134

2-Phenyl-3-oxa-1-azaspiro[4.5]dec-1-en-4-one

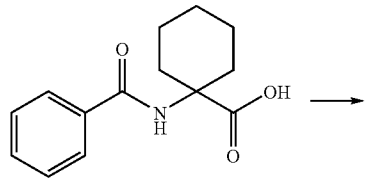
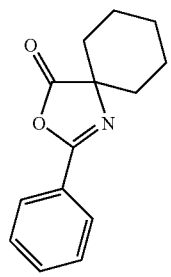

742 mg (3 mmol) of 1-[(benzoyl)amino]cyclohexanecarboxylic acid was used instead of 1-[(phenylacetyl)amino]cyclohexanecarboxylic acid in the process according to Reference example 132 to obtain 633 mg (92%) of the title compound.

1H-NMR (CDCl₃, δ): 1.52-1.58 (1H, m), 1.63-1.78 (3H, m), 1.79-1.89 (6H, m), 7.47 (1H, td, J=7 Hz, 1 Hz), 7.49 (1H, td, J=7 Hz, 1 Hz), 7.56 (1H, td, J=7 Hz, 1 Hz), 8.02 (2H, m)

Reference Example 135

2-(4-Biphenyl)-3-oxa-1-azaspiro[4.5]dec-1-en-4-one

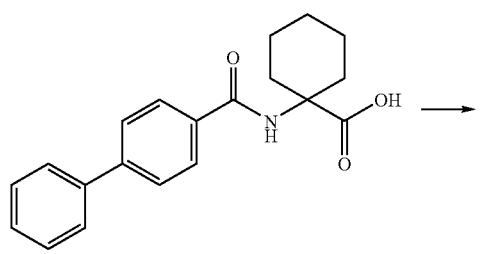
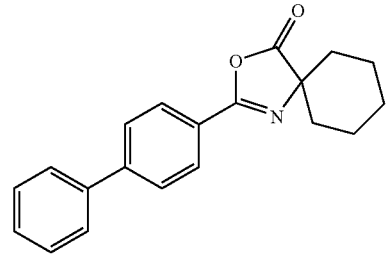

970 mg (3 mmol) of 1-[(4-biphenylcarbonyl)amino]cyclohexanecarboxylic acid was used instead of 1-[(phenylacetyl) amino]cyclohexanecarboxylic acid in the process according to Reference example 132 to obtain 914 mg (quantitative) of the title compound.

1H-NMR (CDCl₃, δ): 1.52 (2H, m), 1.63-1.71 (1H, m), 1.72-1.80 (2H, m), 1.81-1.90 (5H, m), 7.39-7.42 (1H, m), 7.47-7.50 (2H, m), 7.63 (1H, dd, J=7 Hz, 1 Hz), 7.65 (1H, dd, J=7 Hz, 1 Hz), 7.71 (1H, d, J=7 Hz, 1 Hz), 7.72 (1H, dd, J=7 Hz, 1 Hz), 8.07 (1H, dd, J=7 Hz, 1 Hz), 8.08 (1H, dd, J=7 Hz, 1 Hz)

Reference Example 136

2-(2-Naphthyl)-3-oxa-1-azaspiro[4.5]dec-1-en-4-one

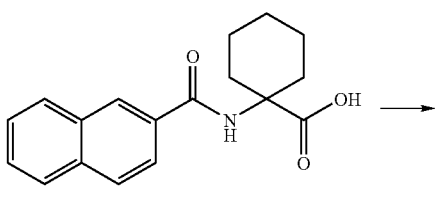
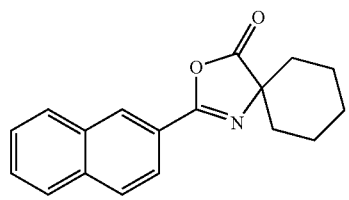

595 mg (2 mmol) of 1-[(2-naphthylcarbonyl)amino]cyclohexanecarboxylic acid was used instead of 1-[(phenylacetyl)amino]cyclohexanecarboxylic acid in the process according to Reference example 132 to obtain 562 mg (quantitative) of the title compound.

1H-NMR (CDCl₃, δ): 1.54-1.68 (1H, m), 1.69-1.76 (1H, m), 1.78-1.94 (8H, m), 7.26-7.62 (2H, m), 7.89 (1H, d, J=8 Hz), 7.92 (1H, dd, J=8 Hz, 1 Hz), 7.95 (1H, dd, J=8 Hz, 1 Hz), 8.09 (1H, dd, J=8 Hz, 1 Hz), 8.49 (1H, d, J=1 Hz)

Reference Example 137

2-(1-Naphthyl)-3-oxa-1-azaspiro[4.5]dec-1-en-4-one

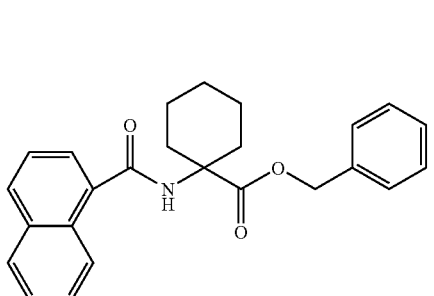
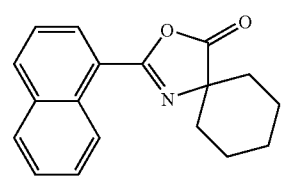

1.35 g (3.5 mmol) of 1-[(1-naphthylcarbonyl)amino]cyclohexanecarboxylic acid phenylmethyl ester obtained in Reference example 11 was dissolved in 50 ml of methanol, 150 mg of 10% palladium-carbon was added thereto, and the mixture was stirred under a hydrogen atmosphere at room temperature overnight. After the reaction solution was filtered, the filtrate was concentrated under reduced pressure. The obtained residue was dissolved in 30 ml of methylene chloride, and 633 mg (3.3 mmol) of 1-ethyl-3-(3-dimethylaminopropyl)carbodiimide hydrochloride was added thereto. After the mixture was stirred at room temperature for 4 hours, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. The solvent was distilled off under reduced pressure to obtain 738 mg (88%) of the title compound.

1H-NMR (CDCl$_3$, δ): 1.50-1.68 (3H, m), 1.70-2.00 (7H, m), 7.53-7.60 (2H, m), 7.67 (1H, td, 7 Hz, 1 Hz), 7.92 (1H, dd, J=7 Hz, 1 Hz), 8.03 (1H, d, J=7 Hz), 8.17 (1H, dd, J=7 Hz, 1 Hz), 9.33 (1H, dd, J=7 Hz, 1 Hz)

Reference Example 138

2-[(RS)-2,3-Tetrahydrofuran-2-yl]-3-oxa-1-azaspiro[4.5]dec-1-en-4-one

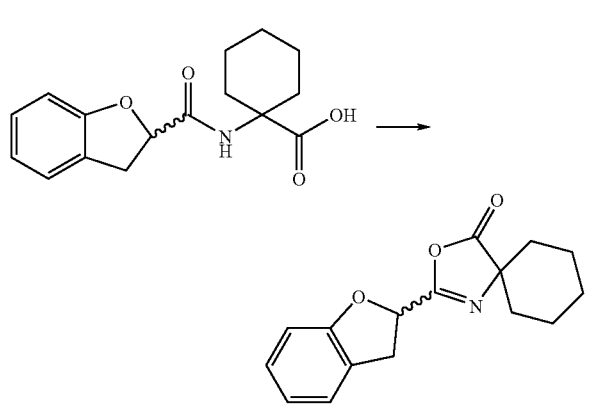

868 mg (3 mmol) of 1-[[[(RS)-2,3-tetrahydrobenzofuran-2-yl]carbonyl]amino]cyclohexanecarboxylic acid was used instead of 1-[(phenylacetyl)amino]cyclohexanecarboxylic acid in the process according to Reference example 132 to obtain 686 mg (87%) of the title compound.

1H-NMR (CDCl$_3$, δ): 1.43-1.82 (10H, m), 3.56 (2H, d, J=9 Hz) 5.46 (½H, d, J=10 Hz), 5.48 (½H, d, J=10 Hz), 6.89 (1H, td, 8 Hz, 1 Hz), 6.93 (1H, dd, H=8 Hz, 1 Hz), 7.16 (1H, td, J=8 Hz, 1 Hz), 7.21 (1H, dd, J=8 Hz, 1 Hz)

Reference Example 139

2-(2-Furanyl)-3-oxa-1-azaspiro[4.5]dec-1-en-4-one

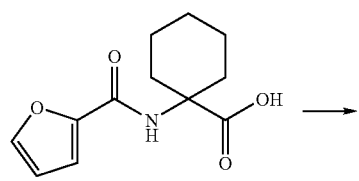

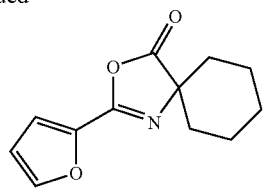

53.2 g (224 mmol) of 1-[(2-furanylcarbonyl)amino]cyclohexanecarboxylic acid was used instead of 1-[(phenylacetyl)amino]cyclohexanecarboxylic acid in the process according to Reference example 132 to obtain 49.8 g (quantitative) of the title compound.

1H-NMR (CDCl$_3$, δ): 1.53-1.57 (1H, m), 1.66-1.86 (9H, m), 6.58 (1H, dd, J=4 Hz, 2 Hz), 7.09 (1H, dd, J=4 Hz, 1 Hz), 7.65 (1H, dd, J=2 Hz, 1 Hz)

Reference Example 140

2-(3-Furanyl)-3-oxa-1-azaspiro[4.5]dec-1-en-4-one

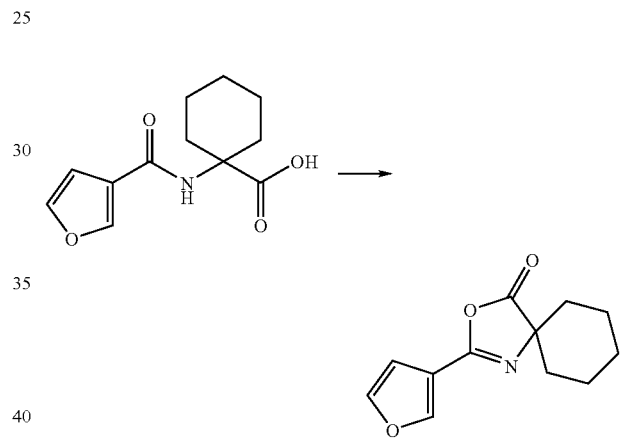

4.48 g (18.9 mmol) of 1-[(3-furanylcarbonyl)amino]cyclohexanecarboxylic acid was used instead of 1-[(phenylacetyl)amino]cyclohexanecarboxylic acid in the process according to Reference example 132 to obtain 4.02 g (97%) of the title compound.

1H-NMR (CDCl$_3$, δ): 1.54-1.57 (1H, m), 1.63-1.86 (9H, m), 6.86 (1H, dd, J=2 Hz, 1 Hz), 7.51 (1H, t, J=2 Hz), 7.99 (1H, dd, J=2 Hz, 1 Hz)

Reference Example 141

2-[2-(2-Furanyl)ethenyl]-3-oxa-1-azaspiro[4.5]dec-1-en-4-one

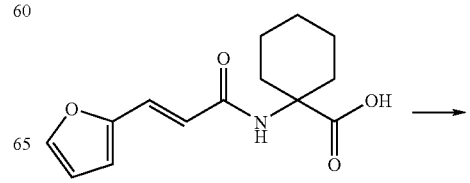

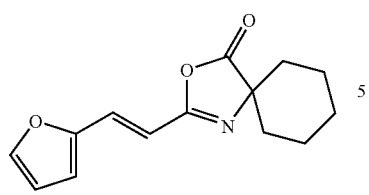

10.0 g (38 mmol) of 1-[[(E)-3-(2-furanyl)-1-oxo-2-propenyl]amino]cyclohexanecarboxylic acid was used instead of 1-[(phenylacetyl)amino]cyclohexanecarboxylic acid in the process according to Reference example 132 to obtain 8.92 g (96%) of the title compound.

1H-NMR (CDCl$_3$, δ): 1.26-1.54 (2H, m), 1.66-1.84 (8H, m), 6.48 (1H, dd, J=2 Hz, 1 Hz), 6.53 (1H, d, J=16 Hz), 6.60 (1H, d, J=2 Hz), 7.22 (1H, d, J=16 Hz), 7.51 (1H, dd, J=2 Hz, 1 Hz)

Reference Example 142

2-Cyclohexyl-3-oxa-1-azaspiro[4.5]dec-1-en-4-one

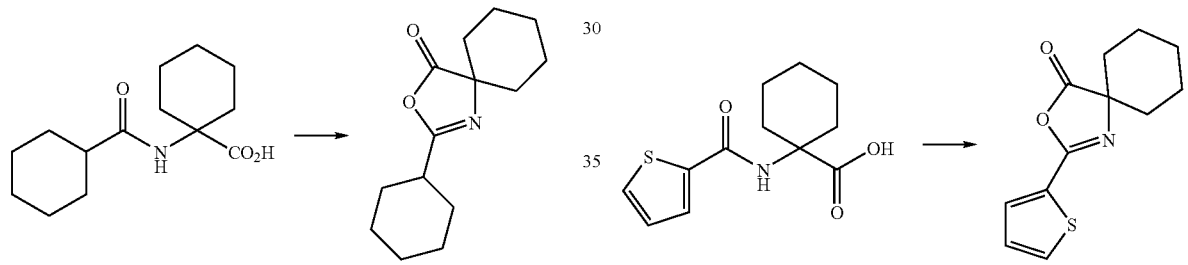

4.15 g (16.3 mmol) of 1-[(cyclohexylcarbonyl)amino]cyclohexanecarboxylic acid was used instead of 1-[(phenylacetyl)amino]cyclohexanecarboxylic acid in the process according to Reference example 132 to obtain 3.75 g (98%) of the title compound.

1H-NMR (CDCl$_3$, δ): 1.24-1.38 (3H, m), 1.44-1.56 (3H, m), 1.56-1.63 (3H, m), 1.63-1.84 (9H, m), 1.92-2.00 (2H, m), 2.43-2.49 (1H, m)

Reference Example 143

2-(6-Benzothiazolyl)-3-oxa-1-azaspiro[4.5]dec-1-en-4-one

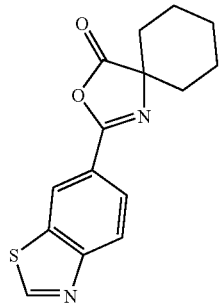

365 mg (1.2 mmol) of 1-[(6-benzothiazolylcarbonyl)amino]cyclohexanecarboxylic acid was used instead of 1-[(phenylacetyl)amino]cyclohexanecarboxylic acid in the process according to Reference example 132 to obtain 287 mg (83%) of the title compound.

1H-NMR (CDCl$_3$, δ): 1.53-1.62 (4H, m), 1.68-1.79 (2H, m), 1.81-1.92 (4H, m), 8.19 (1H, dd, J=9 Hz, 2 Hz), 8.22 (1H, dd, J=9 Hz, 1 Hz), 8.65 (1H, dd, J=2 Hz, 1 Hz), 9.15 (1H, s)

Reference Example 144

2-(2-Thienyl)-3-oxa-1-azaspiro[4.5]dec-1-en-4-one

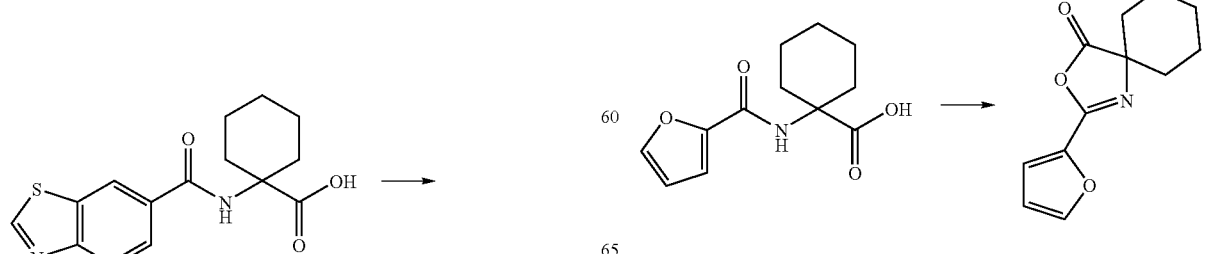

5.0 g (20 mmol) of 1-[(2-thienylcarbonyl)amino]cyclohexanecarboxylic acid was used instead of 1-[(phenylacetyl)amino]cyclohexanecarboxylic acid in the process according to Reference example 132 to obtain 4.46 g (96%) of the title compound.

1H-NMR (CDCl$_3$, δ): 1.51-1.59 (1H, m), 1.61-1.69 (1H, m), 1.71-1.88 (8H, m), 7.14 (1H, dd, J=5 Hz, 4 Hz), 7.57 (1H, dd, J=5 Hz, 1 Hz), 7.70 (1H, dd J=4 Hz, 1 Hz)

Reference Example 145

2-(2-Furanyl)-3-oxa-1-azaspiro[4.5]dec-1-en-4-one 6.0 g (44 mmol) of isobutyl chloroformate was added dropwise to a solution of 10 g (42 mmol) of 1-[(2-furanylcarbonyl)

amino]cyclohexanecarboxylic acid obtained in Reference example 14 and 6.1 ml (44 mmol) of triethylamine in tetrahydrofuran (80 ml), and the mixture was stirred at room temperature for 1 hour. The precipitated crystal was removed by filtration and the filtrate was concentrated. The obtained crystal was washed with water to give 8.95 g (97%) of the title compound.

1H-NMR (CDCl$_3$, δ): 1.53-1.57 (1H, m), 1.66-1.86 (9H, m), 6.58 (1H, dd, J=4 Hz, 2 Hz), 7.09 (1H, dd, J=4 Hz, 1 Hz), 7.65 (1H, dd, J=2 Hz, 1 Hz)

Reference Example 146

2-(1,3-Benzodioxol-5-yl)-3-oxa-1-azaspiro[4.5]dec-1-en-4-one

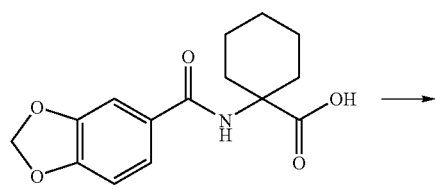

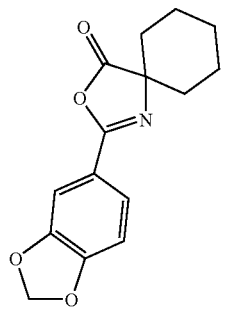

5.8 g (20 mmol) of 1-[[(1,3-benzodioxole)-5-carbonyl] amino]cyclohexanecarboxylic acid was used instead of 1-[(phenylacetyl)amino]cyclohexanecarboxylic acid in the process according to Reference example 132 to obtain 4.9 g (90%) of the title compound.

1H-NMR (CDCl$_3$, δ): 1.51-1.57 (1H, m), 1.63-1.75 (3H, m), 1.76-1.88 (6H, m), 6.05 (2H, s), 6.87 (1H, d, J=8 Hz), 7.46 (1H, d, J=2 Hz), 7.55 (1H, dd, J=8 Hz, 2 Hz)

Reference Example 147

2-(2-Benzofuranyl)-3-oxa-1-azaspiro[4.5]dec-1-en-4-one

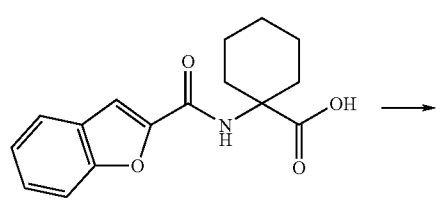

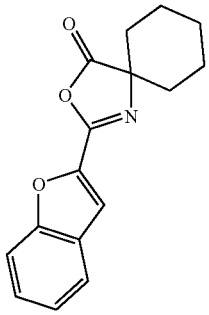

3.8 g (13 mmol) of 1-[[(2-benzofuranyl)carbonyl]amino] cyclohexanecarboxylic acid was used instead of 1-[(phenylacetyl)amino]cyclohexanecarboxylic acid in the process according to Reference example 132 to obtain 3.4 g (96%) of the title compound.

1H-NMR (CDCl$_3$, δ): 1.51-1.74 (2H, m), 1.78-1.94 (8H, m), 7.33 (1H, ddd, J=8 Hz, 7 Hz, 1 Hz), 7.44 (1H, d, J=1 Hz), 7.46 (1H, ddd, J=8 Hz, 7 Hz, 1 Hz), 7.63 (1H, ddd, J=8 Hz, 2 Hz, 1 Hz), 7.70 (1H, ddd, J=8 Hz, 2 Hz, 1 Hz)

Reference Example 148

2-(2-Pyridinyl)-3-oxa-1-azaspiro[4.5]dec-1-en-4-one

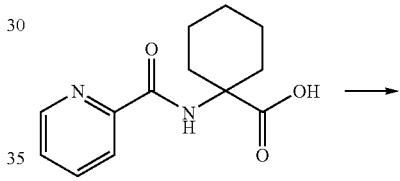

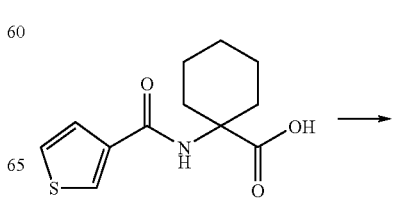

511 mg (2 mmol) of 1-[(2-pyridinylcarbonyl)amino]cyclohexanecarboxylic acid was used instead of 1-[(phenylacetyl) amino]cyclohexanecarboxylic acid in the process according to Reference example 132 to obtain 405 mg (85%) of the title compound.

1H-NMR (CDCl$_3$, δ): 1.54-1.77 (3H, m), 1.78-1.92 (7H, m), 7.62 (1H, ddd, J=7 Hz, 5 Hz, 2 Hz), 7.87 (1H, dt, J=7 Hz, 2 Hz), 8.04 (1H, dd, J=5 Hz, 2 Hz), 8.82 (1H, dd, J=5 Hz, 2 Hz)

Reference Example 149

2-(3-Thienyl)-3-oxa-1-azaspiro[4.5]dec-1-en-4-one

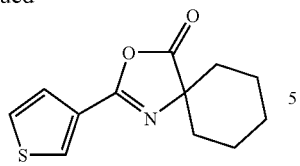

253 mg (1 mmol) of 1-[(3-thienylcarbonyl)amino]cyclohexanecarboxylic acid was used instead of 1-[(phenylacetyl)amino]cyclohexanecarboxylic acid in the process according to Reference example 132 to obtain 234 mg (quantitative) of the title compound.

1H-NMR (CDCl₃, δ): 1.52-1.87 (10H, m), 7.40 (1H, dd, J=5 Hz, 3 Hz), 7.60 (1H, dd, J=5 Hz, 1 Hz), 8.00 (1H, dd, J=3 Hz, 1 Hz)

Reference Example 150

2-(3-Ethoxy-2-thienyl)-3-oxa-1-azaspiro[4.5]dec-1-en-4-one

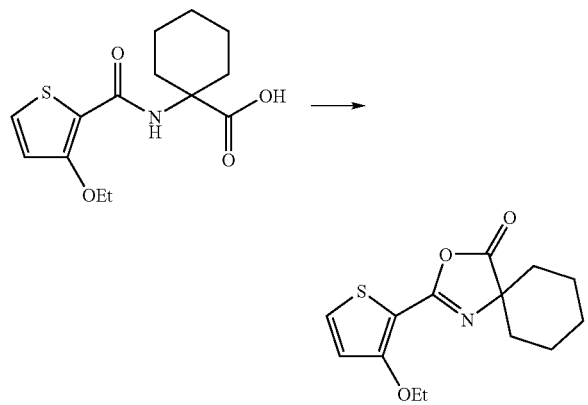

327 mg (1 mmol) of 1-[[(3-ethoxy-2-thienyl)carbonyl]amino]cyclohexanecarboxylic acid was used instead of 1-[(phenylacetyl)amino]cyclohexanecarboxylic acid in the process according to Reference example 132 to obtain 307 mg (quantitative) of the title compound.

1H-NMR (CDCl₃, δ): 1.46 (3H, t, J=7 Hz), 1.49-1.84 (10H, m) 4.22 (2H, q, J=7 Hz), 6.86 (1H, d, J=6 Hz), 7.42 (1H, d, J=6 Hz)

Reference Example 151

2-[2-[(S)-1-Phenylethyl]]-3-oxa-1-azaspiro[4.5]dec-1-en-4-one

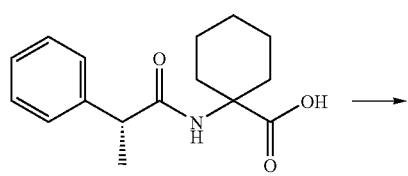

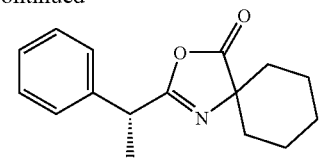

275 mg (1 mmol) of 1-[[(S)-1-oxo-2-phenylpropyl]amino]cyclohexanecarboxylic acid was used instead of 1-[(phenylacetyl)amino]cyclohexanecarboxylic acid in the process according to Reference example 132 to obtain 257 mg (quantitative) of the title compound.

1H-NMR (CDCl₃, δ): 1.51-1.78 (13H, m), 3.89 (1H, q, J=7 Hz), 7.26-7.35 (5H, m)

Reference Example 152

2-(2-Pyrazinyl)-3-oxa-1-azaspiro[4.5]dec-1-en-4-one

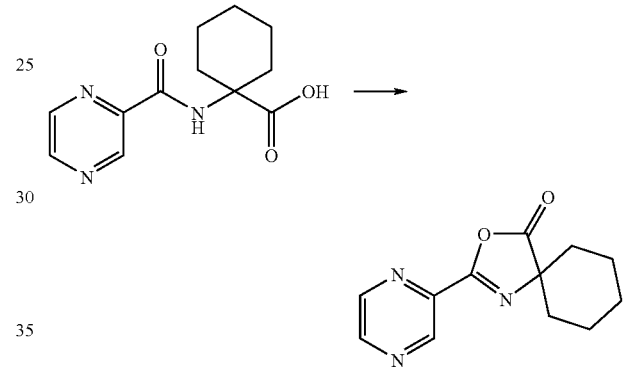

249 mg (1 mmol) of 1-[(2-pyrazinylcarbonyl)amino]cyclohexanecarboxylic acid was used instead of 1-[(phenylacetyl)amino]cyclohexanecarboxylic acid in the process according to Reference example 132 to obtain 231 mg (quantitative) of the title compound.

1H-NMR (CDCl₃, δ): 1.56-1.93 (10H, m), 8.78 (2H, m), 9.28 (1H, t, J=3 Hz)

Reference Example 153

2-(5-Methylisoxazol-4-yl)-3-oxa-1-azaspiro[4.5]dec-1-en-4-one

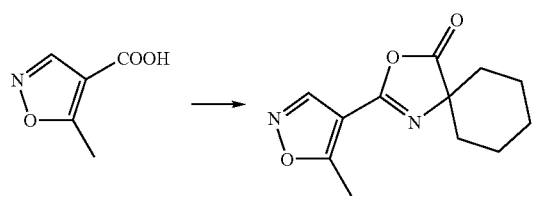

1 g (7.87 mmol) of 5-methylisoxazole-4-carboxylic acid was added to 3 ml of thionyl chloride, and the mixture was stirred overnight. The reaction solution was concentrated under reduced pressure, and the obtained residue was added to a solution of 1.13 g (7.87 mmol) of 1-aminocyclohexanecarboxylic acid and 6.6 g (79 mmol) of sodium hydrogencarbonate in 30 ml of toluene-30 ml of water. After the mixture was stirred at room temperature overnight, the toluene layer was separated. The aqueous layer was neutralized by potassium hydrogensulfate and extracted with ethyl acetate. After the obtained organic layer was washed with saturated brine, the layer was dried with anhydrous sodium sulfate. The solvent was distilled off under reduced pressure, methylene chloride was added thereto, and 332 mg (1.73 mmol) of 1-ethyl-3-(3-dimethylaminopropyl)carbodiimide hydrochloride was added thereto under ice-cooling. After the mixture was stirred at room temperature overnight, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. The solvent was distilled off under reduced pressure to obtain 295 mg (16%) of the title compound.

1H-NMR (CDCl$_3$, δ): 1.50-1.59 (1H, m), 1.64-1.72 (2H, m), 1.76-1.83 (7H, m), 2.75 (3H, s), 8.55 (1H, s)

Reference Example 154

2-cyclopentyl-3-oxa-1-azaspiro[4.5]dec-1-en-4-one

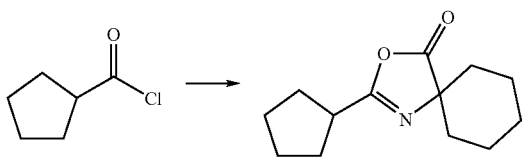 [SMILES: O=C(Cl)C1CCCC1 ; O=C1OC(C2CCCC2)=NC12CCCCC2]

1.98 g (15 mmol) of cyclopentanecarbonyl chloride was added to a solution of 2.16 g (15 mmol) of 1-aminocyclohexanecarboxylic acid and 4.8 g (45 mmol) of sodium carbonate in 50 ml of ethyl acetate-50 ml of water under ice-cooling. After the mixture was stirred at room temperature overnight, ethyl acetate was added thereto, and the mixture was washed with a 10% aqueous potassium hydrogensulfate solution, a saturated aqueous sodium bicarbonate solution, and then saturated brine. After the obtained organic layer was washed with saturated brine, the layer was dried with anhydrous sodium sulfate. The solvent was distilled off under reduced pressure, methylene chloride was added thereto, and 1.59 g (8.3 mmol) of 1-ethyl-3-(3-dimethylaminopropyl)carbodiimide hydrochloride was added thereto under ice-cooling. After the mixture was stirred at room temperature overnight, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. The solvent was distilled off under reduced pressure to obtain 1.41 g (42%) of the title compound.

1H-NMR (CDCl$_3$, δ): 1.53-1.65 (5H, m), 1.67-1.76 (4H, m), 1.86-1.95 (8H, m), 2.80-2.89 (2H, m)

Reference Example 155

2-(5-Methyl-2-thienyl)-3-oxa-1-azaspiro[4.5]dec-1-en-4-one

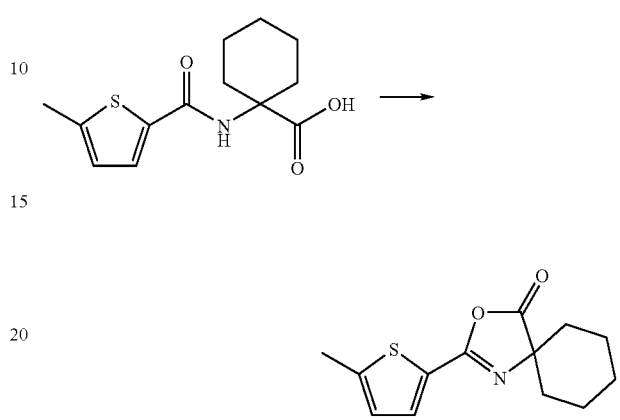

294 mg (1.1 mmol) of 1-[[(5-methyl-2-thienyl)carbonyl]amino]cyclohexanecarboxylic acid was used instead of 1-[(phenylacetyl)amino]cyclohexanecarboxylic acid in the process according to Reference example 132 to obtain 273 mg (quantitative) of the title compound.

1H-NMR (CDCl$_3$, δ): 1.53-1.62 (3H, m), 1.71-1.84 (7H, m), 2.55 (3H, s), 6.79 (1H, d, J=3 Hz), 7.50 (1H, d, J=3 Hz)

Reference Example 156

2-(4-Methoxyphenyl)-3-oxa-1-azaspiro[4.5]dec-1-en-4-one

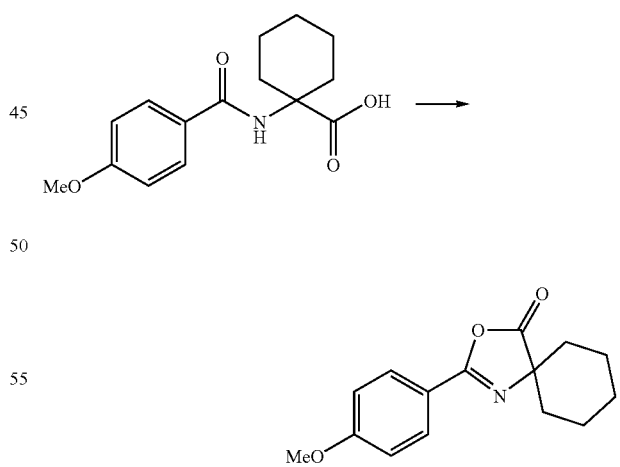

305 mg (1.1 mmol) of 1-[[(4-methoxyphenyl)carbonyl]amino]cyclohexanecarboxylic acid was used instead of 1-[(phenylacetyl)amino]cyclohexanecarboxylic acid in the process according to Reference example 132 to obtain 288 mg (90%) of the title compound.

1H-NMR (CDCl₃, δ): 1.51-1.60 (1H, m), 1.61-1.73 (3H, m), 1.76-1.90 (6H, m), 3.87 (3H, s), 6.96 (2H, dd, J=7 Hz, 2 Hz), 7.94 (2H, dd, J=7 Hz, 2 Hz)

Reference Example 157

2-(3-Methyl-2-thienyl)-3-oxa-1-azaspiro[4.5]dec-1-en-4-one

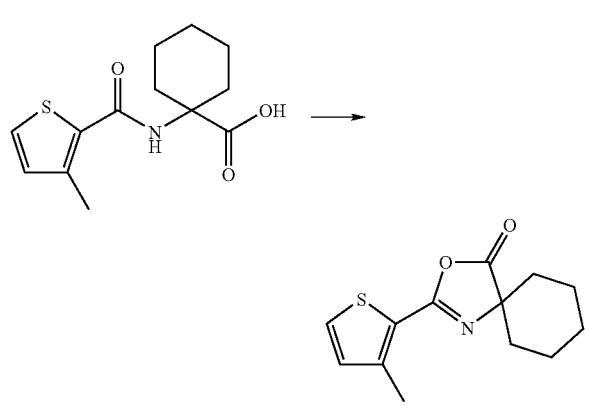

249 mg (1.1 mmol) of 1-[[(3-methyl-2-thienyl)carbonyl]amino]cyclohexanecarboxylic acid was used instead of 1-[(phenylacetyl)amino]cyclohexanecarboxylic acid in the process according to Reference example 132 to obtain 249 mg (quantitative) of the title compound.

1H-NMR (CDCl₃, δ): 1.50-1.60 (1H, m), 1.65-1.78 (3H, m), 1.78-1.90 (6H, m), 2.58 (3H, s), 6.95 (1H, d, J=5 Hz), 7.42 (1H, d, J=5 Hz)

Reference Example 158

2-(3-Methyl-2-furanyl)-3-oxa-1-azaspiro[4.5]dec-1-en-4-one

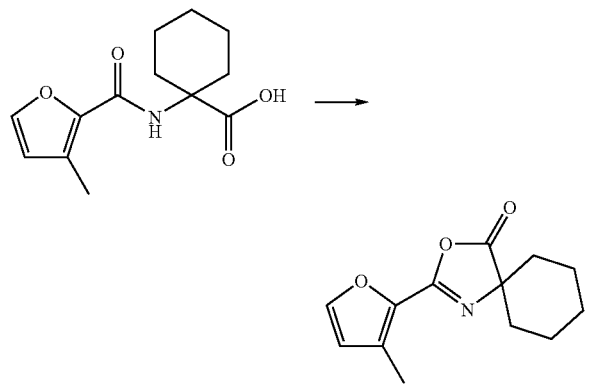

902 mg (3.59 mmol) of 1-[[(3-methyl-2-furanyl)carbonyl]amino]cyclohexanecarboxylic acid was used instead of 1-[(phenylacetyl)amino]cyclohexanecarboxylic acid in the process according to Reference example 132 to obtain 233 mg (quantitative) of the title compound.

1H-NMR (CDCl₃, δ): 1.48-1.61 (1H, m), 1.62-1.89 (9H, m), 2.36 (3H, s), 6.40 (1H, d, J=1 Hz), 7.52 (1H, d, J=1 Hz)

Reference Example 159

2-(3-Pyridinyl)-3-oxa-1-azaspiro[4.5]dec-1-en-4-one

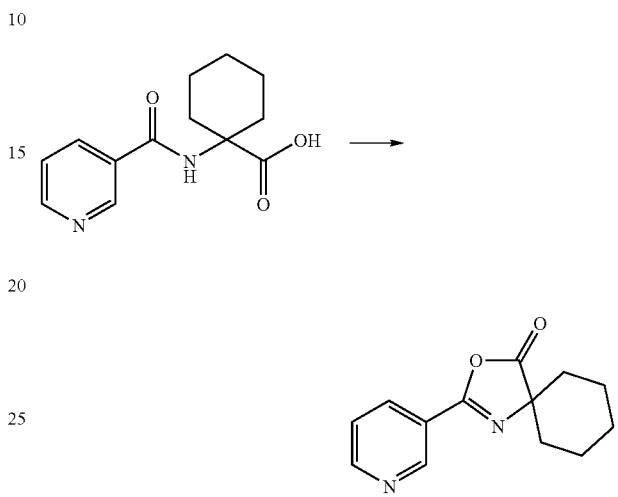

523 mg (2.11 mmol) of 1-[(3-pyridinylcarbonyl)amino]cyclohexanecarboxylic acid was used instead of 1-[(phenylacetyl)amino]cyclohexanecarboxylic acid in the process according to Reference example 132 to obtain 486 mg (quantitative) of the title compound.

1H-NMR (CDCl₃, δ): 1.50-1.90 (10H, m), 7.42 (1H, dd, J=8 Hz, 5 Hz), 8.27 (1H, d, J=8 Hz), 8.78 (1H, d, J=5 Hz), 9.00 (1H, s)

Reference Example 160

2-(1-Methyl-1H-pyrrol-2-yl)-3-oxa-1-azaspiro[4.5]dec-1-en-4-one

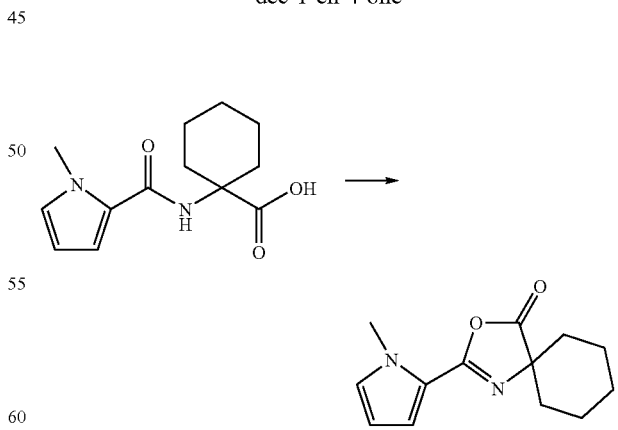

187 mg (0.75 mmol) of 1-[[(1-methyl-1H-pyrrol-2-yl)carbonyl]amino]cyclohexanecarboxylic acid was used instead of 1-[(phenylacetyl)amino]cyclohexanecarboxylic acid in the process according to Reference example 132 to obtain 172 mg (quantitative) of the title compound.

1H-NMR (CDCl$_3$, δ): 1.44-1.85 (10H, m), 3.40 (3H, s), 6.18 (1H, dd, J=4 Hz, 3 Hz), 6.82-6.86 (2H, m)

Reference Example 161

2-[(R)-1-Phenylethyl]-3-oxa-1-azaspiro[4.5]dec-1-en-4-one

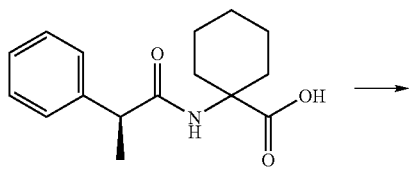

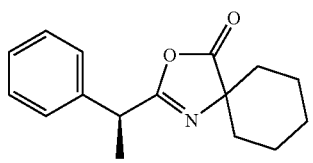

303 mg (1.1 mmol) of 1-[((R)-1-oxo-2-phenylpropyl)amino]cyclohexanecarboxylic acid was used instead of 1-[(phenylacetyl)amino]cyclohexanecarboxylic acid in the process according to Reference example 132 to obtain 257 mg (90%) of the title compound.

1H-NMR (CDCl$_3$, δ): 1.45-1.65 (7H, m), 1.67-1.80 (6H, m), 3.89 (1H, q, J=7 Hz), 7.26-7.34 (5H, m)

Reference Example 162

2-(1H-Indol-5-ylcarbonyl)-3-oxa-1-azaspiro[4.5]dec-1-en-4-one

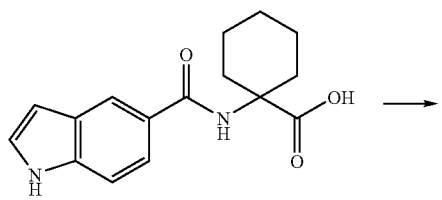

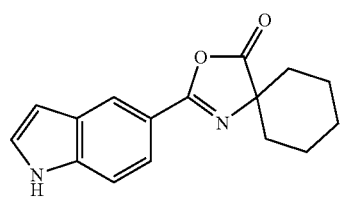

329 mg (1.2 mmol) of 1-[(1H-indol-5-ylcarbonyl)amino]cyclohexanecarboxylic acid was used instead of 1-[(phenylacetyl)amino]cyclohexanecarboxylic acid in the process according to Reference example 132 to obtain 258 mg (80%) of the title compound.

1H-NMR (CDCl$_3$, δ): 1.56-1.89 (10H, m), 6.65 (1H, dd, J=3 Hz, 2 Hz), 7.26-7.36 (1H, m), 7.46 (1H, d, J=9 Hz), 7.88 (1H, dd, J=9 Hz, 2 Hz), 8.32 (1H, s), 8.35 (1H, br-s)

Reference Example 163

2-(1-Cyclopentenylcarbonyl)-3-oxa-1-azaspiro[4.5]dec-1-en-4-one

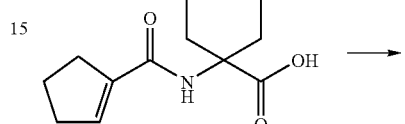

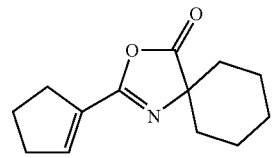

237 mg (1 mmol) of 1-[(1-cyclopentenylcarbonyl)amino]cyclohexanecarboxylic acid was used instead of 1-[(phenylacetyl)amino]cyclohexanecarboxylic acid in the process according to Reference example 132 to obtain 219 mg (quantitative) of the title compound.

1H-NMR (CDCl$_3$, δ): 1.53-1.82 (10H, m), 1.99-2.10 (2H, m), 2.55-2.69 (2H, m), 2.69-2.80 (2H, m), 6.65-6.67 (1H, m)

Reference Example 164

2-(4-Pyridinyl)-3-oxo-1-azaspiro[4.5]dec-1-en-4-one

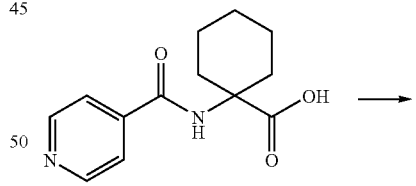

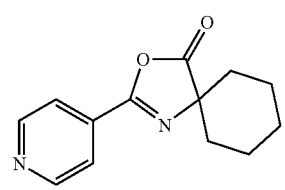

552 mg (2.2 mmol) of 1-[(4-pyridinylcarbonyl)amino]cyclohexanecarboxylic acid was used instead of 1-[(phenylacetyl)amino]cyclohexanecarboxylic acid in the process according to Reference example 132 to obtain 450 mg (88%) of the title compound.

1H-NMR (CDCl₃, δ): 1.50-1.92 (10H, m), 7.85 (2H, dd, J=5 Hz, 2 Hz), 8.80 (2H, dd, J=5 Hz, 2 Hz)

Reference Example 165

2-(1H-Pyrrol-2-yl)-3-oxa-1-azaspiro[4.5]dec-1-en-4-one

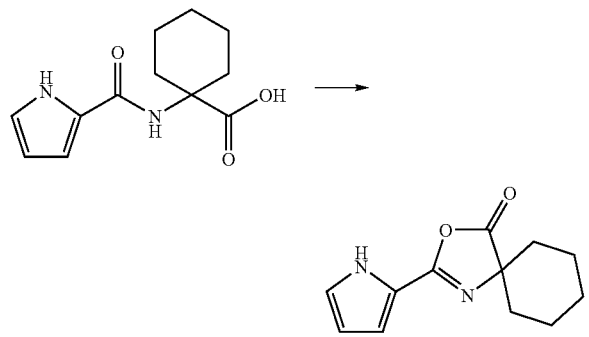

200 mg (0.85 mmol) of 1-[[(1H-pyrrol-2-yl)carbonyl]amino]cyclohexanecarboxylic acid was used instead of 1-[(phenylacetyl)amino]cyclohexanecarboxylic acid in the process according to Reference example 132 to obtain 184 mg (quantitative) of the title compound.

1H-NMR (CDCl₃, δ): 1.51-1.65 (1H, m), 1.65-1.86 (9H, m), 6.32 (1H, dd, J=4 Hz, 2 Hz), 6.87 (1H, dd, J=4 Hz, 2 Hz), 7.01 (1H, dd, J=4 Hz, 2 Hz), 9.37 (1H, br-s)

Reference Example 166

2-(6-Hydroxy-2-pyridinyl)-3-oxa-1-azaspiro[4.5]dec-1-en-4-one

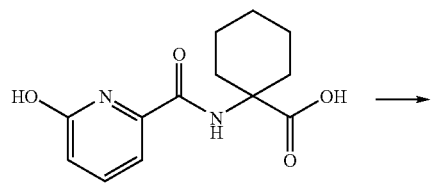

278 mg (1 mmol) of 1-[[(6-hydroxy-2-pyridinyl)carbonyl]amino]cyclohexanecarboxylic acid was used instead of 1-[(phenylacetyl)amino]cyclohexanecarboxylic acid in the process according to Reference example 132 to obtain 250 mg (97%) of the title compound.

1H-NMR (CDCl₃, δ): 1.52 (1H, m), 1.78 (9H, m), 6.85-6.79 (2H, m), 7.50 (1H, dd, J=9 Hz, 7 Hz)

Reference Example 167

2-(2-Hydroxy-3-pyridinyl)-3-oxa-1-azaspiro[4.5]dec-1-en-4-one

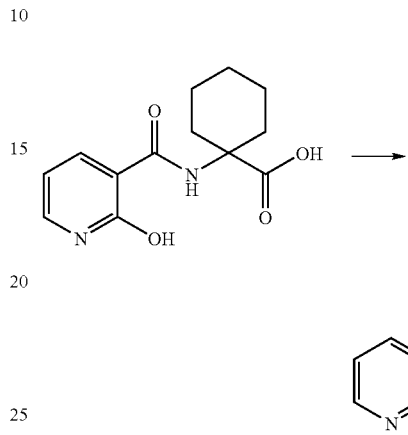

278 mg (1 mmol) of 1-[[(2-hydroxy-3-pyridinyl)carbonyl]amino]cyclohexanecarboxylic acid was used instead of 1-[(phenylacetyl)amino]cyclohexanecarboxylic acid in the process according to Reference example 132 to obtain 257 mg (quantitative) of the title compound.

1H-NMR (CDCl₃, δ): 1.04-2.21 (10H, m), 6.40-6.50 (1H, m), 7.69-7.82 (1H, m), 8.28-8.35 (1H, m)

Reference Example 168

2-(6-Hydroxy-3-pyridinyl)-3-oxa-1-azaspiro[4.5]dec-1-en-4-one

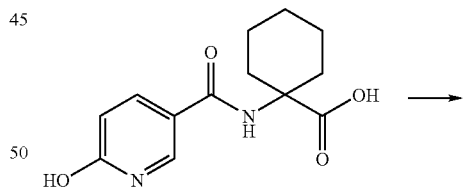

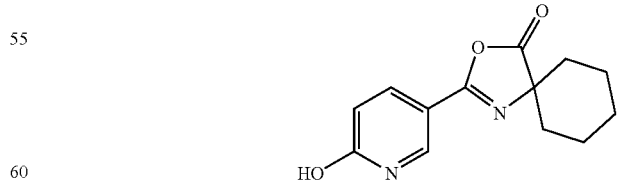

278 mg (1 mmol) of 1-[[(6-hydroxy-3-pyridinyl)carbonyl]amino]cyclohexanecarboxylic acid was used instead of 1-[(phenylacetyl)amino]cyclohexanecarboxylic acid in the process according to Reference example 132 to obtain 257 mg (quantitative) of the title compound.

1H-NMR (CDCl₃, δ): 1.45-1.86 (10H, m), 6.66 (1H, d, J=10 Hz), 8.02 (1H, d, J=2 Hz), 8.05 (1H, dd, J=10 Hz, 2 Hz)

Reference Example 169

2-[2-(2-Furanyl)ethyl]-3-oxa-1-azaspiro[4.5]dec-1-en-4-one

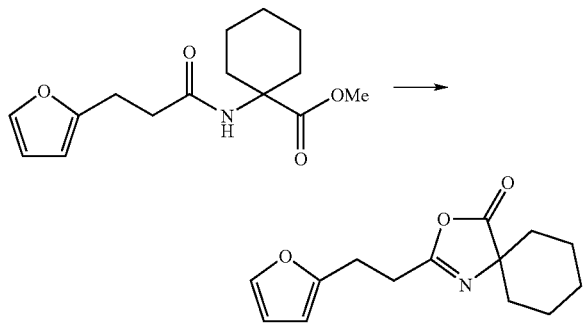

1.7 ml of 2N—NaOH aqueous solution was added to a solution of 478 mg (1.7 mmol) of 1-[[1-oxo-3-(2-furanyl)propyl]amino]cyclohexanecarboxylic acid methyl ester obtained in Reference example 64 in 2 ml of tetrahydrofuran, and the mixture was refluxed under heating for 3 hours. Ether was added to the reaction solution to wash it. After the separated aqueous layer was neutralized by concentrated hydrochloric acid, the layer was extracted with ethyl acetate. After the obtained organic layer was washed with saturated brine, the layer was dried with anhydrous sodium sulfate, and the solvent was distilled off under reduced pressure. Then, 10 ml of methylene chloride and 377 mg (1.82 mmol) of acid 1-ethyl-3-(3-dimethylaminopropyl)carbodiimide hydrochloride were added to the residue, and the mixture was stirred at room temperature overnight. The solvent was distilled off under reduced pressure, ethyl acetate was added thereto, and the mixture was washed with water, a 10% aqueous potassium hydrogensulfate solution, a saturated aqueous sodium hydrogencarbonate solution, and then saturated brine, followed by drying with anhydrous sodium sulfate. The solvent was distilled off under reduced pressure to obtain 198 mg (47%) of the title compound.

1H-NMR (CDCl₃, δ): 1.43-1.60 (4H, m), 1.60-1.80 (6H, m), 2.84 (2H, t, J=7 Hz), 3.05 (2H, t, J=7 Hz), 6.06 (1H, dd, J=2 Hz, 1 Hz), 6.27 (1H, dd, J=2 Hz, 1 Hz), 7.31 (1H, dd, J=2 Hz, 1 Hz)

Reference Example 170

2-[1-[(2-Propoxy)carbonyl]piperidin-4-yl]-3-oxa-1-azaspiro[4.5]dec-1-en-4-one

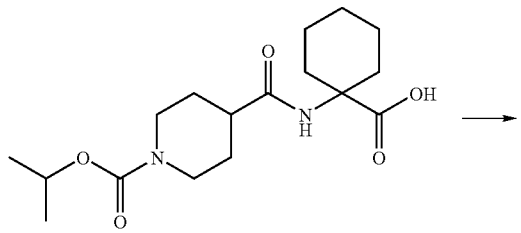

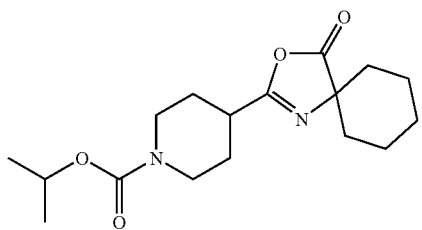

940 mg (2.76 mmol) of 1-[[[1-(2-propoxycarbonyl)piperidin-4-yl]carbonyl]amino]cyclohexanecarboxylic acid was used instead of 1-[(phenylacetyl)amino]cyclohexanecarboxylic acid in the process according to Reference example 132 to obtain 818 mg (92%) of the title compound.

1H-NMR (CDCl₃, δ): 1.24 (6H, d, J=6 Hz), 1.44-1.79 (12H, m), 1.90-1.98 (2H, m), 2.62-2.69 (1H, m), 2.89-2.99 (2H, m), 4.03-4.19 (2H, m), 4.88-4.97 (1H, m)

Reference Example 171

2-[1-(Ethoxycarbonyl)piperidin-4-yl]-3-oxa-1-azaspiro[4.5]dec-1-en-4-one

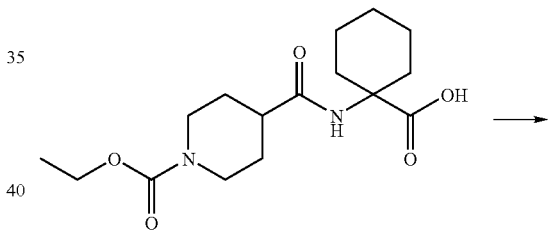

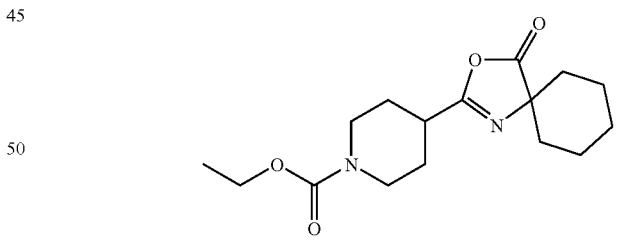

935 mg (2.86 mmol) of 1-[[[1-(ethoxycarbonyl)piperidin-4-yl]carbonyl]amino]cyclohexanecarboxylic acid was used instead of 1-[(phenylacetyl)amino]cyclohexanecarboxylic acid in the process according to Reference example 132 to obtain 730 mg (83%) of the title compound.

1H-NMR (CDCl₃, δ): 1.26 (3H, t, J=7 Hz), 1.45-1.80 (12H, m), 1.92-1.99 (2H, m), 2.62-2.70 (1H, m), 2.90-3.03 (2H, m), 4.03-4.20 (4H, m)

Reference Example 172

2-[1-(2-Furanylcarbonyl)piperidin-4-yl]-3-oxa-1-azaspiro[4.5]dec-1-en-4-one

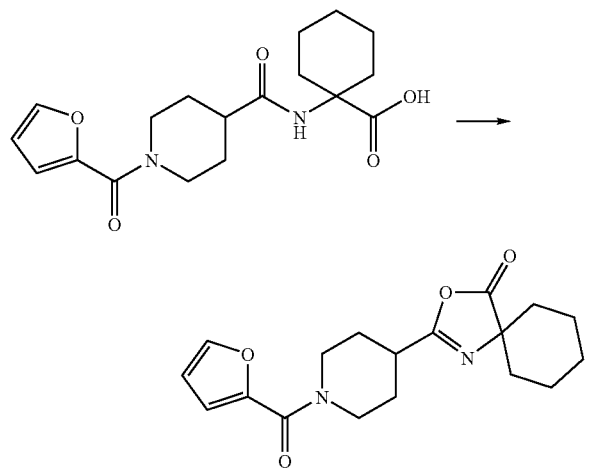

196 mg (0.56 mmol) of 1-[[[1-(2-furanylcarbonyl)piperidin-4-yl]carbonyl]amino]cyclohexanecarboxylic acid was used instead of 1-[(phenylacetyl)amino]cyclohexanecarboxylic acid in the process according to Reference example 132 to obtain 185 mg (quantitative) of the title compound.

1H-NMR (CDCl$_3$, δ): 1.49-1.68 (5H, m), 1.68-1.80 (5H, m), 1.80-1.92 (2H, m), 2.03-2.10 (2H, m), 2.75-2.83 (1H, m), 3.05-3.31 (2H, m), 4.28-4.40 (2H, m), 6.48 (1H, dd, J=3 Hz, 1 Hz), 7.00 (1H, dd, J=3 Hz, 1 Hz), 7.48 (1H, dd, J=3 Hz, 1 Hz)

Reference Example 173

2-[[(2-Furanylcarbonyl)amino]methyl]-3-oxa-1-azaspiro[4.5]dec-1-en-4-one

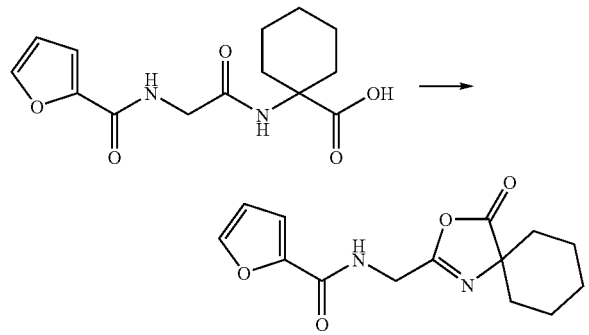

249 mg (1 mmol) of 1-[[[(2-furanylcarbonyl)amino]acetyl]amino]cyclohexanecarboxylic acid was used instead of 1-[(phenylacetyl)amino]cyclohexanecarboxylic acid in the process according to Reference example 132 to obtain 276 mg (quantitative) of the title compound.

1H-NMR (CDCl$_3$, δ): 1.50-1.80 (10H, m), 4.45 (2H, d, J=6 Hz), 6.53 (1H, dd, J=3 Hz, 1 Hz), 6.90 (1H, br-s), 7.18 (1H, ddd, J=3 Hz, 2 Hz, 1 Hz), 7.50 (1H, dd, J=2 Hz, 1 Hz)

Reference Example 174

2-[(Benzoylamino)methyl]-3-oxa-1-azaspiro[4.5]dec-1-en-4-one

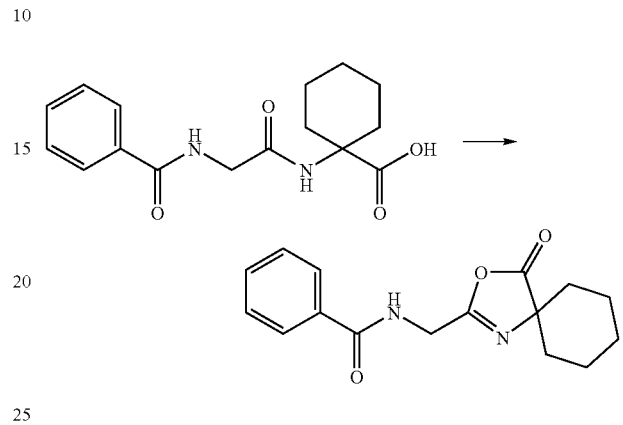

724 mg (2.26 mmol) of 1-[[(benzoylamino)acetyl]amino]cyclohexanecarboxylic acid was used instead of 1-[(phenylacetyl)amino]cyclohexanecarboxylic acid in the process according to Reference example 132 to obtain 631 mg (97%) of the title compound.

1H-NMR (CDCl$_3$, δ): 1.48-1.58 (1H, m), 1.63-1.80 (9H, m), 4.49 (2H, d, J=5 Hz), 6.76 (1H, br-s), 7.48 (2H, m), 7.55 (1H, m), 7.83 (2H, m)

Reference Example 175

2-(4-Fluorophenyl)-3-oxa-1-azaspiro[4.5]dec-1-en-4-one

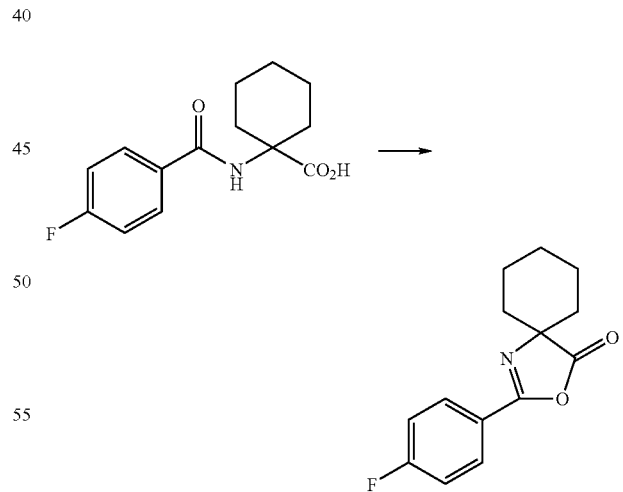

After a suspension of 13.3 g (50 mmol) of 1-[(4-fluorobenzoyl)amino]cyclohexanecarboxylic acid in 30 ml of acetic anhydride was stirred at 100° C. for 30 minutes, the reaction solution was concentrated under reduced pressure. Toluene was added to the residue, and the mixture was washed with water, a saturated aqueous sodium hydrogencarbonate solution, and then saturated brine. After the organic layer was dried with anhydrous sodium sulfate, the solvent was distilled off under reduced pressure. The residue was purified by silica gel column chromatography to obtain 8.5 g (69%) of the title compound.

1H-NMR (CDCl$_3$, δ) 1.49-1.60 (1H, m), 1.63-1.90 (9H, m), 7.13-7.20 (2H, m), 8.00-8.05 (2H, m)

Reference Example 176

2-[4-(4-Propylbdnzopiperazin-1-yl)phenyl]-3-oxa-1-azaspiro[4.5]dec-1-en-4-one

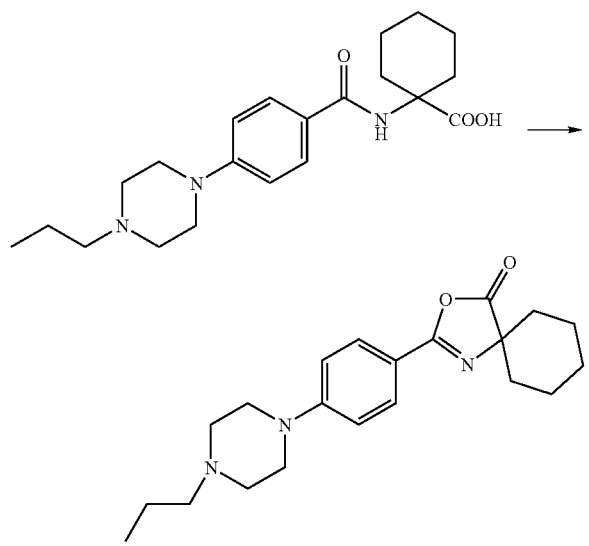

1.43 g (3.86 mmol) of 1-[[[4-(4-propylpiperazin-1-yl)phenyl]carbonyl]amino]cyclohexanecarboxylic acid was used instead of 1-[(phenylacetyl)amino]cyclohexanecarboxylic acid in the process according to Reference example 132 to obtain 1.33 g (98%) of the title compound.

1H-NMR (CDCl$_3$, δ): 0.94 (3H, t, J=8 Hz), 1.50-1.61 (3H, m), 1.61-1.69 (1H, m), 1.69-1.76 (2H, m), 1.79-1.84 (6H, m), 2.35 (1H, t, J=6 Hz), 2.36 (1H, t, J=6 Hz), 2.59 (4H, t, J=5 Hz), 3.35 (4H, t, J=5 Hz), 6.91 (2H, dd, J=2 Hz, 7 Hz), 7.86 (2H, dd, J=2 Hz, 7 Hz)

Reference Example 177

2-[4-(4-Propylpiperazin-1-yl)phenyl]-3-oxa-1-azaspiro[4.5]dec-1-en-4-one hydrochloride

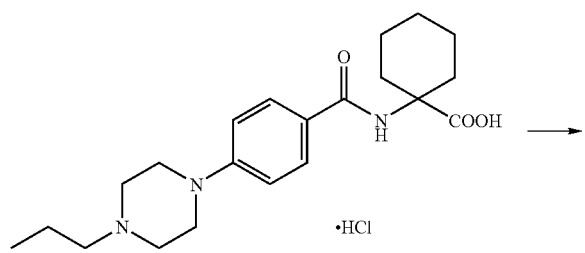

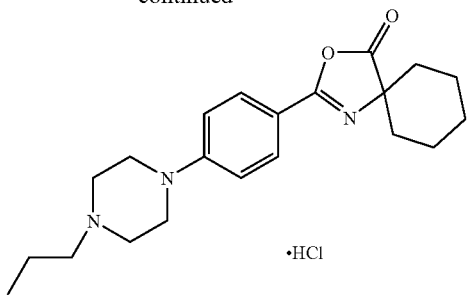

After a suspension of 631 mg (1.54 mmol) of 1-[[[4-(4-propylpiperazin-1-yl)phenyl]carbonyl]amino]cyclohexanecarboxylic acid hydrochloride in 18 ml of acetic anhydride was stirred at 100° C. for 1 hour, the reaction solution was concentrated under reduced pressure. The operation for adding toluene to the obtained residue and distilling off it under reduced pressure was carried out three times, and acetic anhydride was removed by azeotropic distillation to obtain 500 mg (83%) of the title compound.

1H-NMR (CDCl$_3$, δ): 1.05 (3H, t, J=8 Hz), 1.50-1.87 (10H, m), 1.95-2.06 (2H, m), 2.86-3.01, (4H, m), 3.59-3.68 (2H, m), 3.79-3.90 (4H, m), 6.91 (2H, dd, 2 Hz, 7 Hz), 7.91 (2H, dd, J=2 Hz, 7 Hz)

Example 1

N-[[1-[[(Phenylmethoxy)carbonyl]amino]cyclohexyl]carbonyl]-L-valinol

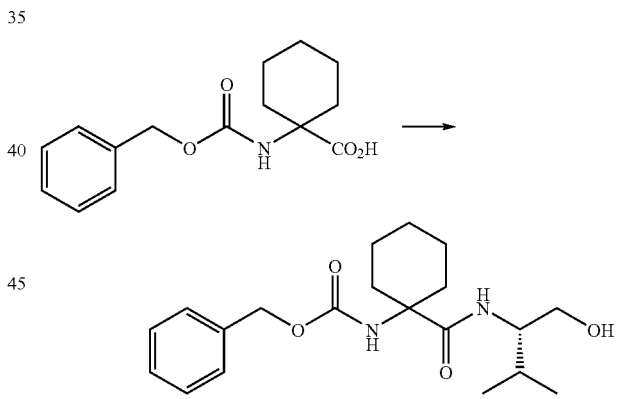

After 422 mg (2.2 mmol) of 1-ethyl-3-(3-dimethylaminopropyl)carbodiimide hydrochloride was added to a solution of 555 mg (2 mmol) of 1-[[(phenylmethoxy)carbonyl]amino] cyclohexanecarboxylic acid, 322 mg (2.1 mmol) of 1-hydroxybenzotriazole and 206 mg (2 mmol) of L-valinol in 20 ml of methylene chloride under ice-cooling, the mixture was stirred at room temperature for 18 hours. The reaction solution was concentrated under reduced pressure, ethyl acetate was added to the residue, and the mixture was washed with water, a 10% aqueous potassium hydrogensulfate solution, a saturated aqueous sodium hydrogencarbonate solution, and then saturated brine. The organic layer was dried with anhydrous sodium sulfate, the solvent was distilled off under reduced pressure. The residue was purified by silica gel column chromatography to obtain 662 mg (91%) of the title compound.

1H-NMR (CDCl₃, δ): 0.87 (3H, d, J=7 Hz), 0.92 (3H, d, J=7 Hz), 1.28-1.46 (3H, m), 1.52-1.70 (3H, m), 1.73-1.82 (1H, m), 1.85-2.03 (4H, m), 2.76 (1H, br-s), 3.42-4.47 (1H, m), 3.65-3.74 (2H, m), 5.02-5.16 (3H, m), 6.36 (1H, d, J=8 Hz), 7.30-7.40 (5H, m)

Example 2

N-[[1-[[(Phenylmethoxy)carbonyl]amino]cyclohexyl]carbonyl]-L-norleucinol

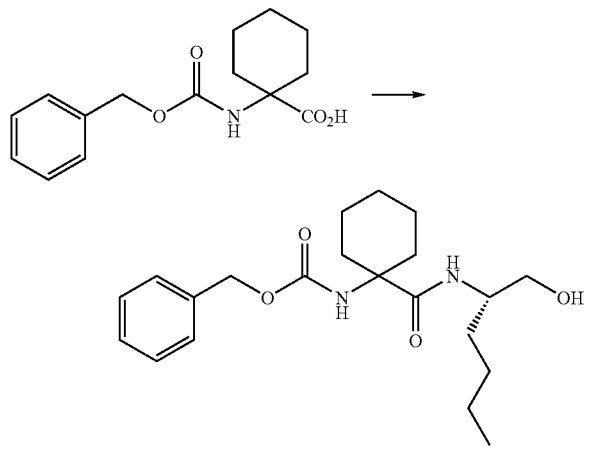

234 mg (2 mmol) of L-norleucinol was used instead of L-valinol in the process according to Example 1 to obtain 350 mg (75%) of the title compound.

1H-NMR (CDCl₃, δ): 0.88 (3H, t, J=7 Hz), 1.23-1.52 (9H, m), 1.58-1.70 (3H, m), 1.83-2.04 (4H, m), 2.83 (1H, br-s), 3.34-3.40 (1H, m), 3.70 (1H, br-s), 3.89 (1H, br-s), 5.02-5.13 (3H, m), 6.26 (1H, d, J=8 Hz), 7.31-7.40 (5H, m)

Example 3

N-[[1-[(2-Furanylcarbonyl)amino]cyclohexyl]carbonyl]-L-valinol

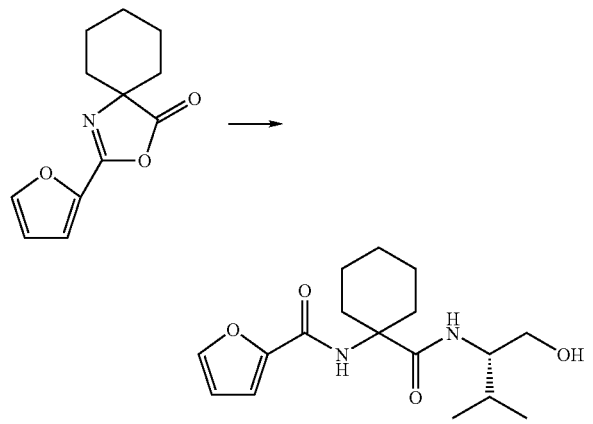

A solution of 8.81 ml (50.6 mmol) of N,N-diisopropylethylamine and 2.09 g (20.2 mmol) of L-valinol in 10 ml of methylene chloride was added to a solution of 3.71 g (16.9 mmol) of 2-(2-furanyl)-3-oxa-1-azaspiro[4.5]dec-1-en-4-one in 100 ml of toluene, and the mixture was refluxed under heating for 14 hours. The reaction solution was concentrated under reduced pressure, ethyl acetate was added to the residue, and the mixture was washed with water, a 10% aqueous potassium hydrogensulfate solution, a saturated aqueous sodium hydrogencarbonate solution, and then saturated brine. The organic layer was dried with anhydrous sodium sulfate, and the solvent was distilled off under reduced pressure. Ethyl acetate was added to the residue, and the mixture was stirred overnight. The obtained crystal was collected by filtration to give 4.06 g (74.7%) of the title compound.

1H-NMR (CDCl₃, δ): 0.93 (3H, d, J=7 Hz), 0.95 (3H, d, J=7 Hz) 1.32-1.56 (3H, m), 1.58-1.76 (3H, m), 1.80-1.90 (1H, m), 1.96-2.08 (2H, m), 2.14-2.24 (2H, m), 3.00-3.06 (1H, m), 3.52-3.58 (1H, m), 3.68-3.78 (2H, m), 6.49 (1H, s), 6.53 (1H, dd, J=4 Hz, 2 Hz), 6.75-6.77 (1H, m), 7.14 (1H, dd, J=4 Hz, 1 Hz), 7.49 (1H, dd, J=2 Hz, 1 Hz)

Example 4

N-[[1-[(2-Furanylcarbonyl)amino]cyclohexyl]carbonyl]-L-valinol

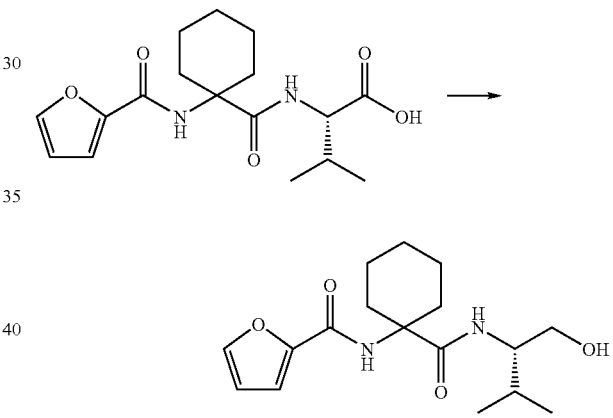

Under an argon atmosphere, 72 mg (0.59 mmol) of isopropyl chlorocarbonate was added to a solution of 200 mg (0.59 mmol) of N-[[1-[(2-furanylcarbonyl)amino]cyclohexyl]carbonyl]-L-valine and 60 mg (0.59 mmol) of triethylamine in 2 ml of tetrahydrofuran under ice-cooling. After the mixture was stirred at 0° C. for 2 hours, the reaction solution was filtered and poured into a solution of 45 mg (1.2 mmol) of sodium borohydride in 1 ml of water, and the mixture was stirred overnight. Ethyl acetate was added to the reaction solution, and the mixture was successively washed with a 10% aqueous potassium hydrogensulfate solution, a saturated aqueous sodium hydrogencarbonate solution and saturated brine, followed by drying with sodium sulfate. After the solvent was distilled off under reduced pressure, the obtained crystal was washed with ether to give 30 mg (16%) of the title compound.

1H-NMR (CDCl₃, δ): 0.93 (3H, d, J=7 Hz), 0.95 (3H, d, J=7 Hz), 1.32-1.56 (3H, m), 1.58-1.76 (3H, m), 1.80-1.90 (1H, m), 1.96-2.08 (2H, m), 2.14-2.24 (2H, m), 3.00-3.06 (1H, m), 3.52-3.58 (1H, m), 3.68-3.78 (2H, m), 6.49 (1H, s), 6.53 (1H, dd, J=4 Hz, 2 Hz), 6.75-6.77 (1H, m), 7.14 (1H, dd, J=4 Hz, 1 Hz), 7.49 (1H, dd, J=2 Hz, 1 Hz)

Example 5

N-[[1-[(2-Furanylcarbonyl)amino]cyclohexyl]carbonyl]-L-valinol

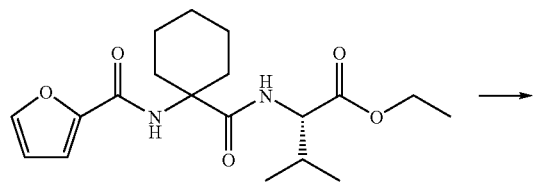

Under an argon atmosphere, 31 mg (0.82 mmol) of lithium aluminum hydride was added to 1 ml of diethyl ether placed in a flask. Under ice-cooling, a solution of 0.3 g (0.82 mmol) of the above compound in 1 ml of tetrahydrofuran was added to the flask, and the mixture was stirred for 1 hour and 30 minutes. Ice water was added to the reaction solution. Ethyl acetate was added thereto, and the mixture was successively washed with a 10% aqueous potassium hydrogensulfate solution, a saturated aqueous sodium hydrogencarbonate solution and saturated brine. After it was dried with sodium sulfate, the solvent was distilled off under reduced pressure. The obtained crystal was washed with ether to give 155 mg (60%) of the title compound.

1H-NMR (CDCl$_3$, δ): 0.93 (3H, d, J=7 Hz), 0.95 (3H, d, J=7 Hz), 1.32-1.56 (3H, m), 1.58-1.76 (3H, m), 1.80-1.90 (1H, m), 1.96-2.08 (2H, m), 2.14-2.24 (2H, m), 3.00-3.06 (1H, m), 3.52-3.58 (1H, m), 3.68-3.78 (2H, m), 6.49 (1H, s), 6.53 (1H, dd, J=4 Hz, 2 Hz), 6.75-6.77 (1H, m), 7.14 (1H, dd, J=4 Hz, 1 Hz), 7.49 (1H, dd, J=2 Hz, 1 Hz)

Example 6

N-[[1-[(4-Morpholinylcarbonyl)amino]cyclohexyl]carbonyl]-L-norleucinol

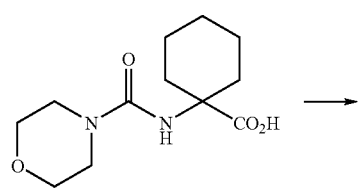

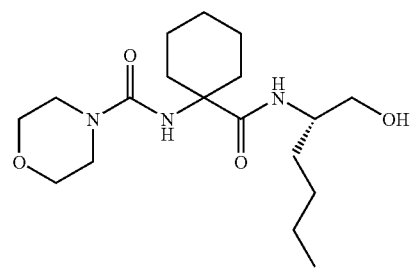

513 mg (2 mmol) of 1-[(4-morpholinylcarbonyl)amino]cyclohexanecarboxylic acid was used instead of 1-[[(phenylmethoxy)carbonyl]amino]cyclohexanecarboxylic acid in the process according to Example 2 to obtain 215 mg (30%) of the title compound.

1H-NMR (CDCl$_3$, δ): 0.89 (3H, t, J=7 Hz), 1.26-1.56 (9H, m), 1.60-1.73 (3H, m), 1.85-2.05 (4H, m), 3.33-3.43 (5H, m), 3.54 (1H, t, J=7 Hz), 3.66-3.73 (4H, m), 3.76-3.82 (1H, m), 3.83-3.93 (1H, m), 4.64 (1H, br-s), 6.35 (1H, d, J=8 Hz)

Reference Example 178

N—[N-[(Phenylmethoxy)carbonyl]-L-leucyl]-L-valinol

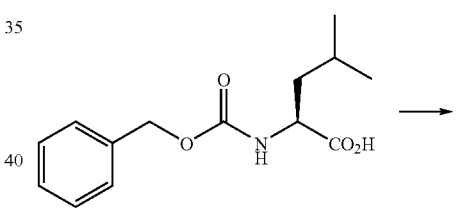

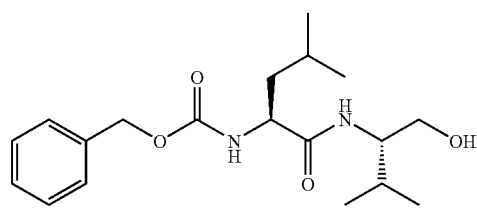

N-[(Phenylmethoxy)carbonyl]-L-leucine was used instead of 1-[[(phenylmethoxy)carbonyl]amino]cyclohexanecarboxylic acid in the process according to Example 1 to obtain 659 mg (94%) of the title compound.

1H-NMR (CDCl$_3$, δ): 0.83-0.99 (12H, m), 1.46-1.74 (3H, m), 1.78-1.90 (1H, m), 2.42 (1H, br-s), 3.57-3.72 (3H, m), 4.10-4.17 (1H, m), 5.04-5.17 (3H, m), 6.22 (1H, d, J=7 Hz), 7.27-7.39 (5H, m)

Reference Example 179

N—[N-[(Phenylmethoxy)carbonyl]-L-leucyl]-L-norleucinol

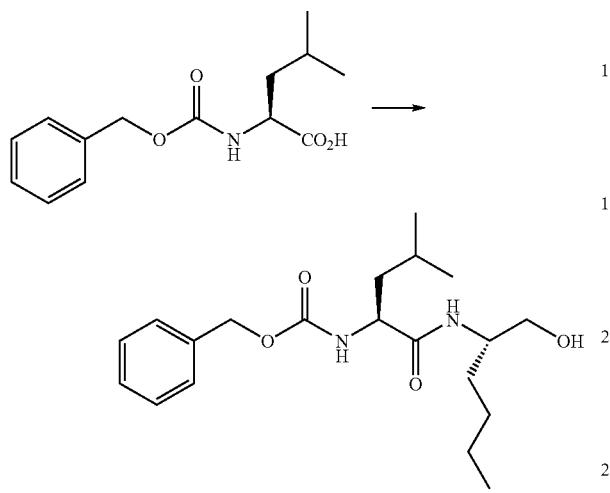

N-[(Phenylmethoxy)carbonyl]-L-leucine was used instead of 1-[[(phenylmethoxy)carbonyl]amino]cyclohexanecarboxylic acid and L-norleucinol was used instead of L-valinol in the process according to Example 1 to obtain 421 mg (58%) of the title compound.

1H-NMR (CDCl$_3$, δ): 0.88 (3H, t, J=7 Hz), 0.95 (6H, d, J=7 Hz), 1.23-2.72 (9H, m), 2.44 (1H, br-s), 3.47-3.71 (2H, m), 3.89 (1H, br-s), 4.10-4.17 (1H, m), 5.08-5.16 (3H, m), 6.10 (1H, d, J=6 Hz), 7.31-7.39 (5H, m)

Reference Example 180

N—[N-(4-Morpholinylcarbonyl)-L-leucyl]-L-norleucinol

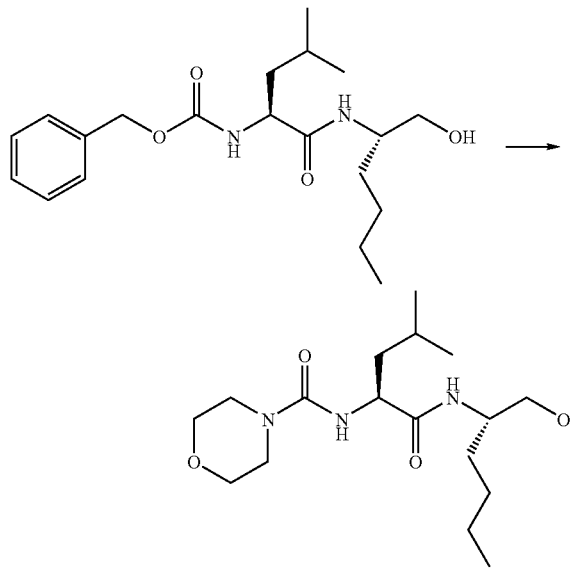

70 mg of 10% palladium-carbon was added to a solution of 700 mg (2 mmol) of N—[N-[(phenylmethoxy)carbonyl]-L-leucyl]-L-norleucinol obtained in Reference example 179 in 10 ml of methanol, and the mixture was stirred under a hydrogen atmosphere at room temperature overnight. After the reaction solution was filtered, the filtrate was concentrated under reduced pressure. 20 ml of methylene chloride and 404 mg (4 mmol) of triethylamine were added to the residue. A solution of 299 mg (2 mmol) of 4-morpholinecarbonyl chloride in 3 ml of methylene chloride was added to the mixture solution under ice-cooling. The reaction solution was returned to room temperature and stirred overnight. After the reaction solution was washed with water and then saturated brine, it was dried with anhydrous sodium sulfate, and the solvent was distilled off under reduced pressure. Ether was added to the residue to wash it to obtain 488 mg (71%) of the title compound.

1H-NMR (CDCl$_3$, δ): 0.89 (3H, t, J=7 Hz), 0.94 (3H, d, J=7 Hz), 0.96 (3H, d, J=7 Hz), 1.23-1.37 (4H, m), 1.43-1.72 (5H, m), 2.67 (1H, br-s), 3.31-3.44 (4H, m), 3.52-3.60 (1H, m), 3.65-3.73 (5H, m), 3.82-3.89 (1H, m), 4.24-4.32 (1H, m), 4.82 (1H, d, J=8 Hz), 6.31 (1H, d, J=8 Hz)

Reference Example 181

N—[N-(2-Furanylcarbonyl)-L-leucyl]-L-valinol

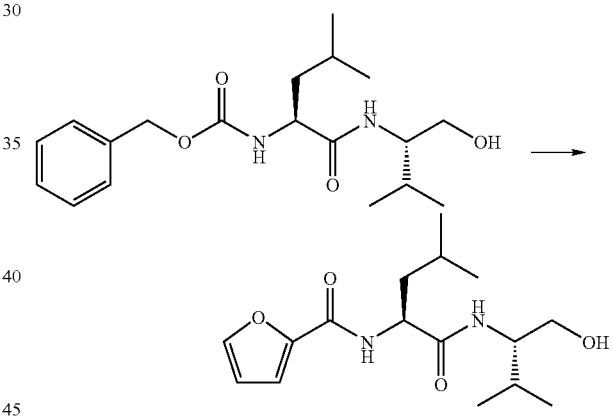

30 mg of 10% palladium-carbon was added to a solution of 350 mg (1 mmol) of N—[N-[(phenylmethoxy)carbonyl]-L-leucyl]-L-valinol obtained in Reference example 178 in 10 ml of methanol, and the mixture was stirred under a hydrogen atmosphere at room temperature overnight. After the reaction solution was filtered, the filtrate was concentrated under reduced pressure. 10 ml of ethyl acetate, 10 ml of water and further 159 mg (1.5 mmol) of sodium carbonate were added to the residue. A solution of 131 mg (1 mmol) of 2-furancarbonyl chloride in 3 ml of ethyl acetate was added to the mixture solution under ice-cooling. The reaction solution was returned to room temperature and stirred overnight. The aqueous layer of reaction solution was separately collected and extracted with ethyl acetate. The organic layer was combined and after it was washed with 10% potassium hydrogensulfate, and then saturated brine, it was dried with anhydrous sodium sulfate. The solvent was distilled off under reduced pressure, ether was added to the residue, and the crystal was washed to obtain 268 mg (86%) of the title compound.

1H-NMR (CDCl$_3$, δ): 0.91 (3H, t, J=7 Hz), 0.93 (3H, t, J=7 Hz), 0.97 (3H, t, J=7 Hz), 0.99 (3H, t, J=7 Hz), 1.65-1.94 (4H, m), 2.47 (1H, t, J=5 Hz), 3.63-3.74 (3H, m), 4.54-4.62 (1H, m), 6.42 (1H, d, J=7 Hz), 6.52 (1H, dd, J=4 Hz, 2 Hz), 6.68 (1H, d, J=8 Hz), 7.14 (1H, dd, J=4 Hz, 1 Hz), 7.47 (1H, dd, J=2 Hz, 1 Hz)

Reference Example 182

N-[[1-[(2-Furanylcarbonyl)amino]cyclohexyl]carbonyl]-L-valine ethyl ester

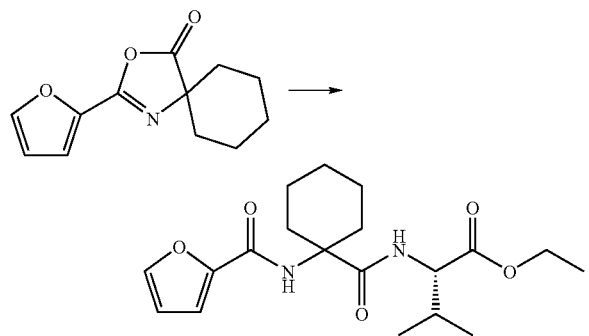

30 ml of dimethylformamide was added to a flask charged with 5 g (27 mmol) of L-valine ethyl ester hydrochloride and 5 g (22.8 mmol) of 2-(2-furanyl)-3-oxa-1-azaspiro[4.5]dec-1-en-4-one. Then, 3.53 g (27.4 mmol) of diisopropylethylamine was added thereto, and the mixture was stirred for 3 days. After the solvent was distilled off under reduced pressure, ethyl acetate was added thereto, and the mixture was successively washed with a 10% aqueous potassium hydrogensulfate solution and saturated brine, followed by drying with sodium sulfate. After the solvent was distilled off under reduced pressure, it was purified by silica gel chromatography to obtain 8.3 g (quantitative) of the title compound.

1H-NMR (CDCl$_3$, δ): 0.89 (3H, d, J=7 Hz), 0.94 (3H, d, J=7 Hz), 1.25 (3H, t, J=7 Hz), 1.35-1.70 (6H, m), 1.98-2.01 (2H, m), 2.19-2.23 (2H, m), 2.31-2.39 (1H, m), 4.11-4.19 (2H, m), 4.49 (1H, dd, J=9 Hz, 5 Hz), 6.34 (1H, s), 6.53 (1H, dd, J=3 Hz, 1 Hz), 7.15 (1H, dd, J=3 Hz, 1 Hz), 7.48 (1H, dd, J=2 Hz, 1 Hz), 7.58 (1H, d, J=9 Hz)

Reference Example 183

N-[[1-[(2-Furanylcarbonyl)amino]cyclohexyl]carbonyl]-L-valine

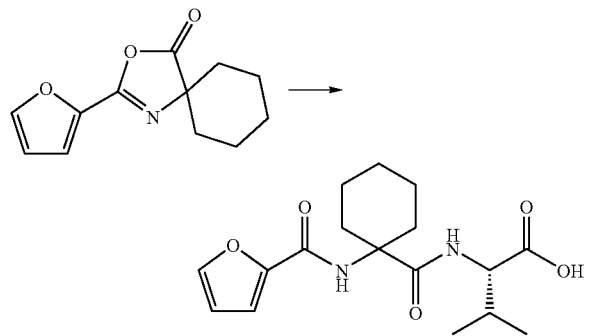

10 ml of N-methylmorpholine was added to 1.0 g (9.1 mmol) of L-valine and 2.0 g (9.1 mmol) of 2-(2-furanyl)-3-oxa-1-azaspiro[4.5]dec-1-en-4-one, and the mixture was refluxed under heating overnight. The reaction solution was distilled off under reduced pressure, ethyl acetate was added thereto, and the mixture was washed with a 10% aqueous potassium hydrogensulfate solution and then saturated brine, followed by drying with anhydrous sodium sulfate. The solvent was distilled off under reduced pressure and the residue was purified by silica gel chromatography to obtain 384 mg (12.5%) of the title compound.

1H-NMR (CDCl$_3$, δ): 0.93 (3H, d, J=7 Hz), 0.97 (3H, d, J=7 Hz), 1.33-1.48 (3H, m), 1.64-1.73 (3H, m), 1.98 (2H, dt, J=14 Hz, 4 Hz), 2.22-2.30 (3H, m), 4.46 (1H, m), 6.43 (1H, s), 6.53 (1H, dd, J=3 Hz, 2 Hz), 7.17 (1H, dd, J=3 Hz, 1 Hz), 7.48 (1H, dd, J=2 Hz, 1 Hz), 7.55 (1H, d, J=8 Hz)

Example 7

N-[[1-[[(Phenylmethoxy)carbonyl]amino]cyclohexyl]carbonyl]-L-valinal

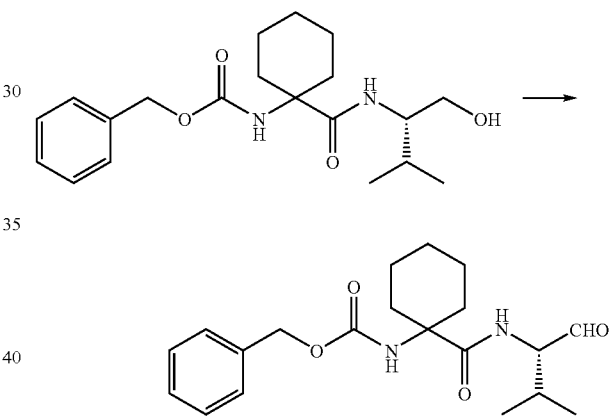

Under an argon atmosphere, 1.22 g (9.44 mmol) of N,N-diisopropylethylamine was added dropwise to a solution of 1.50 g (9.44 mmol) of sulfur trioxide-pyridine complex in 10 ml of anhydrous dimethyl sulfoxide and 5 ml of anhydrous methylene chloride under ice-cooling, the mixture was stirred for 15 minutes. Further, a solution of 570 mg (1.57 mmol) of N-[[1-[[(phenylmethoxy)carbonyl]amino]cyclohexyl]carbonyl]-L-valinol in 3 ml of anhydrous dimethyl sulfoxide was added to the reaction solution under ice-cooling, and the mixture was stirred at the same temperature for 2 hours. The reaction solution was poured into ice water and extracted with ethyl acetate twice. The organic layer was washed with a 10% aqueous citric acid solution, a saturated aqueous sodium hydrogencarbonate solution, and then saturated brine, and after it was dried with anhydrous magnesium sulfate, the solvent was distilled off under reduced pressure. 20 ml of diisopropyl ether was added to the residue, and the mixture was stirred at room temperature for 18 hours. The obtained crystal was collected by filtration to give 435 mg (77%) of the title compound.

1H-NMR (CDCl$_3$, δ): 0.88 (3H, d, J=7 Hz), 0.97 (3H, d, J=7 Hz), 1.22-1.44 (3H, m), 1.59-1.70 (3H, m), 1.85-2.15

(4H, m), 2.22-2.34 (1H, m), 4.48 (1H, s), 4.96 (1H, s), 5.11 (2H, s), 7.10-7.41 (6H, m), 9.59 (1H, s)

Example 8

N-[[1-[[(Phenylmethoxy)carbonyl]amino]cyclohexyl]carbonyl]-L-norleucinal

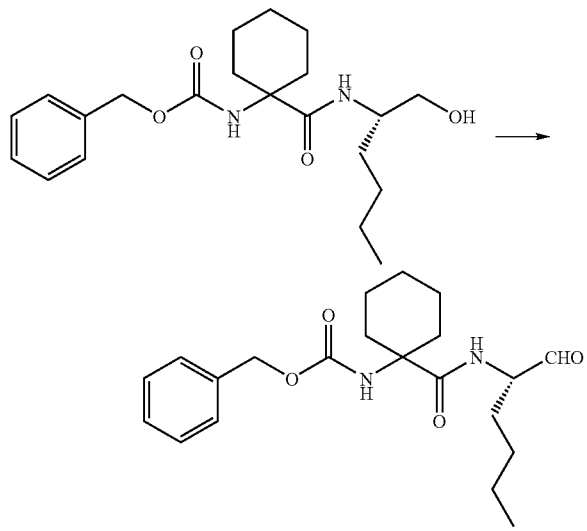

465 mg of (1.24 mmol) of N-[[1-[[(phenylmethoxy)carbonyl]amino]cyclohexyl]carbonyl]-L-norleucinol was used instead of N-[[1-[[(phenylmethoxy)carbonyl]amino]cyclohexyl]carbonyl]-L-valinol in the process according to Example 7 to obtain 350 mg (75%) of the title compound.

1H-NMR (CDCl$_3$, δ): 0.88 (3H, d, J=7 Hz), 1.19-1.43 (7H, m), 1.51-1.70 (4H, m), 1.82-2.13 (5H, m), 4.42 (1H, br-s), 4.95 (1H, s), 5.10 (2H, s), 7.10 (1H, br-s), 7.29-7.42 (5H, m), 9.53 (1H, s)

Example 9

N-[[1-[(2-Furanylcarbonyl)amino]cyclohexyl]carbonyl]-L-valinal

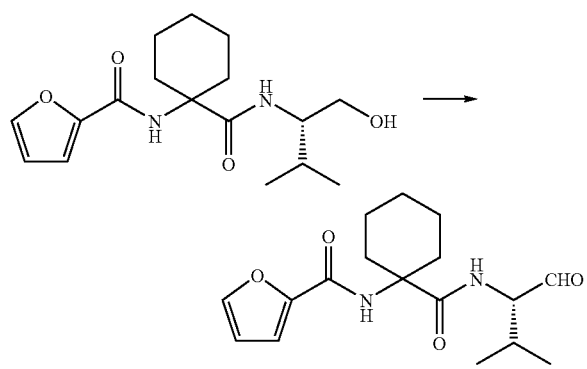

3.50 g (10.9 mmol) of N-[[1-[(2-furanylcarbonyl)amino]cyclohexyl]carbonyl]-L-valinol was used instead of N-[[1-[[(phenylmethoxy)carbonyl]amino]cyclohexyl]carbonyl]-L-valinol in the process according to Example 7 to obtain 3.14 g (90.3%) of the title compound.

1H-NMR (CDCl$_3$, δ): 0.94 (3H, d, J=7 Hz), 1.01 (3H, d, J=7 Hz), 1.30-1.40 (1H, m), 1.41-1.54 (2H, m), 1.62-1.76 (3H, m), 1.95-2.04 (2H, m), 2.20-2.26 (1H, m), 2.28-2.36 (2H, m), 4.44 (1H, dd, J=8 Hz, 5 Hz,), 6.38 (1H, br-s), 6.54 (1H, dd, J=4 Hz, 2 Hz), 7.15 (1H, dd, J=4 Hz, 1 Hz), 7.49 (1H, dd, J=2 Hz, 1 Hz), 7.68 (1H, d, J=8 Hz), 9.60 (1H, s)

Example 10

N-[[1-[(4-Morpholinylcarbonyl)amino]cyclohexyl]carbonyl]-L-norleucinal

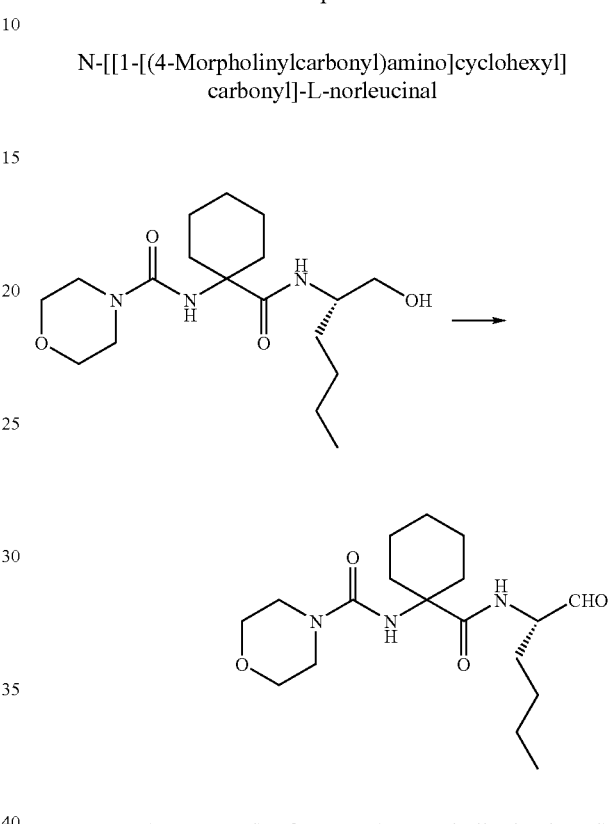

205 mg (0.58 mmol) of N-[[1-[(4-morpholinylcarbonyl)amino]cyclohexyl]carbonyl]-L-norleucinol was used instead of N-[[1-[[(phenylmethoxy)carbonyl]amino]cyclohexyl]carbonyl]-L-valinol in the process according to Example 7 to obtain 125 mg (61%) of the title compound.

1H-NMR (CDCl$_3$, δ): 0.89 (3H, t, J=7 Hz), 1.23-1.42 (7H, m), 1.52-1.71 (4H, m), 1.83-1.98 (3H, m), 2.05-2.18 (2H, m), 3.34-3.42 (4H, m), 3.65-3.76 (4H, m), 4.37 (1H, dt, J=7 Hz, 7 Hz), 4.48 (1H, s), 7.81 (1H, d, J=7 Hz), 9.55 (1H, s)

Reference Example 184

N—[N-[(Phenylmethoxy)carbonyl]-L-leucyl]-L-valinal

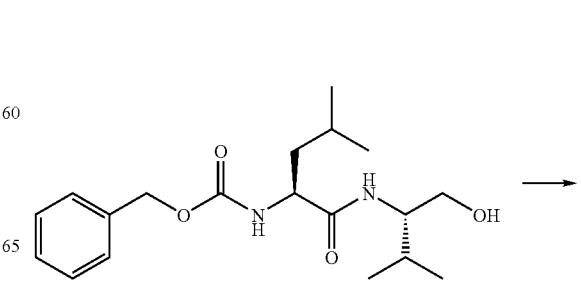

-continued

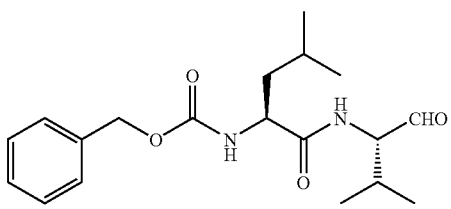

280 mg (0.8 mmol) of N—[N-[(phenylmethoxy)carbonyl]-L-leucyl]-L-valinol was used instead of N-[[1-[[(phenylmethoxy)carbonyl]amino]cyclohexyl]carbonyl]-L-valinol in the process according to Example 7 to obtain 278 mg (quantitative) of the title compound.

1H-NMR (CDCl₃, δ): 0.83-1.01 (12H, m), 1.48-1.59 (1H, m), 1.62-1.74 (2H, m), 2.28-2.37 (1H, m), 4.19-4.28 (1H, m), 4.51-4.56 (1H, m), 5.05-5.17 (3H, m), 6.51 (1H, d, J=7 Hz), 7.27-7.39 (5H, m), 9.64 (1H, s)

Reference Example 185

N—[N-[(Phenylmethoxy)carbonyl]-L-leucyl]-L-norleucinal

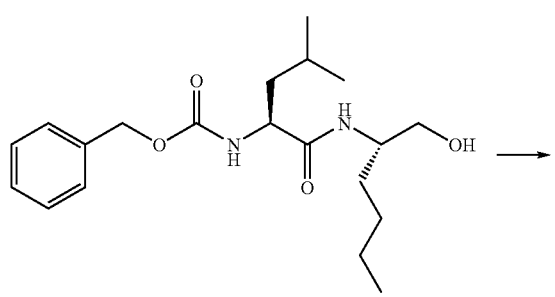

253 mg (0.7 mmol) of N—[N-[(phenylmethoxy)carbonyl]-L-leucyl]-L-norleucinol was used instead of N-[[1-[[(phenylmethoxy)carbonyl]amino]cyclohexyl]carbonyl]-L-valinol in the process according to Example 7 to obtain 195 mg (78%) of the title compound.

1H-NMR (CDCl₃, δ): 0.89 (3H, t, J=7 Hz), 0.95 (6H, d, J=7 Hz), 1.22-1.39 (4H, m), 1.47-1.72 (4H, m), 1.83-1.97 (1H, m), 4.19-4.26 (1H, m), 4.45-4.53 (1H, m), 5.08-5.17 (3H, m), 6.46 (1H, br-s), 7.29-7.39 (5H, m), 9.57 (1H, s)

Reference Example 186

N—[N-(4-Morpholinylcarbonyl)-L-leucyl]-L-norleucinal

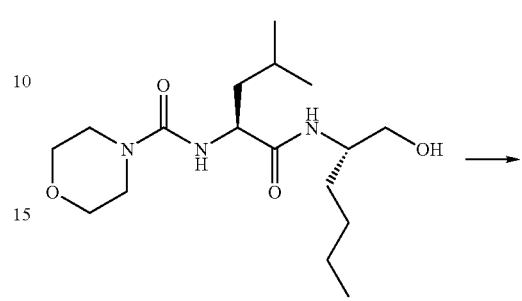

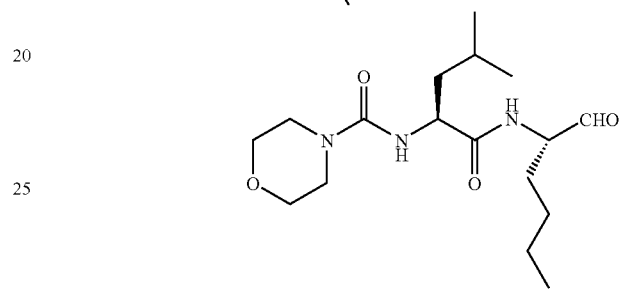

473 mg (1.4 mmol) of N—[N-(4-morpholinylcarbonyl)-L-leucyl]-L-norleucinol was used instead of N-[[1-[[(phenylmethoxy)carbonyl]amino]cyclohexyl]carbonyl]-L-valinol in the process according to Example 7 to obtain 315 mg (67%) of the title compound.

1H-NMR (CDCl₃, δ): 0.90 (3H, t, J=7 Hz), 0.96 (3H, d, J=6 Hz), 0.97 (3H, d, J=6 Hz), 1.23-1.39 (4H, m), 1.50-1.76 (4H, m), 1.85-1.96 (1H, m), 3.32-3.43 (4H, m), 3.63-3.72 (4H, m), 4.37-4.46 (2H, m), 4.86 (1H, d, J=8 Hz), 6.69 (1H, d, J=7 Hz), 9.56 (1H, s)

Reference Example 187

N—[N-(2-Furanylcarbonyl)-L-leucyl]-L-valinal

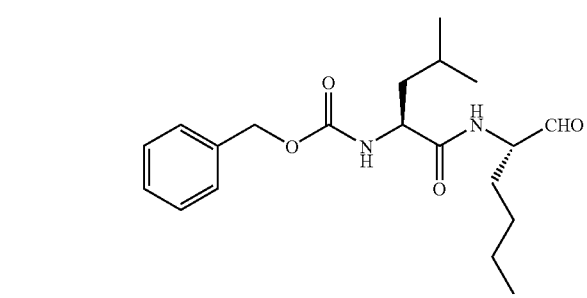

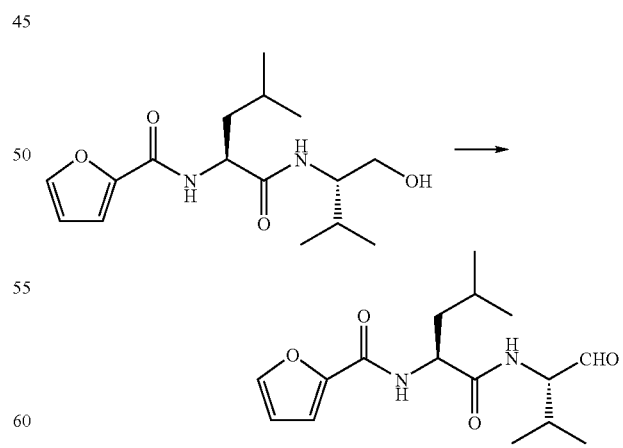

256 mg (0.8 mmol) of N—[N-(2-furanylcarbonyl)-L-leucyl]-L-valinol was used instead of N-[[1-[[(phenylmethoxy)carbonyl]amino]cyclohexyl]carbonyl]-L-valinol in the process according to Example 7 to obtain 175 mg (72%) of the title compound.

1H-NMR (CDCl₃, δ): 0.90-1.02 (12H, m), 1.64-1.82 (3H, m), 2.29-2.36 (1H, m), 4.52 (1H, dd, J=8 Hz, 5 Hz), 4.67 (1H, td, J=8 Hz, 6 Hz), 6.51 (1H, dd, J=4 Hz, 2 Hz), 6.67-6.73 (2H, m), 7.14 (1H, dd, J=4 Hz, 1 Hz), 7.46 (1H, dd, J=2 Hz, 1 Hz), 9.65 (1H, s)

Reference Example 188

1-[(2-Benzothienylcarbonyl)amino]cyclohexanecarboxylic acid phenylmethyl ester

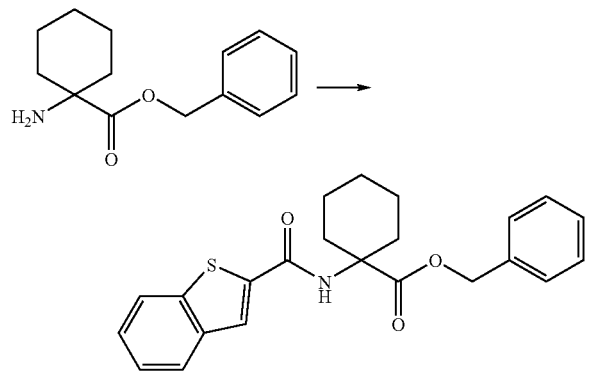

Under ice-cooling, 5.9 g (31 mmol) of 1-ethyl-3-(3-dimethylaminopropyl)carbodiimide hydrochloride was added to a solution of 5 g (28 mmol) of 2-benzothiophenecarboxylic acid, 6.5 g (28 mmol) of 1-aminocyclohexanecarboxylic acid phenylmethyl ester and 4.5 g (29 mmol) of 1-hydroxybenzotriazole in methylenechloride. After the mixture was stirred at room temperature overnight, the reaction solvent was distilled off under reduced pressure. Water was added to the residue and the mixture was extracted with ethyl acetate twice. The obtained organic layer was washed with a 10% aqueous potassium hydrogensulfate solution, a saturated aqueous sodium hydrogencarbonate solution, and then saturated brine, followed by drying with anhydrous sodium sulfate. The solvent was distilled off under reduced pressure, and diethyl ether was added to the obtained residue, followed by stirring of the mixture overnight. The crystal was collected by filtration and was heated and dried under reduced pressure to obtain 10 g (91%) of the title compound.

1H-NMR (CDCl₃, δ): 1.25-1.78 (6H, m), 1.93-2.05 (2H, m), 2.12-2.25 (2H, m), 5.18 (2H, s), 6.24 (1H, s), 7.20-7.38 (5H, m), 7.38-7.51 (2H, m), 7.77 (1H, s), 7.80-7.91 (2H, m)

Reference Example 189

1-[(2-Benzothienylcarbonyl)amino]cyclohexanecarboxylic acid

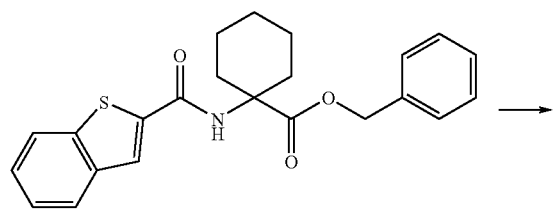

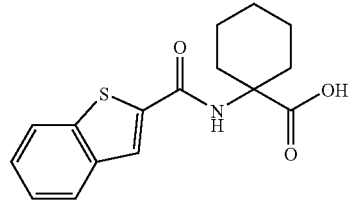

42 ml of 2N sodium hydroxide aqueous solution was added to a solution of 10 g (24 mmol) of 1-[(2-benzothienylcarbonyl)amino]cyclohexanecarboxylic acid phenylmethyl ester in 20 ml of tetrahydrofuran, and the mixture was refluxed under heating for 3 days. After ether was added to the reaction solution to wash it, the aqueous layer was neutralized by concentrated hydrochloric acid, and the precipitated crystal was collected by filtration. The obtained crystal was dried under reduced pressure to give 6.1 g (80%) of the title compound.

1H-NMR (CDCl₃, δ): 1.31-1.85 (6H, m), 1.91-2.08 (2H, m), 2.21-2.35 (2H, m), 6.22 (1H, s), 7.38-7.53 (2H, m), 7.80-7.93 (3H, m)

Reference Example 190

2-(2-Benzothienyl)-3-oxa-1-azaspiro[4.5]dec-1-en-4-one 4.1 g (21 mmol) of 1-ethyl-3-(3-dimethylaminopropyl)carbodiimide hydrochloride was added to a solution of 5 g (16 mmol) of 1-[(2-benzothienylcarbonyl)amino]cyclohexanecarboxylic acid in 50 ml of methylene chloride. After the mixture was stirred at room temperature for 4 hours, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine. The organic layer was dried with anhydrous sodium sulfate and the solvent was distilled off under reduced pressure to obtain 3.5 g (75%) of the title compound.

1H-NMR (CDCl₃, δ): 1.45-1.98 (10H, m), 7.38-7.51 (2H, m), 7.80-7.91 (2H, m), 7.93 (1H, s)

Reference Example 191

1-[[[4-(Chloromethyl)phenyl]carbonyl]amino]cyclohexanecarboxylic acid methyl ester

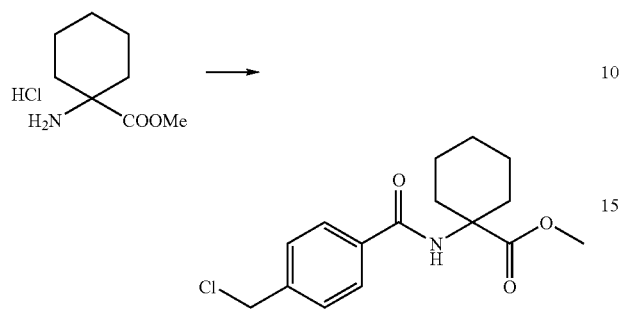

Under ice-cooling, 9.96 g (52 mmol) of 1-ethyl-3-(3-dimethylaminopropyl)carbodiimide hydrochloride was added to a solution of 8.8 g (52 mmol) of 4-(chloromethyl)benzoic acid, 10 g (52 mmol) of 1-aminocyclohexanecarboxylic acid methyl ester hydrochloride, 15 g (152 mmol) of triethylamine and 8.63 g (56 mmol) of 1-hydroxybenzotriazole in methylene chloride. After the mixture was stirred at room temperature overnight, the reaction solvent was distilled off under reduced pressure. Water was added to the residue and the mixture was extracted with ethyl acetate twice. The obtained organic layer was washed with a 10% aqueous potassium hydrogensulfate solution, a saturated aqueous sodium hydrogencarbonate solution, and then saturated brine, followed by drying with anhydrous sodium sulfate. The obtained residue was purified by silica gel column chromatography to give 8.5 g (53%) of the title compound.

1H-NMR (CDCl$_3$, δ): 1.25-1.73 (6H, m), 1.83-2.00 (2H, m), 2.08-2.21 (2H, m), 3.71 (3H, s), 5.56 (2H, s), 6.30 (1H, s), 7.44 (2H, dd, J=8 Hz, 2 Hz), 7.75 (2H, dd, J=8 Hz, 2 Hz)

Reference Example 192

1-[[[4-(Hydroxymethyl)phenyl]carbonyl]amino]cyclohexanecarboxylic acid phenylmethyl ester

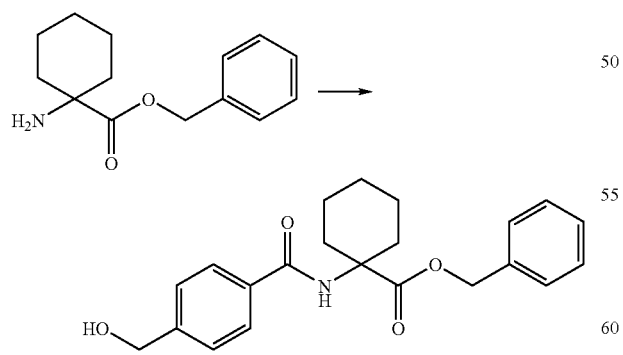

Under ice-cooling, 6.94 g (36 mmol) of 1-ethyl-3-(3-dimethylaminopropyl)carbodiimide hydrochloride was added to a solution of 5 g (33 mmol) of 4-(hydroxymethyl)benzoic acid, 7.7 g (33 mmol) of 1-aminocyclohexanecarboxylic acid phenylmethyl ester and 5.29 g (35 mmol) of 1-hydroxybenzotriazole in methylene chloride. After the mixture was stirred at room temperature overnight, the reaction solvent was distilled off under reduced pressure. Water was added to the residue and the mixture was extracted with ethyl acetate twice. The obtained organic layer was washed with a 10% aqueous potassium hydrogensulfate solution, a saturated aqueous sodium hydrogencarbonate solution, and then saturated brine, followed by drying with anhydrous sodium sulfate. The obtained residue was purified by silica gel column chromatography to give 6.83 g (56%) of the title compound.

1H-NMR (CDCl$_3$, δ): 1.23-1.79 (6H, m), 1.82-2.23 (4H, m), 4.73 (2H, m), 5.16 (2H, s), 6.25 (1H, s), 7.20-7.32 (5H, m), 7.32-7.43 (2H, m), 7.62-7.79 (2H, m)

Reference Example 193

1-[[[4-[(Dimethylamino)methyl]phenyl]carbonyl]amino]cyclohexanecarboxylic acid methyl ester

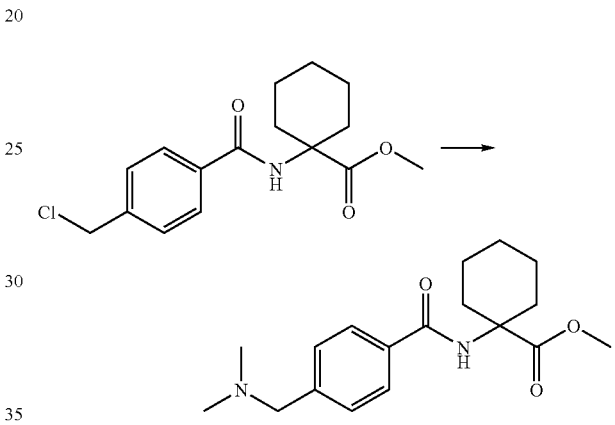

30 ml of 40% aqueous dimethylamine solution was added to 4.5 g (14.5 mmol) of 1-[[[4-(chloromethyl)phenyl]carbonyl]amino]cyclohexanecarboxylic acid methyl ester, and the mixture was refluxed under heating for 3 hours. The reaction solution was distilled off under reduced pressure, a saturated aqueous sodium bicarbonate solution was added thereto, and the mixture was extracted with ethyl acetate. The organic layer was washed with saturated brine and dried with anhydrous sodium sulfate. The solvent was distilled off under reduced pressure, diisopropyl ether was added to the residue, and the mixture was stirred overnight. The precipitated solid was collected by filtration to obtain 2.3 g (50%) of the title compound.

1H-NMR (CDCl$_3$, δ): 1.30-2.19 (10H, m), 2.24 (6H, s), 3.46 (2H, s), 3.76 (3H, s), 6.22 (1H, s), 7.38 (2H, d, J=9 Hz), 7.73 (2H, d, J=9 Hz)

Reference Example 194

1-[[[4-[(Dimethylamino)methyl]phenyl]carbonyl]amino]cyclohexanecarboxylic acid phenylmethyl ester

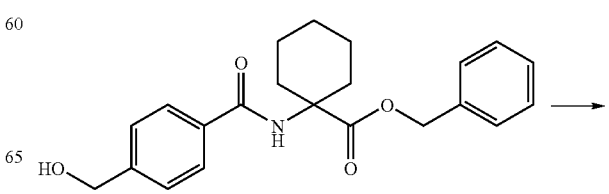

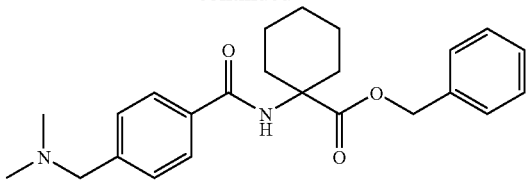

Under ice-cooling, 1 g (9 mmol) of methanesulfonyl chloride was added dropwise to a solution of 3 g (8 mmol) of 1-[[[4-(hydroxymethyl)phenyl]carbonyl]amino]cyclohexanecarboxylic acid phenylmethyl ester and 2.46 g (24 mmol) of triethylamine in methylene chloride. After the reaction mixture was stirred at room temperature for 1 hour, 20 ml of 2N dimethylamine-tetrahydrofuran solution was added, and the mixture was stirred overnight. The reaction solution was distilled off under reduced pressure, a saturated aqueous sodium bicarbonate solution was added thereto, and the mixture was extracted with ethyl acetate. The organic layer was washed with saturated brine and dried with anhydrous sodium sulfate. The solvent was distilled off under reduced pressure and it was purified by silica gel column chromatography to obtain 700 mg (22%) of the title compound.

1H-NMR (CDCl$_3$, δ): 1.30-2.01 (9H, m), 2.12-2.28 (1H, m), 2.24 (6H, s), 3.46 (2H, s), 5.17 (2H, s), 6.25 (1H, s), 7.21-7.32 (5H, m), 7.37 (2H, dd, J=9 Hz, 2 Hz), 7.10 (2H, dd, J=9 Hz, 2 Hz)

Reference Example 195

2-[4-[(Dimethylamino)methyl]phenyl]-3-oxa-1-azaspiro[4.5]dec-1-en-4-one

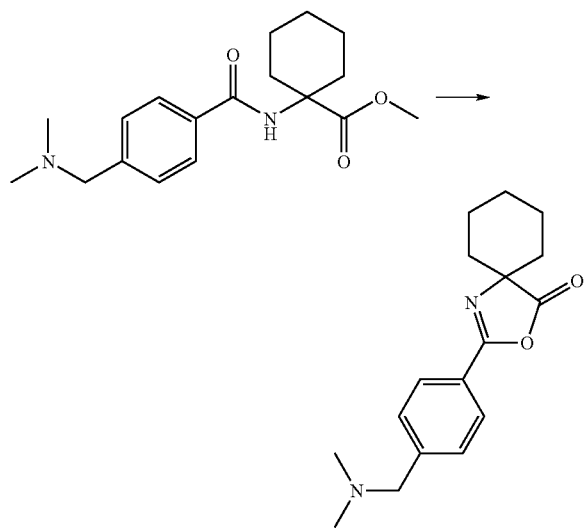

29 ml of 2N aqueous sodium hydroxide solution was added to a solution of 1.85 g (5.8 mmol) of 1-[[[4-[(dimethylamino)methyl]phenyl]carbonyl]amino]cyclohexanecarboxylic acid methyl ester in 29 ml of tetrahydrofuran, and the mixture was refluxed under heating overnight. After the mixture was neutralized by concentrated hydrochloric acid, the reaction mixture was distilled off under reduced pressure. 30 ml of methylene chloride, 1.76 g (17 mmol) of triethylamine and 1.67 g (8.7 mmol) of 1-ethyl-3-(3-dimethylaminopropyl)carbodiimide hydrochloride were added to the residue, and the mixture was stirred for 1 hour. The reaction solution was distilled off under reduced pressure, a saturated aqueous sodium bicarbonate solution was added thereto, and the mixture was extracted with ethyl acetate. The organic layer was washed with a saturated aqueous sodium bicarbonate solution and dried with anhydrous sodium sulfate. The solvent was distilled off under reduced pressure to obtain 1.33 g (80%) of the title compound.

1H-NMR (CDCl$_3$, δ): 1.50-1.88 (10H, m), 2.25 (6H, s), 3.48 (2H, s), 7.43 (2H, dd, J=9 Hz, 2 Hz), 7.96 (2H, dd, J=9 Hz, 2 Hz)

Reference Example 196

2-[4-[(Dimethylamino)methyl]phenyl]-3-oxa-1-azaspiro[4.5]dec-1-en-4-one

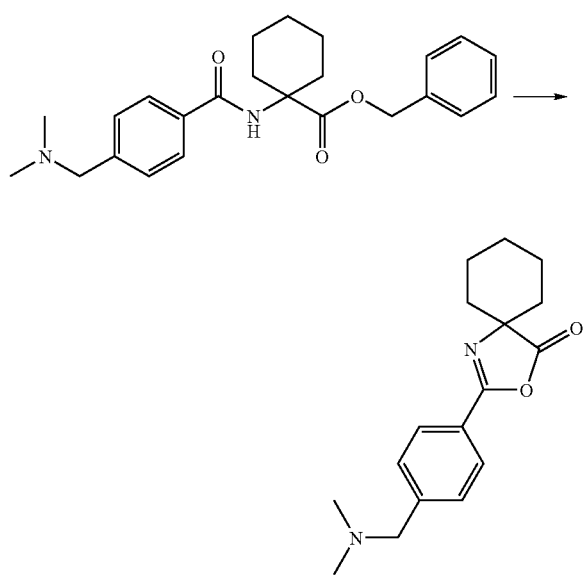

0.7 ml of 2N aqueous sodium hydroxide solution was added to a solution of 100 mg (0.25 mmol) of 1-[[[4-[(dimethylamino)methyl]phenyl]carbonyl]amino]cyclohexanecarboxylic acid phenylmethyl ester in 1 ml of tetrahydrofuran, and the mixture was refluxed under heating overnight. After the mixture was neutralized by concentrated hydrochloric acid, the reaction mixture was distilled off under reduced pressure. 3 ml of methylene chloride, 126 mg (1.25 mmol) of triethylamine and 96 mg (0.5 mmol) 1-ethyl-3-(3-dimethylaminopropyl)carbodiimide hydrochloride were added to the residue, the mixture was stirred for 1 hour. The reaction mixture was distilled off under reduced pressure, an aqueous sodium bicarbonate solution was added thereto, and the mixture was extracted with ethyl acetate. The organic layer was washed with a saturated aqueous sodium bicarbonate solution and dried with anhydrous sodium sulfate. The solvent was distilled off under reduced pressure to obtain 52 mg (68%) of the title compound.

1H-NMR (CDCl$_3$, δ): 1.50-1.88 (10H, m), 2.25 (6H, s), 3.48 (2H, s), 7.43 (2H, dd, J=9 Hz, 2 Hz), 7.96 (2H, dd, J=9 Hz, 2 Hz)

Reference Example 197

1-[[[4-(4-Morpholinylmethyl)phenyl]carbonyl]amino]cyclohexanecarboxylic acid phenylmethyl ester

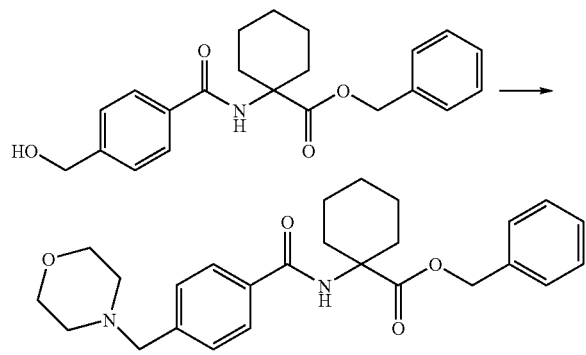

Under ice-cooling, 628 mg (5.5 mmol) of methanesulfonyl chloride was added dropwise to a solution of 1.83 g (5 mmol) of 1-[[[4-(hydroxymethylphenyl]carbonyl]amino]cyclohexanecarboxylic acid phenylmethyl ester and 1.52 g (15 mmol) of triethylamine in methylene chloride. After the mixture was stirred at room temperature for 1 hour, 5 ml of morpholine was added thereto, and the mixture was stirred overnight. The reaction mixture was distilled off under reduced pressure, a saturated aqueous sodium bicarbonate solution was added thereto, and the mixture was extracted with ethyl acetate. The organic layer was washed with saturated brine and dried with anhydrous sodium sulfate. The solvent was distilled off under reduced pressure and it was purified by silica gel column chromatography to obtain 1 g (57%) of the title compound.

1H-NMR (CDCl$_3$, δ): 1.25-1.79 (6H, m), 1.89-2.03 (2H, m), 2.15-2.29 (2H, m), 2.43 (4H, t, J=5 Hz), 3.53 (2H, s), 3.70 (4H, t, J=5 Hz), 5.17 (2H, s), 6.21 (1H, s), 7.21-7.38 (5H, m), 7.39 (2H, d, J=8 Hz), 7.71 (2H, d, J=8 Hz)

Reference Example 198

1-[[[4-(4-Morpholinylmethyl)phenyl]carbonyl]amino]cyclohexanecarboxylic acid methyl ester

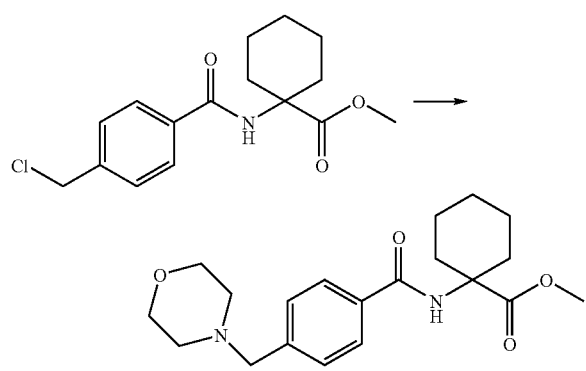

30 ml of morpholine was added to 4 g (13 mmol) of 1-[[[4-(chloromethyl)phenyl]carbonyl]amino]cyclohexanecarboxylic acid methyl ester, and the mixture was refluxed under heating for 1 hour. The reaction solution was distilled off under reduced pressure, a saturated aqueous sodium bicarbonate solution was added thereto, and the mixture was extracted with ethyl acetate. The organic layer was washed with saturated brine and dried with anhydrous sodium sulfate. The solvent was distilled off under reduced pressure, diethyl ether was added to the residue, and the mixture was stirred overnight. The precipitated solid was collected by filtration to obtain 3.8 g (83%) of the title compound.

1H-NMR (CDCl$_3$, δ): 1.28-1.80 (6H, m), 1.80-1.99 (2H, m), 2.11-2.21 (2H, m), 2.38-2.49 (4H, m), 3.54 (2H, s), 3.63-3.74 (4H, m), 3.73 (3H, s), 6.22 (1H, s), 7.41 (2H, d, J=8 Hz), 7.73 (2H, d, J=8 Hz)

Reference Example 199

2-[4-(4-Morpholinylmethyl)phenyl]-3-oxa-1-azaspiro[4.5]dec-1-en-4-one

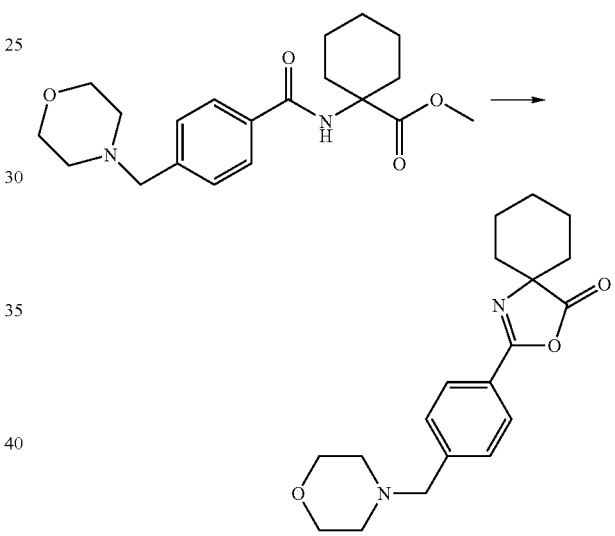

18 ml of 2N sodium hydroxide aqueous solution was added to a solution of 2.07 g (5.7 mmol) of 1-[[[4-(4-morpholinylmethyl)phenyl]carbonyl]amino]cyclohexanecarboxylic acid methyl ester in 18 ml of tetrahydrofuran, and the mixture was refluxed under heating overnight. After the mixture was neutralized by concentrated hydrochloric acid, the reaction solution was distilled off under reduced pressure. 30 ml of methylene chloride, 1.74 g (17 mmol) of triethylamine and 1.65 g (8.6 mmol) of 1-ethyl-3-(3-dimethylaminopropyl)carbodiimide hydrochloride were added to the residue, and the mixture was stirred for 1 hour. The reaction solution was distilled off under reduced pressure, a saturated aqueous sodium bicarbonate solution was added thereto, and the mixture was extracted with ethyl acetate. The organic layer was washed with a saturated aqueous sodium bicarbonate solution and dried with anhydrous sodium sulfate. The solvent was distilled off under reduced pressure to obtain 1.27 g (60%) of the title compound.

1H-NMR (CDCl$_3$, δ): 1.42-1.80 (10H, m), 2.44 (4H, t, J=5 Hz) 3.56 (2H, s), 3.71 (4H, t, J=5 Hz), 7.45 (2H, d, J=8 Hz), 7.96 (2H, d, J=8 Hz)

Reference Example 200

2-[4-(4-Morpholinylmethyl)phenyl]-3-oxa-1-aza-spiro[4.5]dec-1-en-4-one

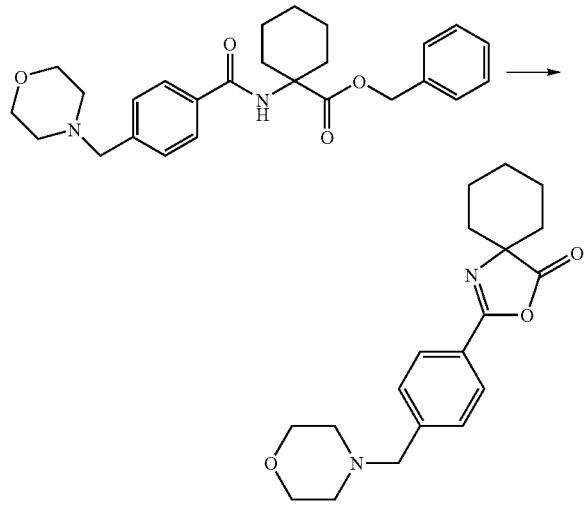

2 ml of 2N aqueous sodium hydroxide solution was added to a solution of 300 mg (0.69 mmol) of 1-[[[4-(4-morpholinylmethyl)phenyl]carbonyl]amino]cyclohexanecarboxylic acid phenylmethyl ester in 2 ml of tetrahydrofuran, and the mixture was refluxed under heating overnight. After the mixture was neutralized by concentrated hydrochloric acid, the reaction solution was distilled off under reduced pressure. 3 ml of methylene chloride, 698 mg (6.9 mmol) of triethylamine and 264 mg (1.38 mmol) of 1-ethyl-3-(3-dimethylaminopropyl)carbodiimide hydrochloride were added to the residue, and the mixture was stirred for 1 hour. The reaction mixture was distilled off under reduced pressure, a saturated aqueous sodium bicarbonate solution was added thereto, and the mixture was extracted with ethyl acetate. The organic layer was washed with a saturated aqueous sodium bicarbonate solution and dried with anhydrous sodium sulfate. The solvent was distilled off under reduced pressure to obtain 191 mg (80%) of the title compound.

1H-NMR (CDCl$_3$, δ): 1.42-1.80 (10H, m), 2.44 (4H, t, J=5 Hz), 3.56 (2H, s), 3.71 (4H, t, J=5 Hz), 7.45 (2H, d, J=8 Hz), 7.96 (2H, d, J=8 Hz)

Reference Example 201

1-[[[4-[2-(4-Methyl-1-piperazinyl)-4-thiazolyl]phenyl]carbonyl]amino]cyclohexanecarboxylic acid phenylmethyl ester

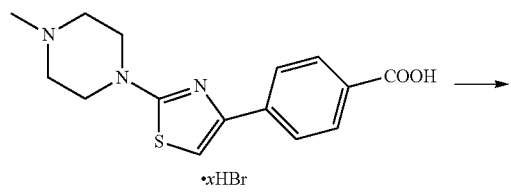

·xHBr

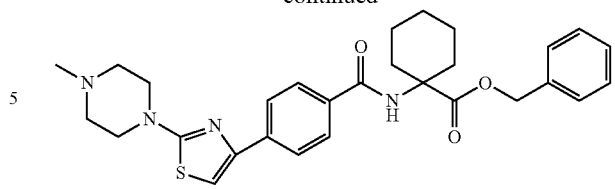

Under ice-cooling, 5.29 g (374 mmol) of 1-ethyl-3-(3-dimethylaminopropyl)carbodiimide hydrochloride was added to a solution of 8.84 g (23.0 mmol) of 4-[2-(4-methyl-1-piperazinyl)-4-thiazolyl]benzoic acid hydrobromide, 4.19 g (27.6 mmol) of 1-hydroxybenzotriazole, 6.44 g (27.6 mmol) of 1-aminocyclohexanecarboxylic acid phenylmethyl ester and 11.9 g (92 mmol) of N,N-diisopropylethylamine in 120 ml of dimethylformamide. After the mixture was stirred at room temperature overnight, the reaction solution was concentrated under reduced pressure, ethyl acetate was added thereto, and the mixture was successively washed with water, a saturated aqueous sodium hydrogencarbonate solution and saturated brine, followed by drying with anhydrous sodium sulfate. After the solvent was distilled off under reduced pressure, ether was added to the residue and a crystal was washed to obtain 11.8 g (quantitative) of the title compound.

1H-NMR (CDCl$_3$, δ): 1.30-1.42 (1H, m), 1.45-1.61 (2H, m), 1.62-1.75 (3H, m), 1.91-2.01 (2H, m), 2.18-2.24 (2H, m), 2.37 (3H, s), 2.56 (4H, t, J=5 Hz), 3.59 (4H, t, J=5 Hz), 5.18 (2H, s), 6.23 (1H, br-s), 6.88 (1H, s), 7.25-7.34 (5H, m), 7.76 (2H, dd, J=8 Hz, 2 Hz), 7.90 (2H, dd, J=8 Hz, 2 Hz)

Reference Example 202

1-[[[4-[2-(4-Methyl-1-piperazinyl)-4-thiazolyl]phenyl]carbonyl]amino]cyclohexanecarboxylic acid

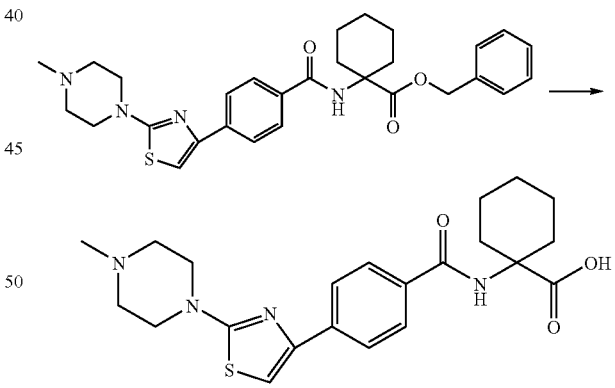

35 ml of 2N sodium hydroxide aqueous solution was added to a solution of 11.8 g (23.0 mmol) of 1-[[[4-[2-(4-methyl-1-piperazinyl)-4-thiazolyl]phenyl]carbonyl]amino]cyclohexanecarboxylic acid phenylmethyl ester in 120 ml of tetrahydrofuran, and the mixture was refluxed under heating for 15 hours. Ether was added to the reaction mixture, and the aqueous layer was separated. Concentrated hydrochloric acid was added to the separated aqueous layer to neutralize it and the precipitated crystal was collected by filtration to obtain 6.60 g (67%) of the title compound.

1H-NMR (CDCl$_3$, δ): 1.28-1.38 (1H, m), 1.40-1.51 (2H, m), 1.58-1.73 (3H, m), 1.85-2.00 (2H, m), 2.10-2.21 (2H, m), 2.47 (3H, s), 2.66-2.75 (4H, m), 3.54-4.04 (4H, m), 6.38 (1H, br-s), 6.83 (1H, s), 7.69 (2H, d, J=8 Hz), 7.76 (2H, d, J=8 Hz)

Reference Example 203

2-[4-[2-(4-Methyl-1-piperazinyl)-4-thiazolyl]phenyl]-3-oxa-1-azaspiro[4.5]dec-1-en-4-one

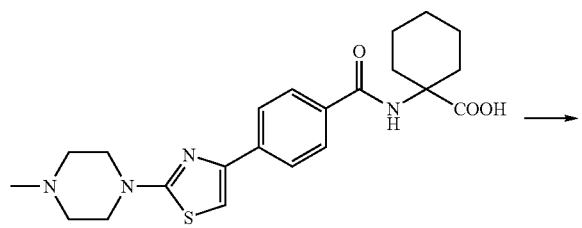

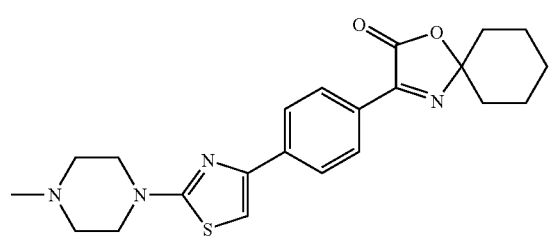

450 mg (2.5 mmol) of 1-ethyl-3-(3-dimethylaminopropyl) carbodiimide hydrochloride was added to a solution of 910 mg (2.1 mmol) of 1-[[[4-[2-(4-methyl-1-piperazinyl)-4-thiazolyl]phenyl]carbonyl]amino]cyclohexanecarboxylic acid in 20 ml of dimethylformamide. After the mixture was stirred at room temperature for 4 hours, the reaction solution was concentrated under reduced pressure, ethyl acetate was added thereto, and the mixture was successively washed with water, a saturated aqueous sodium hydrogencarbonate solution and saturated brine, followed by drying with anhydrous sodium sulfate. The solvent was distilled off under reduced pressure to obtain 577 mg (67%) of the title compound.

1H-NMR (CDCl₃, δ): 1.51-1.62 (1H, m), 1.62-1.71 (1H, m), 1.71-1.78 (2H, m), 1.78-1.90 (6H, m), 2.37 (3H, s), 2.56 (4H, t, J=5 Hz), 3.60 (4H, t, J=5 Hz), 6.92 (1H, s), 7.94 (2H, d, J=8 Hz), 8.00 (2H, d, J=8 Hz)

Reference Example 204

4-[[2-(4-Morpholinyl)-1-piperazinyl]-4-thiazolyl]benzoic acid hydrobromide

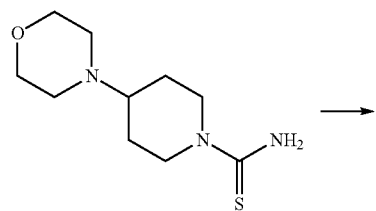

-continued

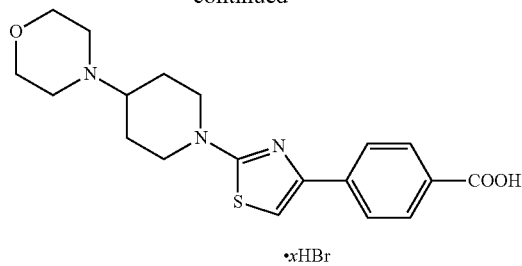

After a solution of 2.47 g (16.9 mmol) of 4-(4-morpholinyl)piperidine-1-thiocarboxamide and 4.08 g (16.9 mmol) of 4-(bromoacetyl)benzoic acid in 150 ml of ethanol was refluxed under heating for 2 hours, the mixture was cooled to room temperature. After 150 ml of ether was added to the reaction solution and the mixture was stirred at 4° C. overnight, the precipitated crystal was collected by filtration to obtain 4.64 g (95%) of the title compound.

1H-NMR (DMSO-d6, δ): 1.68-1.80 (2H, m), 2.17-2.25 (2H, m), 3.07-3.20 (4H, m), 3.21-3.63 (5H, m), 3.64-3.78 (1H, m), 3.98-4.10 (1H, m), 4.10-4.18 (2H, m), 7.51 (1H, s), 7.95-7.99 (4H, m)

Reference Example 205

1-[[[4-[2-[4-(4-Morpholinyl)-1-piperazinyl]-4-thiazolyl]phenyl]carbonyl]amino]cyclohexanecarboxylic acid methyl ester

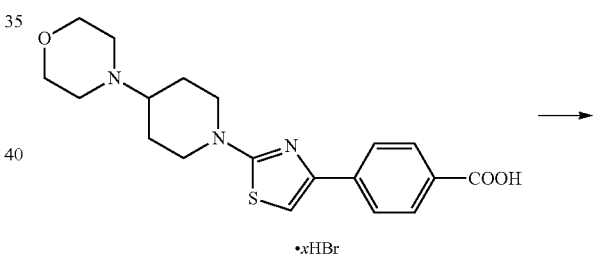

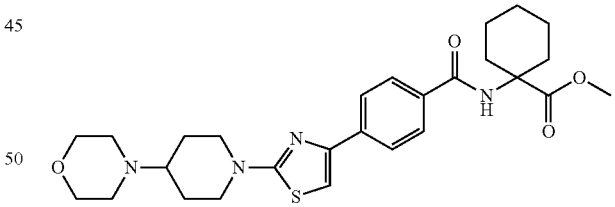

4.50 g (9.90 mmol) of 4-[2-[4-(4-morpholinyl)-1-piperazinyl]-4-thiazolyl]benzoic acid hydrobromide was used instead of 4-[2-(4-methyl-1-piperazinyl)-4-thiazolyl]benzoic acid hydrobromide and 1.57 g (9.90 mmol) of 1-aminocyclohexanecarboxylic acid methyl ester was used instead of 1-aminocyclohexanecarboxylic acid phenylmethyl ester in the process according to Reference example 201 to obtain 5.08 g (quantitative) of the title compound.

1H-NMR (CDCl₃, δ): 1.32-1.42 (1H, m), 1.45-1.74 (7H, m), 1.93-2.01 (4H, m), 2.14-2.21 (2H, m), 2.41-2.50 (1H, m), 2.58 (4H, t, J=5 Hz), 3.07 (2H, dd, J=13 Hz, 13 Hz), 3.73 (4H, t, J=5 Hz), 3.74 (3H, s), 4.13 (2H, d, J=13 Hz), 6.25 (1H, br-s), 6.86 (1H, s), 7.78 (2H, dd, J=8 Hz, 2 Hz), 7.90 (2H, dd, J=8 Hz, 2 Hz)

143

Reference Example 206

1-[[[4-[2-[4-(4-Morpholinyl)-1-piperazinyl]-4-thiazolyl]phenyl]carbonyl]amino]cyclohexanecarboxylic acid

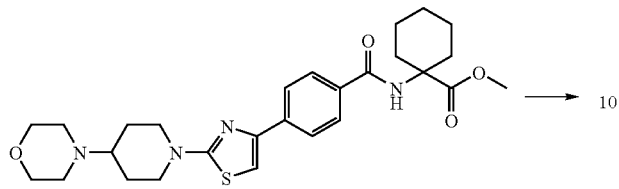

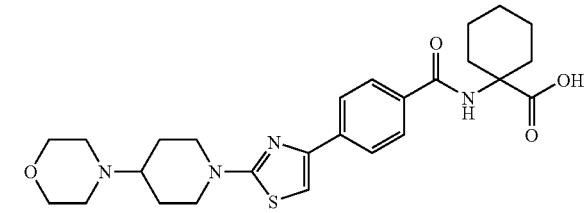

5.08 g (9.90 mmol) of 1-[[[4-[2-[4-(4-morpholinyl)-1-piperazinyl]-4-thiazolyl]phenyl]carbonyl]amino]cyclohexanecarboxylic acid methyl ester was used instead of 1-[[[4-[2-(4-methyl-1-piperazinyl)-4-thiazolyl]phenyl]carbonyl]amino]cyclohexanecarboxylic acid phenylmethyl ester in the process according to Reference example 202 to obtain 4.93 g (quantitative) of the title compound.

1H-NMR (CDCl$_3$, δ): 1.32-1.45 (1H, m), 1.46-1.60 (2H, m), 1.61-1.77 (5H, m), 1.90-2.03 (4H, m), 2.15-2.25 (2H, m), 2.44-2.52 (1H, m), 2.62 (4H, t, J=5 Hz), 3.08 (2H, dd, J=13 Hz, 13 Hz), 3.78 (4H, t, J=5 Hz), 4.14 (2H, d, J=13 Hz), 6.70 (1H, br-s), 6.88 (1H, s), 7.79 (2H, d, J=8 Hz), 7.90 (2H, d, J=8 Hz)

Reference Example 207

2-[4-[2-[4-(4-Morpholinyl)-1-piperidinyl]-4-thiazolyl]phenyl]-3-oxa-1-azaspiro[4.5]dec-1-en-4-one

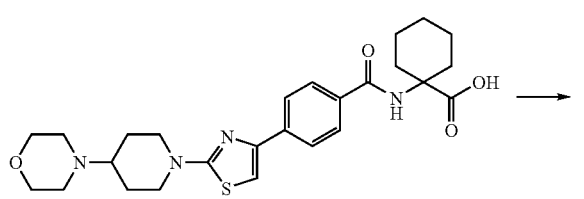

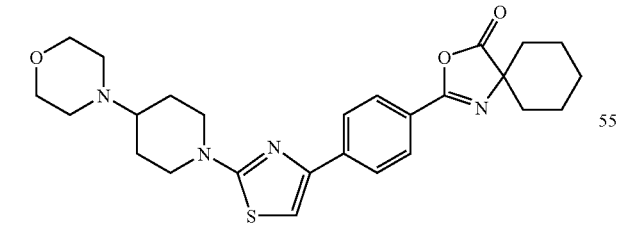

4.93 g (9.90 mmol) of 1-[[[4-[2-[4-(4-morpholinyl)-1-piperazinyl]-4-thiazolyl]phenyl]carbonyl]amino]cyclohexanecarboxylic acid was used instead of 1-[[[4-[2-(4-methyl-1-piperazinyl)-4-thiazolyl]phenyl]carbonyl]amino]cyclohexanecarboxylic acid in the process according to Reference example 203 to obtain 3.00 g (63%) of the title compound.

144

1H-NMR (CDCl$_3$, δ): 1.50-1.61 (1H, m), 1.61-1.71 (3H, m), 1.71-1.79 (2H, m), 1.79-1.89 (5H, m), 1.91-2.00 (2H, m), 2.40-2.48 (1H, m), 2.59 (4H, t, J=5 Hz), 3.09 (2H, d, J=12 Hz), 3.74 (4H, t, J=5 Hz), 4.13 (2H, d, J=12 Hz), 6.90 (1H, s), 7.96 (2H, dd, J=7 Hz, 2 Hz), 8.00 (2H, dd, J=7 Hz, 2 Hz)

Example 11

N-[[1-[(2-Benzothienylcarbonyl)amino]cyclohexyl]carbonyl]-L-phenylglycinol

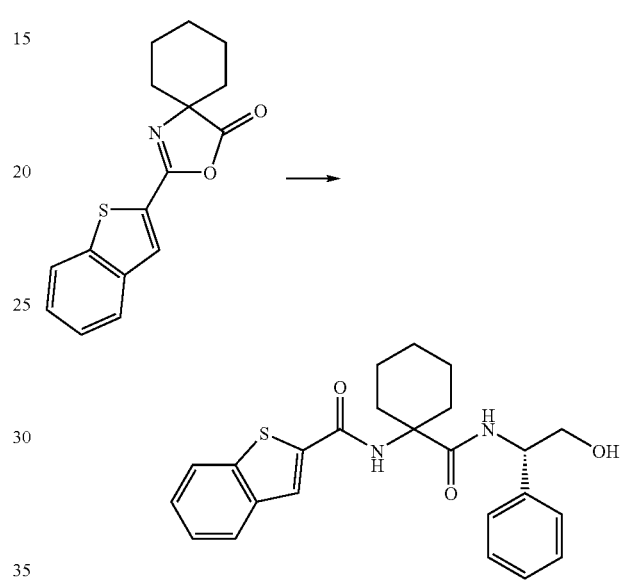

288 mg (2 mmol) of L-phenylglycinol was added to a solution of 500 mg (1.75 mmol) of 2-(2-benzothienyl)-3-oxa-1-azaspiro[4.5]dec-1-en-4-on in 3 ml of N,N-dimethylformamide, and the mixture was stirred overnight. Water was slowly added to the mixture and the precipitated crystal was collected by filtration. The obtained crystal was dried under reduced pressure to give 730 mg (98%) of the title compound.

1H-NMR (CDCl$_3$, δ): 1.29-1.80 (6H, m), 1.91-2.12 (2H, m), 2.19-2.38 (2H, m), 2.91 (1H, br-s), 3.73-3.83 (1H, m), 3.89-4.02 (1H, m), 5.07-5.20 (1H, m), 6.26 (1H, s), 7.20-7.49 (8H, m), 7.83 (1H, s), 7.84-7.92 (2H, m)

Example 12

N-[[1-[(2-Benzothienylcarbonyl)amino]cyclohexyl]carbonyl]-L-phenylglycinal

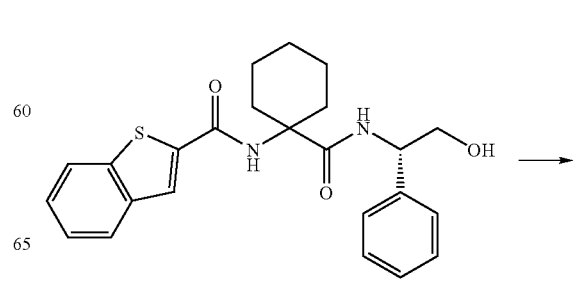

-continued

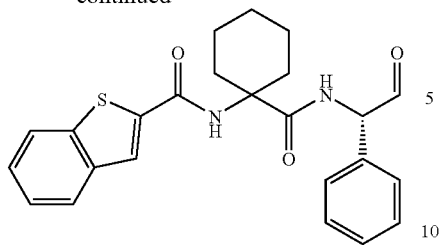

Under ice-cooling, 585 mg (1.38 mmol) of Des Martin periodinane was added to a solution of 100 mg (0.23 mmol) of N-[[1-[(2-benzothienylcarbonyl)amino]cyclohexyl]carbonyl]-L-phenylglycinol in 5 ml of methylene chloride, and the mixture was stirred for 1 hour. At the same temperature, 10 ml of ethyl acetate and 10 ml of a saturated aqueous sodium bicarbonate solution were added thereto. Sodium thiosulfate was added thereto until the solution became transparent, and the mixture was extracted with ethyl acetate. The organic layer was washed with a saturated aqueous sodium bicarbonate solution and saturated brine and dried with anhydrous sodium sulfate. The solvent was distilled off under reduced pressure, ethyl acetate was added to the obtained residue, and the mixture was stirred for 1 hour. The precipitated solid was collected by filtration to obtain 55 mg (57%) of the title compound.

1H-NMR (CDCl$_3$, δ): 1.21-1.80 (6H, m), 1.83-2.18 (2H, m), 2.23-2.40 (2H, m), 5.51 (1H, d, J=5 Hz), 6.10 (1H, s), 7.21-7.52 (7H, m), 7.83 (1H, s), 7.84-7.96 (2H, m), 8.18 (1H, d, J=5 Hz), 9.55 (1H, s)

Example 13

N-[[1-[(2-Benzothienylcarbonyl)amino]cyclohexyl]carbonyl]-L-methioninol

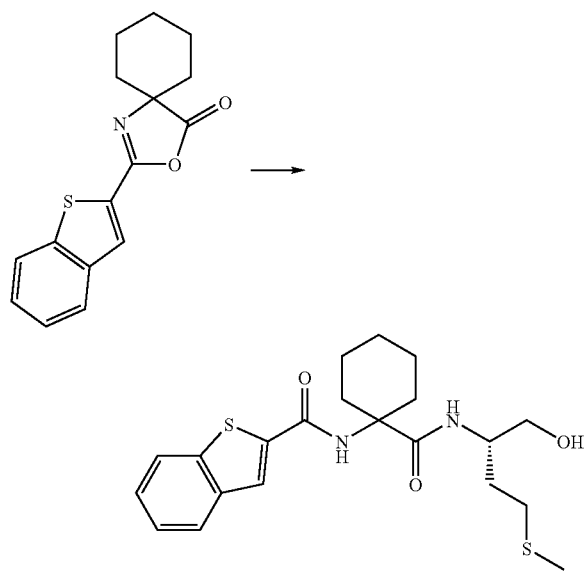

284 mg (2.1 mmol) of L-methioninol was added to a solution of 500 mg (1.75 mmol) of 2-(2-benzothienyl)-3-oxa-1-azaspiro[4.5]dec-1-en-4-one in 3 ml of N,N-dimethylformamide, and the mixture was stirred overnight. Water was slowly added to the mixture and the precipitated crystal was collected by filtration. The obtained crystal was dried under reduced pressure to give 722 mg (98%) of the title compound.

1H-NMR (CDCl$_3$, δ): 1.31-2.29 (16H, m), 2.45-2.63 (1H, m), 3.06 (1H, br-s), 3.45-3.61 (1H, m), 3.73-3.82 (1H, m), 3.97-4.05 (1H, m), 6.29 (1H, s), 6.85 (1H, br-s), 7.38-7.50 (2H, m), 7.82 (1H, s), 7.83-7.90 (2H, m)

Example 14

N-[[1-[(2-Benzothienylcarbonyl)amino]cyclohexyl]carbonyl]-L-methioninal

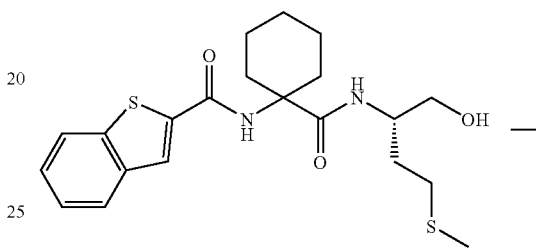

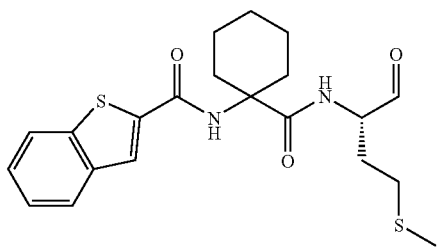

Under an argon gas atmosphere, 245 mg (1.9 mmol) of N,N-diisopropylethylamine was added dropwise to a solution of 297 mg (1.9 mmol) of sulfur trioxide-pyridine complex in 10 ml of anhydrous dimethyl sulfoxide and 5 ml of anhydrous methylene chloride under ice-cooling, the mixture was stirred for 15 minutes. Further, under ice-cooling, 100 mg (0.23 mmol) of N-[[1-[(2-benzothienylcarbonyl)amino]cyclohexyl]carbonyl]-L-methioninol was added to the reaction solution, and the mixture was stirred at the same temperature for 2 hours. The reaction solution was poured into ice-water, and the mixture was extracted with ethyl acetate twice. After the organic layer was washed with a 10% aqueous citric acid solution, a saturated aqueous sodium hydrogencarbonate solution and then saturated brine and dried with anhydrous magnesium sulfate, the solvent was distilled off under reduced pressure. 20 ml of diisopropyl ether was added to the residue, and the mixture was stirred at room temperature for 18 hours. The obtained crystal was collected by filtration to quantitatively give the title compound.

1H-NMR (CDCl$_3$, δ): 1.36-1.80 (9H, m), 1.91-2.09 (5H, m), 2.20-2.35 (2H, m), 2.50-2.63 (1H, m), 4.43-4.59 (1H, m), 6.19 (1H, s), 7.38-7.52 (2H, m), 7.67 (1H, d, J=7 Hz), 7.71 (1H, s), 7.80-7.89 (2H, m), 9.61 (1H, s)

Example 15

N-[[1-[[[4-(4-Morpholinylmethyl)phenyl]carbonyl]amino]cyclohexyl]carbonyl]-L-phenylglycinol

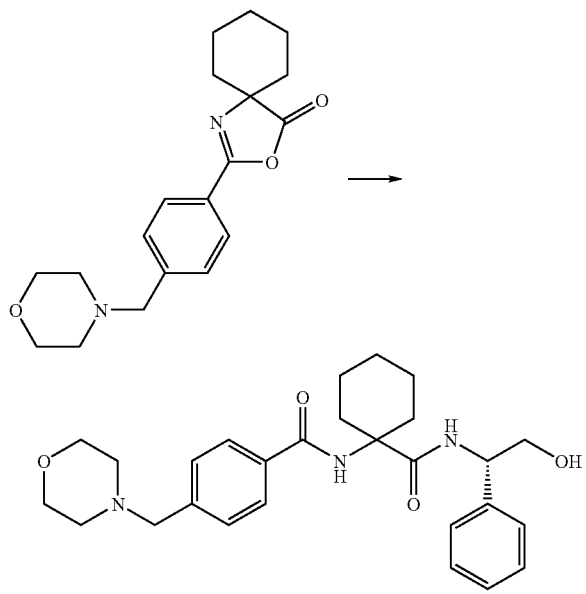

44 mg (0.32 mmol) of L-phenylglycinol was added to a solution of 100 mg (0.29 mmol) of 2-[4-(4-morpholinylmethyl)phenyl]-3-oxa-1-azaspiro[4.5]dec-1-en-4-one in 3 ml of N,N-dimethylformamide, and the mixture was stirred overnight. Water was slowly added and the precipitated crystal was collected by filtration. The obtained crystal was dried under reduced pressure to give 46 mg (34%) of the title compound.

1H-NMR (CDCl₃, δ): 1.25-1.80 (6H, m), 1.92-2.10 (2H, m), 2.18-2.32 (2H, m), 2.37-2.50 (4H, m), 2.99 (1H, br-s), 3.55 (2H, s), 3.62-3.71 (4H, m), 3.71-3.83 (1H, m), 3.91-4.02 (1H, m), 5.05-5.18 (1H, m), 6.24 (1H, s), 7.17-7.37 (6H, m), 7.44 (2H, d, J=8 Hz), 7.73 (2H, d, J=8 Hz)

Example 16

N-[[1-[[[4-(4-Morpholinylmethyl)phenyl]carbonyl]amino]cyclohexyl]carbonyl]-L-phenylglycinal

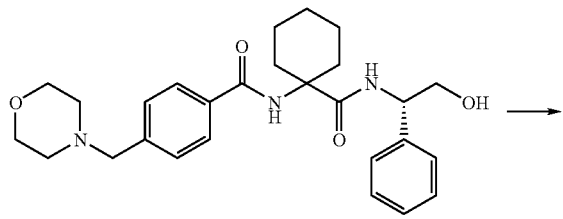

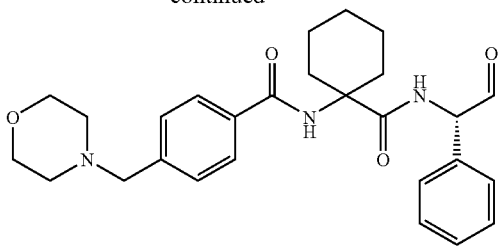

Under ice-cooling, 254 mg (0.6 mmol) of Des Martin periodinane was added to a solution of 46 mg (0.1 mmol) of N-[[1-[[[4-(4-morpholinylmethyl)phenyl]carbonyl]amino]cyclohexyl]carbonyl]-L-phenylglycinol in 5 ml of methylene chloride, and the mixture was stirred for 1 hour. At the same temperature, 10 ml of ethyl acetate and 10 ml of a saturated aqueous sodium bicarbonate solution were added to the reaction mixture. Sodium thiosulfate was added thereto until the solution became transparent, and the mixture was extracted with ethyl acetate. The organic layer was washed with a saturated aqueous sodium bicarbonate solution and saturated brine and dried with anhydrous sodium sulfate. The solvent was distilled off under reduced pressure, ethyl acetate was added to the obtained residue, and the mixture was stirred for 1 hour. The precipitated solid was collected by filtration to obtain 30 mg (60%) of the title compound.

1H-NMR (CDCl₃, δ): 1.20-2.37 (10H, m), 2.37-2.60 (4H, m), 3.55 (2H, s), 3.61-3.80 (4H, m), 5.49 (1H, d, J=6 Hz), 6.16 (1H, s), 7.20-7.58 (7H, m), 7.75 (2H, d, J=8 Hz), 8.27 (1H, d, J=6 Hz), 9.54 (1H, s)

Example 17

N-[[1-[[[4-(4-Morpholinylmethyl)phenyl]carbonyl]amino]cyclohexyl]carbonyl]-L-methioninol

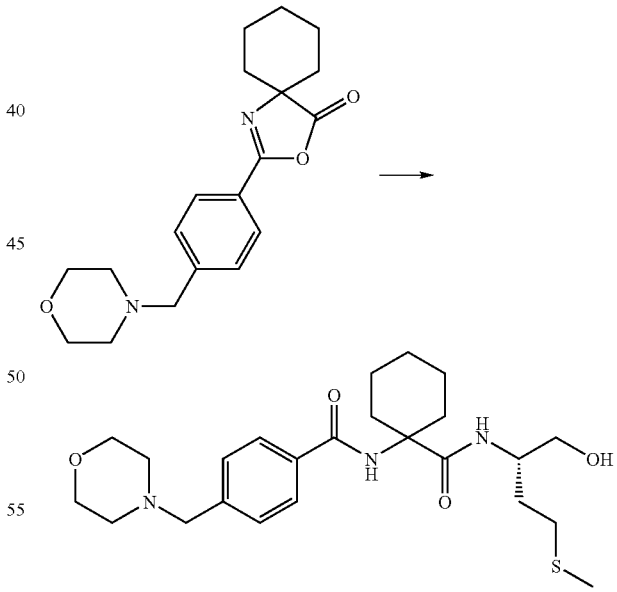

43 mg (0.32 mmol) of L-methioninol was added to a solution of 100 mg (0.29 mmol) of 2-[4-(4-morpholinylmethyl)phenyl]-3-oxa-1-azaspiro[4.5]dec-1-en-4-one in 3 ml of N,N-dimethylformamide, and the mixture was stirred overnight. Water was slowly added thereto and the precipitated crystal was collected by filtration. The obtained crystal was dried under reduced pressure to give 65 mg (49%) of the title compound.

1H-NMR (CDCl₃, δ): 1.31-2.23 (15H, m), 2.35-2.45 (4H, m), 2.45-2.62 (2H, m), 3.12 (1H, br-s), 3.40-3.60 (3H, m), 3.60-3.82 (5H, m), 3.95-4.05 (1H, m), 6.28 (1H, s), 6.80 (1H, d, J=8 Hz), 7.43 (2H, d, J=8 Hz), 7.72 (2H, d, J=8 Hz)

Example 18

N-[[1-[[[4-(4-Morpholinylmethyl)phenyl]carbonyl]amino]cyclohexyl]carbonyl]-L-methioninal

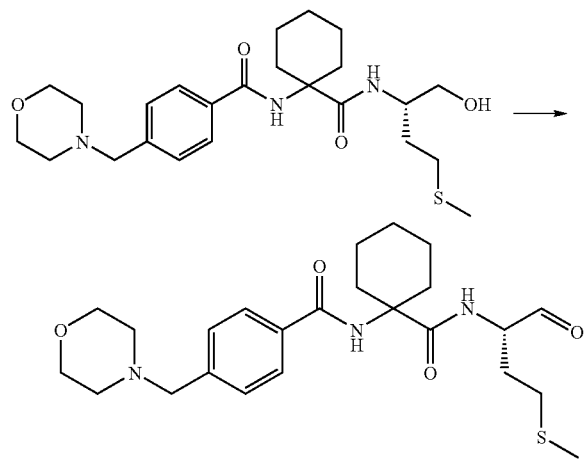

Under ice-cooling, 356 mg (0.84 mmol) of Des Martin periodinane was added to a solution of 65 mg (0.14 mmol) of N-[[1-[[[4-(4-morpholinylmethyl)phenyl]carbonyl]amino]cyclohexyl]carbonyl]-L-methioninol in 5 ml of methylene chloride, and the mixture was stirred for 1 hour. At the same temperature, 10 ml of ethyl acetate and 10 ml of a saturated aqueous sodium bicarbonate solution were added to the reaction solution. Sodium thiosulfate was added thereto until the solution became transparent, and the mixture was extracted with ethyl acetate. The organic layer was washed with a saturated aqueous sodium bicarbonate solution and saturated brine and dried with anhydrous sodium sulfate. The solvent was distilled off under reduced pressure to obtain 55 mg (85%) of the title compound.

1H-NMR (CDCl₃, δ): 1.20-2.80 (21H, m), 3.56 (2H, s), 3.60-3.81 (4H, m), 4.40-4.58 (1H, m), 5.12 (1H, d, J=7 Hz), 6.18 (1H, s), 7.44 (2H, d, J=8 Hz), 7.73 (2H, d, J=8 Hz), 9.59 (1H, s)

Example 19

N-[[1-[[[4-[2-(4-Methyl-1-piperazinyl)-4-thiazolyl]phenyl]carbonyl]amino]cyclohexyl]carbonyl]-L-methioninol

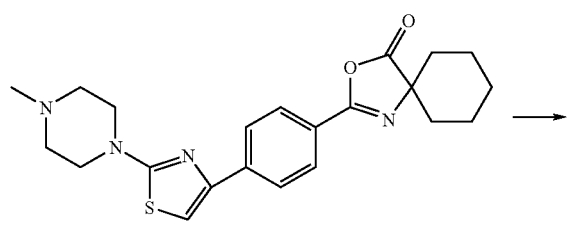

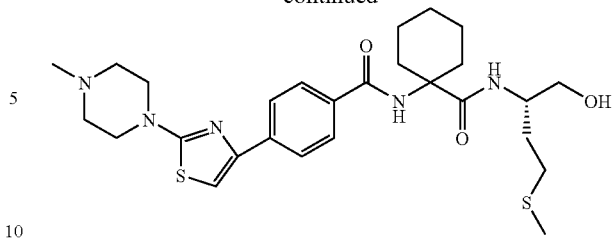

100 mg (0.74 mmol) of L-methioninol was added to a solution of 250 mg (0.68 mmol) of 2-[4-[2-(4-methyl-1-piperazinyl)-4-thiazolyl]phenyl]-3-oxa-1-azaspiro[4.5]dec-1-en-4-one in 20 ml of dimethylformamide. After the mixture was stirred at 80° C. for 15 hours, the reaction solution was concentrated under reduced pressure, ethyl acetate was added thereto, and the mixture was successively washed with water, a saturated aqueous sodium hydrogencarbonate solution and saturated brine, followed by drying with anhydrous sodium sulfate. After the solvent was distilled off under reduced pressure, diisopropyl ether was added to the residue. The crystal was washed to obtain 319 mg (86%) of the title compound.

1H-NMR (CDCl₃, δ): 1.37-1.61 (3H, m), 1.65-1.80 (3H, m), 1.80-1.86 (2H, m), 1.96-2.05 (2H, m), 2.07 (3H, s), 2.15-2.29 (2H, m), 2.37 (3H, s), 2.51-2.60 (2H, m), 2.56 (4H, t, J=5 Hz), 3.14-3.21 (1H, m), 3.50-3.56 (1H, m), 3.59 (4H, t, J=5 Hz), 3.77-3.84 (1H, m), 4.00-4.06 (1H, m), 6.30 (1H, br-s), 6.85 (1H, d, J=7 Hz), 6.90 (1H, s), 7.76 (2H, dd, J=8 Hz, 2 Hz), 7.92 (2H, dd, J=8 Hz, 2 Hz)

Example 20

N-[[1-[[[4-[2-(4-Methyl-1-piperazinyl)-4-thiazolyl]phenyl]carbonyl]amino]cyclohexyl]carbonyl]-L-methioninal

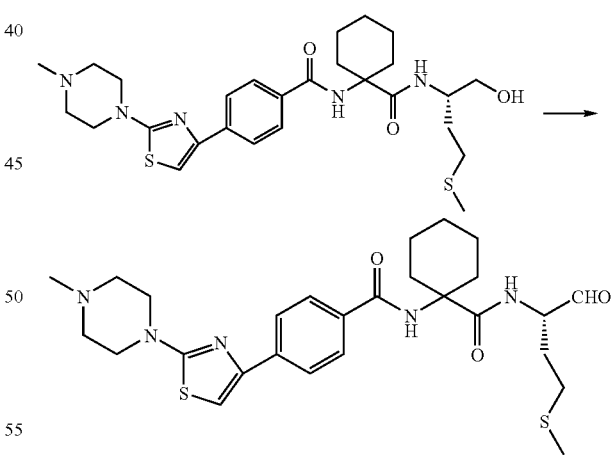

Under an argon gas atmosphere, 453 mg (3.5 mmol) of N,N-diisopropylethylamine was added dropwise to a solution of 658 mg (3.5 mmol) of sulfur trioxide-pyridine complex in 10 ml of anhydrous dimethyl sulfoxide and 5 ml of anhydrous methylene chloride under ice-cooling, and the mixture was stirred for 15 minutes. Further, under ice-cooling, a solution of 319 mg (0.58 mmol) of N-[[1-[[[4-[2-(4-methyl-1-piperazinyl)-4-thiazolyl]phenyl]carbonyl]amino]cyclohexyl]carbonyl]-L-methioninol in 3 ml of anhydrous dimethyl sulfoxide was added to the reaction solution, and the mixture was stirred at the same temperature for 2 hours. The reaction solution was poured into ice-water, and the mixture was extracted with ethyl acetate twice. The organic layer was washed with a saturated aqueous sodium hydrogencarbonate solution and then saturated brine and dried with anhydrous magnesium sulfate. Thereafter, the solvent was distilled off under reduced pressure. 20 ml of diisopropyl ether was added to the residue, and the mixture was stirred at room temperature for 18 hours. The obtained crystal was collected by filtration to give 203 mg (64%) of the title compound.

1H-NMR (CDCl₃, δ): 1.36-1.78 (6H, m), 1.98-2.08 (3H, m), 2.02 (3H, s), 2.21-2.57 (3H, m), 2.38 (3H, s), 2.55 (4H, t, J=5 Hz), 2.56 (2H, m), 3.61 (4H, t, J=5 Hz), 4.49 (1H, dt, J=8 Hz, 5 Hz), 6.17 (1H, br-s), 6.90 (1H, s), 7.78 (2H, d, J=8 Hz), 7.84 (1H, d, J=8 Hz), 7.92 (2H, d, J=8 Hz), 9.62 (1H, s)

Example 21

N-[[1-[[[4-[2-(4-Methyl-1-piperazinyl)-4-thiazolyl]phenyl]carbonyl]amino]cyclohexyl]carbonyl]-L-phenylglycinol

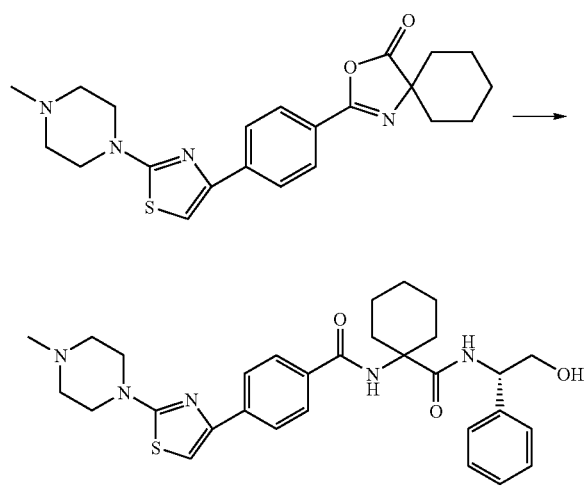

96 mg (0.7 mmol) of L-phenylglycinol was used instead of L-methioninol in the process according to Example 19 to obtain 220 mg (57%) of the title compound.

1H-NMR (CDCl₃, δ): 1.34-1.43 (1H, m), 1.42-1.61 (2H, m), 1.61-1.79 (3H, m), 1.96-2.10 (2H, m), 2.20-2.29 (1H, m), 2.30-2.36 (1H, m), 2.37 (3H, s), 2.56 (4H, t, J=5 Hz), 3.01-3.08 (1H, m), 3.60 (4H, t, J=5 Hz), 3.76-3.85 (1H, m), 3.92-4.01 (1H, m), 5.09-5.15 (1H, m), 6.27 (1H, br-s), 6.90 (1H, s), 7.24-7.30 (3H, m), 7.31-7.36 (2H, m), 7.37 (1H, d, J=7 Hz), 7.78 (2H, d, J=8 Hz) 7.92 (2H, d, J=8 Hz)

Example 22

N-[[1-[[[4-[2-(4-Methyl-1-piperazinyl)-4-thiazolyl]phenyl]carbonyl]amino]cyclohexyl]carbonyl]-L-phenylglycinal

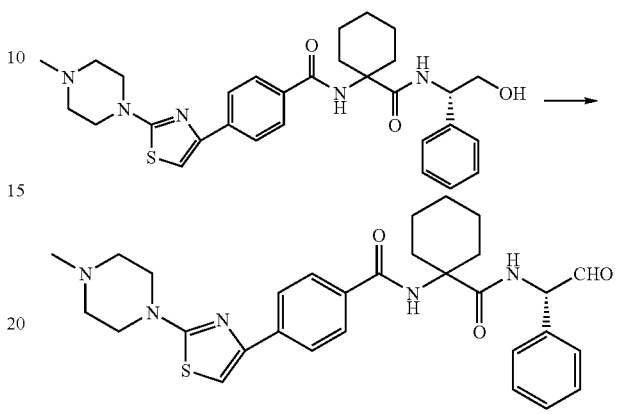

Under an argon gas atmosphere, 310 mg (2.4 mmol) of N,N-diisopropylethylamine was added dropwise to a solution of 382 mg (2.4 mmol) of sulfur trioxide-pyridine complex in 10 ml of anhydrous dimethyl sulfoxide and 5 ml of anhydrous methylene chloride under ice-cooling, and the mixture was stirred for 15 minutes. Further, under ice-cooling, a solution of 220 mg (0.4 mmol) of N-[[1-[[[4-[2-(4-methyl-1-piperazinyl)-4-thiazolyl]phenyl]carbonyl]amino]cyclohexyl]carbonyl]-L-phenylglycinol in 3 ml of anhydrous dimethyl sulfoxide was added to the reaction solution, and the mixture was stirred at the same temperature for 30 minutes. After the reaction, under ice-cooling, 200 ml of water was added to the reaction solution, and thereafter the mixture was stirred at room temperature for 3 hours. The precipitated crystal was washed with diethyl ether again to obtain 67 mg (31%) of the title compound.

1H-NMR (CDCl₃, δ): 1.35-1.82 (6H, m), 2.25-2.39 (2H, m), 2.50-2.59 (1H, m), 2.62 (3H, s), 2.75 (4H, t, J=5 Hz), 3.06-3.15 (1H, m), 3.72 (4H, t, J=5 Hz), 5.51 (1H, d, J=6 Hz), 6.16 (1H, br-s), 6.91 (1H, s), 7.21-7.38 (5H, m), 7.38 (1H, d, J=6 Hz), 7.79 (2H, d, J=8 Hz), 7.92 (2H, d, J=8 Hz), 9.56 (1H, s)

Example 23

N-[[1-[[[4-[2-[4-(4-Morpholinyl)-1-piperazinyl]-4-thiazolyl]phenyl]carbonyl]amino]cyclohexyl]carbonyl]-L-methioninol

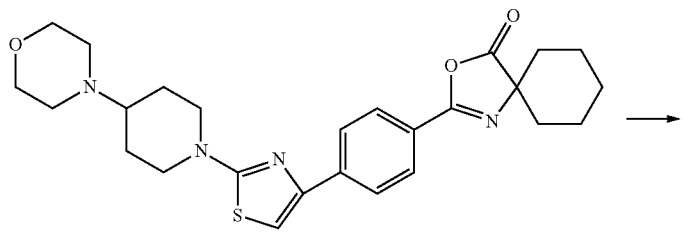

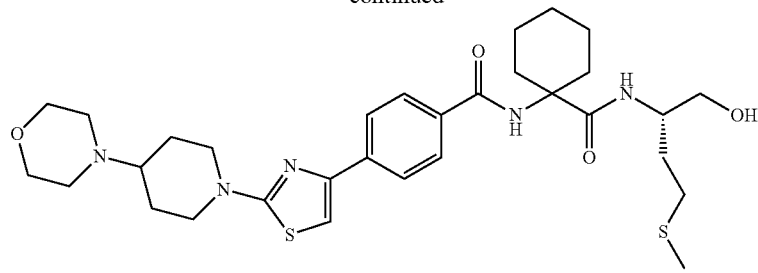

481 mg (1.00 mmol) of 2-[4-[2-[4-(4-morpholinyl)-1-piperidinyl]-4-thiazolyl]phenyl]-3-oxa-1-azaspiro[4.5]dec-1-en-4-one was used instead of 2-[4-[2-(4-methyl-1-piperazinyl)-4-thiazolyl]phenyl]-3-oxa-1-azaspiro[4.5]dec-1-en-4-one in the process according to Example 19 to obtain 501 mg (81%) of the title compound.

1H-NMR (CDCl₃, δ): 1.35-1.80 (7H, m), 1.81-1.89 (2H, m), 1.92-2.09 (4H, m), 2.07 (3H, s), 2.15-2.23 (3H, m), 2.41-2.49 (1H, m), 2.54 (2H, t, J=6 Hz), 2.57 (4H, t, J=5 Hz), 3.08 (2H, dd, J=13 Hz, 13 Hz), 3.18 (1H, t, J=7 Hz), 3.50-3.58 (1H, m), 3.74 (4H, t, J=5 Hz), 3.77-3.85 (1H, m), 4.00-4.08 (1H, m), 4.12 (2H, d, J=13 Hz), 6.30 (1H, br-s), 6.83 (1H, d, J=8 Hz), 6.88 (1H, s), 7.77 (2H, d, J=8 Hz), 7.96 (2H, d, J=8 Hz)

Example 24

N-[[1-[[[4-[2-[4-(4-Morpholinyl)-1-piperazinyl]-4-thiazolyl]phenyl]carbonyl]amino]cyclohexyl]carbonyl]-L-methioninal 501 mg (0.81 mmol) of N-[[1-[[[4-[2-[(4-morpholinyl)-1-piperazinyl]-4-thiazolyl]phenyl]carbonyl]amino]cyclohexyl]carbonyl]-L-methioninol was used instead of N-[[1-[[[4-[2-(4-methyl-1-piperazinyl)-4-thiazolyl]phenyl]carbonyl]amino]cyclohexyl]carbonyl]-L-methioninol in the process according to Example 20 to obtain 100 mg (20%) of the title compound.

1H-NMR (CDCl₃, δ): 1.36-1.56 (3H, m), 1.61-1.79 (6H, m), 1.93-2.07 (5H, m), 2.02 (3H, s), 2.04-2.15 (2H, m), 2.40-2.49 (1H, m), 2.45 (2H, t, J=6 Hz), 2.58 (4H, t, J=5 Hz), 3.08 (2H, dd, J=12 Hz, 12 Hz), 3.74 (4H, t, J=5 Hz), 4.12 (2H, d, J=12 Hz), 4.49 (1H, dd, J=8 Hz, 5 Hz,), 6.15 (1H, br-s), 6.88 (1H, s), 7.78 (2H, d J=8 Hz), 7.85 (1H, d, J=8 Hz), 7.93 (2H, d, J=8 Hz), 9.62 (1H, s)

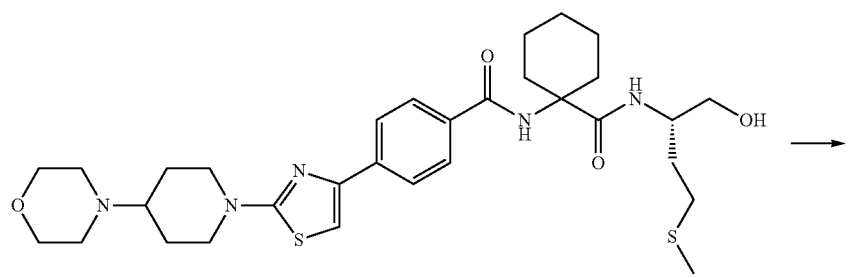

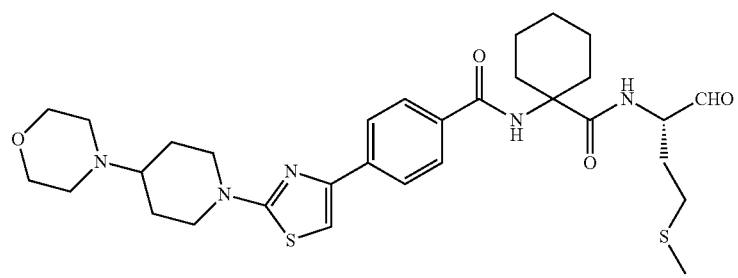

Example 25

N-[[1-[[[4-[2-[4-(4-Morpholinyl)-1-piperazinyl]-4-thiazolyl]phenyl]carbonyl]amino]cyclohexyl]carbonyl]-L-phenylglycinol

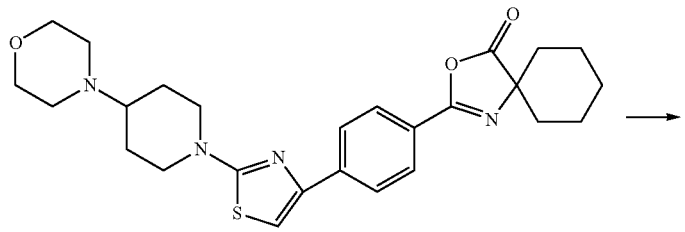

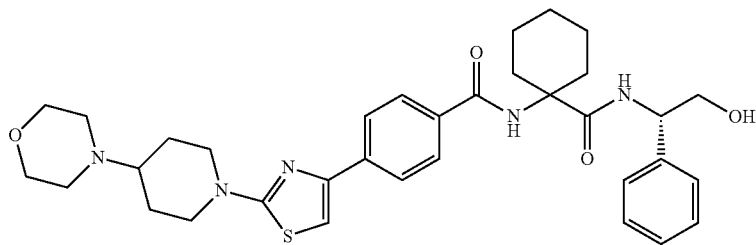

481 mg (1.00 mmol) of 2-[4-[2-[4-(4-morpholinyl)-1-piperidinyl]-4-thiazolyl]phenyl]-3-oxa-1-azaspiro[4.5]dec-1-en-4-one was used instead of 2-[4-[2-(4-methyl-1-piperazinyl)-4-thiazolyl]phenyl]-3-oxa-1-azaspiro[4.5]dec-1-en-4-one and 137 mg (1.00 mmol) of L-phenylglycinol was used instead of L-methioninol in the process according to Example 19 to obtain 324 mg (52%) of the title compound.

1H-NMR (CDCl₃, δ): 1.32-1.78 (9H, m), 1.95-2.11 (4H, m), 2.20-2.27 (1H, m), 2.29-2.36 (1H, m), 2.40-2.49 (1H, m) 2.59 (4H, t, J=5 Hz), 3.09 (2H, dd, J=13 Hz, 13 Hz), 3.74 (4H, t, J=5 Hz), 3.78-3.82 (1H, m), 3.96-4.00 (1H, m), 4.12 (2H, d, J=13 Hz), 5.09-5.14 (1H, m), 6.28 (1H, br-s), 6.88 (1H, s), 7.25-7.30 (1H, m) 7.30-7.35 (4H, m), 7.78 (1H, d, J=8 Hz), 7.78 (2H, dd, J=7 Hz, 2 Hz), 7.92 (2H, dd, J=7 Hz, 2 Hz)

Example 26

N-[[1-[[[4-[2-[4-(4-Morpholinyl)-1-piperazinyl]-4-thiazolyl]phenyl]carbonyl]amino]cyclohexyl]carbonyl]-L-phenylglycinal

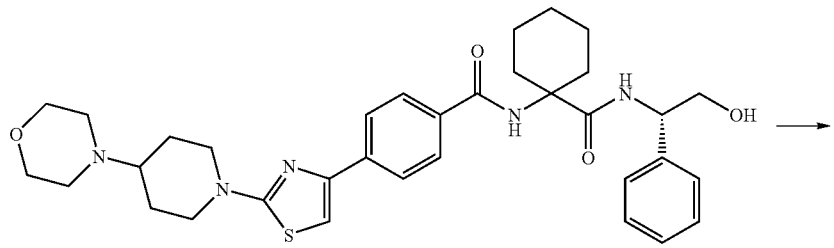

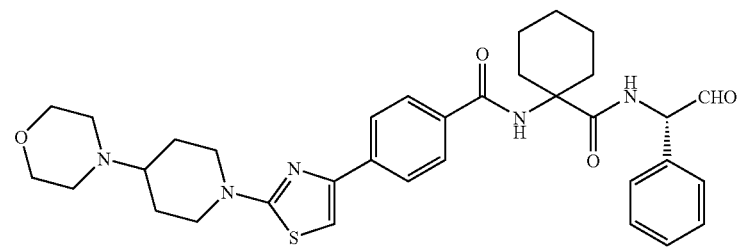

324 mg (0.52 mmol) of N-[[1-[[[4-[2-[4-(4-morpholinyl)-1-piperazinyl]-4-thiazolyl]phenyl]carbonyl]amino]cyclohexyl]carbonyl]-L-phenylglycinol was used instead of N-[[1-[[[4-[2-(4-methyl-1-piperazinyl)-4-thiazolyl]phenyl]carbonyl]amino]cyclohexyl]carbonyl]-L-methioninol in the process according to Example 20 to obtain 128 mg (40%) of the title compound.

1H-NMR (CDCl₃, δ): 1.30-1.85 (8H, m), 1.92-2.13 (4H, m), 2.25-2.50 (3H, m), 2.59 (4H, t, J=5 Hz), 3.08 (2H, dd, J=12 Hz, 12 Hz), 3.74 (4H, t, J=5 Hz), 4.13 (2H, d, J=12 Hz), 5.51 (1H, d, J=6 Hz), 6.14 (1H, br-s), 6.88 (1H, s), 7.30-7.41 (5H, m), 7.79 (2H, d, J=8 Hz), 7.93 (2H, d, J=8 Hz), 8.34 (1H, d, J=6 Hz), 9.56 (1H, s)

Reference Example 208

N-[[1-[(2-Benzothienylcarbonyl)amino]cyclohexyl]carbonyl]-L-phenylglycine methyl ester

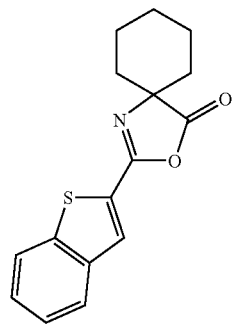

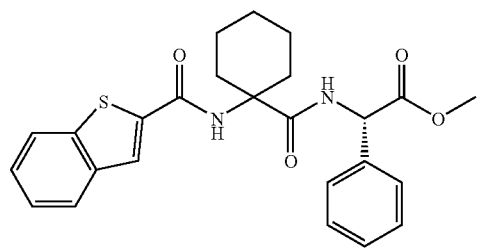

679 mg (5.3 mmol) of diisopropylethylamine was added to a suspension of 423 mg (2 mmol) of L-phenylglycine methyl ester hydrochloride and 500 mg (1.75 mmol) of 2-(2-benzothienyl)-3-oxa-1-azaspiro[4.5]dec-1-en-4-one in 10 ml of toluene, and the mixture was refluxed under heating overnight. After the solvent was distilled off under reduced pressure, ethyl acetate was added thereto, and the mixture was washed with a 10% aqueous potassium hydrogensulfate solution and saturated brine and dried with anhydrous sodium sulfate. After the solvent was distilled off under reduced pressure, diethyl ether was added thereto, and the mixture was stirred overnight. The precipitated solid was collected by filtration and dried under reduced pressure to obtain 670 mg (91%) of the title compound.

1H-NMR (CDCl₃, δ): 1.25-1.80 (6H, m), 1.90-2.08 (2H, m), 2.23-2.40 (2H, m), 3.69 (3H, s), 5.53 (1H, d, J=7 Hz), 6.10 (1H, s), 7.23-7.49 (7H, m), 7.81 (1H, s), 7.83-7.91 (2H, m), 8.13 (1H, d, J=7 Hz)

Reference Example 209

N-[[1-[(2-Benzothienylcarbonyl)amino]cyclohexyl]carbonyl]-L-methionine methyl ester

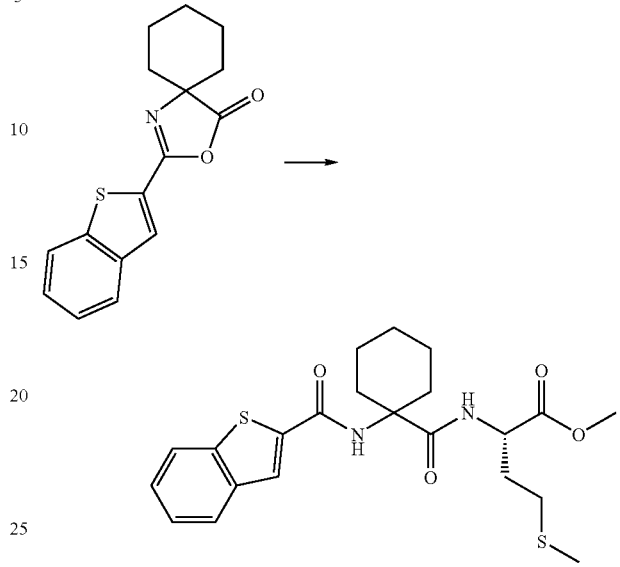

679 mg (5.3 mmol) of diisopropylethylamine was added to a suspension of 419 mg (2 mmol) of L-methionine methyl ester hydrochloride and 500 mg (1.75 mmol) of 2-(2-benzothienyl)-3-oxa-1-azaspiro[4.5]dec-1-en-4-one in 10 ml of toluene, and the mixture was refluxed under heating overnight. After the solvent was distilled off under reduced pressure, ethyl acetate was added thereto, and the mixture was washed with a 10% aqueous potassium hydrogensulfate solution and saturated brine and dried with anhydrous sodium sulfate. After the solvent was distilled off under reduced pressure, diethyl ether was added thereto, and the mixture was stirred overnight. The precipitated solid was collected by filtration and dried under reduced pressure to obtain 678 mg (86%) of the title compound.

1H-NMR (CDCl₃, δ): 1.30-1.81 (8H, m), 1.95-2.09 (5H, m), 2.11-2.39 (2H, m), 2.43-2.61 (2H, m), 3.71 (3H, s), 4.61-4.73 (1H, m), 6.16 (1H, s), 7.38-7.45 (2H, m), 7.59 (1H, d, J=8 Hz), 7.80 (1H, s), 7.82-7.90 (2H, m)

Reference Example 210

N-[[1-[[[4-[(Dimethylamino)methyl]phenyl]carbonyl]amino]cyclohexyl]carbonyl]-L-phenylglycine methyl ester

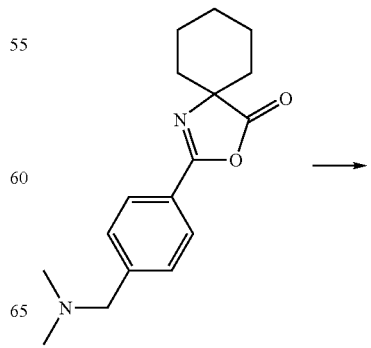

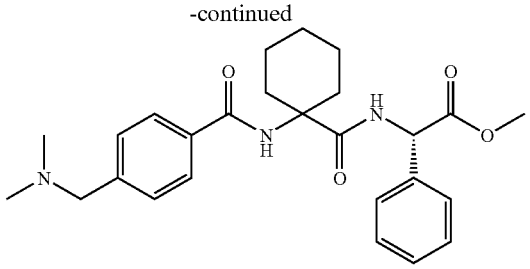

129 mg (1 mmol) of diisopropylethylamine was added to a suspension of 85 mg (0.42 mmol) of L-phenylglycine methyl ester hydrochloride and 100 mg (0.35 mmol) of 2-[4-[(dimethylamino)methyl]phenyl]-3-oxa-1-azaspiro[4.5]dec-1-en-4-one in 3 ml of toluene, and the mixture was refluxed under heating overnight. After the solvent was distilled off under reduced pressure, ethyl acetate was added thereto, and the mixture was washed with saturated brine and dried with anhydrous sodium sulfate. After the solvent was distilled off under reduced pressure, diethyl ether was added thereto, and the mixture was stirred overnight. The precipitated solid was collected by filtration and dried under reduced pressure to obtain 62 mg (39%) of the title compound.

1H-NMR (CDCl$_3$, δ): 1.27-1.80 (7H, m), 1.83-2.09 (2H, m), 2.18-2.39 (1H, m), 2.25 (6H, s), 3.47 (2H, s), 3.69 (3H, s), 5.53 (1H, d, J=7 Hz), 6.07 (1H, s), 7.10-7.25 (7H, m), 7.73 (2H, d, J=8 Hz), 8.28 (1H, d, J=7 Hz)

Reference Example 211

N-[[1-[[[4-[(Dimethylamino)methyl]phenyl]carbonyl]amino]cyclohexyl]carbonyl]-L-methionine methyl ester

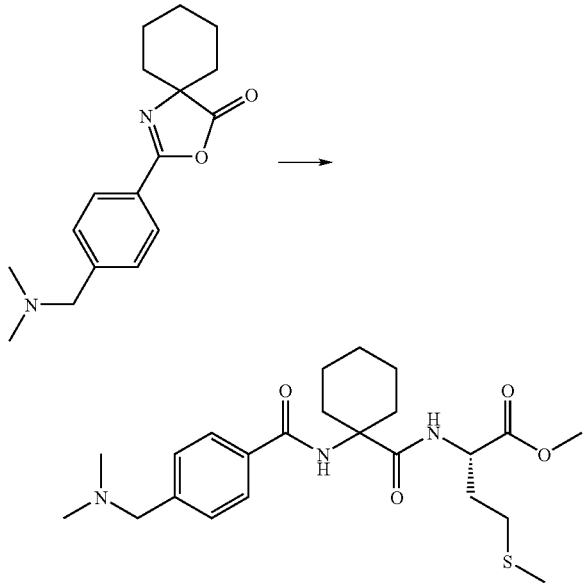

129 mg (1 mmol) of diisopropylethylamine was added to a suspension of 84 mg (0.42 mmol) of L-methionine methyl ester hydrochloride and 100 mg (0.35 mmol) of 2-[4-[(dimethylamino)methyl]phenyl]-3-oxa-1-azaspiro[4.5]dec-1-en-4-one in 3 ml of toluene, and the mixture was refluxed under heating overnight. After the solvent was distilled off under reduced pressure, ethyl acetate was added thereto, and the mixture was washed with saturated brine and dried with sodium sulfate. After the solvent was distilled off under reduced pressure, diethyl ether was added thereto, and the mixture was stirred overnight. The precipitated solid was collected by filtration and dried under reduced pressure to obtain 93 mg (59%) of the title compound.

1H-NMR (CDCl$_3$, δ): 1.29-1.58 (4H, m), 1.58-1.79 (4H, m), 1.92-2.35 (7H, m), 2.25 (6H, s), 2.43-2.59 (2H, m), 3.47 (2H, s), 3.71 (3H, s), 4.61-4.72 (1H, m), 6.10 (1H, s), 7.41 (2H, d, J=8 Hz), 7.69 (1H, d, J=8 Hz), 7.73 (2H, d, J=8 Hz)

Reference Example 212

N-[[1-[[[4-[2-(4-Methyl-1-piperazinyl)-4-thiazolyl]phenyl]carbonyl]amino]cyclohexyl]carbonyl]-L-methionine methyl ester

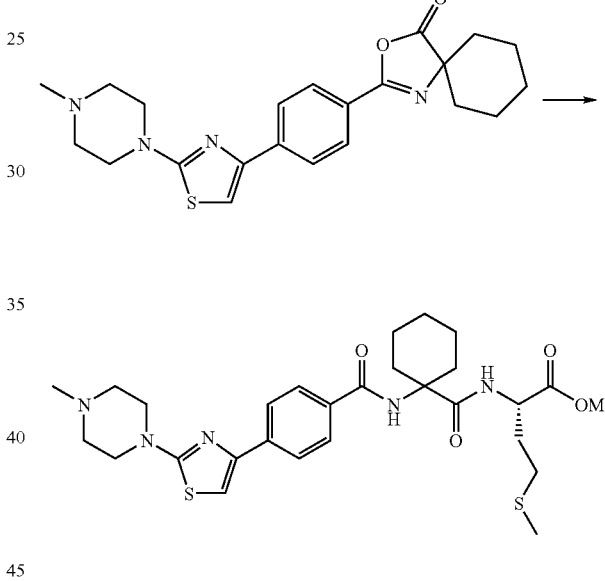

200 mg (1.00 mmol) of L-methionine methyl ester hydrochloride was added to a solution of 411 mg (1.00 mmol) of 2-[4-[2-(4-methyl-1-piperazinyl)-4-thiazolyl]phenyl]-3-oxa-1-azaspiro[4.5]dec-1-en-4-one and 258 mg (2.00 mmol) of N,N-diisopropylethylamine in 20 ml of dimethylformamide. After the mixture was stirred at 80° C. for 15 hours, the reaction solution was concentrated under reduced pressure, ethyl acetate was added thereto, and the mixture was successively washed with water, a saturated aqueous sodium hydrogencarbonate solution and saturated brine and dried with anhydrous sodium sulfate. After the solvent was distilled off under reduced pressure, it was purified by silica gel chromatography to obtain 191 mg (33%) of the title compound.

1H-NMR (CDCl$_3$, δ): 1.33-1.60 (3H, m), 1.63-1.78 (3H, m), 1.97-2.05 (3H, m), 2.05 (3H, s), 2.15-2.35 (3H, m), 2.37 (3H, s), 2.50-2.58 (2H, m), 2.56 (4H, t, J=5 Hz), 3.59 (4H, t, J=5 Hz), 3.71 (3H, s), 4.69 (1H, dt, J=7 Hz, 5 Hz), 6.13 (1H, br-s), 6.90 (1H, s), 7.72 (1H, d, J=7 Hz), 7.78 (2H, dd, J=8 Hz, 2 Hz), 7.92 (2H, dd, J=8 Hz, 2 Hz)

Reference Example 213

N-[[1-[[[4-[2-(4-Methyl-1-piperazinyl)-4-thiazolyl]phenyl]carbonyl]amino]cyclohexyl]carbonyl]-L-phenylglycine methyl ester

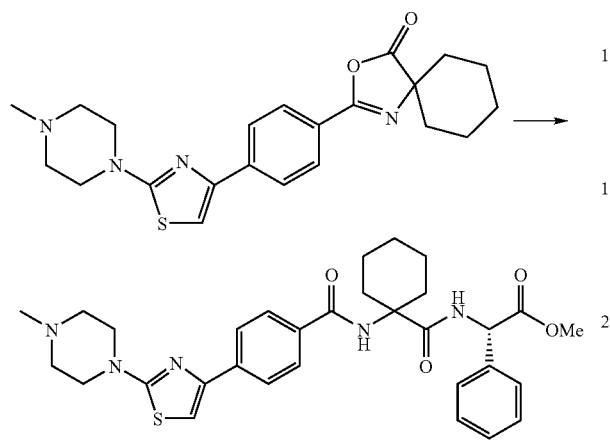

202 mg (1.00 mmol) of L-phenylglycine methyl ester hydrochloride was used instead of L-methionine methyl ester hydrochloride in the process according to Reference example 212 to obtain 156 mg (24%) of the title compound.

1H-NMR (CDCl$_3$, δ): 1.25-1.41 (1H, m), 1.41-1.55 (2H, m), 1.60-1.76 (3H, m), 1.94-2.05 (2H, m), 2.25-2.40 (2H, m), 2.37 (3H, s), 2.56 (4H, t, J=5 Hz), 3.59 (4H, t, J=5 Hz), 3.69 (3H, s), 5.54 (1H, d, J=7 Hz), 6.08 (1H, br-s), 6.89 (1H, s), 7.26-7.35 (3H, m), 7.38-7.41 (2H, m), 7.78 (2H, d, J=8 Hz), 7.92 (2H, d, J=8 Hz), 8.29 (1H, d, J=7 Hz)

Reference Example 214

N-[[1-[[[4-[2-[4-(4-Morpholinyl)-1-piperidinyl]-4-thiazolyl]phenyl]carbonyl]amino]cyclohexyl]carbonyl]-L-methionine methyl ester

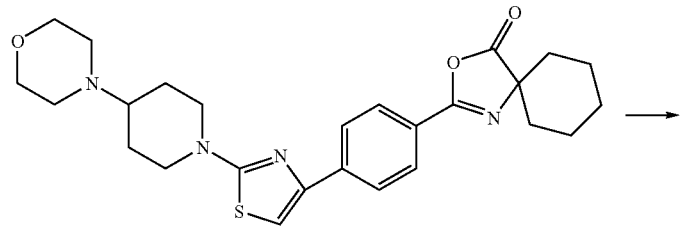

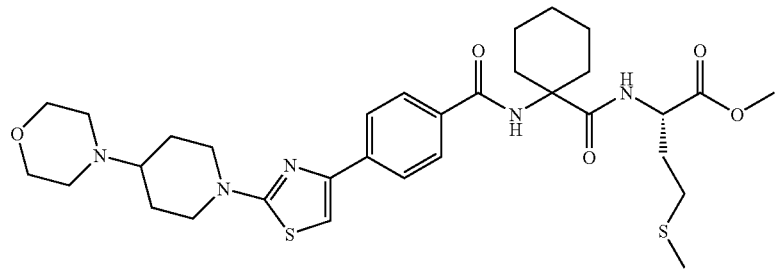

481 mg (1.00 mmol) of 2-[4-[2-[4-(4-morpholinyl)-1-piperidinyl]-4-thiazolyl]phenyl]-3-oxa-1-azaspiro[4.5]dec-1-en-4-one was used instead of 2-[4-[2-(4-methyl-1-piperazinyl)-4-thiazolyl]phenyl]-3-oxa-1-azaspiro[4.5]dec-1-en-4-one in the process according to Reference example 212 to obtain 439 mg (68%) of the title compound.

1H-NMR (CDCl$_3$, δ): 1.31-1.79 (8H, m), 1.92-2.05 (5H, m), 2.05 (3H, s), 2.15-2.34 (3H, m), 2.40-2.49 (1H, m), 2.53 (2H, t, J=7 Hz), 2.59 (4H, t, J=5 Hz), 3.08 (2H, dd, J=12 Hz, 12 Hz), 3.71 (3H, s), 3.74 (4H, t, J=5 Hz), 4.13 (2H, d, J=12 Hz), 4.69 (1H, dt, J=8 Hz, 5 Hz), 6.12 (1H, br-s), 6.88 (1H, s), 7.72 (1H, d, J=8 Hz), 7.78 (2H, d, J=8 Hz), 7.92 (2H, d, J=8 Hz)

Reference Example 215

N-[[1-[[[4-[2-[4-(4-Morpholinyl)-1-piperidinyl]-4-thiazolyl]phenyl]carbonyl]amino]cyclohexyl]carbonyl]-L-phenylglycine methyl ester

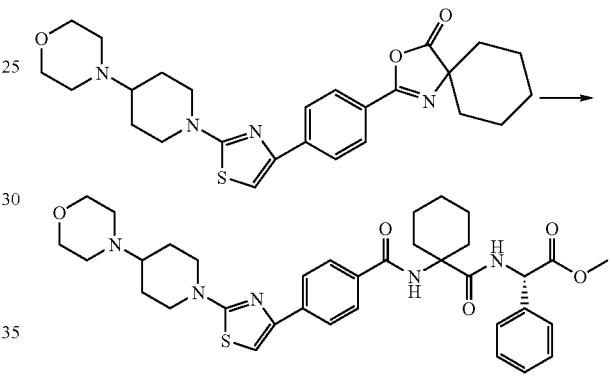

481 mg (1.00 mmol) of 2-[4-[2-[4-(4-morpholinyl)-1-piperidinyl]-4-thizolyl]phenyl]-3-oxa-1-azaspiro[4.5]dec-1-en-4-one was used instead of 2-[4-[2-(4-methyl-1-piperazinyl)-4-thiazolyl]phenyl]-3-oxa-1-azaspiro[4.5]dec-1-en-4-one and 202 mg (1.00 mmol) of L-phenylglycine methyl ester hydrochloride was used instead of L-methionine methyl ester hydrochloride in the process according to Reference example 212 to obtain 156 mg (24%) of the title compound.

1H-NMR (CDCl₃, δ): 1.30-1.41 (1H, m), 1.42-1.60 (3H, m), 1.61-1.77 (4H, m), 1.92-2.08 (4H, m), 2.25-2.37 (2H, m), 2.40-2.49 (1H, m), 2.59 (4H, t, J=5 Hz), 3.08 (2H, dd, J=12 Hz, 12 Hz), 3.69 (3H, s), 3.74 (4H, t, J=5 Hz), 4.12 (2H, d, J=12H), 5.54 (1H, d, J=7 Hz), 6.07 (1H, br-s), 6.87 (1H, s), 7.26-7.36 (3H, m), 7.37-7.42 (2H, m), 7.77 (2H, d, J=8 Hz), 7.91 (2H, d, J=8 Hz), 8.30 (1H, d, J=8 Hz)

Reference Example 216

N-[[1-[(2-Benzothienylcarbonyl)amino]cyclohexyl]carbonyl]-L-phenylglycine

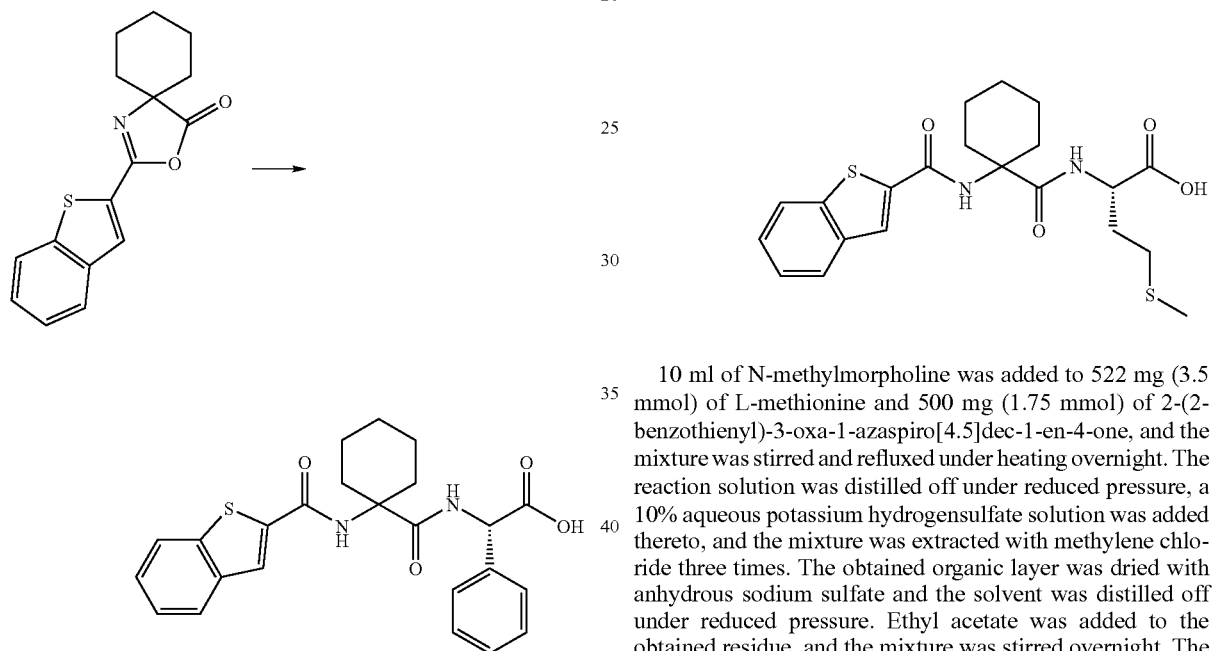

10 ml of N-methylmorpholine was added to 530 mg (3.5 mmol) of L-phenylglycine and 500 mg (1.75 mmol) of 2-(2-benzothienyl)-3-oxa-1-azaspiro[4.5]dec-1-en-4-one, and the mixture was stirred and refluxed under heating overnight. The reaction solution was distilled off under reduced pressure, a 10% aqueous potassium hydrogensulfate solution was added thereto, and the mixture was extracted with methylene chloride three times. The obtained organic layer was dried with anhydrous sodium sulfate and the solvent was distilled off under reduced pressure. Ethyl acetate was added to the obtained residue, and the mixture was stirred overnight. The precipitated solid was collected by filtration and dried under reduced pressure to obtain 259 mg (34%) of the title compound.

1H-NMR (CDCl₃, δ): 1.25-1.80 (6H, m), 1.83-2.03 (2H, m), 2.12-2.40 (2H, m), 4.47 (1H, d, J=5 Hz), 6.11 (1H, s), 7.18-7.55 (8H, m), 7.79 (1H, s), 7.80-7.91 (2H, m)

Reference Example 217

N-[[1-[(2-Benzothienylcarbonyl)amino]cyclohexyl]carbonyl]-L-methionine

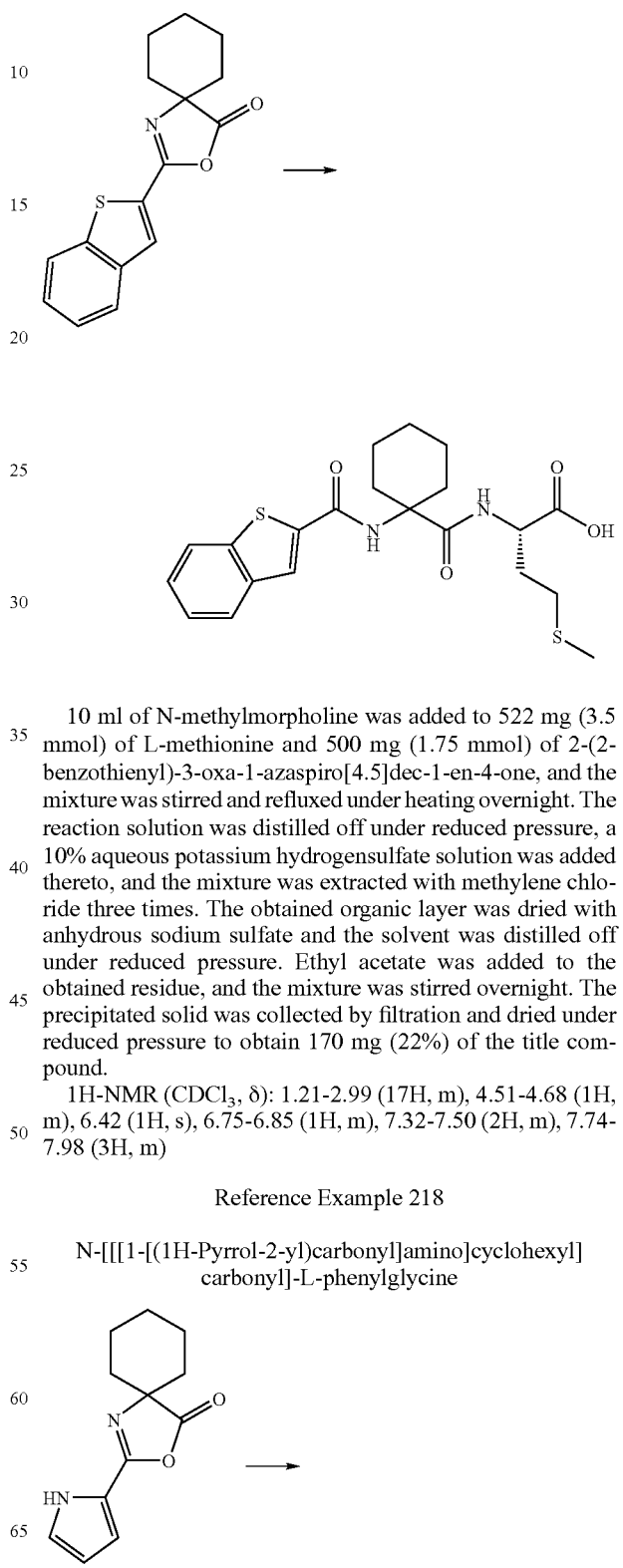

10 ml of N-methylmorpholine was added to 522 mg (3.5 mmol) of L-methionine and 500 mg (1.75 mmol) of 2-(2-benzothienyl)-3-oxa-1-azaspiro[4.5]dec-1-en-4-one, and the mixture was stirred and refluxed under heating overnight. The reaction solution was distilled off under reduced pressure, a 10% aqueous potassium hydrogensulfate solution was added thereto, and the mixture was extracted with methylene chloride three times. The obtained organic layer was dried with anhydrous sodium sulfate and the solvent was distilled off under reduced pressure. Ethyl acetate was added to the obtained residue, and the mixture was stirred overnight. The precipitated solid was collected by filtration and dried under reduced pressure to obtain 170 mg (22%) of the title compound.

1H-NMR (CDCl₃, δ): 1.21-2.99 (17H, m), 4.51-4.68 (1H, m), 6.42 (1H, s), 6.75-6.85 (1H, m), 7.32-7.50 (2H, m), 7.74-7.98 (3H, m)

Reference Example 218

N-[[[1-[(1H-Pyrrol-2-yl)carbonyl]amino]cyclohexyl]carbonyl]-L-phenylglycine

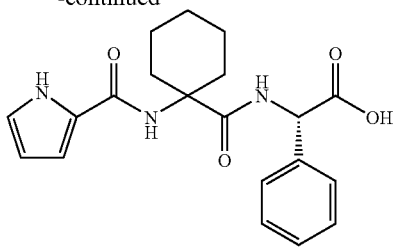

10 ml of N-methylmorpholine was added to 583 mg (3.9 mmol) of L-phenylglycine and 500 mg (1.9 mmol) of 2-(1H-pyrrol-2-yl)-3-oxa-1-azaspiro[4.5]dec-1-en-4-one, and the mixture was stirred and refluxed under heating overnight. The reaction solution was distilled off under reduced pressure, a 10% aqueous potassium hydrogensulfate solution was added thereto, and the mixture was extracted with methylene chloride three times. The obtained organic layer was dried with anhydrous sodium sulfate and the solvent was distilled off under reduced pressure. The obtained residue was purified by silica gel column chromatography to give 120 mg (17%) of the title compound.

1H-NMR (CDCl₃, δ): 1.18-2.08 (9H, m), 2.18-2.30 (1H, m), 5.63 (1H, d, J=7 Hz), 6.16-6.23 (1H, m), 6.25 (1H, s), 6.61-6.83 (2H, m), 7.17-7.35 (3H, m), 7.41 (2H, d, J=8 Hz), 7.83 (1H, d, J=7 Hz), 10.92 (1H, s)

Reference Example 219

N-[[[1-[(1H-Pyrrol-2-yl)carbonyl]amino]cyclohexyl]carbonyl]-L-methionine

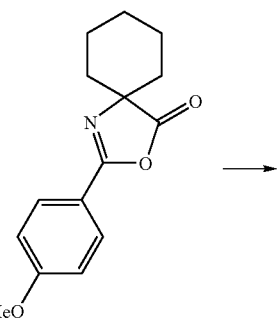

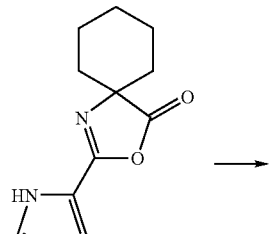

10 ml of N-methylmorpholine was added to 575 mg (3.9 mmol) of L-methionine and 500 mg (1.9 mmol) of 2-(1H-pyrrol-2-yl)-3-oxa-1-azaspiro[4.5]dec-1-en-4-one, and the mixture was stirred and refluxed under heating overnight. The reaction solution was distilled off under reduced pressure, a 10% aqueous potassium hydrogensulfate solution was added thereto, and the mixture was extracted with methylene chloride three times. The obtained organic layer was dried with anhydrous sodium sulfate and the solvent was distilled off under reduced pressure. Ethyl acetate was added to the obtained residue, and the mixture was stirred overnight. The precipitated solid was collected by filtration and dried under reduced pressure to obtain 503 mg (72%) of the title compound.

1H-NMR (CDCl₃, δ): 1.20-2.33 (15H, m), 2.42-2.61 (2H, m), 4.58-4.72 (1H, m), 6.21 (1H, dd, J=5 Hz, 3 Hz), 6.28 (1H, s), 6.69 (1H, d, J=3 Hz), 6.78 (1H, d, J=5 Hz), 7.29 (1H, d, J=8 Hz)

Reference Example 220

N-[[[1-[(4-Methoxyphenyl)carbonyl]amino]cyclohexyl]carbonyl]-L-phenylglycine

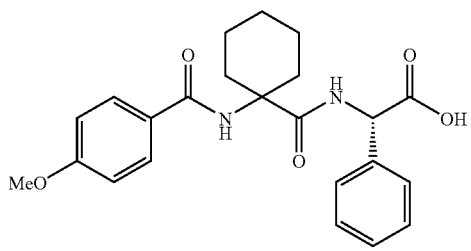

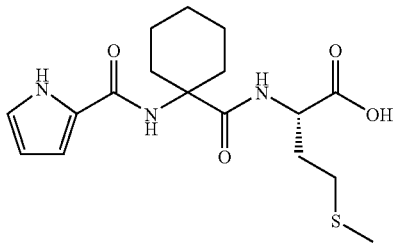

10 ml of N-methylmorpholine was added to 583 mg (3.9 mmol) of L-phenylglycine and 500 mg (1.9 mmol) of 2-(4-methoxyphenyl)-3-oxa-1-azaspiro[4.5]dec-1-en-4-one, and the mixture was stirred and refluxed under heating overnight. The reaction solution was distilled off under reduced pressure, a 10% aqueous potassium hydrogensulfate solution was added thereto, and the mixture was extracted with methylene chloride three times. The obtained orgnanic layer was dried with anhydrous sodium hydrogensulfate and the solvent was distilled off under reduced pressure. The obtained residue was purified by silica gel column chromatography to give 92 mg (22%) of the title compound.

1H-NMR (CDCl₃, δ): 1.25-1.58 (3H, m), 1.60-1.81 (3H, m), 1.85-2.05 (2H, m), 2.17-2.39 (2H, m), 3.86 (3H, s), 4.45 (1H, d, J=6 Hz), 6.01 (1H, s), 6.82-7.00 (3H, m), 7.19-7.38 (4H, m), 7.57-7.83 (3H, m)

Reference Example 221

N-[[1-[[(4-Methoxyphenyl)carbonyl]amino]cyclo-hexyl]carbonyl]-L-methionine

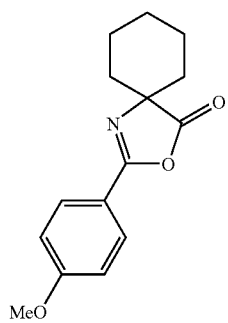

↓

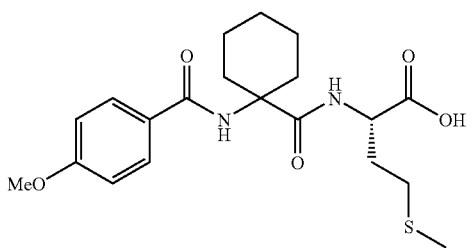

10 ml of N-methylmorpholine was added to 298 mg (2 mmol) of L-methionine and 259 mg (1 mmol) of 2-(4-methoxyphenyl)-3-oxa-1-azaspiro[4.5]dec-1-en-4-one, and the mixture was stirred and refluxed under heating overnight. The reaction solution was distilled off under reduced pressure, a 10% aqueous potassium hydrogensulfate solution was added thereto, and the mixture was extracted with methylene chloride three times. The obtained organic layer was dried with anhydrous sodium hydrogensulfate and the solvent was distilled off under reduced pressure. Ethyl acetate was added to the obtained residue, and the mixture was stirred overnight. The precipitated solid was collected by filtration and dried under reduced pressure to obtain 52 mg (13%) of the title compound.

1H-NMR (CDCl$_3$, δ): 1.20-2.62 (17H, m), 3.86 (3H, s), 4.56-4.71 (1H, m), 6.27 (1H, s), 6.95 (2H, d, J=9 Hz), 7.75 (2H, d, J=9 Hz), 7.86 (1H, d, J=8 Hz)

Reference Example 222

N-[[1-[[(E)-3-(2-Furanyl)-1-oxo-2-propenyl]amino]cyclohexyl]carbonyl]-L-methionine

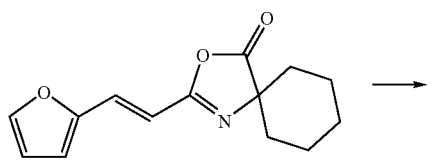

↓

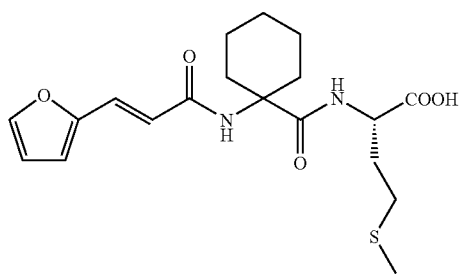

A solution of 491 mg (2 mmol) of 2-[(E)-2-(2-furanyl)ethenyl]-3-oxo-1-azaspiro[4.5]dec-1-en-4-one and 597 mg (4 mmol) of L-methionine in 20 ml of N-methylmorpholine was refluxed under heating for 15 hours. After ethyl acetate and water was added to the reaction solution, it was acidified using concentrated hydrochloric acid. The organic layer was separated and was successively washed with water and saturated brine, followed by drying with anhydrous sodium sulfate. After the solvent was distilled off under reduced pressure, the residue was purified by silica gel chromatography to obtain 74 mg (9%) of the title compound.

1H-NMR (CDCl$_3$, δ): 1.24-1.48 (3H, m), 1.59-1.71 (3H, m), 1.87-1.98 (2H, m), 2.00-2.25 (4H, m), 2.05 (3H, s), 2.51-2.63 (2H, m), 4.63 (1H, dt, J=8 Hz, 5H), 6.00 (1H, br-s), 6.40 (1H, d, J=15 Hz), 6.46 (1H, dd, J=3 Hz, 2 Hz), 6.59 (1H, d, J=3 Hz), 7.40 (1H, d, J=15 Hz), 7.45 (1H, d, J=2 Hz), 7.76 (1H, d, J=8 Hz)

Example 27

N-[[1-[[(2-Furanylmethoxy)carbonyl]amino]cyclohexyl]carbonyl]-L-valinol

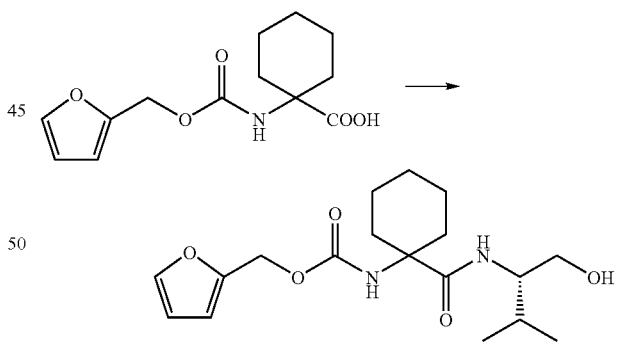

2.00 g (7.48 mmol) of 1-[[(2-furanylmethoxy)carbonyl]amino]cyclohexanecarboxylic acid was used instead of 2-benzothiophenecarboxylic acid and 772 mg (7.48 mmol) of L-valinol was used instead of 1-aminocyclohexanecarboxylic acid phenylmethyl ester in the process according to Reference example 188 to obtain 2.64 g (quantitative) of the title compound.

1H-NMR (CDCl$_3$, δ): 0.90 (3H, d, J=7 Hz), 0.95 (3H, d, J=7 Hz) 1.29-1.46 (3H, m), 1.56-1.72 (3H, m), 1.78-1.85 (1H, m), 1.88-1.96 (2H, m), 1.96-2.06 (2H, m), 2.75-2.90 (1H, br-s), 3.48-3.55 (1H, m), 3.68-3.78 (2H, m), 5.06 (1H, br-s), 5.00 (1H, d, J=13 Hz), 5.10 (1H, d, J=13 Hz), 6.35 (1H, br-s), 6.37 (1H, dd, J=3 Hz, 2 Hz), 6.43 (1H, dd, J=3 Hz, 1 Hz), 7.43 (1H, dd, J=2 Hz, 1 Hz)

Example 28

N-[[1-[[(2-Furanylmethoxy)carbonyl]amino]cyclohexyl]carbonyl]-L-valinal

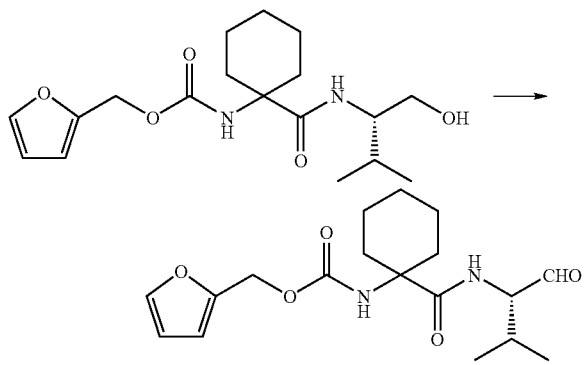

2.67 g of N-[[1-[[(2-furanylmethoxy)carbonyl]amino]cyclohexyl]carbonyl]-L-valinol, obtained above, was used instead of N-[[1-[(2-benzothienylcarbonyl)amino]cyclohexyl]carbonyl]-L-methioninol in the process according to Example 14 to obtain 2.08 g (83.7%, 2 steps) of the title compound.

1H-NMR (CDCl$_3$, δ): 0.92 (3H, d, J=7 Hz), 1.00 (3H, d, J=7 Hz), 1.26-1.46 (3H, m), 1.52-1.70 (3H, m), 1.86-1.96 (2H, m), 1.96-2.04 (1H, m), 2.05-2.14 (1H, m), 2.28-2.36 (1H, m), 4.46-4.52 (1H, m), 4.92-4.99 (1H, br-s), 5.04 (1H, d, J=13 Hz), 5.09 (1H, d, J=13 Hz), 6.36 (1H, dd, J=3 Hz, 2 Hz), 6.41 (1H, d, J=3 Hz), 7.04-7.16 (1H, m), 7.42 (1H, d, J=2 Hz), 9.61 (1H, s)

Example 29

N-[[1-[[(E)-3-(2-Furanyl)-1-oxo-2-propenyl]amino]cyclohexyl]carbonyl]-L-valinol

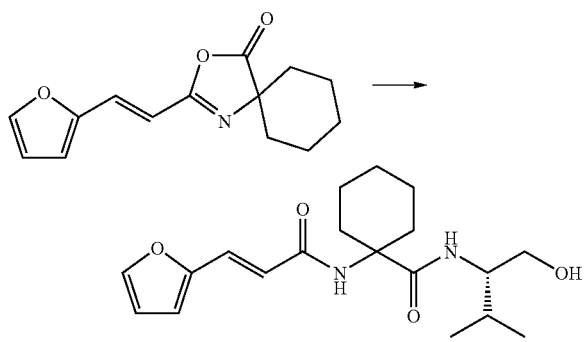

1.07 ml (6.12 mmol) of diisopropylamine was added to a solution of 252 mg (2.45 mmol) of L-valinol and 500 mg (2.04 mmol) of 2-[(E)-2-(2-furanyl)ethenyl]-3-oxo-1-azaspiro[4.5]dec-1-en-4-one in 15 ml of toluene, and the mixture was stirred and refluxed under heating for 4 days. The reaction solution was distilled off under reduced pressure and purified by silica gel chromatography to obtain 481 mg (67.7%) of the title compound.

1H-NMR (CDCl$_3$, δ): 0.93 (3H, d, J=7 Hz), 0.95 (3H, d, J=7 Hz), 1.34-1.52 (3H, m), 1.60-1.74 (3H, m), 1.80-1.88 (1H, m), 1.94-2.06 (2H, m), 2.08-2.18 (2H, m), 3.16-3.21 (1H, m), 3.51-3.57 (1H, m), 3.68-3.78 (2H, m), 5.72 (1H, br-s), 6.35 (1H, d, 15 Hz), 6.47 (1H, dd, J=3 Hz, 2 Hz), 6.58 (1H, dd, J=3 Hz, 1 Hz), 6.73 (1H, br-d, J=9 Hz), 7.41 (1H, d, J=15 Hz), 7.46 (1H, dd, J=2 Hz, 1 Hz)

Example 30

N-[[1-[[(E)-3-(2-Furanyl)-1-oxo-2-propenyl]amino]cyclohexyl]carbonyl]-L-valinal

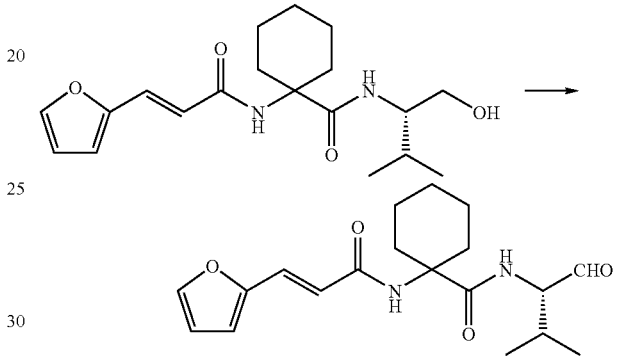

481 mg (1.38 mmol) of N-[[1-[[(E)-3-(2-furanyl)-1-oxo-2-propenyl]amino]cyclohexyl]carbonyl]-L-valinol was used instead of N-[[1-[(2-benzothienylcarbonyl)amino]cyclohexyl]carbonyl]-L-methioninol in the process according to Example 14 to obtain 449 mg (93.9%) of the title compound.

1H-NMR (CDCl$_3$, δ): 0.95 (3H, d, J=7 Hz), 1.01 (3H, d, J=7 Hz), 1.30-1.74 (6H, m), 1.92-2.02 (2H, m), 2.14-2.22 (1H, m), 2.22-2.30 (1H, m), 2.28-2.36 (1H, m), 4.42 (1H, ddd, J=8 Hz, 5 Hz, 1 Hz), 5.55 (1H, br-s), 6.38 (1H, d, J=15 Hz), 6.47 (1H, dd, J=3 Hz, 2 Hz), 6.58 (1H, d, J=3 Hz, 1 Hz), 7.42 (1H, d, J=15 Hz), 7.46 (1H, dd, J=2 Hz, 1 Hz), 7.83 (1H, d, J=8 Hz), 9.59 (1H, d, 1 Hz)

Example 31

N-[[1-[(3-Furanylcarbonyl)amino]cyclohexyl]carbonyl]-L-valinol

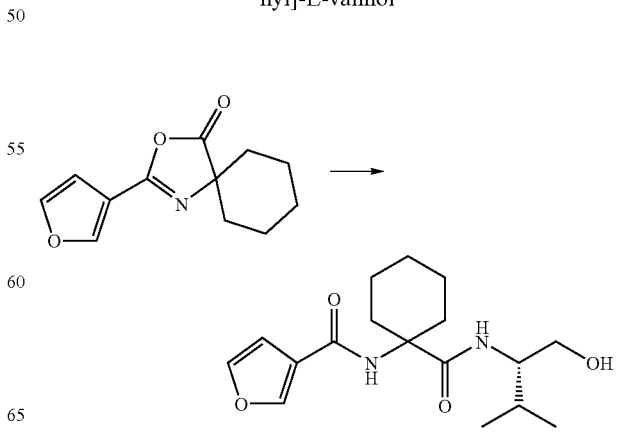

0.52 ml (3.01 mmol) of diisopropylamine was added to a solution of 124 mg (1.20 mmol) of L-valinol and 222 mg (1.00 mmol) of 2-(3-furanyl)-3-oxo-1-azaspiro[4.5]dec-1-en-4-one in 10 ml of toluene, and the solution was stirred and refluxed under heating for 4 days. The reaction mixture was distilled off under reduced pressure and purified by silica gel chromatography to obtain 340 mg (quantitative) of the title compound.

1H-NMR (CDCl$_3$, δ): 0.93 (3H, d, J=7 Hz), 0.96 (3H, d, J=7 Hz), 1.35-1.54 (3H, m), 1.56-1.76 (3H, m), 1.82-1.90 (1H, m), 1.96-2.06 (2H, m), 2.13-2.20 (2H, m), 3.05 (1H, br-s), 3.54-3.59 (1H, m), 3.69-3.78 (2H, m), 5.88 (1H, br-s), 6.60 (1H, dd, J=2 Hz, 1 Hz), 6.80 (1H, br-d, J=8 Hz), 7.46 (1H, dd, J=2 Hz, 2 Hz), 7.96 (1H, dd, J=2 Hz, 1 Hz)

Example 32

N-[[1-[(3-Furanylcarbonyl)amino]cyclohexyl]carbonyl]-L-valinal

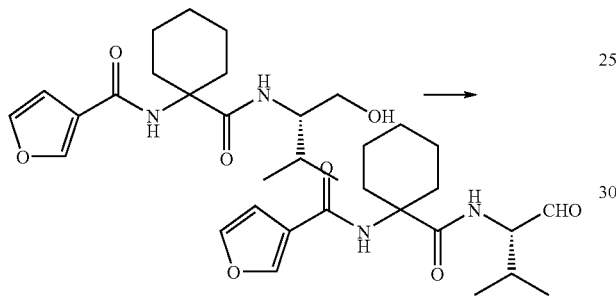

340 mg of the above obtained N-[[1-[(3-furanylcarbonyl)amino]cyclohexyl]carbonyl]-L-valinol was used instead of N-[[1-[(2-benzothienylcarbonyl)amino]cyclohexyl]carbonyl]-L-methioninol in the process according to Example 14 to give 282 g (87.6%, 2 steps) of the title compound.

1H-NMR (CDCl$_3$, δ): 0.95 (3H, d, J=7 Hz), 1.02 (3H, d, J=7 Hz), 1.32-1.52 (3H, m), 1.60-1.76 (3H, m), 1.95-2.06 (2H, m), 2.18-2.24 (1H, m), 2.26-2.36 (2H, m), 4.46 (1H, ddd, J=8 Hz, 5 Hz, 1 Hz), 5.74 (1H, br-s), 6.62 (1H, dd, J=2 Hz, 1 Hz), 7.47 (1H, dd, J=2 Hz, 1 Hz), 7.71 (1H, d, J=8 Hz), 7.97 (1H, dd, J=1 Hz, 1 Hz), 9.61 (1H, d, J=1 Hz)

Example 33

N-[[1-[[(4-Methoxyphenyl)carbonyl]amino]cyclohexyl]carbonyl]-L-valinol

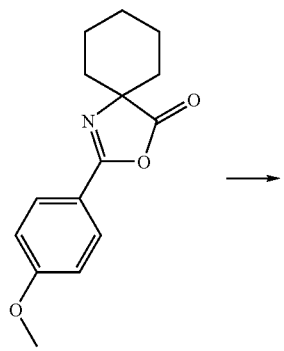

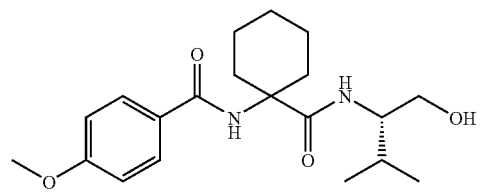

260 mg (1.00 mmol) of 2-(4-methoxyphenyl)-3-oxo-1-azaspiro[4.5]dec-1-en-4-one was added to a solution of 252 mg (2.45 mmol) of L-valinol in 5 ml of ethyl acetate, and the mixture was stirred at room temperature for 4 days. The reaction solution was distilled off under reduced pressure and the residue was washed with diethyl ether to obtain 243.5 mg (66.7%) of the title compound.

1H-NMR (CDCl$_3$, δ): 0.93 (3H, d, J=7 Hz), 0.96 (3H, d, J=7 Hz), 1.36-1.80 (7H, m), 1.80-1.88 (1H, m), 1.98-2.10 (2H, m), 2.16-2.26 (2H, m), 3.55 (1H, dd, J=11 Hz, 6 Hz), 3.69-3.74 (1H, m), 3.77 (1H, dd, J=11 Hz, 3 Hz), 3.86 (3H, s), 6.17 (1H, br-s), 6.84 (1H, br-d, J=9 Hz), 6.95 (2H, dd, J=7 Hz, 2 Hz), 7.74 (2H, dd, J=7 Hz, 2 Hz)

Example 34

N-[[1-[[(4-Methoxyphenyl)carbonyl]amino]cyclohexyl]carbonyl]-L-valinal

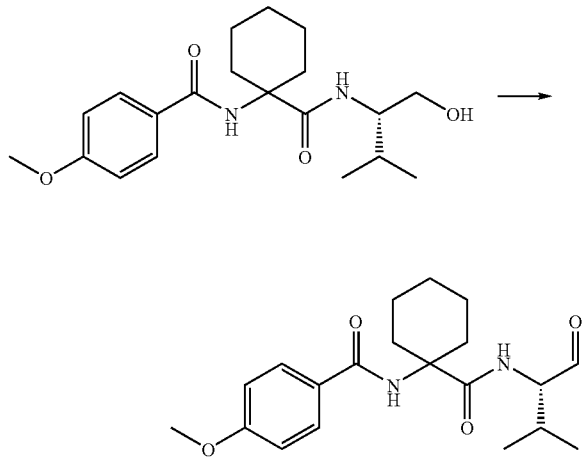

243 mg (0.67 mmol) of N-[[1-[[(4-methoxyphenyl)carbonyl]amino]cyclohexyl]carbonyl]-L-valinol was used instead of N-[[1-[(2-benzothienylcarbonyl)amino]cyclohexyl]carbonyl]-L-methioninol in the process according to Example 14 to obtain 240 mg (98.9%) of the title compound.

1H-NMR (CDCl$_3$, δ): 0.95 (3H, d, J=7 Hz), 1.02 (3H, d, J=7 Hz), 1.34-1.54 (3H, m), 1.63-1.78 (3H, m), 1.96-2.05 (2H, m), 2.24-2.37 (3H, m), 3.87 (3H, s), 4.43 (1H, ddd, J=8 Hz, 5 Hz, 1 Hz), 6.03 (1H, br-s), 6.96 (2H, dd, J=7 Hz, 2 Hz), 7.75 (2H, dd, J=7 Hz, 2 Hz), 7.87 (1H, d, J=8 Hz), 9.60 (1H, s)

Example 35

N-[[1-[[(1H-Pyrrol-2-yl)carbonyl]amino]cyclohexyl]carbonyl]-L-valinol

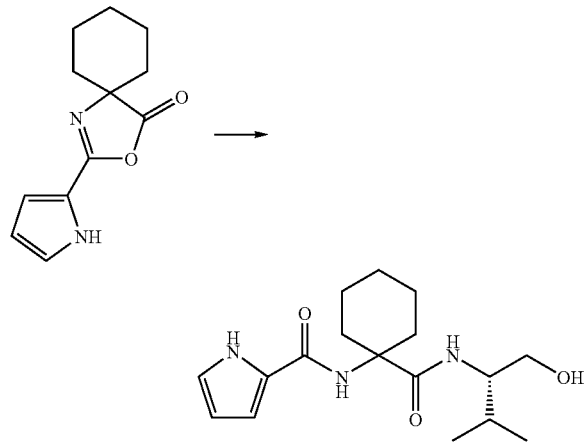

220 mg (1.01 mmol) of 2-(1H-pyrrol-2-yl)-3-oxo-1-azaspiro[4.5]dec-1-en-4-one was added to a solution of 252 mg (2.45 mmol) of L-valinol in 5 ml of ethyl acetate, and the mixture was stirred at room temperature for 4 days. The reaction solution was distilled off under reduced pressure and purified by silica gel chromatography to obtain 247 mg (76.4%) of the title compound.

1H-NMR (CDCl$_3$, δ): 0.93 (3H, d, J=7 Hz), 0.94 (3H, d, J=7 Hz), 1.34-1.52 (3H, m), 1.62-2.14 (8H, m), 2.16-2.22 (1H, m), 3.51 (1H, dd, J=12 Hz, 7 Hz), 3.69-3.76 (2H, m), 6.03 (1H, br-s), 6.27 (1H, ddd, J=4 Hz, 3 Hz, 3 Hz), 6.60-6.66 (2H, m), 6.97 (1H, ddd, J=3 Hz, 3 Hz, 1 Hz), 9.48 (1H, br-s)

Example 36

N-[[1-[[(1H-Pyrrol-2-yl)carbonyl]amino]cyclohexyl]carbonyl]-L-valinal

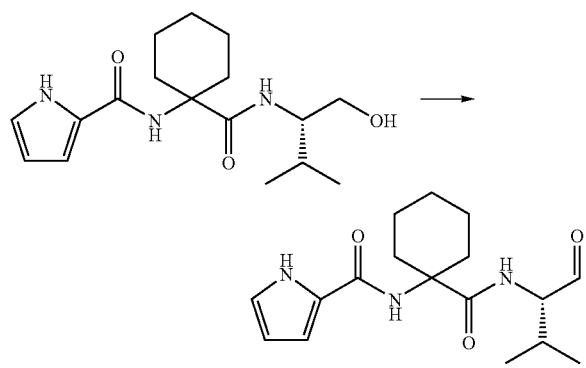

247 mg (0.77 mmol) of N-[[1-[[(1H-pyrrol-2-yl)carbonyl]amino]cyclohexyl]carbonyl]-L-valinol was used instead of N-[[1-[(2-benzothienylcarbonyl)amino]cyclohexyl]carbonyl]-L-methioninol in the process according to Example 14 to obtain 217 mg (88.2%) of the title compound.

1H-NMR (CDCl$_3$, δ): 0.93 (3H, d, J=7 Hz), 1.00 (3H, d, J=7 Hz), 1.32-1.52 (3H, m), 1.60-1.76 (3H, m), 1.94-2.03 (2H, m), 2.18-2.25 (1H, m), 2.26-2.34 (2H, m), 4.45 (1H, dd, J=8 Hz, 5 Hz), 5.84 (1H, br-s), 6.28 (1H, ddd, J=4 Hz, 3 Hz, 3 Hz), 6.63 (1H, ddd, J=4 Hz, 3 Hz, 1 Hz), 6.96 (1H, ddd, J=3 Hz, 3 Hz, 1 Hz), 7.75 (1H, br-d, J=8 Hz), 9.33 (1H, br-s), 9.59 (1H, s)

Test Example 1

Measurement of Cathepsin K Inhibitory Activity

Active enzyme was produced by expressing cathepsin K as a proenzyme in a cell culture from a baculovirus expression system using Sf21 insect cells, followed by incubating for 1 hour at 40° C.[1]. Cathepsin K activity was measured based on decomposition of the fluorescent substrate Z-Gly-Pro-Arg-MCA (Peptide Institute, Inc.) following the method of Aibe et al.[2]. Namely, the decomposition of 20 mM Z-Gly-Pro-Arg-MCA by cathepsin K was measured in 100 mM sodium/potassium phosphate, 1 mM EDTA and 8 mM cysteine at pH 6.0. The reaction was carried out for 30 minutes at 37° C., and stopped by the addition of $2\times10^{-5}$ M Calpeptin. After stopping the reaction, fluorescent intensity was measured at an excitation wavelength of 355 nm and measurement wavelength of 460 nm. Inhibition of cathepsin K by the compounds was examined using the reaction system described above. The 50% inhibitory concentrations on cathepsin K of the compounds of the examples are shown in Table 1.

Test Example 2

Measurement of Cathepsin B Inhibitory Activity

Human cathepsin B (Calbiochem Corp.) was used for measurement. Activity was measured based on decomposition of the fluorescent substrate Z-Arg-Arg-MCA (Peptide Institute, Inc.) following the method of Barrett et al.[3]. Namely, the decomposition of 20 mM Z-Arg-Arg-MCA by cathepsin B was measured in 100 mM sodium/potassium phosphate, 1 mM EDTA, 8 mM cysteine and 0.005% Brij35 at pH 6.0. The reaction was carried out for 30 minutes at 30° C., and stopped by the addition of $2\times10^{-5}$ M Calpeptin. After stopping the reaction, fluorescent intensity was measured at an excitation wavelength of 355 nm and measurement wavelength of 460 nm. Inhibition of cathepsin B by the compounds was examined using the reaction system described above. The 50% inhibitory concentrations on cathepsin B of the compounds of the examples are shown in Table 1.

Test Example 3

Measurement of Cathepsin L Inhibitory Activity

Human cathepsin L (Calbiochem Corp.) was used for measurement. Activity was measured based on decomposition of the fluorescent substrate Z-Phe-Arg-MCA (Peptide Institute, Inc.) following the method of Barrett et al.[3]. Namely, the decomposition of 20 mM Z-Phe-Arg-MCA by cathepsin L was measured in 100 mM sodium acetate, 5 mM EDTA, 4 mM urea, 8 mM cysteine and 0.005% Brij35 at pH 5.5. The reaction was carried out for 30 minutes at 30° C., and stopped by the addition of $2\times10^{-5}$ M Calpeptin. After stopping the reaction, fluorescent intensity was measured at an excitation wavelength of 355 nm and measurement wavelength of 460 nm. Inhibition of cathepsin L by the compounds was examined using the reaction system described above. The 50% inhibitory concentrations on cathepsin L of the compounds of the examples are shown in Table 1.

REFERENCE

Tezuka et al., J. Biol. Chem., 269, 1106-1109 (1994)
Aibe et al., Biol. Pharm. Bull., 19, 1026-1031 (1996)
Barrett, A. J. & Kirschke, H. Methods Enzymol. 80, 535-561 (1981)

| Compound No. | Structural Formula | IC$_{50}$ (M) | | |
|---|---|---|---|---|
| | | Cathepsin K | human Cathepsin B | human Cathepsin L |
| Reference Example 184 | (structure) | $1.9 \times 10^{-9}$ | $1.1 \times 10^{-7}$ B/K 58 | $1.4 \times 10^{-7}$ L/K 74 |
| Example 7 | (structure) | $1.7 \times 10^{-9}$ | $3.9 \times 10^{-7}$ B/K 230 | $6.8 \times 10^{-7}$ L/K 400 |
| Reference Example 185 | (structure) | $3.5 \times 10^{-9}$ | $4.0 \times 10^{-8}$ B/K 11 | $5.3 \times 10^{-8}$ L/K 15 |
| Example 8 | (structure) | $4.0 \times 10^{-9}$ | $1.4 \times 10^{-7}$ B/K 35 | $2.0 \times 10^{-7}$ L/K 50 |
| Reference Example 186 | (structure) | $3.0 \times 10^{-9}$ | $1.3 \times 10^{-8}$ B/K 4.3 | $2.2 \times 10^{-8}$ L/K 7.3 |
| Example 10 | (structure) | $2.2 \times 10^{-8}$ | $2.6 \times 10^{-7}$ B/K 12 | $4.7 \times 10^{-7}$ L/K 21 |

| Compound No. | Structural Formula | IC$_{50}$ (M) Cathepsin K | human Cathepsin B | human Cathepsin L |
|---|---|---|---|---|
| Reference Example 187 | | $1.9 \times 10^{-9}$ | $5.7 \times 10^{-8}$ B/K 30 | $6.7 \times 10^{-8}$ L/K 35 |
| Example 9 | | $5.4 \times 10^{-10}$ | $4.7 \times 10^{-8}$ B/K 87 | $2.0 \times 10^{-7}$ L/K 370 |

The invention claimed is:

1. A cycloalkane carboxamide compound of formula (I):

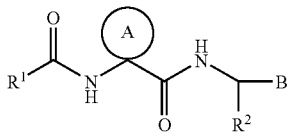

(I)

or a pharmaceutically acceptable salt thereof, wherein $R^1$ is a substituted or unsubstituted monocyclic or polycyclic $C_{6-18}$ aromatic hydrocarbon group or a substituted or unsubstituted 3- to 7-membered heterocyclic ring group containing at least one nitrogen atom, oxygen atom or sulfur atom as a ring-member atom, or a group $R^4O-$, $R^2$ and $R^4$ are respectively and independently a substituted or unsubstituted alkyl group selected from $C_{1-12}$ linear alkyl and $C_{3-12}$ branched or cyclic alkyl, a substituted or unsubstituted alkenyl group selected from $C_{2-12}$ linear alkenyl and $C_{3-12}$ branched or cyclic alkenyl, a substituted or unsubstituted alkynyl group selected from $C_{2-12}$ linear alkynyl and $C_{3-12}$ branched or cyclic alkynyl, a substituted or unsubstituted aromatic hydrocarbon group selected from monocyclic or polycyclic $C_{6-18}$ aromatic hydrocarbon, or a substituted or unsubstituted heterocyclic group selected from 3- to 7-membered heterocyclic rings containing at least one nitrogen atom, oxygen atom or sulfur atom as a ring-member atom; ring A is a cyclohexane-1,1-diyl group; and B is a formyl group;

wherein the alkyl of $R^2$, if substituted, is substituted with a hydroxyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group;

the alkyl of $R^4$, if substituted, is substituted with a hydroxyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group;

the alkenyl of $R^2$ and $R^4$, if substituted, respectively and independently are substituted with a hydroxyl group, an alkyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group;

the alkynyl of $R^2$ and $R^4$, if substituted, respectively and independently are substituted with a hydroxyl group, an alkyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group;

the aromatic hydrocarbon of $R^1$, $R^2$, and $R^4$, if substituted, respectively and independently are substituted with a hydroxyl group, an alkyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group; and the heterocycle of $R^1$, $R^2$, and $R^4$, if substituted, respectively and independently are substituted with a hydroxyl group, an alkyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group.

2. The cycloalkane carboxamide compound according to claim 1, or a pharmaceutically acceptable salt thereof, wherein $R^1$ is a substituted or unsubstituted monocyclic or polycyclic $C_{6-18}$ aromatic hydrocarbon group, or a substituted or unsubstituted 3- to 7-membered heterocyclic ring group containing at least one nitrogen atom, oxygen atom or sulfur atom as a ring-member atom, and $R^2$ is a substituted or unsubstituted $C_{1-12}$ linear alkyl, substituted or unsubstituted $C_{3-12}$ branched or cyclic alkyl, or a substituted or unsubstituted monocyclic or polycyclic $C_{6-18}$ aromatic hydrocarbon group.

3. A cycloalkane carboxamide compound of formula (I):

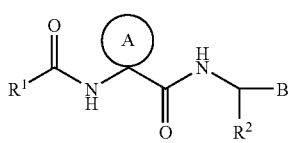

or a pharmaceutically acceptable salt thereof, wherein $R^1$ is a 3- to 7-membered substituted or unsubstituted heterocyclic group containing at least one nitrogen atom, oxygen atom or sulfur atom as a ring-member atom, or a substituted aromatic hydrocarbon group; ring A is a cyclohexane-1,1-diyl group; $R^2$ is a substituted or unsubstituted $C_{1-4}$ alkyl group; and B is a hydroxymethyl group.

4. The cycloalkane carboxamide compound according to claim 1, or a pharmaceutically acceptable salt thereof, wherein $R^2$ is an unsubstituted alkyl group selected from $C_{1-12}$ linear alkyl and $C_{3-12}$ branched or cyclic alkyl, a substituted or unsubstituted alkenyl group selected from $C_{1-12}$ linear alkenyl and $C_{3-12}$ branched or cyclic alkenyl, a substituted or unsubstituted alkynyl group selected from linear $C_{2-12}$ alkynyl and $C_{3-12}$ branched or cyclic alkynyl, a substituted or unsubstituted aromatic hydrocarbon group selected from monocyclic or polycyclic $C_{6-18}$ aromatic hydrocarbon, or a substituted or unsubstituted heterocyclic group selected from 3- to 7-membered heterocyclic rings containing at least one nitrogen atom, oxygen atom or sulfur atom.

5. The cycloalkane carboxamide compound according to claim 4, or a pharmaceutically acceptable salt thereof, wherein $R^1$ is monocyclic or polycyclic $C_{6-18}$ aromatic hydrocarbon or 3- to 7-membered heterocyclic ring containing at least one nitrogen atom, oxygen atom or sulfur atom as a ring-member atom, and $R^2$ is an unsubstituted alkyl group selected from $C_{1-12}$ linear alkyl and $C_{3-12}$ branched or cyclic alkyl, or a substituted or unsubstituted aromatic hydrocarbon group selected from monocyclic or polycyclic $C_{6-18}$ aromatic hydrocarbon.

6. A cycloalkane carboxamide compound of the formula (I):

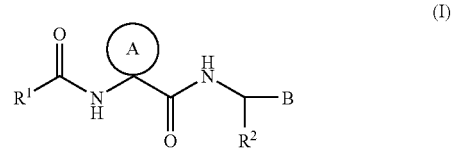

or a pharmaceutically acceptable salt thereof, wherein $R^1$ is a substituted or unsubstituted aromatic hydrocarbon group selected from a monocyclic or polycyclic $C_{6-18}$ aromatic hydrocarbon group, a substituted or unsubstituted heterocyclic group selected from a 3- to 7-membered heterocyclic ring group containing at least one nitrogen atom, oxygen atom or sulfur atom as a ring-member atom, or a group $R^4O—$, $R^2$ is an unsubstituted alkyl group selected from 7 linear alkyl and $C_{3-12}$ branched or cyclic alkyl, a substituted or unsubstituted alkenyl group selected from $C_{2-12}$ linear alkenyl and $C_{3-12}$ branched or cyclic alkenyl, a substituted or unsubstituted alkynyl group selected from $C_{2-12}$ linear alkynyl and $C_{3-17}$ branched or cyclic alkynyl, a substituted or unsubstituted aromatic hydrocarbon selected from monocyclic or polycyclic $C_{6-18}$ aromatic hydrocarbon, or a substituted or unsubstituted heterocyclic group selected from 3- to 7-membered heterocyclic rings containing at least one nitrogen atom, oxygen atom or sulfur atom as a ring-member atom;

$R^4$ is a substituted or unsubstituted alkyl group selected from $C_{1-12}$ linear alkyl and $C_{3-12}$ branched or cyclic alkyl, a substituted or unsubstituted alkenyl group selected from $C_{2-12}$ linear alkenyl and $C_{3-12}$ branched or cyclic alkenyl, a substituted or unsubstituted alkynyl group selected from C$_{2-12}$ linear alkynyl and C$_{3-12}$ branched or cyclic alkynyl, a substituted or unsubstituted aromatic hydrocarbon selected from monocyclic or polycyclic C$_{6-18}$ aromatic hydrocarbon, or a substituted or unsubstituted heterocyclic group selected from 3- to 7-membered heterocyclic rings containing at least one nitrogen atom, oxygen atom or sulfur atom as a ring-member atom;

ring A is a cyclohexane-1,1-diyl group; and B is a hydroxymethyl group, wherein the alkyl of R$^4$, if substituted, is substituted with a hydroxyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group;

the alkenyl of R$^2$ and R$^4$, if substituted, respectively and independently are substituted with a hydroxyl group, an alkyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group;

the alkynyl of R$^2$ and R$^4$, if substituted, respectively and independently are substituted with a hydroxyl group, an alkyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group;

the aromatic hydrocarbon of R$^1$, R$^2$ and R$^4$, if substituted, respectively and independently are substituted with a hydroxyl group, an alkyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group; and the heterocycle of R$^1$, R$^2$ and R$^4$, if substituted, respectively and independently are substituted with a hydroxyl group, an alkyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an aryloxy group, an azido group, a sulfonamido group, a mercapto group, an alkoxycarbonylamino group or a group Rx(Ry)N, wherein Rx and Ry respectively and independently are a hydrogen atom, an alkyl group, an alkenyl group, an alkynyl group, an aromatic hydrocarbon group or a heterocyclic group.

7. The cycloalkane carboxamide compound according to claim 1 or 6, or a pharmaceutically acceptable salt thereof, wherein R$^1$ is a substituted or unsubstituted C$_{6-18}$ aromatic hydrocarbon group, or a substituted or unsubstituted 3- to 7-membered heterocyclic group, and R$^2$ is an unsubstituted alkyl group, or a substituted or unsubstituted C$_{6-18}$ aromatic hydrocarbon group.

8. The cycloalkane carboxamide compound according to claim 3, or a pharmaceutically acceptable salt thereof, wherein the 3- to 7-membered heterocyclic group of R$^1$ is substituted with a hydroxyl group, an alkyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfa group, a cyano group, a nitro group, an acyloxy group, an azido group, a sulfonamide group, a mercapto group, an alkoxycarbonylamino group or a group Rx(Ry)N, the aromatic hydrocarbon group of R$^1$ is substituted with a hydroxyl group, an alkyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carboxyl group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, the C$_{1-4}$ alkyl of R$^2$ is subsituted with a hydroxyl group, an alkenyl group, an alkynyl group, a halogen atom, an aromatic hydrocarbon group, a heterocyclic group, an alkoxy group, a guanidino group, an alkylthio group, an alkoxycarbonyl group, an aryloxy group, an arylthio group, an acyl group, a sulfonyl group, a heterocyclyloxy group, a heterocyclylthio group, an amido group, a ureido group, a carbamoyl group, an oxo group, a sulfamoyl group, a sulfo group, a cyano group, a nitro group, an acyloxy group, an azido group, a sulfonamido group, a mercapto group, an alkoxycarbonylamino group or a group Rx(Ry)N, and Rx and Ry respectively and independently are a hydrogen atom, an alkyl group, an alkenyl group, an alkynyl group, an aromatic hydrocarbon group or a heterocyclic group.

* * * * *